United States Patent
Keller et al.

(10) Patent No.: US 11,389,456 B2
(45) Date of Patent: Jul. 19, 2022

(54) COMPOUNDS AND METHODS FOR TREATING OXALATE-RELATED DISEASES

(71) Applicant: OxaluRx, Inc., St. Louis, MO (US)

(72) Inventors: Bradley T. Keller, Chesterfield, MO (US); John J. Talley, St. Louis, MO (US)

(73) Assignee: OxaluRx, Inc., St. Louis, MO (US)

( * ) Notice: Subject to any disclaimer, the term of this patent is extended or adjusted under 35 U.S.C. 154(b) by 142 days.

(21) Appl. No.: 16/971,825

(22) PCT Filed: Feb. 22, 2019

(86) PCT No.: PCT/US2019/019070
§ 371 (c)(1),
(2) Date: Aug. 21, 2020

(87) PCT Pub. No.: WO2019/165159
PCT Pub. Date: Aug. 29, 2019

(65) Prior Publication Data
US 2020/0390778 A1  Dec. 17, 2020

Related U.S. Application Data

(60) Provisional application No. 62/634,669, filed on Feb. 23, 2018.

(51) Int. Cl.
| | | |
|---|---|---|
| *A61K 31/5377* | (2006.01) | |
| *A61P 13/12* | (2006.01) | |
| *A61K 31/4192* | (2006.01) | |
| *A61K 31/4439* | (2006.01) | |
| *A61K 31/444* | (2006.01) | |
| *A61K 31/55* | (2006.01) | |
| *A61K 31/635* | (2006.01) | |
| *A61K 9/00* | (2006.01) | |
| *A61K 45/06* | (2006.01) | |

(52) U.S. Cl.
CPC ...... *A61K 31/5377* (2013.01); *A61K 31/4192* (2013.01); *A61K 31/444* (2013.01); *A61K 31/4439* (2013.01); *A61K 31/55* (2013.01); *A61K 31/635* (2013.01); *A61P 13/12* (2018.01); *A61K 9/0053* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 4,248,879 A | * | 2/1981 | Buckle | ............. C07D 491/04 |
| | | | | 548/255 |
| 2006/0160794 A1 | | 7/2006 | Amegadzie | |
| 2021/0052586 A1 | | 2/2021 | Kabakibi | |

FOREIGN PATENT DOCUMENTS

| | | |
|---|---|---|
| WO | 2017100266 | 6/2017 |
| WO | 2017100268 | 6/2017 |
| WO | 2019133770 | 7/2019 |
| WO | 2019133813 | 7/2019 |
| WO | 2019165159 | 8/2019 |
| WO | 2021035196 | 2/2021 |

OTHER PUBLICATIONS

International Application No. PCT/US2019/019070; International Preliminary Report on Patentability, dated Sep. 3, 2020; 8 pages.
International Application No. PCT/US2019/019070; International Search Report and Written Opinion of the International Searching Authority, dated Jun. 27, 2019; 11 pages.
Cox, J. et al., "Discovery of CHK-336: A First-in-Class, Liver-Targeted, Small Molecule Inhibitor of Lactate Dehydrogenase for the Treatment of Primary Hyperoxaluria", Chinook Therapeutics presentation, 9 pages, (2020).
International Application No. PCT/US2020/047548; International Search Report and Written Opinion of the International Searching Authority, dated Nov. 24, 2020; 8 pages.
Oxlumo™ (Lumasiran) Product Label, Highlights of Prescribing Information, Manufactured for Alnylam Pharmaceuticals, Inc., 10 pages, (revised Nov. 2020).
U.S. Appl. No. 17/000,301; Application as filed, dated Aug. 22, 2020; 279 pages.

* cited by examiner

*Primary Examiner* — Heidi Reese
(74) *Attorney, Agent, or Firm* — Dennis A. Bennett; Cynthia Hathaway; C A Schlecht

(57) ABSTRACT

Disclosed herein are compounds and compositions for modulating glycolate oxidase, useful for treating oxalate-related diseases, such as hyperoxaluria, where modulating glycolate oxidase is expected to be therapeutic to a patent in need thereof. Methods of modulating glycolate oxidase activity in a human or animal subject is also provided.

20 Claims, No Drawings

COMPOUNDS AND METHODS FOR TREATING OXALATE-RELATED DISEASES

This application claims the benefit of priority of U.S. Provisional Application No. 62/634,669, filed Feb. 23, 2018, and entitled "Compound and Methods for Treating Oxalate-Related Disease," the disclosure of which is incorporated by referenced in its entirety for all purposes.

The present disclosure relates to new compounds and compositions, and their application as pharmaceuticals for treating disease. Methods of treating oxalate-related diseases, including hyperoxaluria and related conditions, in a human or animal subject are also provided.

Oxalate-related diseases are characterized by oxalate accumulation and/or dysregulation of glyoxylate metabolism in the subject. Hyperoxaluria is an oxalate-related disease characterized by elevated urinary excretion of oxalate. Primary and secondary hyperoxaluria are two distinct clinical manifestations of hyperoxaluria. Primary hyperoxaluria is an inherited error of metabolism due to mutations in at least one of a several different hepatic enzymes involved in glyoxylate and hydroxyproline (HYP) metabolism. Oxalate is endogenously generated by a pathway in which human glycolate oxidase (GO or hGOX) oxidizes glycolate to glyoxylate and then glyoxylate is subsequently converted to oxalate by lactate dehydrogenase (LDH). Mutations in hepatic enzymes involved in these related metabolic pathways result in excess oxalate being formed and excreted through the kidneys. In contrast, secondary hyperoxaluria is caused by increased dietary ingestion and/or absorption of oxalate, precursors of oxalate or alteration in intestinal microflora. Dietary oxalate comes from spinach, bran, rhubarb, beets, potatoes, nuts, nut butter, and other foods. As urinary oxalate levels increase in hyperoxaluria, insoluble crystals of calcium oxalate begin to form in the urinary tract and deposit in the renal tubules causing kidney function to decline. The disease spectrum of hyperoxaluria extends from recurrent kidney stones (nephrolithiasis), nephrocalcinosis and urinary tract infections to chronic kidney disease and eventually end stage renal disease. When calcium oxalate burden exceeds the renal excretory capacity, calcium oxalate also deposits in various organ systems via systemic oxalosis.

Increased urinary oxalate levels are helpful to establish an initial diagnosis for hyperoxaluria while elevated plasma oxalate levels are likely to be more indicative of when patients develop chronic kidney disease. Definitive diagnosis of primary hyperoxaluria is best achieved by genetic analysis and if genetic studies prove inconclusive, liver biopsy is undertaken to establish diagnosis. Diagnostic clues pointing towards secondary hyperoxaluria are a supportive dietary history and tests to detect increased intestinal absorption of oxalate.

Conservative treatment for both types of hyperoxaluria include vigorous hydration and administration of crystallization inhibitors to decrease calcium oxalate precipitation. Pyridoxine is also found to be helpful in approximately 30% patients with primary hyperoxaluria type 1. Onset of the disease can occur at any point from infancy through adulthood and is typically fatal with early onset in the absence of organ transplant. Liver-kidney and isolated kidney transplantation are the treating choice in primary hyperoxaluria type 1 and type 2 respectively. Data are scarce on the role of transplantation in primary hyperoxaluria type 3.

Currently there are no broadly effective treatment options for primary hyperoxaluria. More and better options are needed, for example, compounds which inhibit glycolate oxidase, thus reducing the concentration of glyoxylate available for conversion to oxalate. Early treatment to inhibit GO (often referred to as "substrate depletion therapy") would decrease urinary oxalate concentrations before organ function is compromised.

Novel compounds and pharmaceutical compositions, certain of which have been found to treat oxalate-related diseases, including all types of hyperoxaluria, have been discovered, together with methods of synthesizing and using the compounds including methods for treating hyperoxaluria in a patient by administering the compounds.

Accordingly, disclosed herein are new compositions and methods for targeting glycolate oxidase inhibition and treating hyperoxaluria.

Certain compounds disclosed herein possess useful glycolate oxidase inhibitory activity and may be used to treat or in prophylaxis of oxalate-related diseases. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating glycolate oxidase. Other embodiments provide methods for treating an oxalate-related disease in a patient in need of such treatment, comprising administering to said patient a therapeutically effective amount of a compound or composition as disclosed herein. Also provided is the use of certain compounds disclosed herein for use in the manufacture of a medicament for treating a disease or condition ameliorated by modulating glycolate oxidase.

The present disclosure provides a compound of structural Formula I

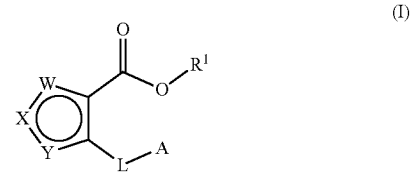

or a salt or prodrug thereof, wherein:
two of W, X and Y are N, and the remaining one is S or NH;
$R^1$ is chosen from hydrogen and $C_1$-$C_6$ alkyl;
L is chosen from NH, $NR^4$, S, O, $CR^4$=$CR^5$, $OCR^4R^5$, and $SCR^4R^5$;
$R^4$ and $R^5$ are each independently chosen from hydrogen or $C_1$-$C_6$ alkyl;
A is chosen from monocyclic or bicyclic aryl, monocyclic or bicyclic heteroaryl, biaryl, and biheteroaryl, any of which is optionally substituted with one or more $R^2$ groups; and
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

In certain embodiments, W and X are N, and Y is NH. In certain embodiments, W and Y are N, and X is NH. In certain embodiments, X and Y are N, and W is NH.

In particular, the present disclosure provides a compound of structural Formula Ia

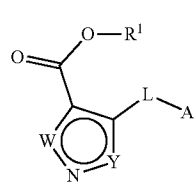

(Ia)

or a salt or prodrug thereof, wherein:
W is N or NH;
Y is N if W is NH; Y is NH if W is N;
$R^1$ is chosen from hydrogen and $C_1$-$C_6$ alkyl;
L is chosen from NH, $NR^4$, S, O, $CR^4$=$CR^5$, $OCR^4R^5$, and $SCR^4R^5$;
$R^4$ and $R^5$ are each independently chosen from hydrogen and $C_1$-$C_6$ alkyl;
A is chosen from monocyclic or bicyclic aryl, monocyclic or bicyclic heteroaryl, biaryl, and biheteroaryl, any of which is optionally substituted with one or more $R^2$ groups; and
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

In certain embodiments, the compound of Formula Ia is a structure of Formula Ib:

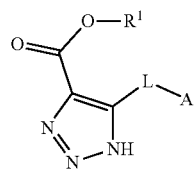

(Ib)

or a salt, ester, or prodrug thereof wherein
$R^1$ is chosen from hydrogen and $C_1$-$C_6$ alkyl;
L is chosen from NH, $NR^4$, S, O, $CR^4$=$CR^5$, $OCR^4R^5$, and $SCR^4R^5$;
$R^4$ and $R^5$ are each independently chosen from hydrogen and $C_1$-$C_6$ alkyl;
A is chosen from monocyclic or bicyclic aryl, monocyclic or bicyclic heteroaryl, biaryl, and biheteroaryl, any of which is optionally substituted with one or more $R^2$ groups; and
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

In certain embodiments, the compound of Formula Ia is a structure of Formula Ic:

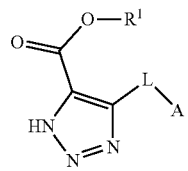

(Ic)

or a salt, ester, or prodrug thereof wherein
$R^1$ is chosen from hydrogen and $C_1$-$C_6$ alkyl;
L is chosen from NH, $NR^4$, S, O, $CR^4$=$CR^5$, $OCR^4R^5$, and $SCR^4R^5$;
$R^4$ and $R^5$ are each independently chosen from hydrogen and $C_1$-$C_6$ alkyl;
A is chosen from monocyclic or bicyclic aryl, monocyclic or bicyclic heteroaryl, biaryl, and biheteroaryl, any of which is optionally substituted with one or more $R^2$ groups; and
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

In certain embodiments, A is monocyclic aryl optionally substituted with one or more $R^2$ groups. In certain embodiments, A is biaryl optionally substituted with one or more $R^2$ groups. In certain embodiments, A is bicyclic aryl optionally substituted with one or more $R^2$ groups. In certain embodiments, A is monocyclic heteroaryl optionally substituted with one or more $R^2$ groups. In certain embodiments, A is bicyclic heteroaryl optionally substituted with one or more $R^2$ groups.

In certain embodiments, A is chosen from phenyl, biphenyl, naphthyl, pyridinylphenyl, phenylpyridinyl, and bipyridinyl any of which is optionally substituted with one or more $R^2$ groups.

In certain embodiments, A is phenyl optionally substituted with one or more $R^2$ groups. In certain embodiments, A is biphenyl optionally substituted with one or more $R^2$ groups. In certain embodiments, A is naphthyl optionally substituted with one or more $R^2$ groups. In certain embodiments, A is pyridinylphenyl optionally substituted with one or more $R^2$ groups. In certain embodiments, A is phenylpyridinyl optionally substituted with one or more $R^2$ groups. In certain embodiments, A is bipyridinyl optionally substituted with one or more $R^2$ groups.

The present disclosure further provides a compound of structural Formula Id

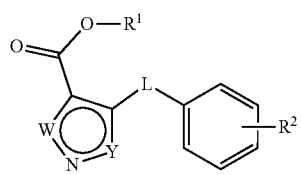

(Id)

or a salt or prodrug thereof, wherein:
W is N or NH;
Y is N if W is NH; Y is NH if W is N;
$R^1$ is chosen from hydrogen and $C_1$-$C_6$ alkyl;
L is chosen from NH, $NR^4$, S, O, CH=CH, $OCH_2$, and $SCH_2$;
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

Also provided are embodiments of any of the above embodiments wherein if A is optionally substituted biphenyl, and the phenyl of the biphenyl that is distal to the core is para-substituted with Br or F, then said phenyl must have at least one additional $R^2$ substituent.

The present disclosure further provides a compound of structural Formula Ie

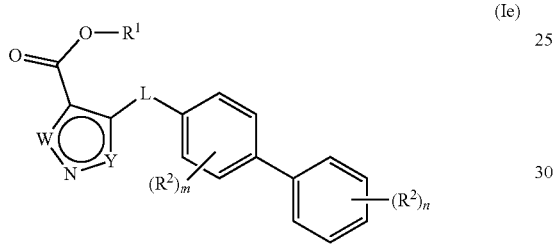

(Ie)

or a salt or prodrug thereof, wherein:
W is N or NH;
Y is N if W is NH; Y is NH if W is N;
$R^1$ is chosen from hydrogen and $C_1$-$C_6$ alkyl;
L is chosen from NH, $NR^4$, S, O, $CR^4$=$CR^5$, $OCR^4R^5$, and $SCR^4R^5$;
$R^4$ and $R^5$ are each independently chosen from hydrogen and $C_1$-$C_6$ alkyl;
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl;
m and n are each independently 1, 2, or 3.

Also provided are embodiments of Formula Ie wherein if $R^2$ is Br or F and is attached in the para position, then n must be 2 or 3 (i.e., there must be an additional $R^2$ substituent).

The present disclosure provides a compound of structural Formula If

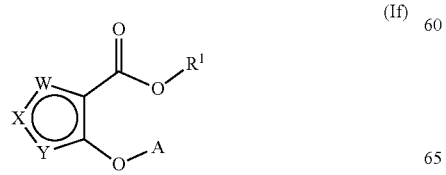

(If)

or a salt or prodrug thereof, wherein:
two of W, X and Y are N, and the remaining one is S or NH;
$R^1$ is chosen from hydrogen and $C_1$-$C_6$ alkyl;
$R^4$ and $R^5$ are each independently chosen from hydrogen and $C_1$-$C_6$ alkyl;
A is chosen from monocyclic or bicyclic aryl, monocyclic or bicyclic heteroaryl, biaryl, and biheteroaryl, any of which is optionally substituted with one or more $R^2$ groups; and
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

In certain embodiments, W and X are N, and Y is NH. In certain embodiments, W and Y are N, and X is NH. In certain embodiments, X and Y are N, and W is NH.

In particular, the present disclosure provides a compound of structural Formula Ig

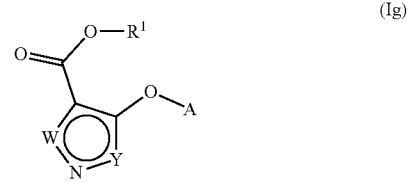

(Ig)

or a salt or prodrug thereof, wherein:
W is N or NH;
Y is N if W is NH; Y is NH if W is N;
$R^1$ is chosen from hydrogen and $C_1$-$C_6$ alkyl;
$R^4$ and $R^5$ are each independently chosen from hydrogen and $C_1$-$C_6$ alkyl;
A is chosen from monocyclic or bicyclic aryl, monocyclic or bicyclic heteroaryl, biaryl, and biheteroaryl, any of which is optionally substituted with one or more $R^2$ groups; and
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, and cyano.

In certain embodiments, the compound of Formula Ia is a structure of Formula Ih:

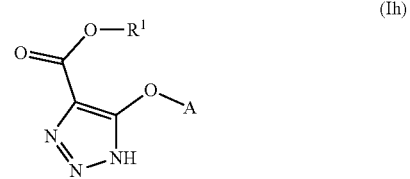

(Ih)

or a salt, ester, or prodrug thereof wherein
$R^1$ is chosen from hydrogen and $C_1$-$C_6$ alkyl;
$R^4$ and $R^5$ are each independently chosen from hydrogen and $C_1$-$C_6$ alkyl;
A is chosen from monocyclic or bicyclic aryl, monocyclic or bicyclic heteroaryl, biaryl, and biheteroaryl, any of which is optionally substituted with one or more $R^2$ groups; and
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

In certain embodiments, the compound of Formula Ia is a structure of Formula Ii:

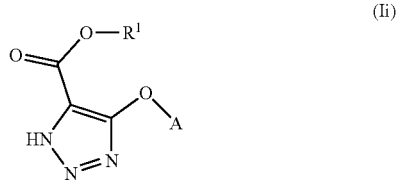

(Ii)

or a salt, ester, or prodrug thereof wherein
$R^1$ is chosen from hydrogen and $C_1$-$C_6$ alkyl;
$R^4$ and $R^5$ are each independently chosen from hydrogen and $C_1$-$C_6$ alkyl;
A is chosen from monocyclic or bicyclic aryl, monocyclic or bicyclic heteroaryl, biaryl, and biheteroaryl, any of which is optionally substituted with one or more $R^2$ groups; and
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

In certain embodiments, A is monocyclic aryl optionally substituted with one or more $R^2$ groups. In certain embodiments, A is biaryl optionally substituted with one or more $R^2$ groups. In certain embodiments, A is bicyclic aryl optionally substituted with one or more $R^2$ groups. In certain embodiments, A is monocyclic heteroaryl optionally substituted with one or more $R^2$ groups. In certain embodiments, A is bicyclic heteroaryl optionally substituted with one or more $R^2$ groups.

In certain embodiments, A is chosen from phenyl, biphenyl, naphthyl, pyridinylphenyl, phenylpyridinyl, and bipyridinyl, any of which is optionally substituted with one or more $R^2$ groups.

In certain embodiments, A is phenyl optionally substituted with one or more $R^2$ groups. In certain embodiments, A is biphenyl optionally substituted with one or more $R^2$ groups. In certain embodiments, A is naphthyl optionally substituted with one or more $R^2$ groups. In certain embodiments, A is pyridinylphenyl optionally substituted with one or more $R^2$ groups. In certain embodiments, A is phenylpyridinyl optionally substituted with one or more $R^2$ groups. In certain embodiments, A is bipyridinyl optionally substituted with one or more $R^2$ groups.

The present disclosure further provides a compound of structural Formula Ij

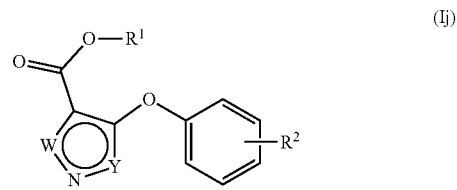

(Ij)

or a salt or prodrug thereof, wherein:
W is N or NH;
Y is N if W is NH; Y is NH if W is N;
$R^1$ is chosen from hydrogen and $C_1$-$C_6$ alkyl;
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

The present disclosure further provides a compound of structural Formula Ik

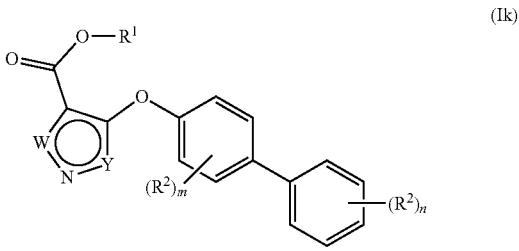

(Ik)

or a salt or prodrug thereof, wherein:
W is N or NH;
Y is N if W is NH; Y is NH if W is N;
$R^1$ is chosen from hydrogen and $C_1$-$C_6$ alkyl;
$R^4$ and $R^5$ are each independently chosen from hydrogen and $C_1$-$C_6$ alkyl;
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl;
m and n are each independently 1, 2, or 3.

The following embodiments are applicable, individually and in combination with each other where not mutually exclusive, to any of Formulae Ia to Ik.

In certain embodiments, $R^1$ is ethyl, methyl or hydrogen. In certain embodiments, $R^1$ is ethyl. In certain embodiments, $R^1$ is methyl. In certain embodiments, $R^1$ is hydrogen.

In certain embodiments, each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

In certain embodiments, the A is substituted with one or more $R^2$ groups chosen from chloro, methyl, methoxy, bromo, dimethyl, fluoro, trifluoromethyl, ethoxy, trifluoromethoxy, difluoromethoxy, methylthio, trifluoromethylthio, cyano, pentafluorosulfaneyl, dichloro, methylsulfinyl, methylsulfonyl, sulfamoyl, methylsulfamoyl, dimethylsulfamoyl, propyl, butyl, cyclobutyl, cyclopentyl, cyclohexyl, pyrrolindyl, piperidinyl, azepanyl, morpholinyl, vinyl, methylpropenyl, and ethynyl.

In certain embodiments, A is phenyl and is substituted with one or more $R^2$ groups chosen from chloro, methyl, methoxy, bromo, dimethyl, fluoro, trifluoromethyl, ethoxy, trifluoromethoxy, difluoromethoxy, methylthio, trifluoromethylthio, cyano, pentafluorosulfaneyl, dichloro, methylsulfinyl, methylsulfonyl, sulfamoyl, methylsulfamoyl, dimethylsulfamoyl, propyl, butyl, cyclobutyl, cyclopentyl, cyclohexyl, pyrrolindyl, piperidinyl, azepanyl, morpholinyl, vinyl, methylpropenyl, and ethynyl.

In certain embodiments, A is biphenyl and is substituted with one or more $R^2$ groups chosen from chloro, methyl, methoxy, bromo, dimethyl, fluoro, trifluoromethyl, ethoxy, trifluoromethoxy, difluoromethoxy, methylthio, trifluoromethylthio, cyano, pentafluorosulfaneyl, dichloro, methylsulfinyl, methylsulfonyl, sulfamoyl, methylsulfamoyl, dimethylsulfamoyl, propyl, butyl, cyclobutyl, cyclopentyl, cyclohexyl, pyrrolindyl, piperidinyl, azepanyl, morpholinyl, vinyl, methylpropenyl, and ethynyl.

In certain embodiments, A is naphthyl and is substituted with one or more $R^2$ groups chosen from chloro, methyl, methoxy, bromo, dimethyl, fluoro, trifluoromethyl, ethoxy, trifluoromethoxy, difluoromethoxy, methylthio, trifluoromethylthio, cyano, pentafluorosulfaneyl, dichloro, methylsulfinyl, methylsulfonyl, sulfamoyl, methylsulfamoyl, dimethylsulfamoyl, propyl, butyl, cyclobutyl, cyclopentyl, cyclohexyl, pyrrolindyl, piperidinyl, azepanyl, morpholinyl, vinyl, methylpropenyl, and ethynyl.

In certain embodiments, A is phenylpyridinyl and is substituted with one or more $R^2$ groups chosen from chloro, methyl, methoxy, bromo, dimethyl, fluoro, trifluoromethyl, ethoxy, trifluoromethoxy, difluoromethoxy, methylthio, trifluoromethylthio, cyano, pentafluorosulfaneyl, dichloro, methylsulfinyl, methylsulfonyl, sulfamoyl, methylsulfamoyl, dimethylsulfamoyl, propyl, butyl, cyclobutyl, cyclopentyl, cyclohexyl, pyrrolindyl, piperidinyl, azepanyl, morpholinyl, vinyl, methylpropenyl, and ethynyl.

In certain embodiments, A is pyridinylphenyl and is substituted with one or more $R^2$ groups chosen from chloro, methyl, methoxy, bromo, dimethyl, fluoro, trifluoromethyl, ethoxy, trifluoromethoxy, difluoromethoxy, methylthio, trifluoromethylthio, cyano, pentafluorosulfaneyl, dichloro, methylsulfinyl, methylsulfonyl, sulfamoyl, methylsulfamoyl, dimethylsulfamoyl, propyl, butyl, cyclobutyl, cyclopentyl, cyclohexyl, pyrrolindyl, piperidinyl, azepanyl, morpholinyl, vinyl, methylpropenyl, and ethynyl.

In certain embodiments, A is bipyridinyl and is substituted with one or more $R^2$ groups chosen from chloro, methyl, methoxy, bromo, dimethyl, fluoro, trifluoromethyl, ethoxy, trifluoromethoxy, difluoromethoxy, methylthio, trifluoromethylthio, cyano, pentafluorosulfaneyl, dichloro, methylsulfinyl, methylsulfonyl, sulfamoyl, methylsulfamoyl, dimethylsulfamoyl, propyl, butyl, cyclobutyl, cyclopentyl, cyclohexyl, pyrrolindyl, piperidinyl, azepanyl, morpholinyl, vinyl, methylpropenyl, and ethynyl.

In certain embodiments, $R^4$ and $R^5$ are independently chosen from methyl and hydrogen.

In certain embodiments, $R^4$ is methyl. In certain embodiments, $R^4$ is hydrogen.

In certain embodiments, $R^5$ is methyl. In certain embodiments, $R^5$ is hydrogen. In certain embodiments, L is NH. In certain embodiments, L is $NR^4$. In certain embodiments, L is S. In certain embodiments, L is O. In certain embodiments, L is $CR^4$=$CR^5$. In certain embodiments, L is CH=CH. In certain embodiments, L is $OCR^4R^5$. In certain embodiments, L is $OCH_2$. In certain embodiments, L is $SCR^4R^5$. In certain embodiments, L is $SCH_2$.

Provided is a compound of Formula I, or a salt or prodrug thereof, for use as a medicament.

Provided is a compound as disclosed herein, or a salt or prodrug thereof, for use in the manufacture of a medicament for preventing or treating an oxalate-related disease.

Provided is a pharmaceutical composition comprising a compound as disclosed herein, or a salt or prodrug thereof, together with a pharmaceutically acceptable carrier. The pharmaceutical composition may be formulated for oral administration. The pharmaceutical composition may additionally comprise another therapeutic agent.

Provided is a method of inhibiting glycolate oxidase (hGOX) activity in a biological sample comprising contacting the biological sample with a compound disclosed herein, or a salt or prodrug thereof.

Provided is method of treating an oxalate-related disease in a subject in need thereof, comprising the step of administering to the subject a compound disclosed herein, or a salt or prodrug thereof. The subject may be a human. Primary hyperoxaluria may be treated.

Provided is a method of treating an oxalate-related disease in a subject in need thereof, comprising the sequential or co-administration of a compound disclosed herein, or a salt or prodrug thereof, and a second therapeutic agent.

Provided is a compound disclosed herein, or a salt or prodrug thereof, for use in human therapy.

Provided is a compound disclosed herein, or a salt or prodrug thereof, for use in treating an oxalate-related disease.

Provided is use of a compound disclosed herein, or a salt or prodrug thereof, for the manufacture of a medicament to treat an oxalate-related disease.

Provided herein is Embodiment 1: A compound of structural Formula Ia

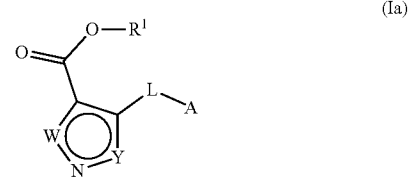

(Ia)

or a salt or prodrug thereof, wherein:
W is N or NH;
Y is N if W is NH; Y is NH if W is N;
$R^1$ is chosen from hydrogen and $C_1$-$C_6$ alkyl;
L is chosen from NH, $NR^4$, S, O, $CR^4$=$CR^5$, $OCR^4R^5$, and $SCR^4R^5$;

$R^4$ and $R^5$ are each independently chosen from hydrogen and $C_1$-$C_6$ alkyl;

A is chosen from monocyclic or bicyclic aryl, monocyclic or bicyclic heteroaryl, biaryl, and biheteroaryl, any of which is optionally substituted with one or more $R^2$ groups; and each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

Also provided are the following further embodiments:

Embodiment 2: The compound of Embodiment 1, wherein structure of Formula I is a structure of Formula Ib

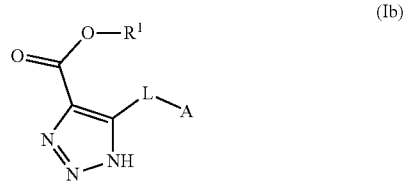

or a salt or prodrug thereof, wherein all groups are as defined in Embodiment 1.

Embodiment 3: The compound of Embodiment 1, wherein structure of Formula I is a structure of Formula Ic

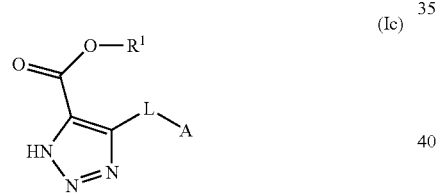

or a salt or prodrug thereof, wherein all groups are as defined in Embodiment 1.

Embodiment 4: The compound of any of Embodiments 1 to 3, wherein A is chosen from aryl, biaryl, and biheteroaryl, any of which is optionally substituted with one or more $R^2$ groups.

Embodiment 5: The compound of Embodiment 4, wherein A is chosen from phenyl, biphenyl, naphthyl, pyridinylphenyl, phenylpyridinyl, and bipyridinyl, any of which is optionally substituted with one or more $R^2$ groups.

Embodiment 6: The compound of Embodiment 5, wherein A is substituted with one or more $R^2$ groups chosen from chloro, methyl, methoxy, bromo, dimethyl, fluoro, trifluoromethyl, ethoxy, trifluoromethoxy, difluoromethoxy, methylthio, trifluoromethylthio, cyano, pentafluorosulfaneyl, dichloro, methylsulfinyl, methylsulfonyl, sulfamoyl, methylsulfamoyl, dimethylsulfamoyl, propyl, butyl, cyclobutyl, cyclopentyl, cyclohexyl, pyrrolindyl, piperidinyl, azepanyl, morpholinyl, vinyl, methylpropenyl, and ethynyl.

Embodiment 7: The compound of Embodiment 6, wherein the phenyl is substituted with one or more $R^2$ groups chosen from chloro, methyl, methoxy, bromo, dimethyl, fluoro, trifluoromethyl, ethoxy, trifluoromethoxy, difluoromethoxy, methylthio, trifluoromethylthio, cyano, pentafluorosulfaneyl, dichloro, methylsulfinyl, methylsulfonyl, sulfamoyl, methylsulfamoyl, dimethylsulfamoyl, propyl, butyl, cyclobutyl, cyclopentyl, cyclohexyl, pyrrolindyl, piperidinyl, azepanyl, morpholinyl, vinyl, methylpropenyl, and ethynyl.

Embodiment 8: The compound of any of Embodiments 1-7, wherein $R^1$ is ethyl, methyl, or hydrogen.

Embodiment 9: The compound of any of Embodiments 1-8, wherein $R^4$ and $R^5$ are independently chosen from methyl and hydrogen.

Embodiment 10: The compound of any of Embodiments 1-9, wherein L is NH.

Embodiment 11: The compound of any of Embodiments 1-9, wherein L is S.

Embodiment 12: The compound of any of Embodiments 1-9, wherein L is O.

Embodiment 13: The compound of any of Embodiments 1-9, wherein L is CH=CH.

Embodiment 14: The compound of any of Embodiments 1-9, wherein L is $OCH_2$.

Embodiment 15: The compound of any of Embodiments 1-9, wherein L is $SCH_2$.

Embodiment 16: The compound of any of Embodiments 1-15, chosen from compounds I-001 through I-311, or a salt or prodrug thereof.

Embodiment 17: A compound of structural Formula Id

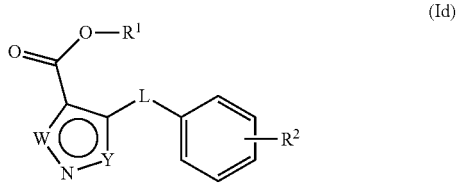

or a salt or prodrug thereof, wherein:

W is N or NH;

Y is N if W is NH; Y is NH if W is N;

$R^1$ is chosen from hydrogen and $C_1$-$C_6$ alkyl;

L is chosen from NH, $NR^4$, S, O, $CR^4$=$CR^5$, $OCR^4R^5$, and $SCR^4R^5$;

$R^4$ and $R^5$ are each independently chosen from hydrogen and $C_1$-$C_6$ alkyl;

each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl.

Embodiment 18: The compound of Embodiment 17, wherein the phenyl is substituted with one or more $R^2$ groups chosen from chloro, methyl, methoxy, bromo, dimethyl, fluoro, trifluoromethyl, ethoxy, trifluoromethoxy, difluoromethoxy, methylthio, trifluoromethylthio, cyano, pentafluorosulfaneyl, dichloro, methylsulfinyl, methylsulfonyl, sulfamoyl, methylsulfamoyl, dimethylsulfamoyl, propyl, butyl, cyclobutyl, cyclopentyl, cyclohexyl, pyrrolindyl, piperidinyl, azepanyl, morpholinyl, vinyl, methylpropenyl, and ethynyl.

Embodiment 19: The compound of Embodiment 16 or 17, wherein $R^1$ is ethyl, methyl, or hydrogen.

Embodiment 20: The compound of any of Embodiments 16-19, wherein $R^4$ and $R^5$ are independently chosen from methyl and hydrogen.

Embodiment 21: The compound of any of Embodiments 16-20, wherein L is NH.

Embodiment 22: The compound of Embodiment 21, chosen from

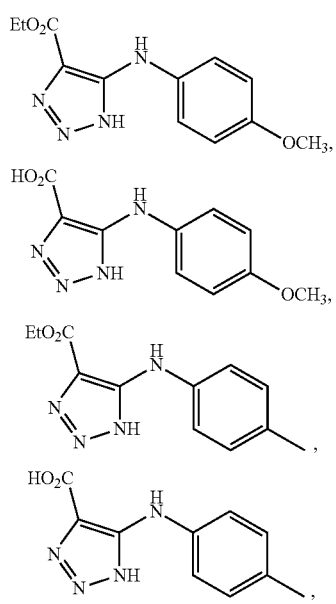

or a salt or prodrug thereof.

Embodiment 23: The compound of any of Embodiments 16-20, wherein L is S.

Embodiment 24: The compound of Embodiment 23, chosen from

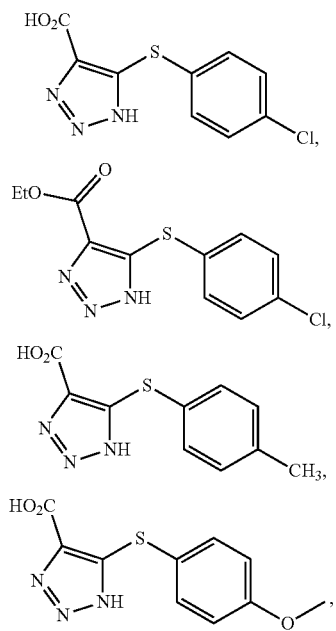

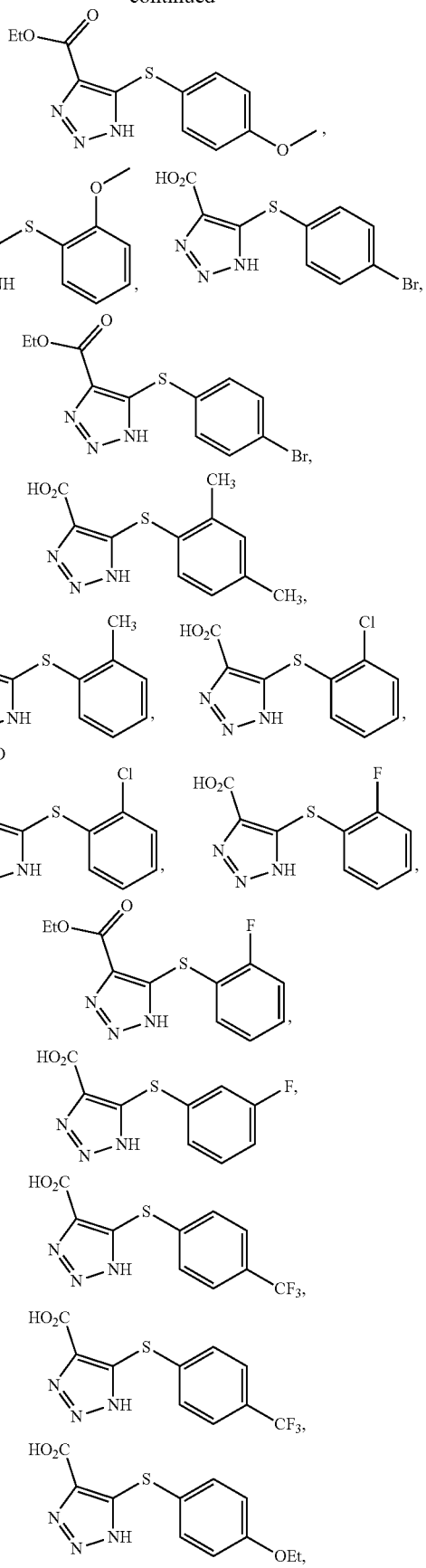

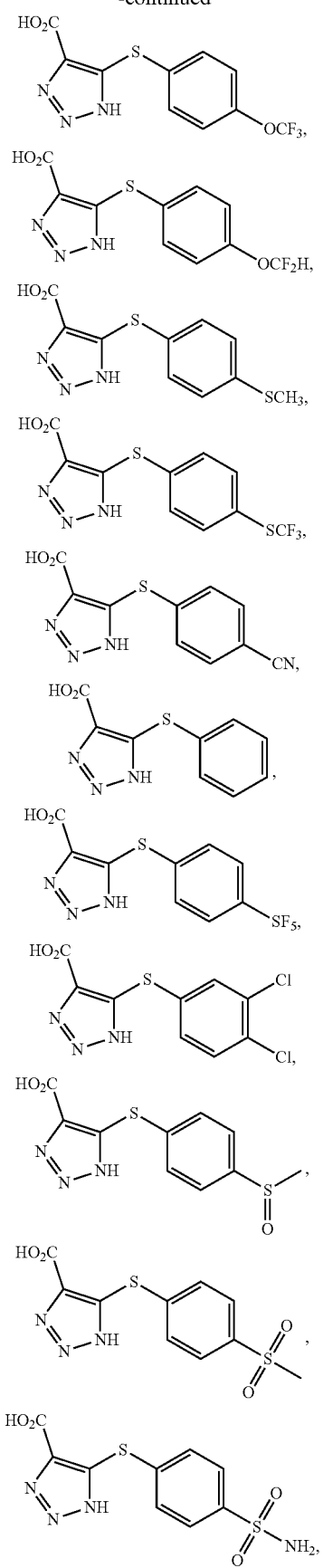
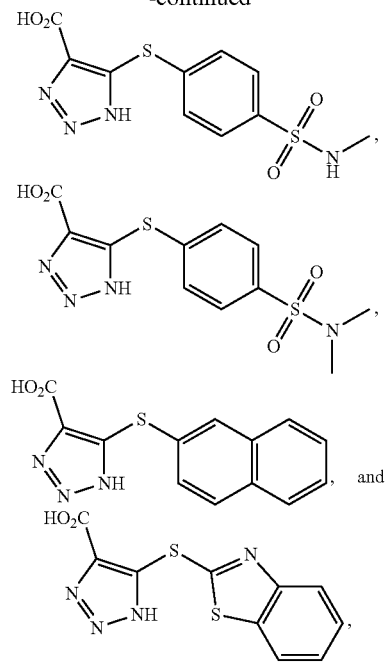
or a salt or prodrug thereof.
Embodiment 25: The compound of any of Embodiments 16-20, wherein L is O.
Embodiment 26: The compound of Embodiment 25, chosen from
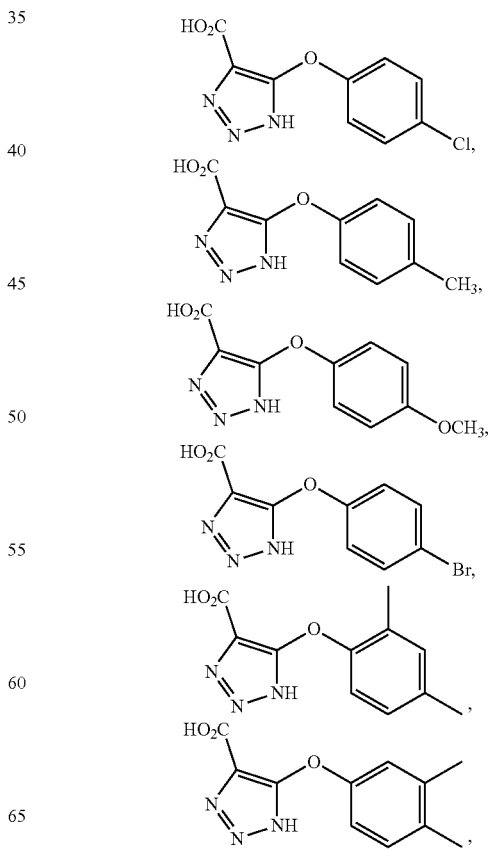

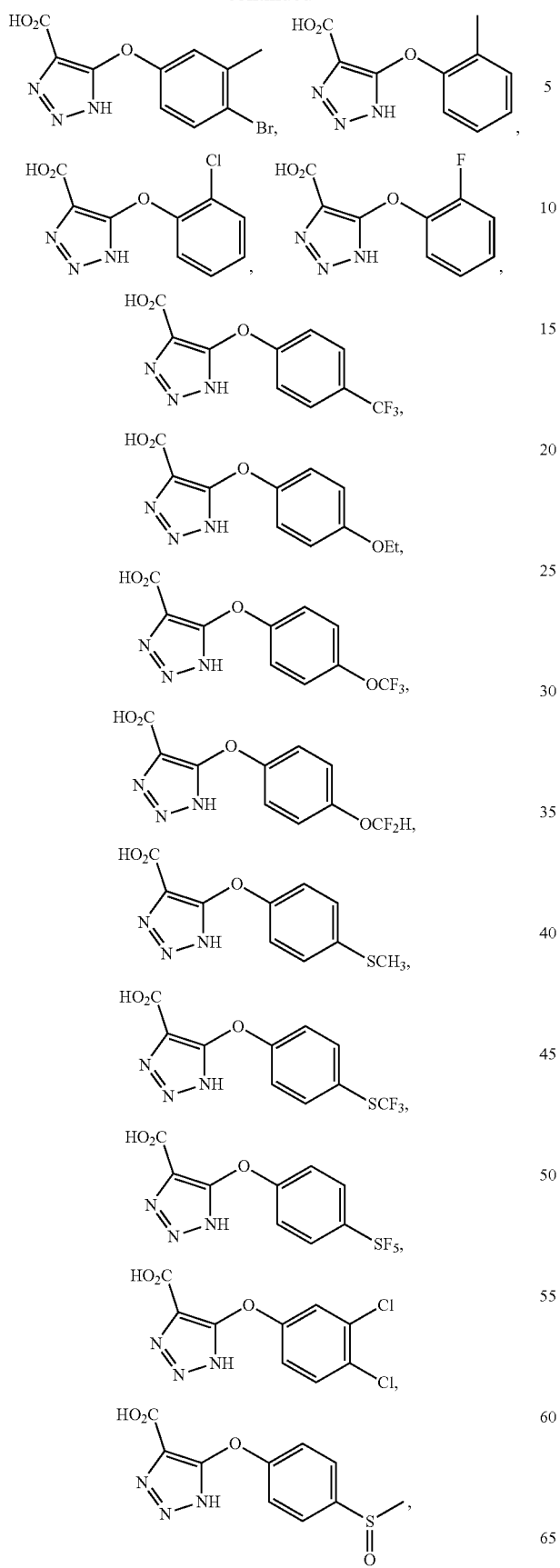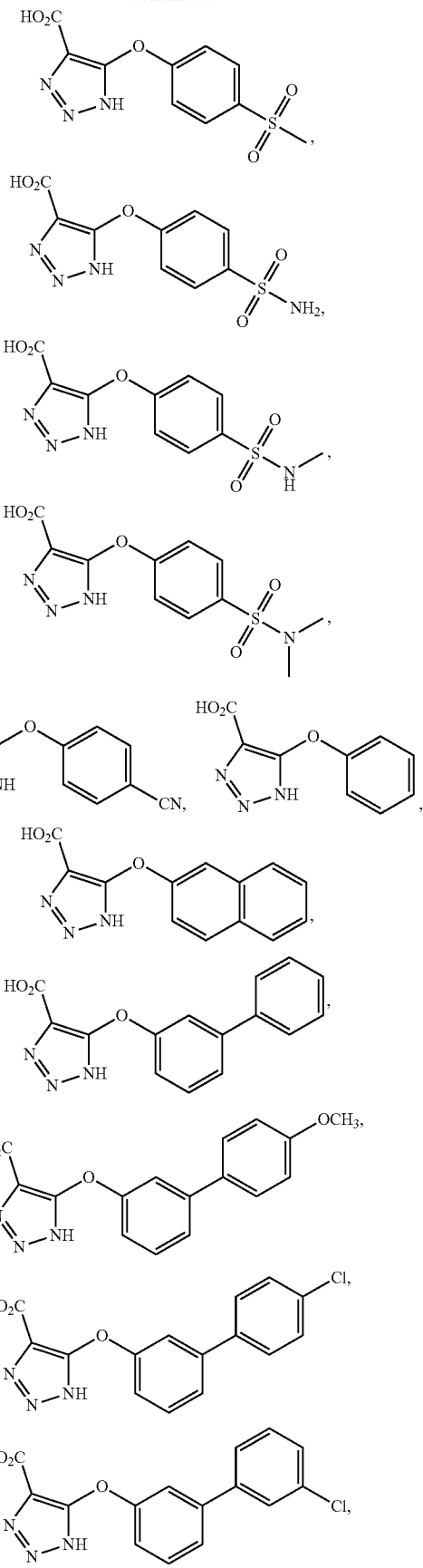

-continued
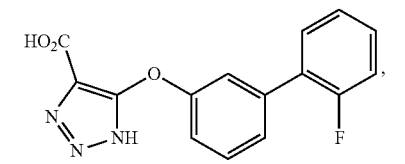
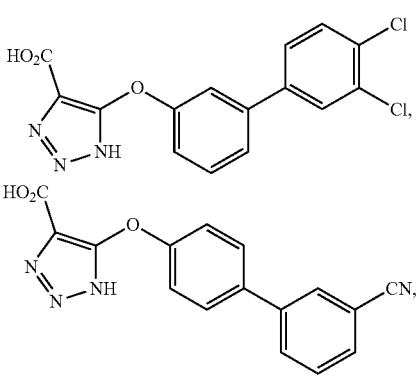
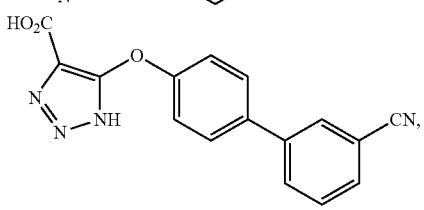
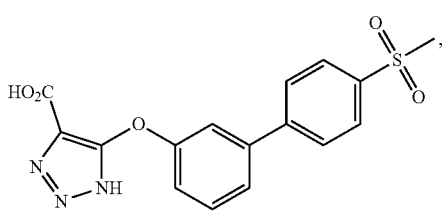
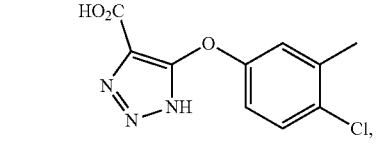
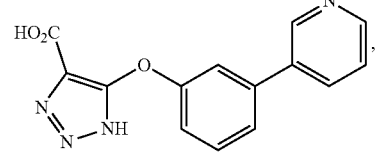
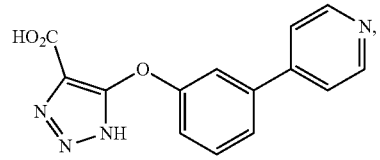
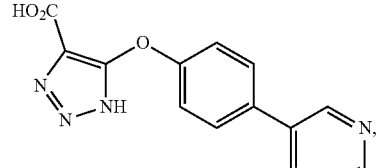
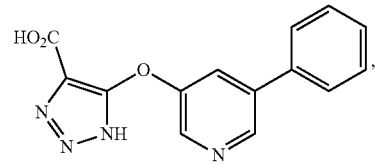
-continued
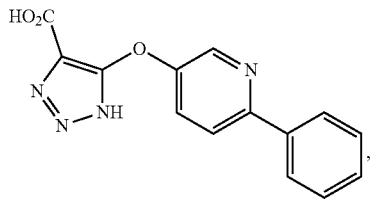
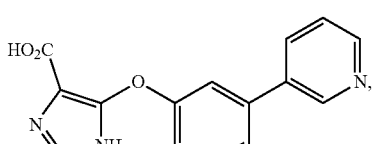
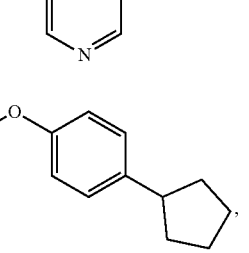
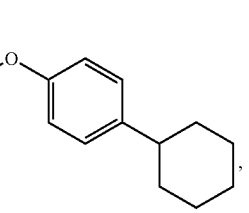
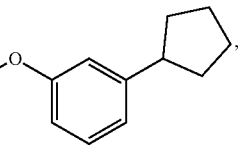
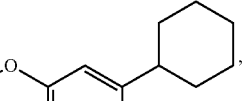
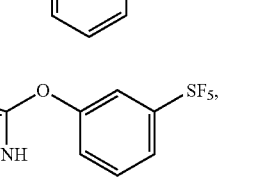
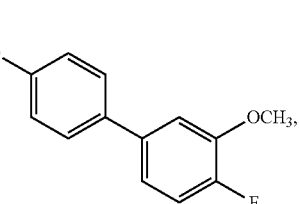
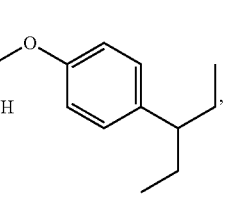

-continued

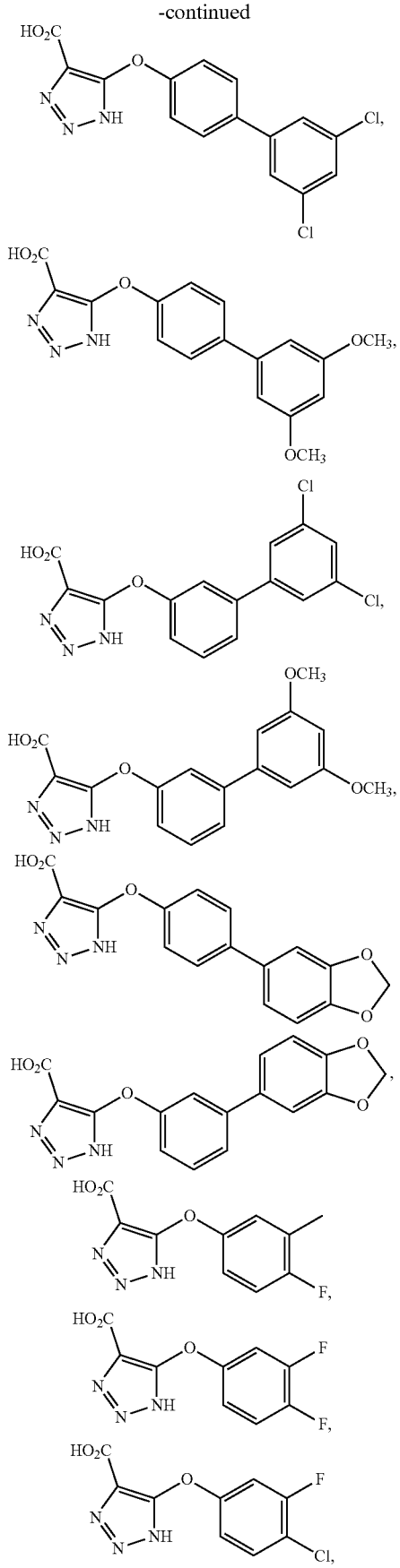
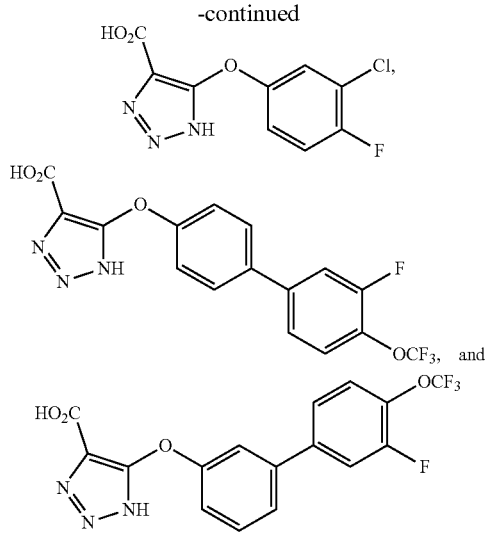
or a salt or prodrug thereof.
Embodiment 27: The compound of any of Embodiments 16-20, wherein L is CH=CH.
Embodiment 28: The compound of Embodiment 27, chosen from
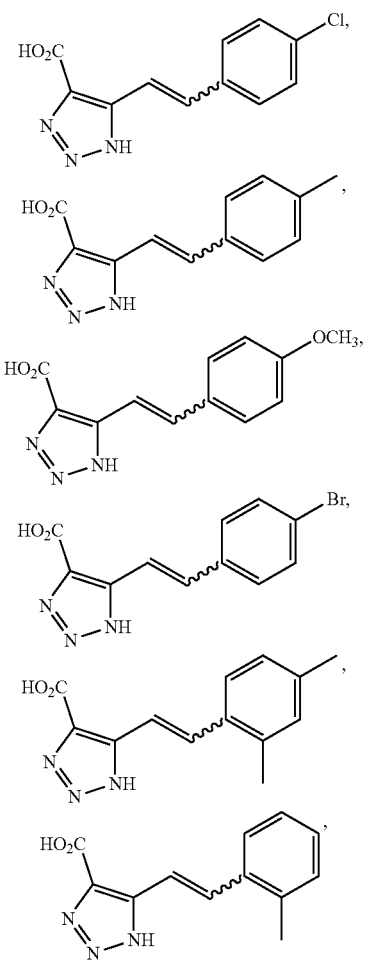

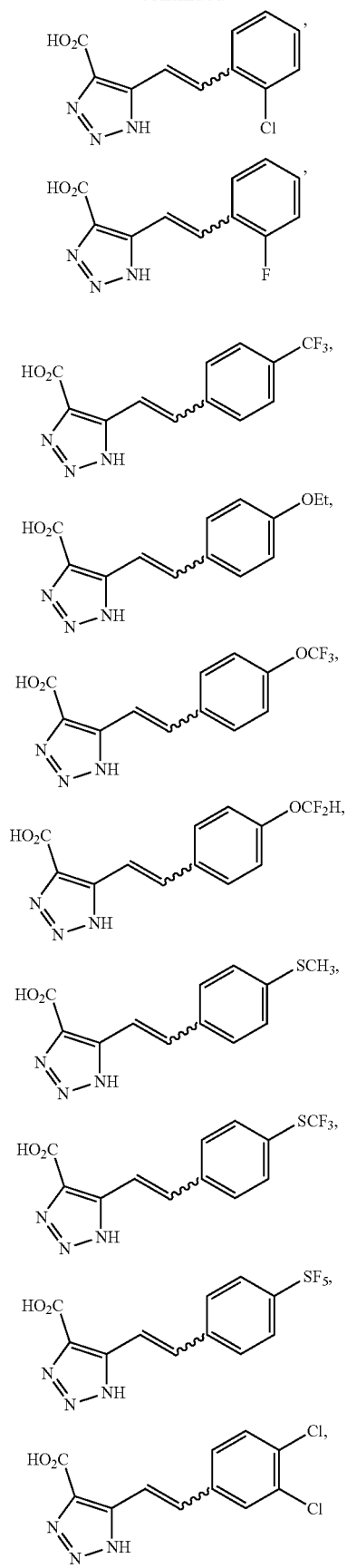
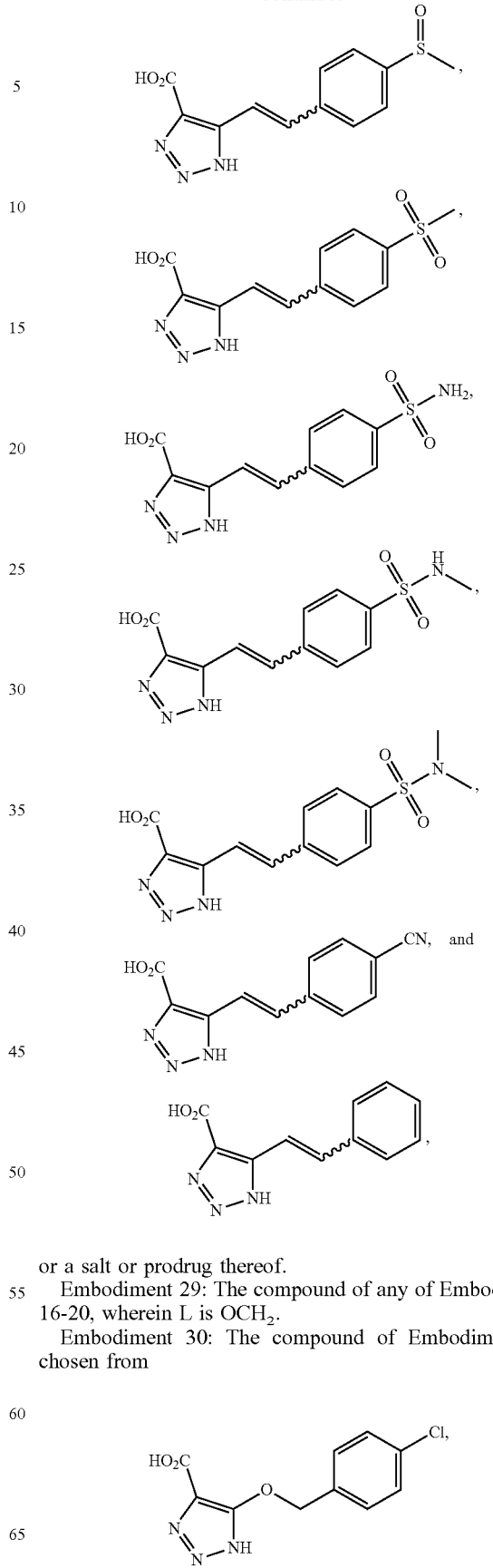
or a salt or prodrug thereof.
Embodiment 29: The compound of any of Embodiments 16-20, wherein L is OCH$_2$.
Embodiment 30: The compound of Embodiment 27, chosen from -continued
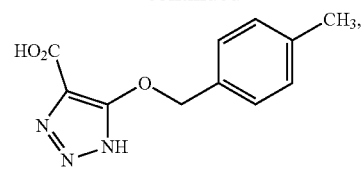
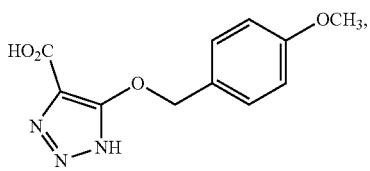
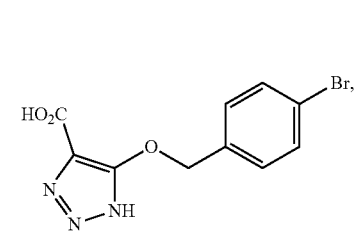
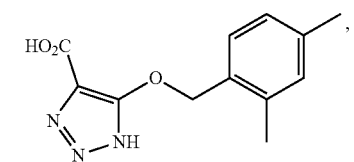
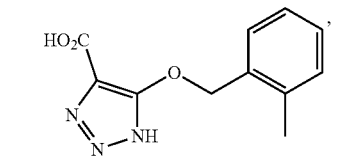
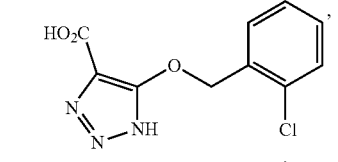
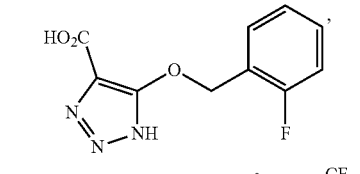
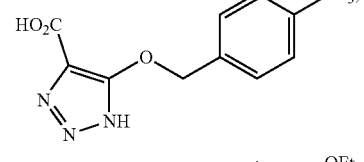
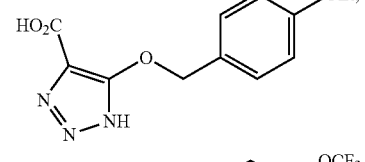
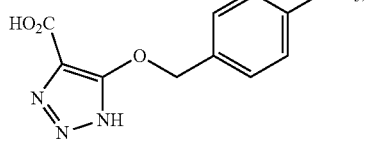
-continued
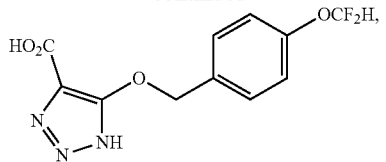
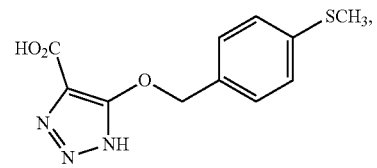
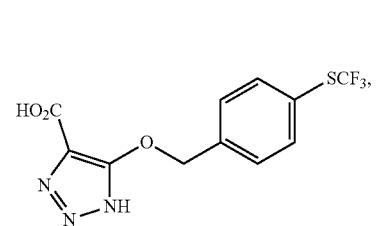
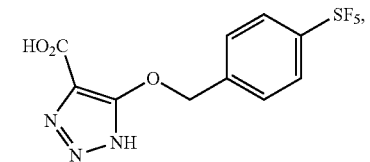
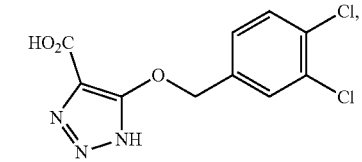
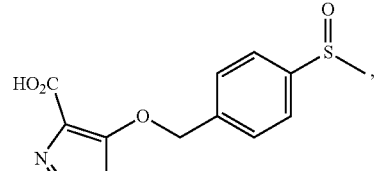
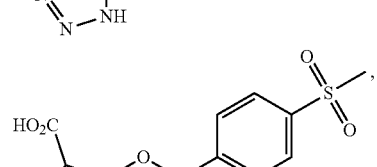
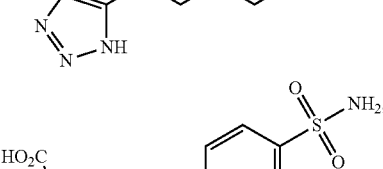
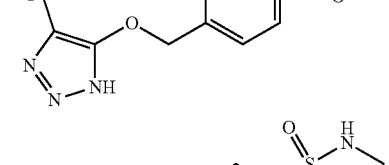
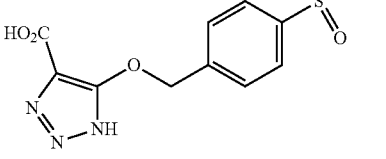

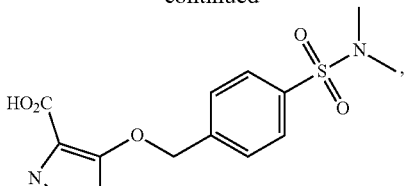
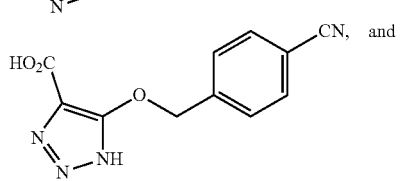
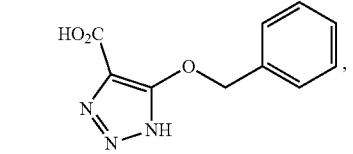 [SMILES: O=C(O)c1nn[nH]c1OCc1ccccc1]
or a salt or prodrug thereof.
Embodiment 31: The compound of any of Embodiments 16-20, wherein L is SCH$_2$.
Embodiment 32: The compound of Embodiment 31, chosen from
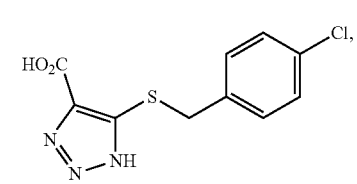
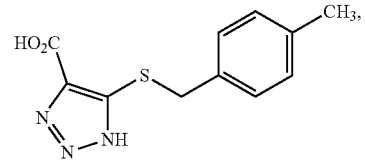
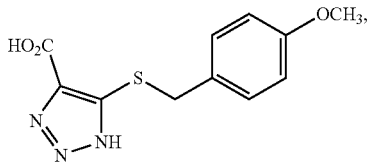
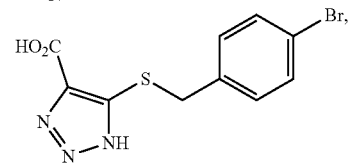
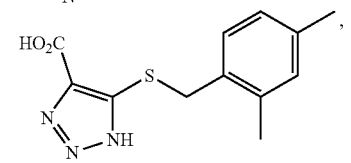
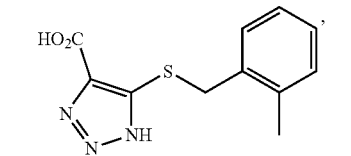 [SMILES: O=C(O)c1nn[nH]c1SCc1ccccc1]
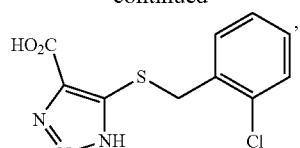
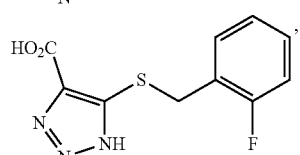
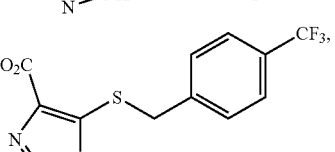
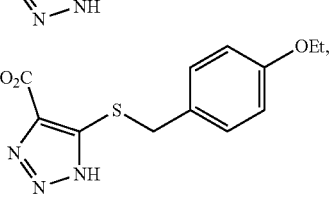
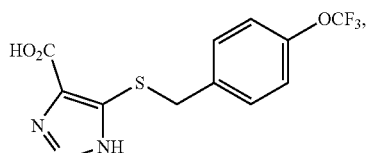
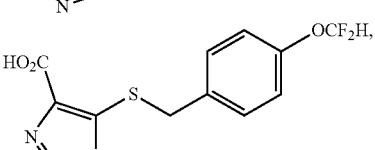
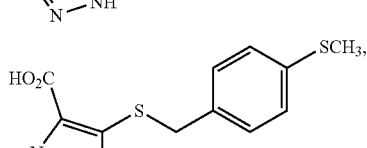
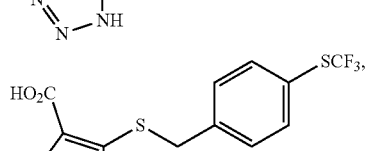
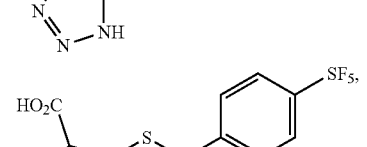
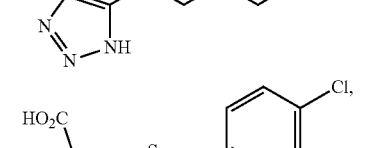

-continued

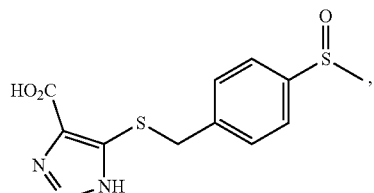

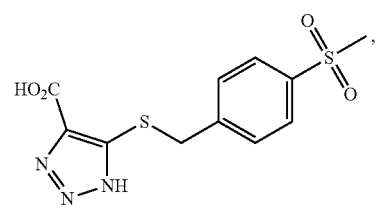

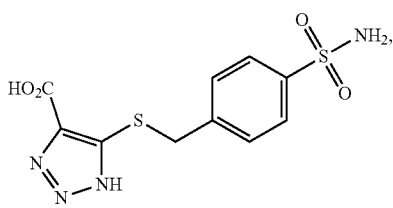

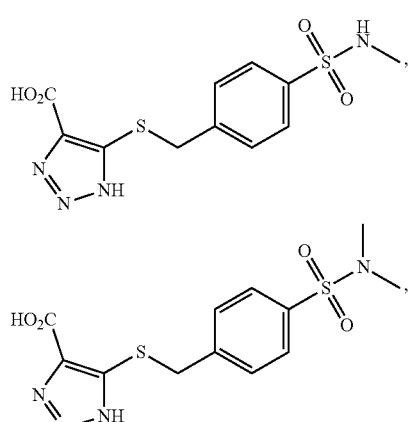

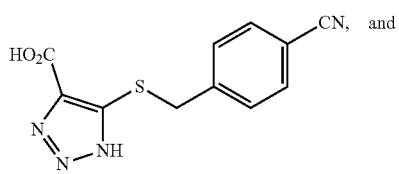

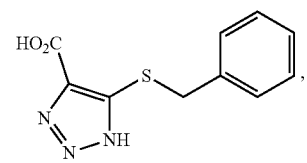

or a salt or prodrug thereof.

Embodiment 33: A compound of structural Formula Ie

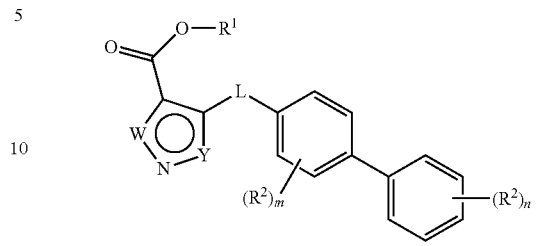

(Ie)

or a salt or prodrug thereof, wherein:
W is N or NH;
Y is N if W is NH; Y is NH if W is N;
$R^1$ is chosen from hydrogen and $C_1$-$C_6$ alkyl;
L is chosen from NH, $NR^4$, S, O, $CR^4$=$CR^5$, $OCR^4R^5$, and $SCR^4R^5$;
$R^4$ and $R^5$ are each independently chosen from hydrogen or $C_1$-$C_6$ alkyl;
each $R^2$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl;
m and n are independently 1, 2, or 3.

Embodiment 34: The compound of Embodiment 33, wherein the biphenyl is substituted with one or more $R^2$ groups chosen from chloro, methyl, methoxy, bromo, dimethyl, fluoro, trifluoromethyl, ethoxy, trifluoromethoxy, difluoromethoxy, methylthio, trifluoromethylthio, cyano, pentafluorosulfaneyl, dichloro, methylsulfinyl, methylsulfonyl, sulfamoyl, methylsulfamoyl, dimethylsulfamoyl, propyl, butyl, cyclobutyl, cyclopentyl, cyclohexyl, pyrrolindyl, piperidinyl, azepanyl, morpholinyl, vinyl, methylpropenyl, and ethynyl.

Embodiment 35: The compound of Embodiment 33 or 34, wherein $R^1$ is ethyl, methyl, or hydrogen.

Embodiment 36: The compound of any of Embodiments 33-35, wherein $R^4$ and $R^5$ are independently chosen from methyl and hydrogen.

Embodiment 37: The compound of any of Embodiments 33-35, wherein L is S.

Embodiment 38: The compound of Embodiment 37, chosen from

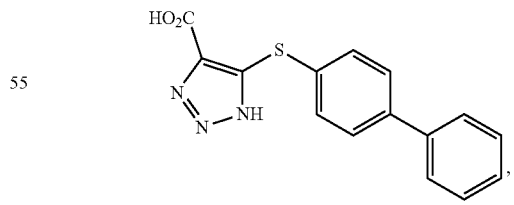

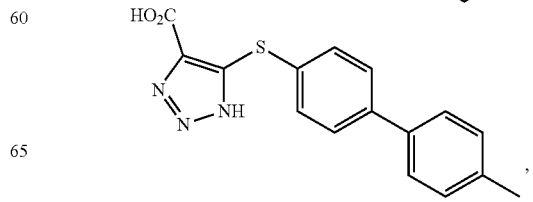

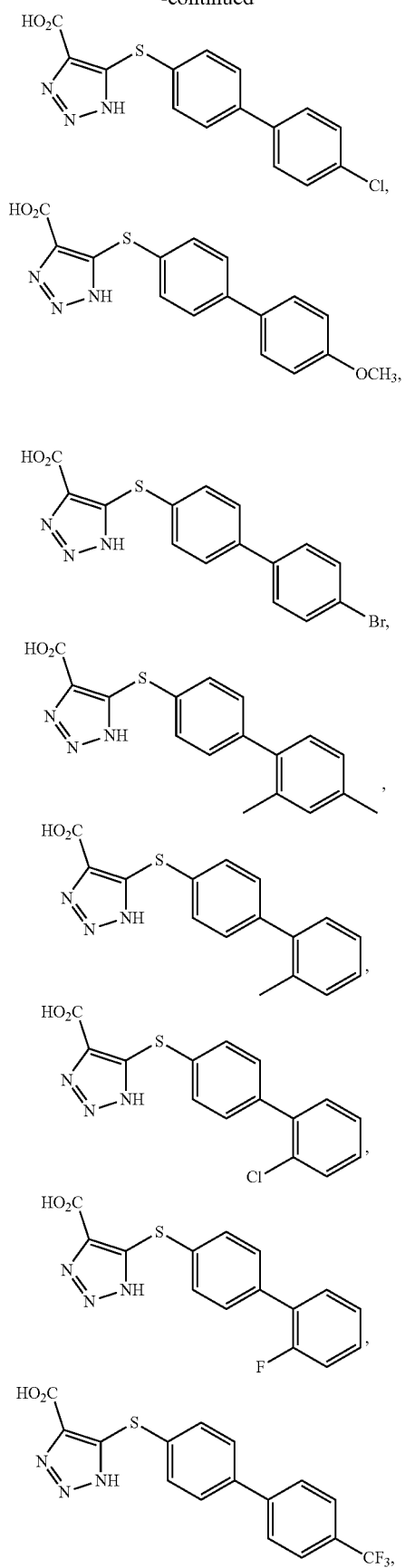
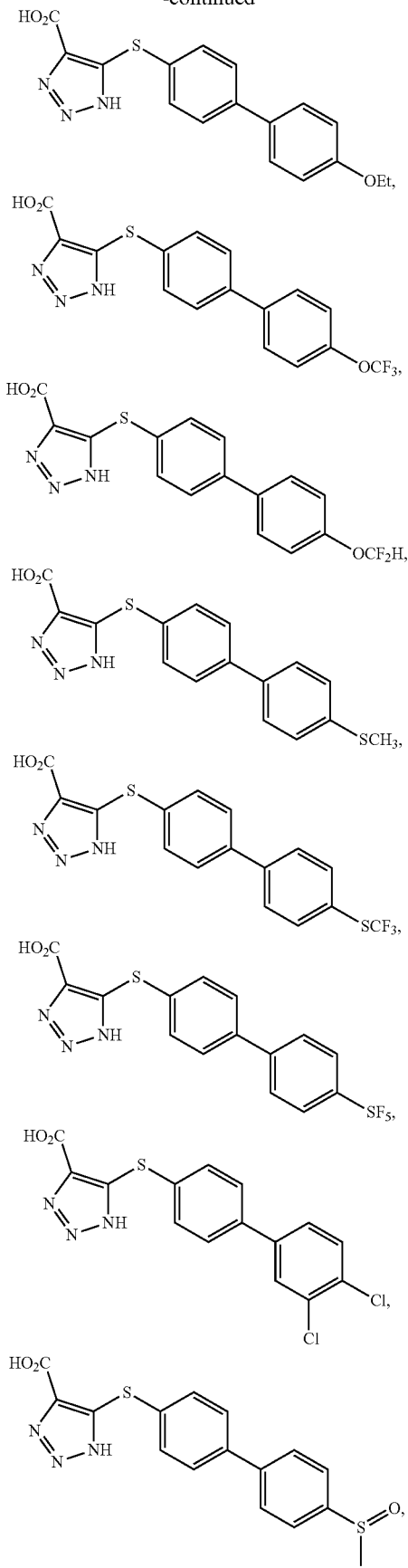

or a salt or prodrug thereof.

Embodiment 39: The compound of any of Embodiments 33-36, wherein L is O.

Embodiment 40: The compound of Embodiment 39, chosen from

-continued (structures omitted)

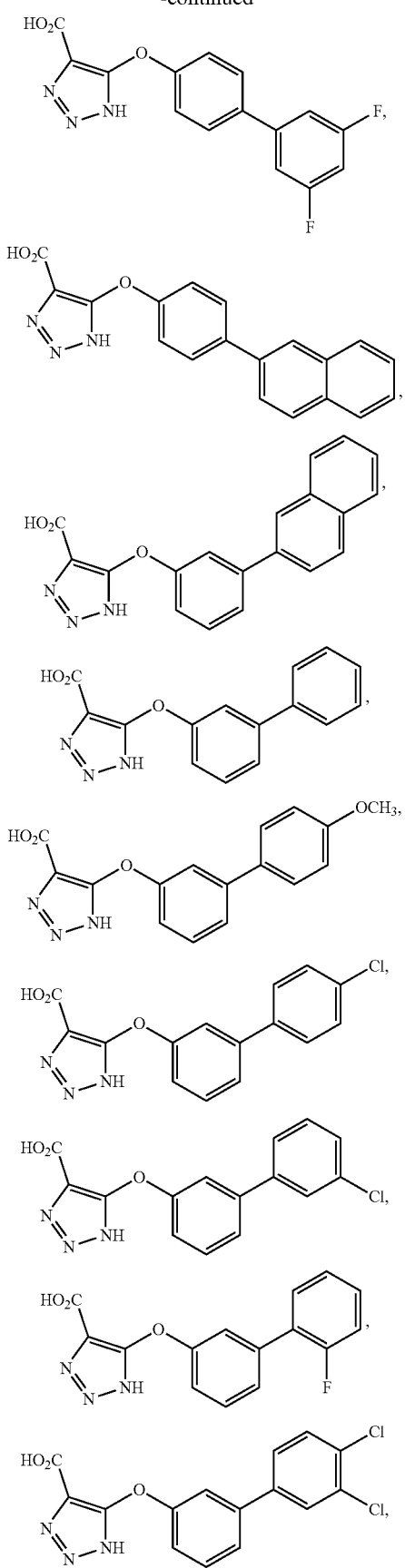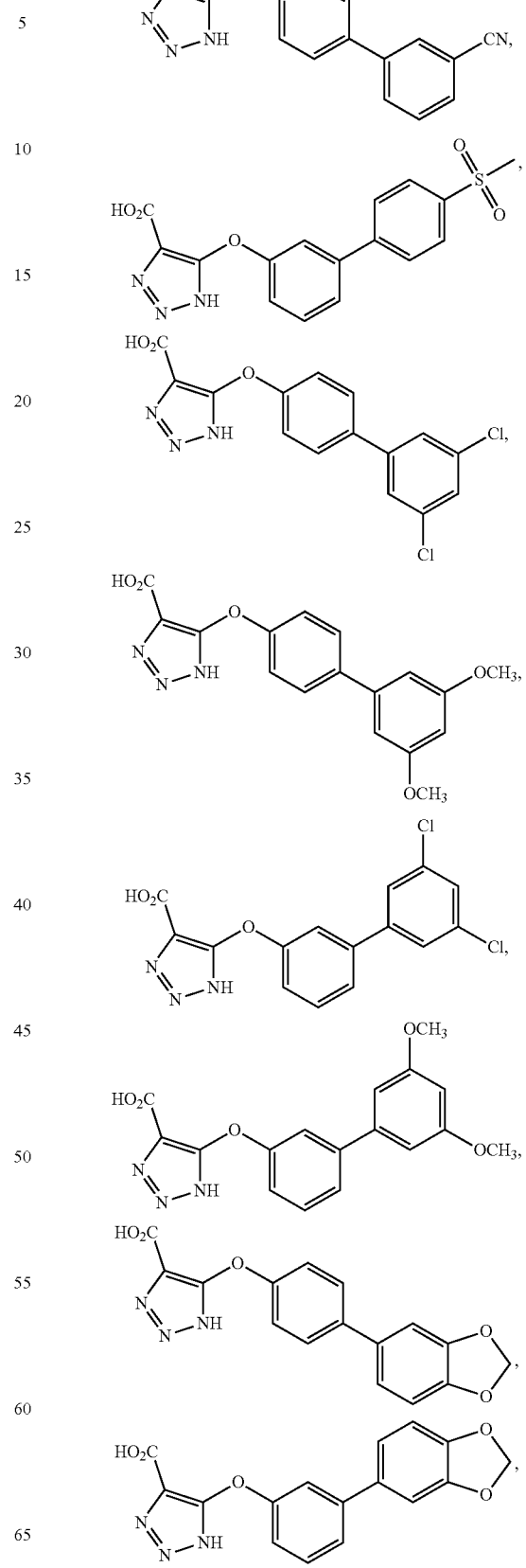

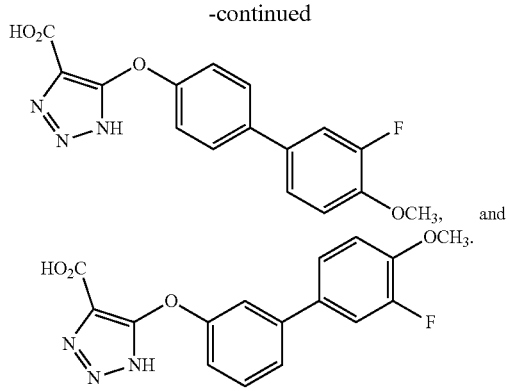
or a salt or prodrug thereof.
Embodiment 41: The compound of any of Embodiments 33-36, wherein L is CH=CH.
Embodiment 42: The compound of Embodiment 41, chosen from
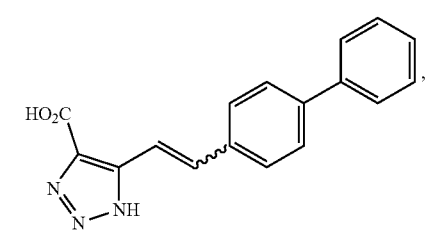
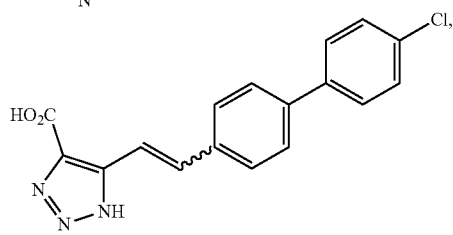
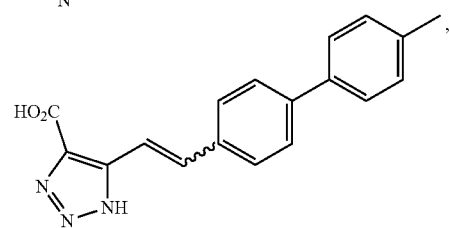
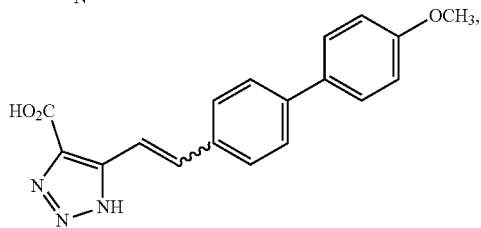
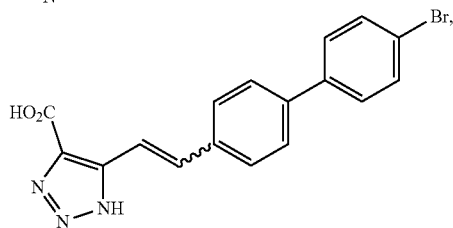
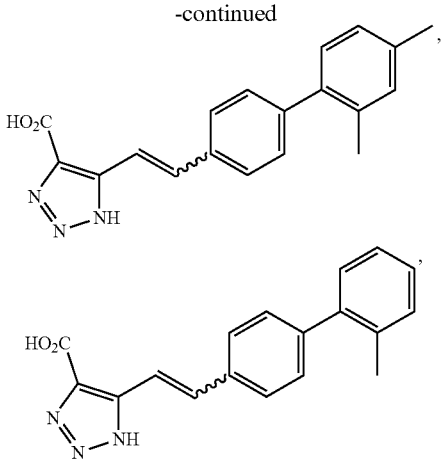
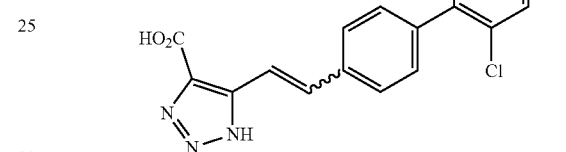
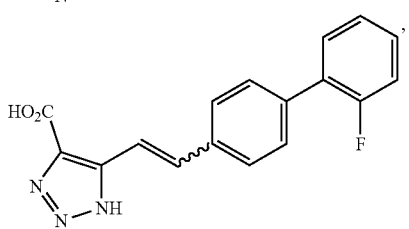
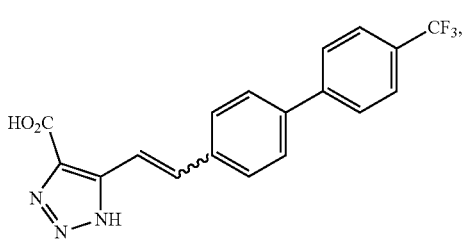
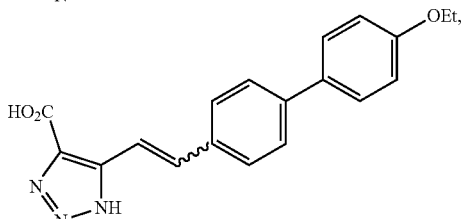
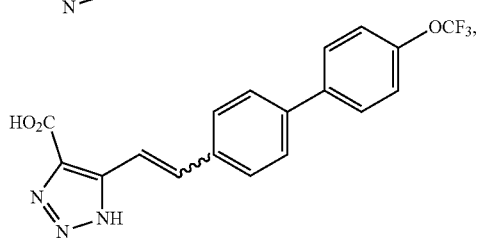

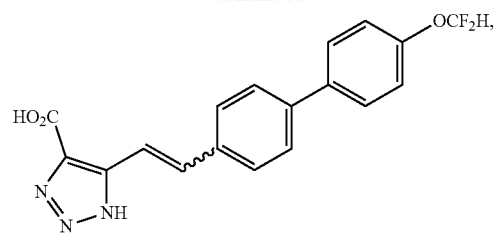
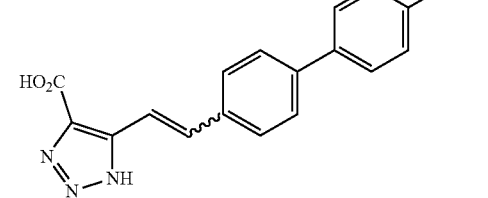
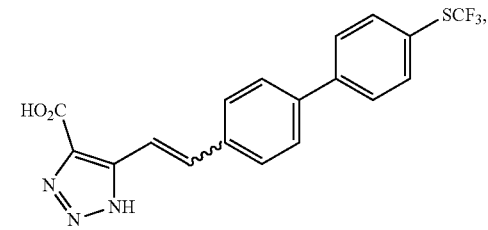
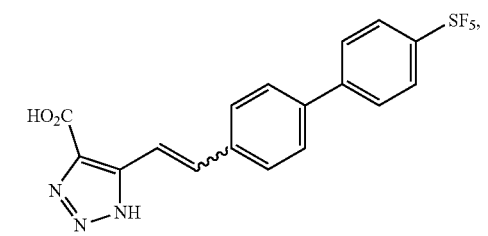
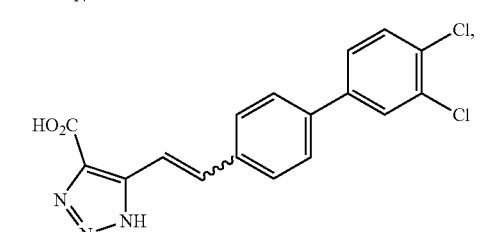
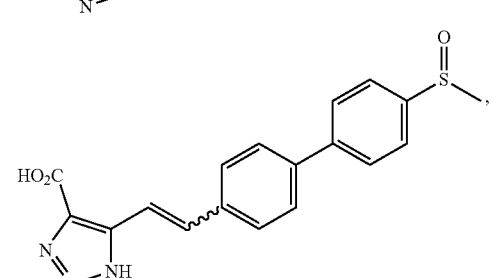
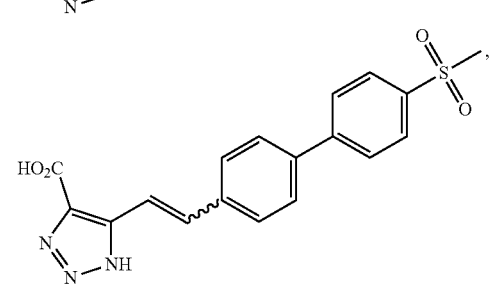
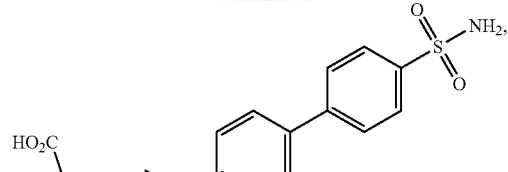
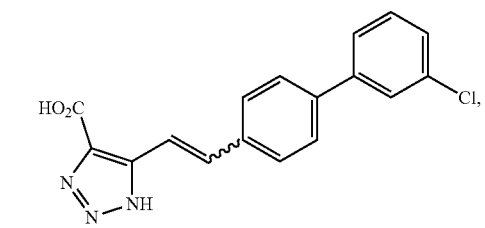
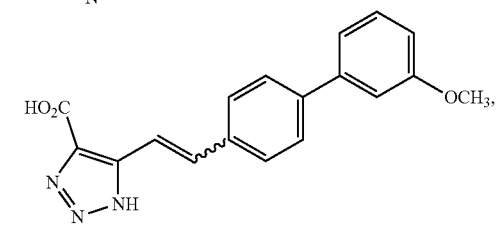
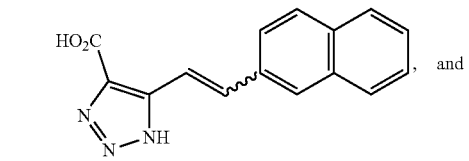
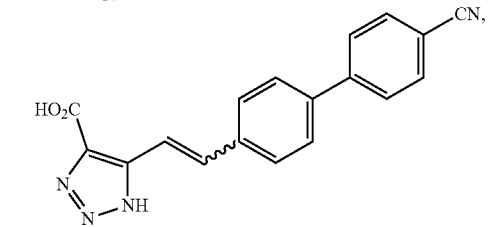
or a salt thereof.
Embodiment 43: The compound of any of Embodiments 33-36, wherein L is OCH$_2$.
Embodiment 44: The compound of Embodiment 43, chosen from
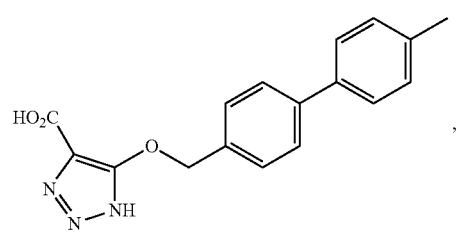

-continued
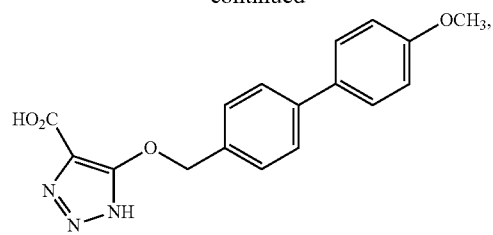
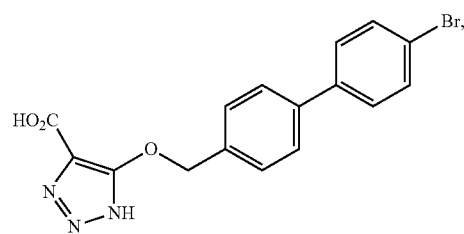
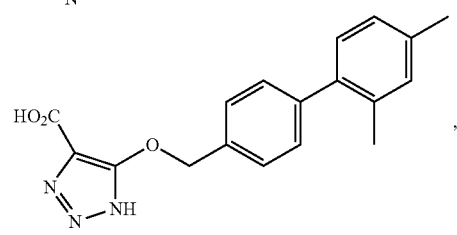
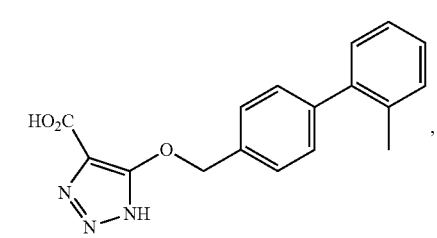
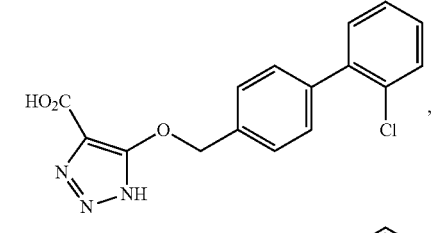
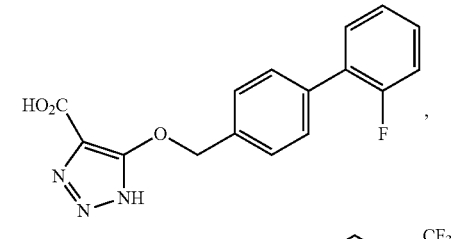
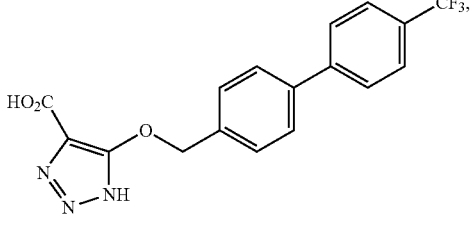
-continued
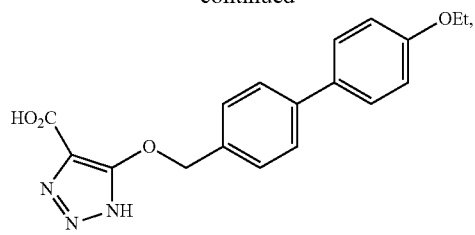
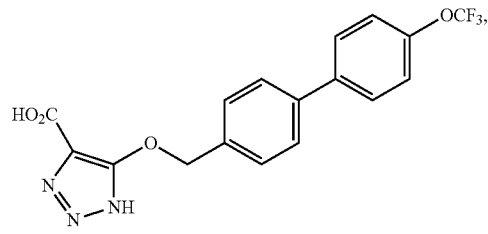
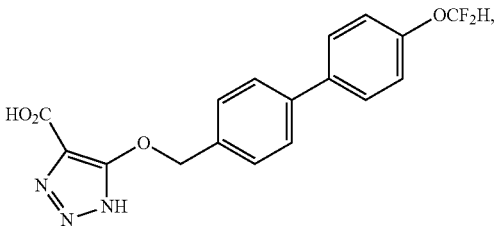
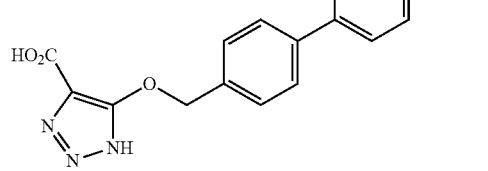
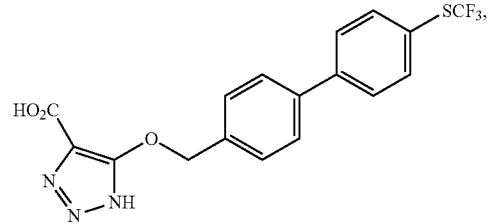
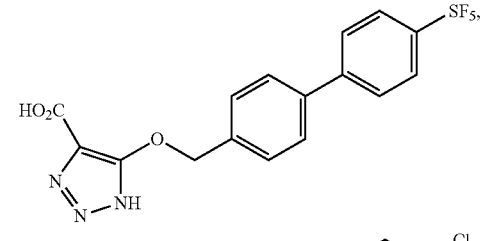
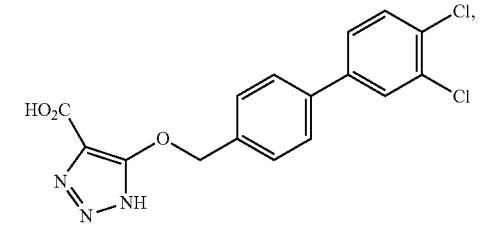

-continued
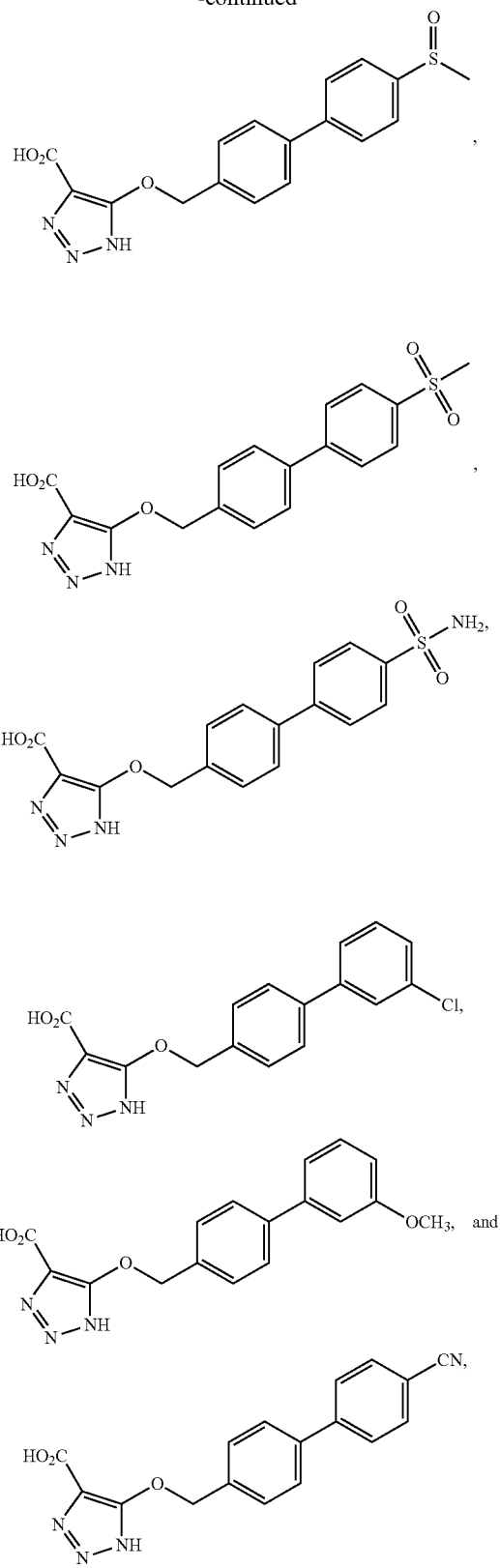
or a salt or prodrug thereof.
Embodiment 45: The compound of any of Embodiments 33-36, wherein L is $SCH_2$.
Embodiment 46: The compound of Embodiment 45, chosen from
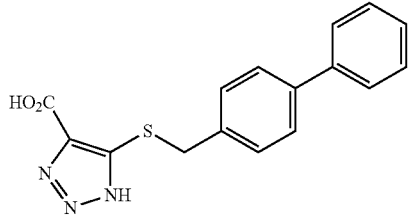
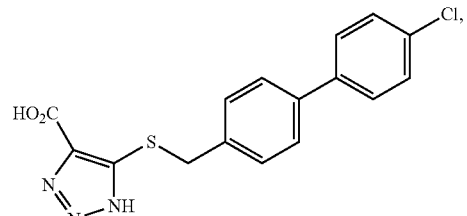
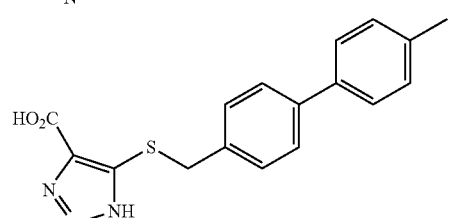
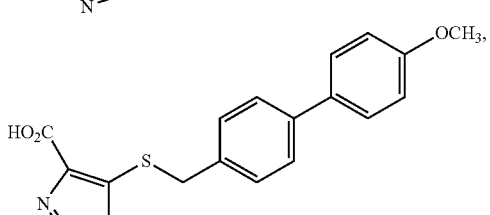
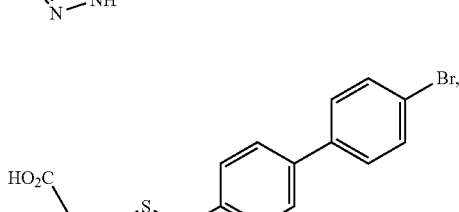
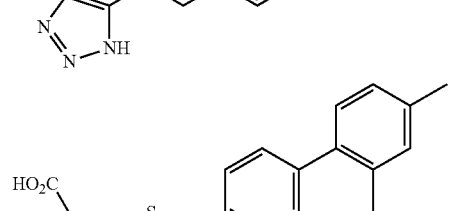
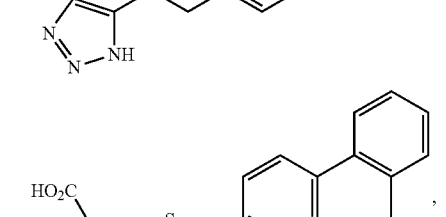
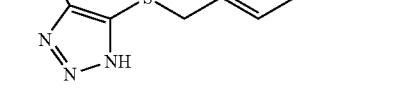

49
-continued
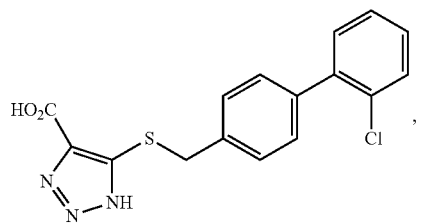
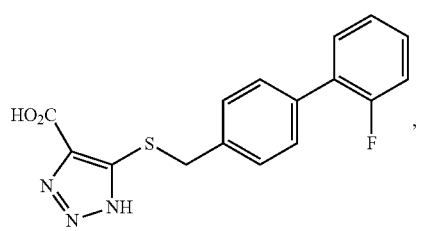
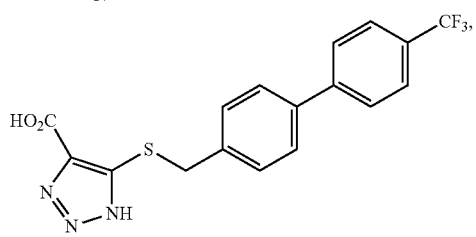
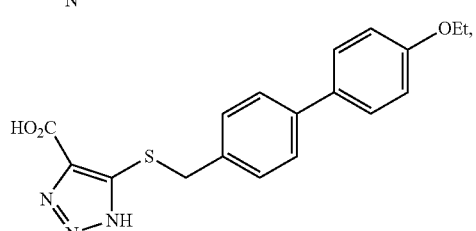
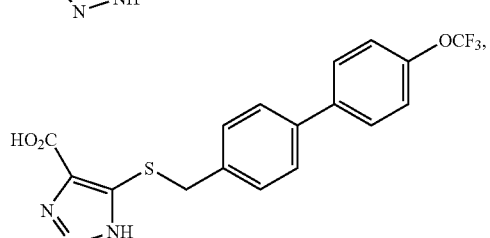
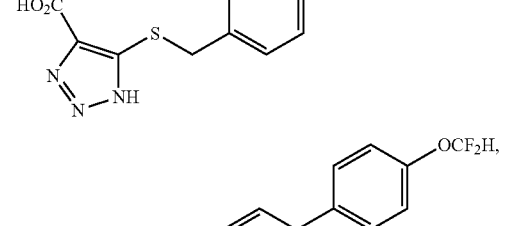
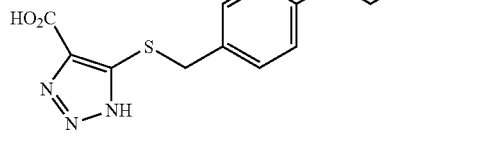
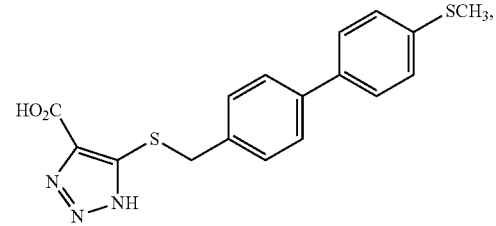
50
-continued
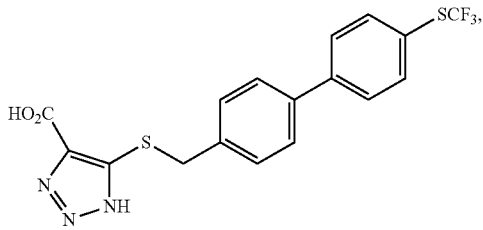
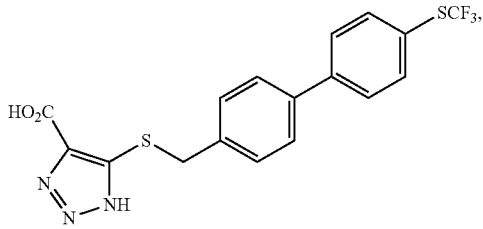
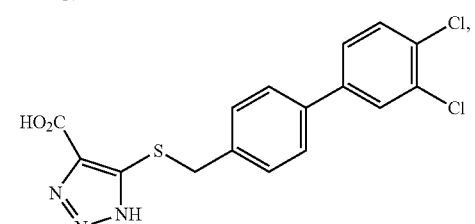
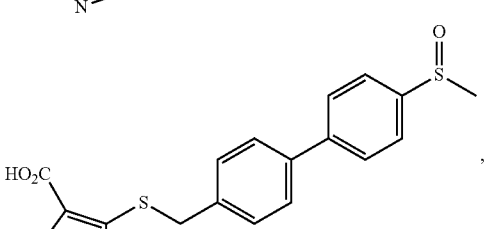
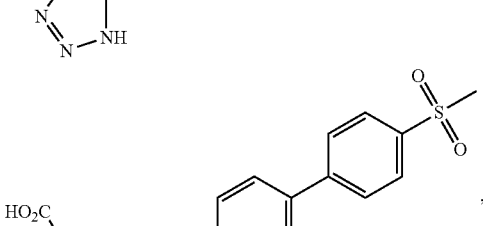
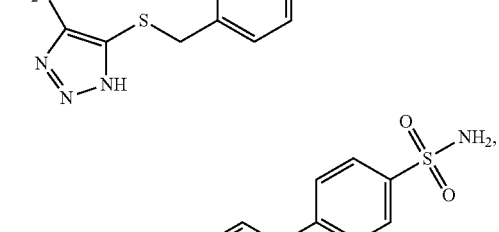
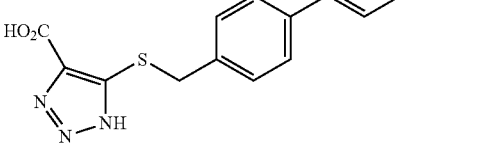
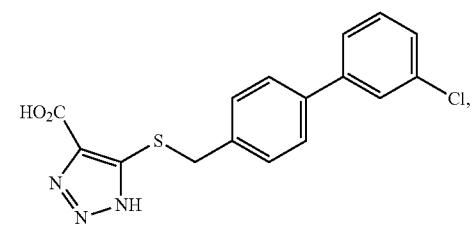

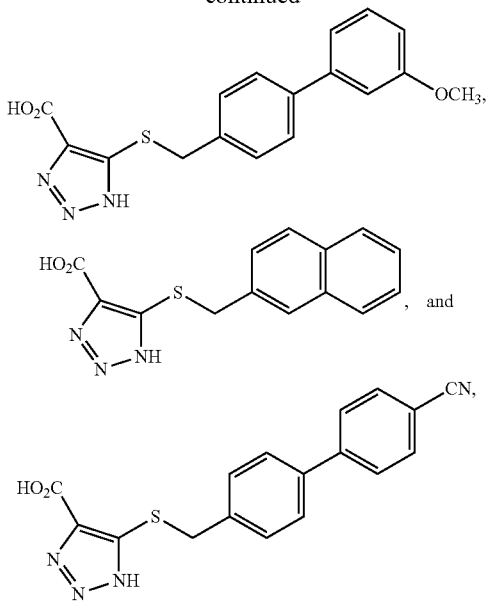

or a salt or prodrug thereof.

Also provided herein are Embodiments 47(1)-47(46): A compound of any of Embodiments 1-46, or a salt or prodrug thereof, for use as a medicament.

Also provided herein are Embodiments 48(1)-48(46): A compound of any of Embodiments 1-46, or a salt or prodrug thereof, for use in the manufacture of a medicament for preventing or treating an oxalate-related disease.

Also provided herein are Embodiments 49(1)-49(46): A pharmaceutical composition comprising a compound of any of Embodiments 1-46, or a salt or prodrug thereof, together with a pharmaceutically acceptable excipient.

Provided herein is Embodiment 50: The pharmaceutical composition of Embodiment 49, formulated for oral administration.

Provided herein is Embodiment 51: The pharmaceutical composition of Embodiment 49, additionally comprising another therapeutic agent.

Also provided herein are Embodiments 52(1)-52(46): A method of inhibiting glycolate oxidase (GOX) activity in a biological sample comprising contacting the biological sample with a compound of any of Embodiments 1-46, or a salt or prodrug thereof.

Also provided herein are Embodiments 53(1)-53(46): A method of treating an oxalate-related disease in a subject in need thereof, comprising the step of administering to the subject a compound of any of Embodiments 1-46, or a salt or prodrug thereof.

Also provided herein are Embodiments 54(1)-54(46): The method of Embodiment 53, wherein the subject is a human.

Also provided herein are Embodiments 55(1)-55(46): The method of Embodiment 53 or 54, wherein the oxalate-related disease is hyperoxaluria.

Also provided herein is Embodiment 56: The method of any of Embodiments 53-55, wherein primary hyperoxaluria is treated.

Also provided herein is Embodiment 57: A method of treating an oxalate-related disease in a subject in need thereof, comprising the sequential or co-administration of a compound of any of Embodiments 1-46, or a salt or prodrug thereof, and a second therapeutic agent.

Also provided herein is Embodiment 58: A compound of any of Embodiments 1-46, or a salt or prodrug thereof, for use in human therapy.

Also provided herein is Embodiment 59: A compound of any of Embodiments 1-46, or a salt or prodrug thereof, for use in treating an oxalate-related disease.

Also provided herein is Embodiment 60: Use of a compound of any of Embodiments 1-46, or a salt or prodrug thereof, for the manufacture of a medicament to treat an oxalate-related disease.

Also provided herein is Embodiment 61: The compound of any of Embodiments 1-9, wherein $R^1$ hydrogen.

Also provided herein is Embodiment 62: The compound of any of Embodiments 1-9, wherein $R^1$ is $C_1$-$C_6$ alkyl.

DETAILED DESCRIPTION

When introducing elements of the present disclosure or the embodiment(s) thereof, the articles "a", "an", "the" and "said" are intended to mean that there are one or more of the elements. The terms "comprising", "including" and "having" are inclusive and mean that there may be additional elements other than the listed elements.

The term "and/or" when in a list of two or more items, means that any of the listed items can be employed by itself or in combination with one or more of the listed items. For example, the expression "A and/or B" means either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about" qualifies the numerical values that it modifies, denoting such a value as variable within a margin of error. When no margin of error, such as a standard deviation to a mean value given in a chart or table of data, is recited, the term "about" means that range which would encompass the recited value and the range which would be included by rounding up or down to that figure, considering significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene (—CH═CH—, —C::C—). Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, the alkyl will comprise from 1 to 10 carbon atoms. In further embodiments, the alkyl will comprise from 1 to 8 carbon atoms. Alkyl groups are optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "straight-chain alkyl" refers to an alkyl radical containing from 1 to 20 carbon atoms in a linear sequence without branches. Examples of straight-chain alkyl radicals include n-octyl (—CH$_2$CH$_2$CH$_2$CH$_2$CH$_2$CH$_2$CH$_2$CH$_2$—), n-butyl (—CH$_2$CH$_2$CH$_2$CH$_2$—), and ethyl (—CH$_2$CH$_2$—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl" refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which is optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylene," as used herein, alone or in combination, refers to an aryl group attached at two or more positions, such as phenylene (—C$_6$H$_4$—, which encompasses

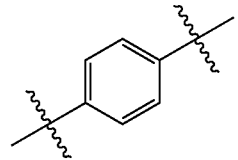 [SMILES: *c1ccc(*)cc1]

and the corresponding meta- and para-isomers). Unless otherwise specified, the term "aryl" may include "arylene" groups.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$═derived from benzene. Examples include benzothiophene and benzimidazole.

The term "biaryl," as used herein, refers to a first aryl group attached to the parent molecular moiety, with the first aryl group substituted with a second aryl group. Examples of biaryl groups include biphenyl, 2-(2-pyridyl)phenyl, and 5-(2-naphthyl)-thien-1-yl.

The term "biheteroaryl," as used herein, refers to a first heteroaryl group attached to the parent molecular moiety, with the first heteroaryl group substituted with a second heteroaryl group. Examples of biaryl groups include 3,3'-bipyridinyl.

The term "carbamate," as used herein, alone or in combination, refers to an ester of carbamic acid (—NHCOO—) which may be attached to the parent molecular moiety from either the nitrogen or acid end, and which is optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl (—C(O)H]) and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "cycloalkylene," refers to a cycloalkyl group attached at two or more positions, such as cyclohexylene (—C$_6$H$_{10}$—), which encompasses,

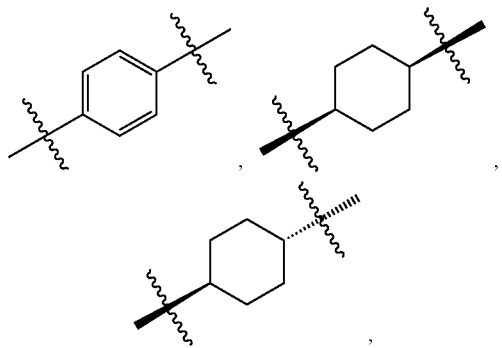

and the corresponding 1,2- and 1,4-isomers). Unless otherwise specified, the term "cycloalkyl" may include "cycloalkylene" groups.

The term "diazanaphthalene," as used herein, alone or in combination, refers to analogues of naphthalene, having formula C$_8$H$_6$N$_2$, in which two >CH groups have been replaced with two >N groups. Examples of diazanaphthalene include cinnoline, phthalazine, and 1,8-diazanaphthalene.

The term "bicyclic ring system" as used herein refers to a group which contains two distinct rings of atoms. In certain embodiments, bicyclic ring systems contain a single atom common to both ring systems. In certain embodiments, bicyclic ring systems contain two or more atoms common to both ring systems. Examples of compounds with bicyclic ring systems include decalin, norbornane, and pinene. Further examples of compounds with bicyclic ring systems are bicyclo[1.1.1]pentane, bicyclo[3.1.0.]hexane, 1,4-diazabicyclo[2.2.2]octane, 1,5-diazabicyclo(4.3.0)non-5-ene, and 7-oxabicyclo[2.2.1]heptadiene.

The term "tricyclic ring system" as used herein refers to a group which contains three distinct rings of atoms. In certain embodiments, bicyclic ring systems contain a single atom common to two rings. In certain embodiments, bicyclic ring systems contain two or more atoms common to two rings. Examples of compounds with tricyclic ring systems include perhydroanthracene, cedrene, and taxadiene. Further examples of compounds with tricyclic ring systems are tricyclo[3.1.0.0$^{2,4}$]hexane, tricyclo[3.3.1.1$^{3,7}$]decane, and cyclopentadiene diepoxide.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichoropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms chosen from O, N, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The term "heteroarylene," as used herein, alone or in combination, refers to a heteroaryl group attached at two or more positions, such as pyrimidinylene (—C$_5$H$_3$N—, which encompasses the 2,3 isomer:

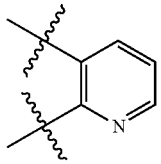 [SMILES: *c1cccnc1*]

as well as the 2,4-, 2,5-, 2,6-, 3,4-, and 3,5-isomers). Unless otherwise specified, the term "heteroaryl" may include "heteroarylene" groups.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each the heteroatom may be independently chosen from nitrogen, oxygen, and sulfur. In certain embodiments, said heterocycloalkyl will comprise a spirocycle ring system. In certain embodiments, said heterocycloalkyl will comprise from 1 to 4 heteroatoms as ring members. In further embodiments, the heterocycloalkyl will comprise from 1 to 2 heteroatoms as ring members. In certain embodiments, the heterocycloalkyl will comprise from 3 to 8 ring members in each ring. In further embodiments, the heterocycloalkyl will comprise from 3 to 7 ring members in each ring. In yet further embodiments, the heterocycloalkyl will comprise from 5 to 6 ring members in each ring. In further embodiments, said heterocycle will comprise a bicyclic ring system. In further embodiments, said heterocycle will comprise a tricyclic ring system. In further embodiments, said heterocycle will comprise a bicyclic ring system, said bicyclic ring system comprising a ring of three atoms. In further embodiments, said heterocycle will comprise a bicyclic ring system, said bicyclic ring system comprising a ring of four atoms. In further embodiments, said heterocycle will comprise a bicyclic ring system, said bicyclic ring system comprising a ring of five atoms. In further embodiments, said heterocycle will comprise a bicyclic ring system, said bicyclic ring system comprising a pyrrolidine ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include 3-azabicyclo[3.1.0] hexan-6-yl, aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups are optionally substituted unless specifically prohibited.

The term "heterocycloalkylene," refers to a heterocycloalkyl group attached at two or more positions, such as piperazinylene (—C$_4$H$_8$N$_2$—). Unless otherwise specified, the term "heterocycloalkyl" may include "heterocycloalkylene" groups.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently chosen from carbon, nitrogen, oxygen and sulfur.

The term "lower," as used herein, alone or in a combination, where not otherwise specifically defined, means containing from 1 to and including 6 carbon atoms (i.e., C$_1$-C$_8$ alkyl).

The term "lower aryl," as used herein, alone or in combination, means phenyl or naphthyl, either of which is optionally substituted as provided.

The term "lower heteroaryl," as used herein, alone or in combination, means either 1) monocyclic heteroaryl comprising five or six ring members, of which between one and four the members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen, alkyl, and lower heteroalkyl, any of which is optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all the hydrogen atoms are replaced by halogen atoms.

The term "perhaloalkyl" as used herein, alone or in combination, refers to an alkyl group where all the hydrogen atoms are replaced by halogen atoms.

The term "spirocycle ring system" refers to a polycyclic ring system comprising two rings such that a single atom is common to both rings.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" or "sulfamoyl" refers to a $RS(=O)_2NR'$— group with R and R' as defined herein.

The term "S-sulfonamido" refers to a —$S(=O)_2NRR'$, group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3CS(O)_2NR$— group with X is a halogen and R as defined herein.

The term "trihalomethanesulfonyl" refers to a $X_3CS(O)_2$— group where X is a halogen.

The term "trihalomethoxy" refers to a $X_3CO$— group where X is a halogen.

The term "trisubstituted silyl," as used herein, alone or in combination, refers to a silicone group substituted at its three free valences with groups as listed herein under the definition of substituted amino. Examples include trimethylsilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which is optionally substituted. Such R and R' groups should be understood to be optionally substituted as defined herein. Whether an R group has a number designation or not, every R group, including R, R' and R" where n=(1, 2, 3, ... n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N (R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. The disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used for treating a disease or disorder or on the effecting of a clinical endpoint.

The term "therapeutically acceptable" refers to those compounds (or salts, prodrugs, tautomers, zwitterionic forms, etc.) suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "therapeutically acceptable salt," as used herein, represents salts or zwitterionic forms of the compounds disclosed herein, which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethanesulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylpropionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

While the disclosed compounds may be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers/excipients thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound disclosed herein or a pharmaceutically acceptable salt, ester, amide, prodrug or solvate thereof ("active ingredient") with the carrier which constitutes one or more accessory ingredients. In general, the formulations are prepared by uniformLy and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately before use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 01% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds may be a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Unit dosage formulations are those containing an effective dose, as herein below recited, or an appropriate fraction thereof, of the active ingredient.

In addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few min to four weeks.

Thus, in another aspect, certain embodiments provide methods for treating glycolate oxidase-mediated disorders in a human or animal subject in need of such treatment comprising administering to said subject an amount of a compound disclosed herein effective to reduce or prevent said disorder in the subject, in combination with at least one additional agent for the treating said disorder that is known in the art. In a related aspect, certain embodiments provide therapeutic compositions comprising at least one compound disclosed herein in combination with one or more additional agents for the treating glycolate oxidase-mediated disorders.

Specific diseases to be treated by the compounds, compositions, and methods disclosed herein include oxalate-related diseases, such as hyperoxaluria, for example primary hyperoxaluria, enteric hyperoxaluria, idiopathic hyperoxaluria, oxalate poisoning, and kidney stones. The disease may be primary hyperoxaluria. The primary hyperoxaluria may be Type 1 (PH1). The primary hyperoxaluria may be Type 2 (PH2). The primary hyperoxaluria may be Type 3 (PH3). The disease may be enteric hyperoxaluria. The disease may be idiopathic hyperoxaluria. The disease may be oxalate poisoning. The condition may be kidney stones.

Hyperoxaluria involves an excessive urinary excretion of oxalate. Individuals with hyperoxaluria often have calcium oxalate kidney stones. It is sometimes called Bird's disease, after Golding Bird, who first described the condition.

There are three known types of primary hyperoxaluria. Without wishing to be bound by theory, type I primary hyperoxaluria (PH1) is caused by alanine-glyoxylate aminotransferase (AGXT), a key enzyme involved in breakdown of oxalate. The AGXT is expressed only in the liver and the encoded protein is localized mostly in the peroxisomes, where it is involved in glyoxylate detoxification. Mutations in this gene, some of which alter subcellular targeting, have been associated with type I primary hyperoxaluria. PH1 is an example of a protein mistargeting disease, wherein AGXT shows a trafficking defect. Instead of being trafficked to peroxisomes, it is targeted to mitochondria, where it is metabolically deficient despite being catalytically active.

Without wishing to be bound by theory, type II primary hyperoxaluria (PH2) is associated with glyoxylate reductase/hydroxypyruvate reductase (GRHPR). Type II hyperoxaluria is caused by mutations in this GRHPR gene. PH2 a complication of jejunoileal bypass, or in any patient who has lost much of the ileum with an intact colon. This is due to excessive absorption of oxalate from the colon.

Without wishing to be bound by theory, type III primary hyperoxaluria (PH3) is associated with mutations in the mitochondrial dihydrodipicolinate synthase-like (DHDPSL) gene on chromosome 10, which encodes 4-hydroxy-2-oxo-glutarate aldolase (HOGA1). This enzyme catalyzes the last step in the metabolic pathway of hydroxyproline. Using heterozygosity mapping, which searched for long heterozygous patterns unique to all patients in each family and overlaps between families, and reconstructed haplotypes, an allelic fragment was determined to be shared by all patients of Ashkenazi Jewish descent and bearing a three-base pair deletion in DHDPSL. Overall, six mutations were detected: four missense mutations, one in-frame deletion, and one splice-site mutation.

The term "systemic oxalosis" refers to significantly elevated levels of oxalate in the systemic circulation of a subject. Systemic oxalosis occurs when the kidneys stop eliminating calcium oxalate crystals from the body through the urine, such as in subjects who have primary and intestinal causes of hyperoxaluria. Because the kidneys stop functioning, oxalate crystals are deposited elsewhere in the body, including blood vessels, bones and body organs, such as the liver and kidney.

Before the present disclosure, the main therapeutic approach to primary hyperoxaluria has been restricted to symptomatic treatment, i.e. liver-kidney transplantation once the disease has already reached mature or terminal stages. Genomics and proteomics approaches have been reported to elucidate some kinetics of AGXT folding, which directly bears on its targeting to appropriate subcellular localization. Secondary hyperoxaluria is much more common than primary hyperoxaluria, and has been treated by limiting dietary oxalate and providing calcium supplementation. A child with primary hyperoxaluria had to be treated with a liver and kidney transplant. A favorable outcome was more likely if a kidney transplant was complemented by a liver transplant, given the disease originates in the liver.

As such, the present disclosure supplies a long-felt but unmet need for treating hyperoxaluria, including Types I, II, and III primary hyperoxaluria and secondary, especially in children. The disclosed compounds and compositions can treat hyperoxaluria before the disease destroys the kidneys and liver, mandating transplantation.

Besides being useful for human treatment, certain compounds and formulations disclosed herein may also be useful for the veterinary treatment of companion animals, exotic animals and farm animals, including mammals, rodents, and the like. More examples of suitable animals include horses, dogs, and cats.

General Synthetic Methods for Preparing Compounds

All experiments were conducted under an atmosphere of dry argon in oven-dried glassware using standard Schlenk techniques unless noted otherwise. Experiments performed in an oil bath were done using Fisher Scientific silicone oil in a Pyrex crystallizing dish on top of an IKA RCT basic model magnetic hotplate stirrer with an ETS-D5 electronic contact thermometer. Glovebox manipulations were performed in an MBraun Unilab glove-box under an atmosphere of dry argon. All reagents were purchased from Sigma-Aldrich or Alfa Aesar and were used without further purification unless noted otherwise. Pre-catalysts were acquired from Total Synthesis Ltd., Toronto, Canada. All reaction vials (screw-cap threaded, caps attached, 15×45 mm) were purchased from Fisher Scientific. Analytical thin layer chromatography (TLC) was performed on EMD 60 F254 pre-coated glass plates and spots were visualized with UV light (254 nm). Column chromatography purifications were carried out using the flash technique on ZEOprep 60 silica gel (40-63 µm).

General Synthetic Methods for Preparing Compounds

The following schemes can generally be used to practice the present disclosure.

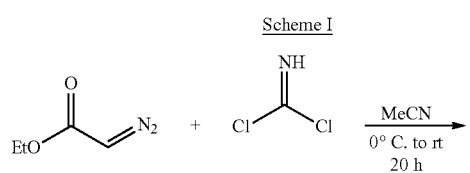
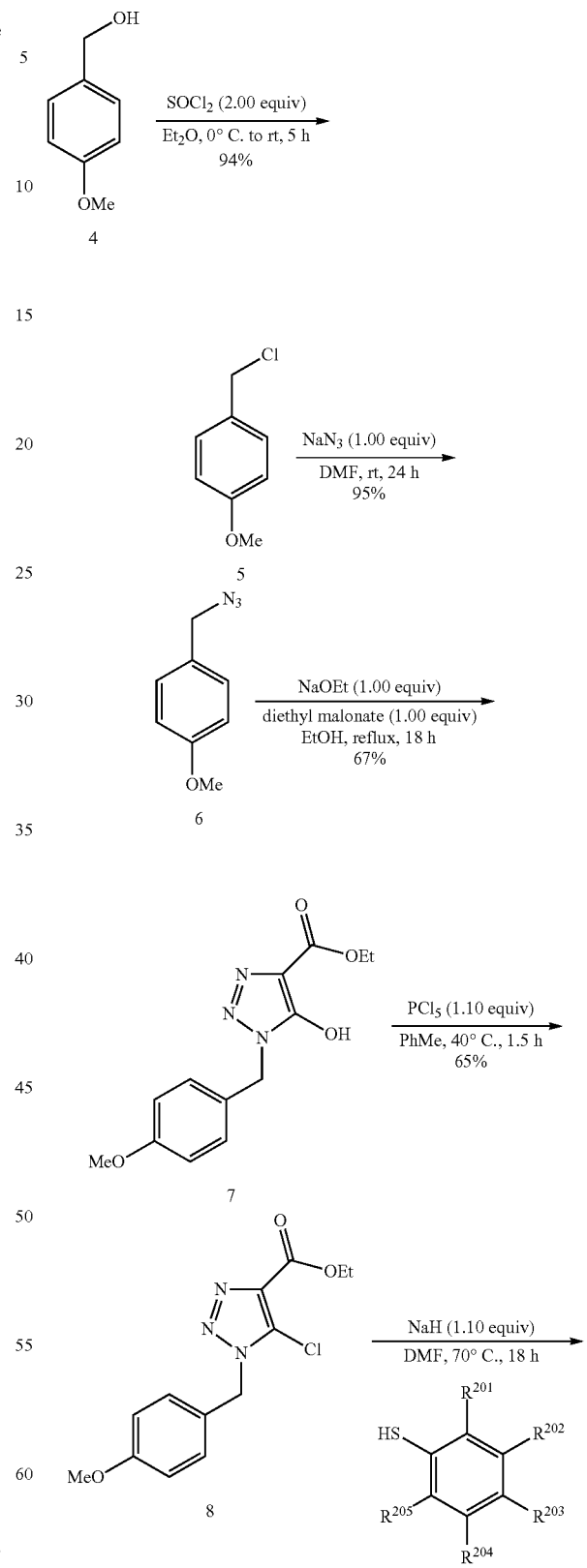

Scheme I depicts the formation of a phenylmercaptotriazole. A chlorotriazole is formed from reacting ethyl diazoacetate and phosgene. The chlorotriazole is then reacted with a thiobenzene under basic conditions to yield the phenylmercaptotriazole.

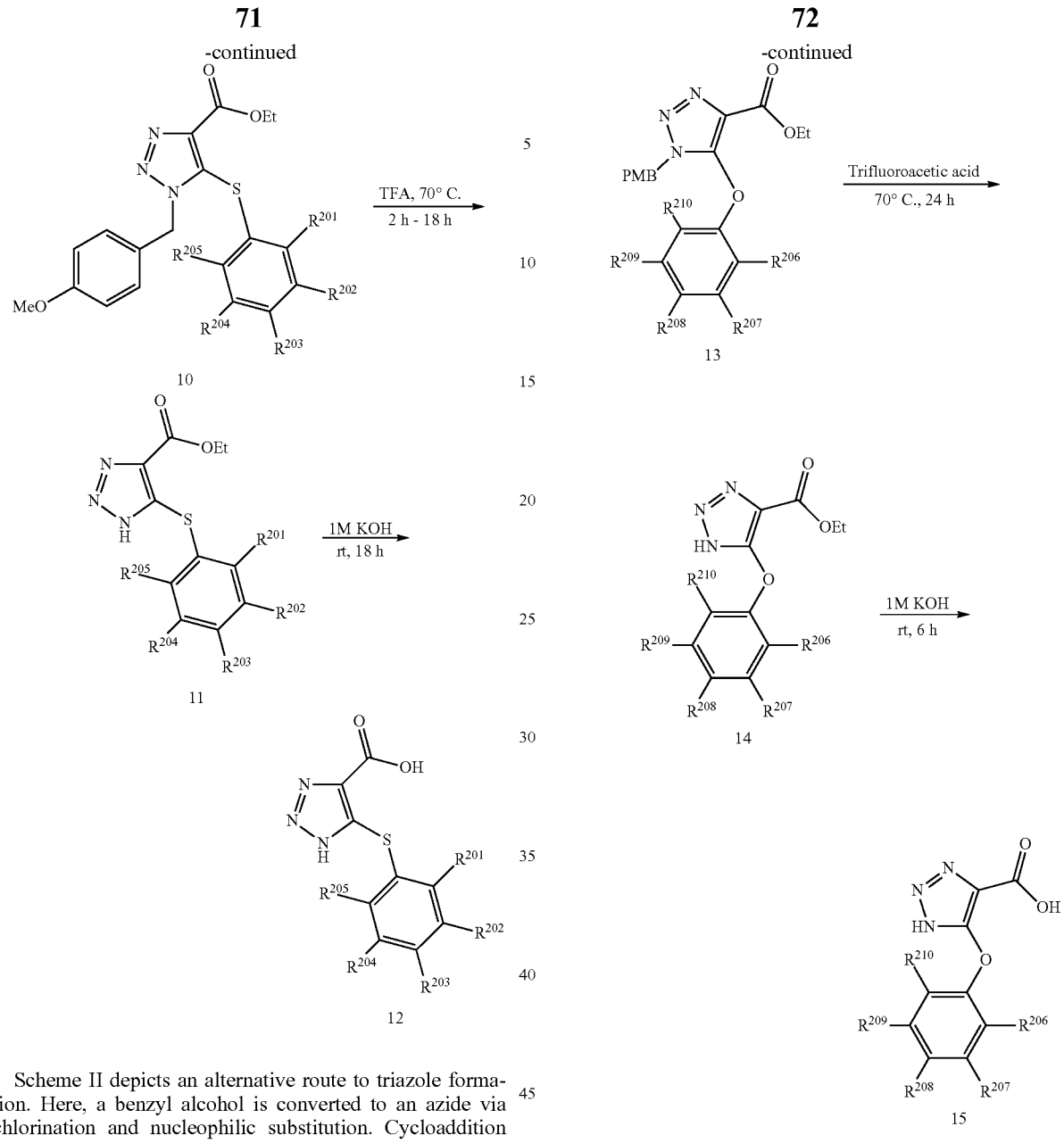

Scheme II depicts an alternative route to triazole formation. Here, a benzyl alcohol is converted to an azide via chlorination and nucleophilic substitution. Cycloaddition between the azide and diethyl malonate yields chlorotriazole. The chlorotriazole is further reacted with a thiobenzene to yield a phenylmercaptotriazole.

Scheme III

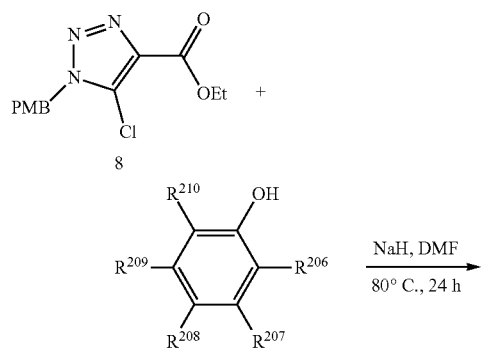

Scheme III depicts reaction of a chlorotriazole with a phenol under basic conditions to yield a phenoxytriazole. The method above can be modified to accommodate an alternate reagent in the first step, for example a substituted or unsubstituted monocyclic or bicyclic aryl, monocyclic or bicyclic heteroaryl, biaryl, and biheteroaryl, such as biphenyl, naphthyl, pyridinylphenyl, phenylpyridinyl, or bipyridinyl.

Scheme IV

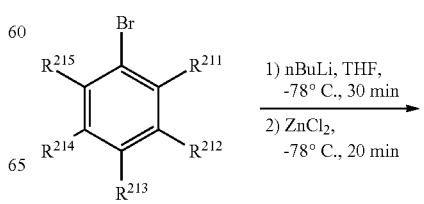

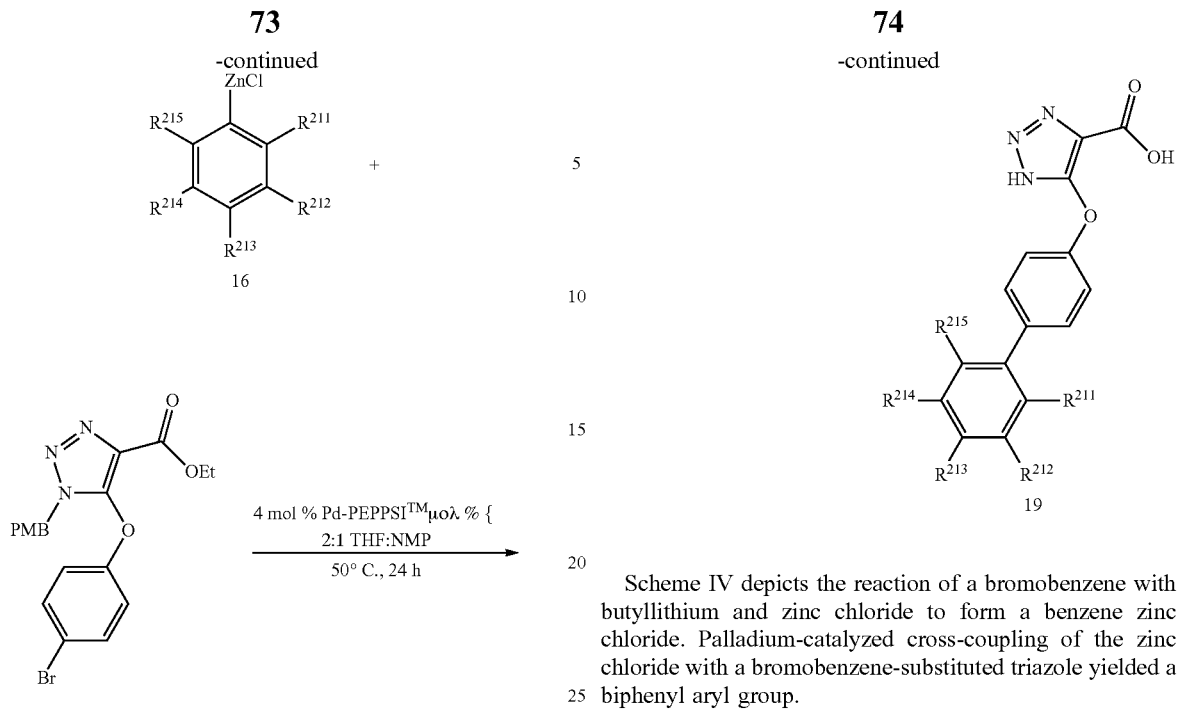
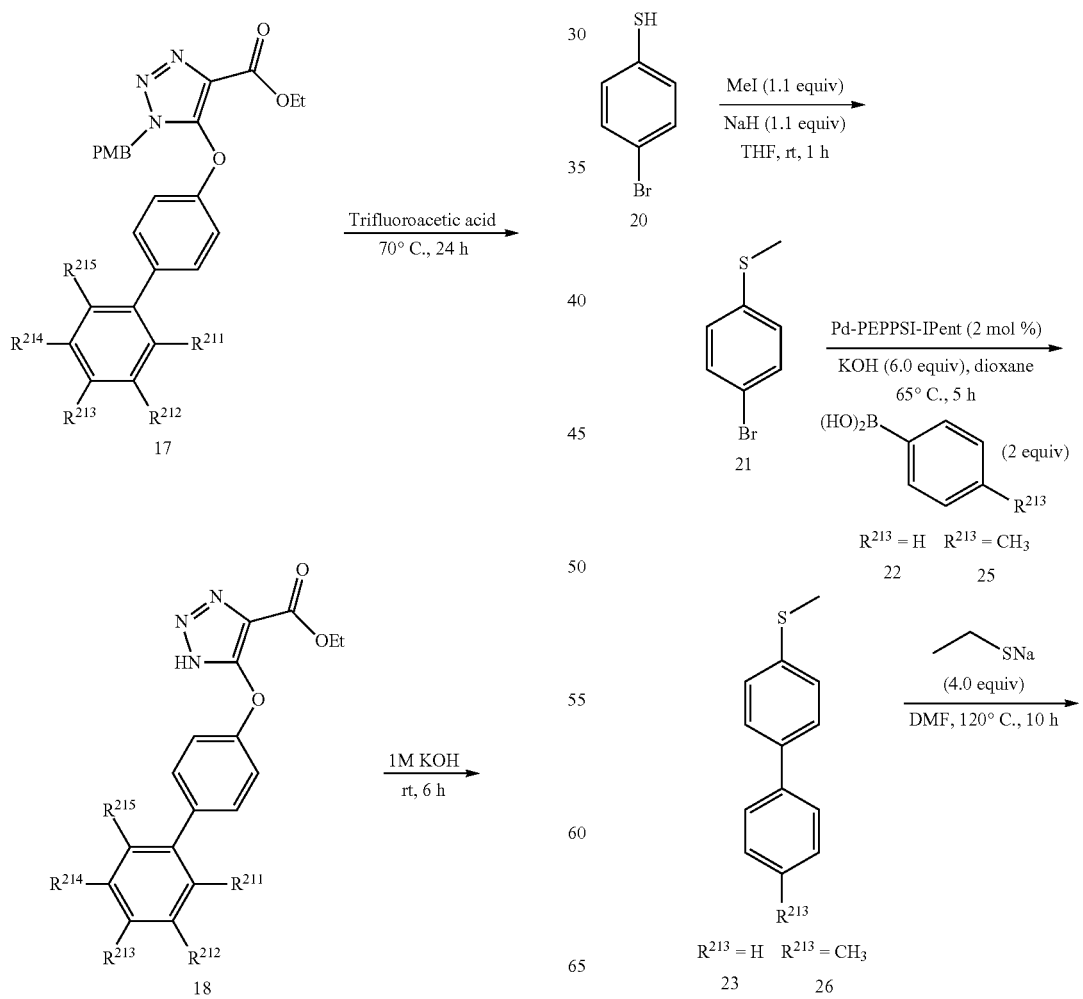
Scheme IV depicts the reaction of a bromobenzene with butyllithium and zinc chloride to form a benzene zinc chloride. Palladium-catalyzed cross-coupling of the zinc chloride with a bromobenzene-substituted triazole yielded a biphenyl aryl group.

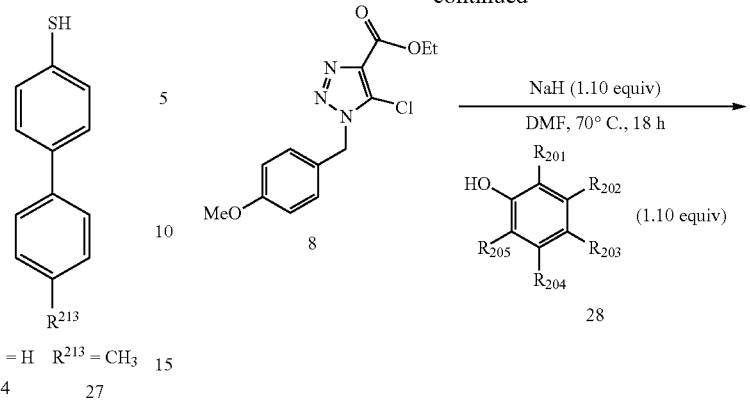

Scheme V depicts a general synthesis for biaryls. Alternate substitution patterns on one or more of the aryl group can be accommodated using variations known in the art.

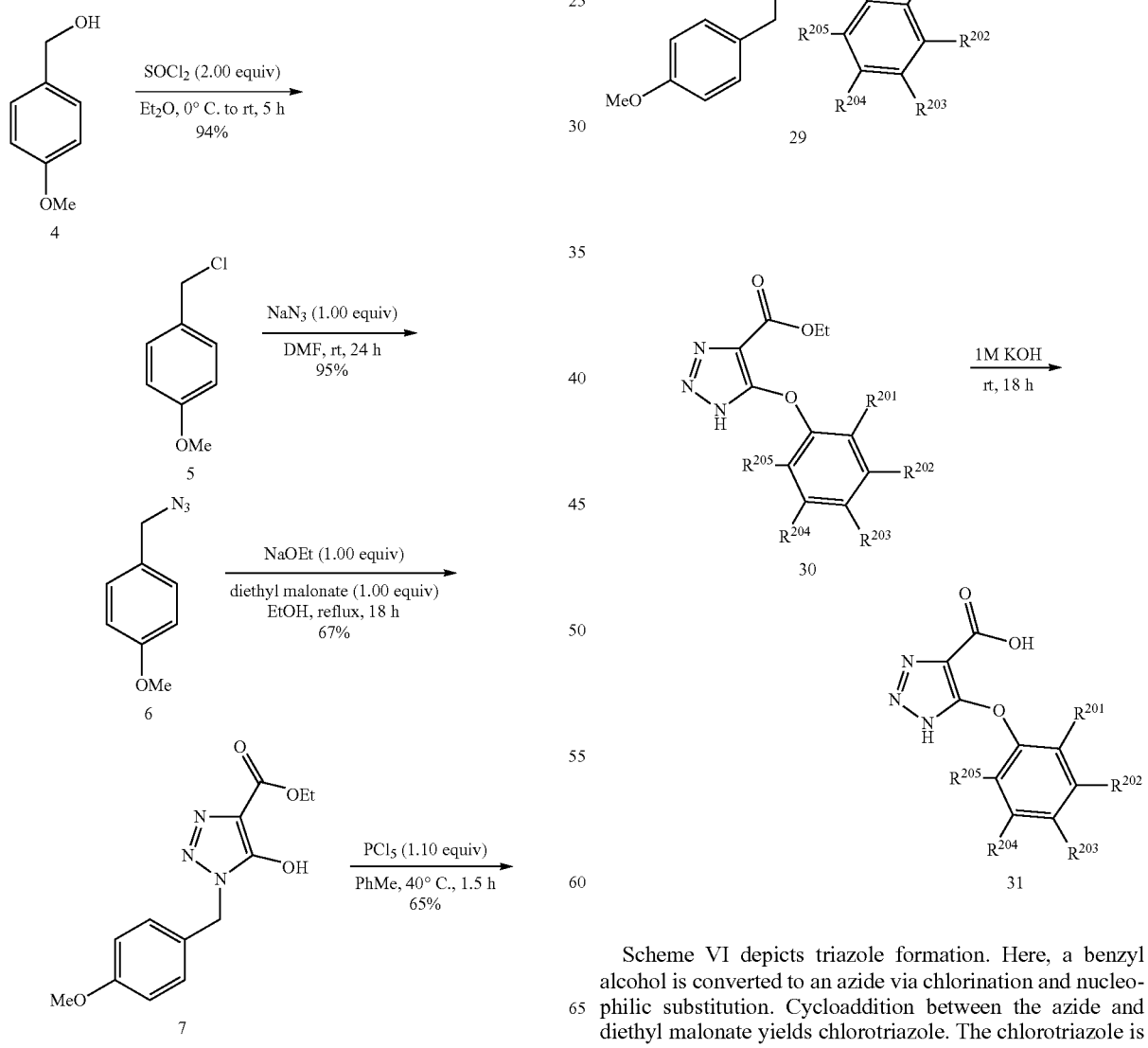

Scheme VI depicts triazole formation. Here, a benzyl alcohol is converted to an azide via chlorination and nucleophilic substitution. Cycloaddition between the azide and diethyl malonate yields chlorotriazole. The chlorotriazole is further reacted with a phenol to yield a phenoxytriazole.

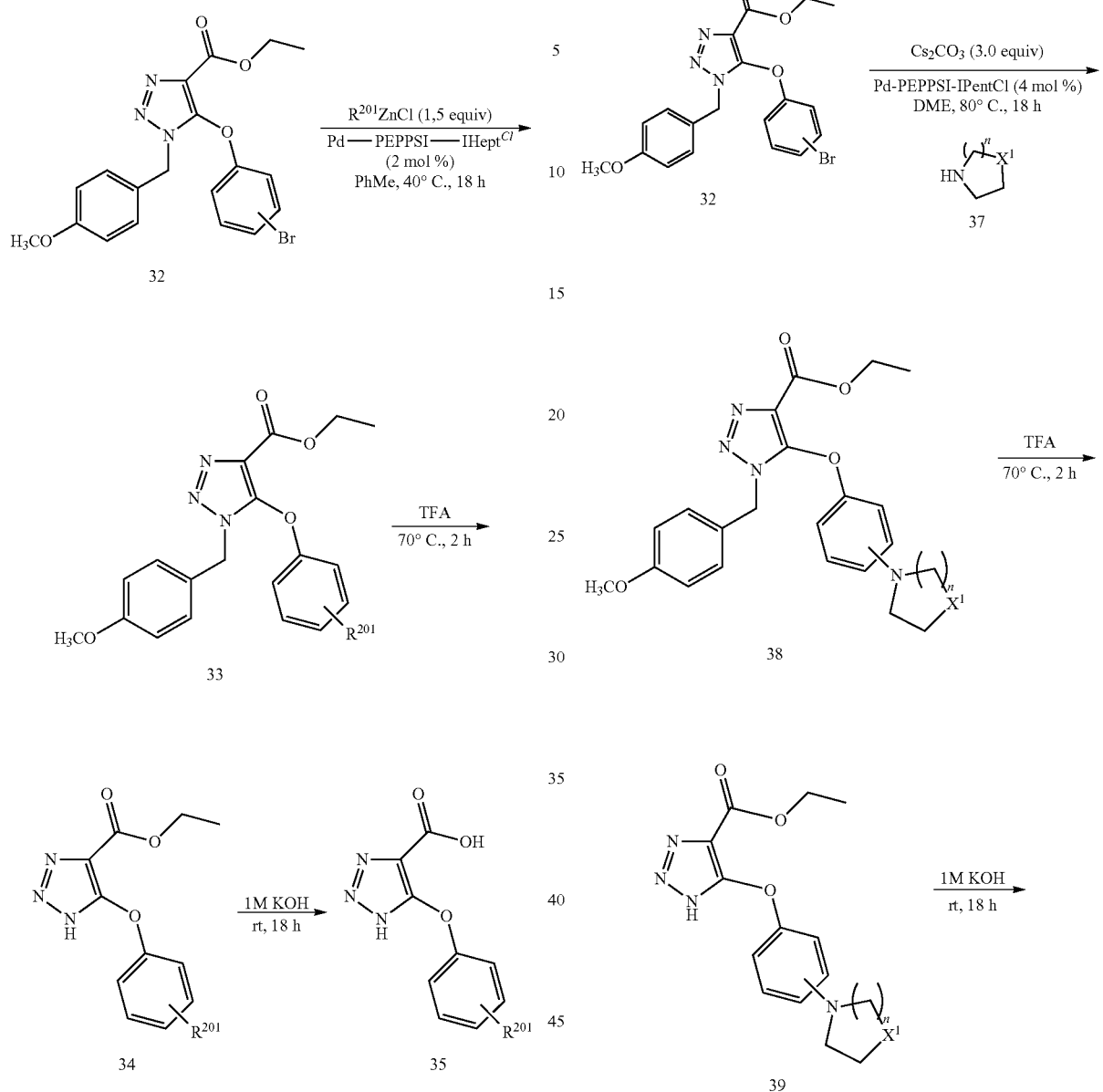
Scheme VII depicts synthetic method for preparing O-linked 1H-1,2,3-triazole-4-carboxylic acids with Negishi cross-coupling.
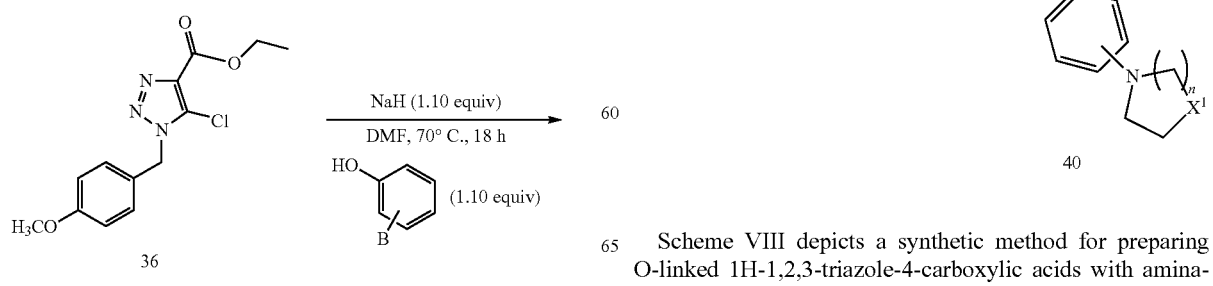
Scheme VIII depicts a synthetic method for preparing O-linked 1H-1,2,3-triazole-4-carboxylic acids with amination. "n" is an integer, such as 0, 1, 2, or 3.

Scheme IX
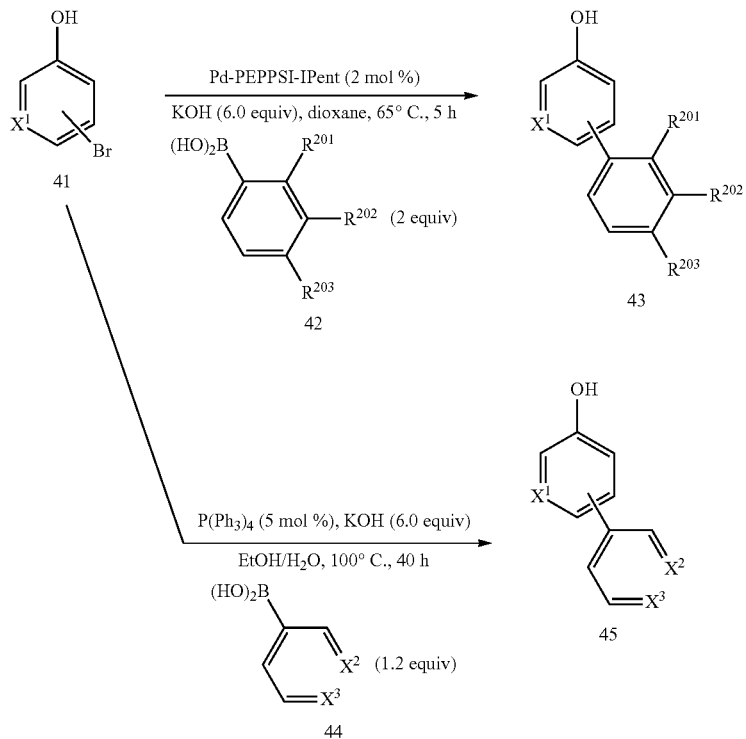
Scheme IX depicts the synthesis of biaryl phenols via Suzuki cross-coupling.
Scheme X
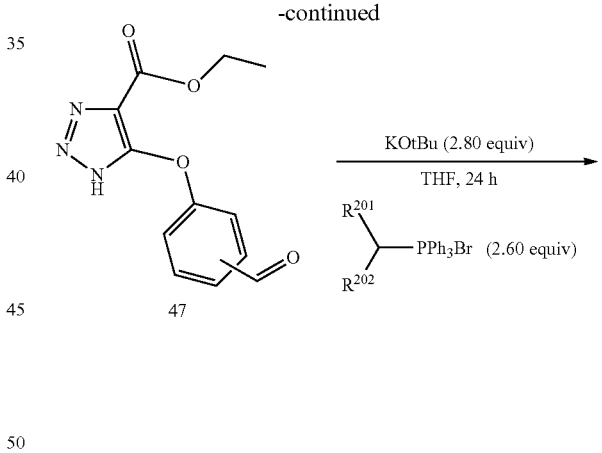
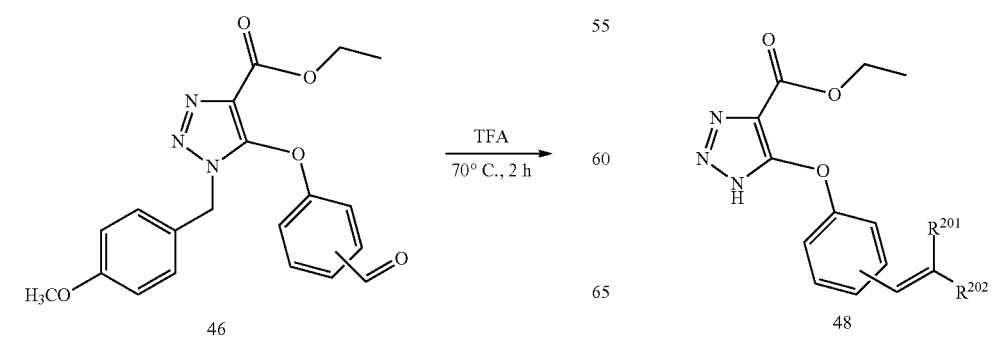

81
-continued
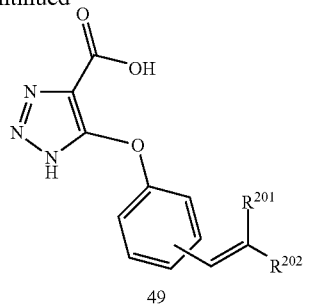
49
Scheme X depicts a general method for the synthesis of alkene-substituted O-linked 1H-1,2,3-triazole-4-carboxylic acids.
Scheme XI
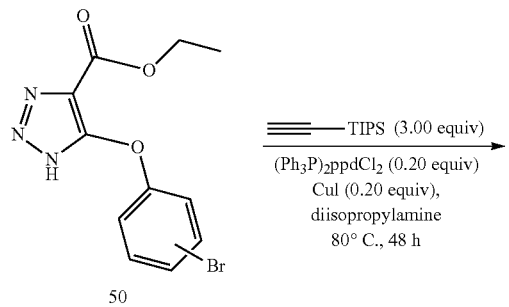
50
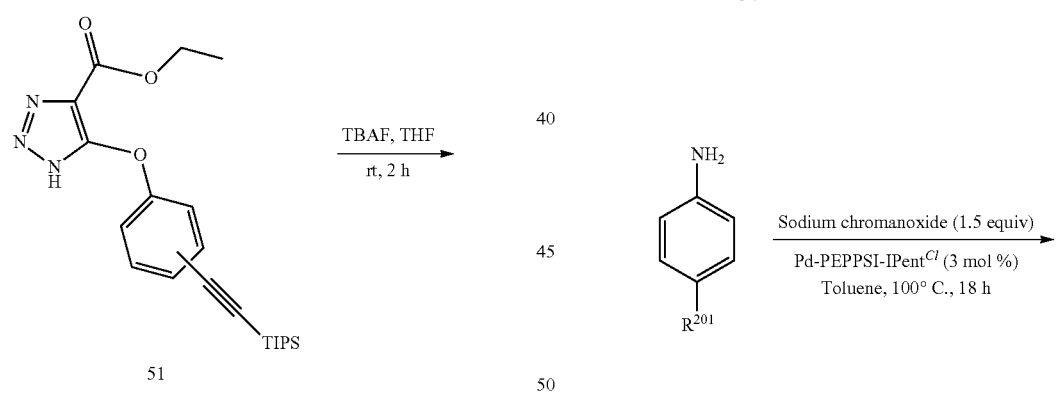
51
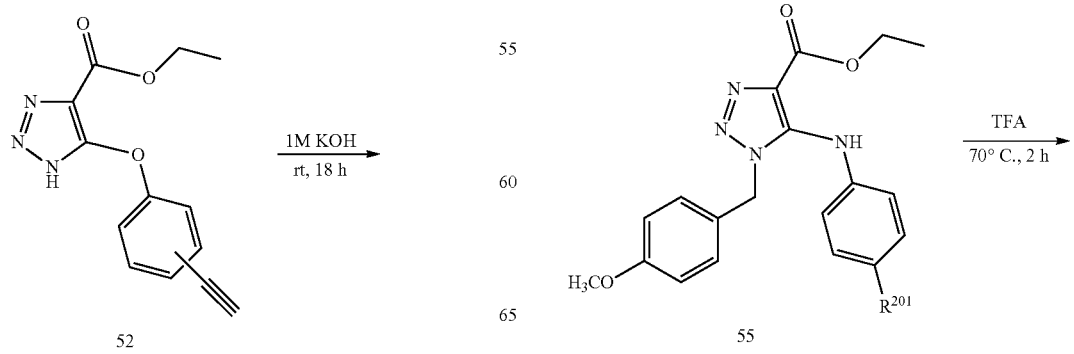
52
82
-continued
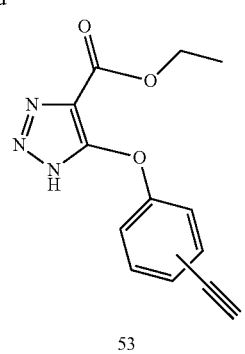
53
Scheme XI depicts a general method for the synthesis of alkyne-substituted O-linked 1H-1,2,3-triazole-4-carboxylic acids.
Scheme XII
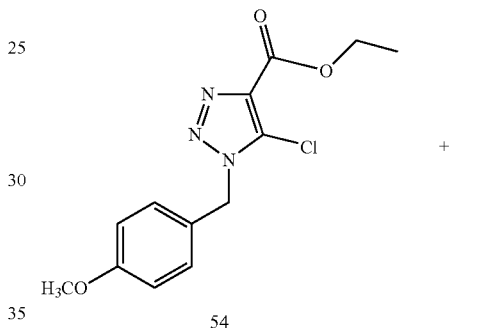
54
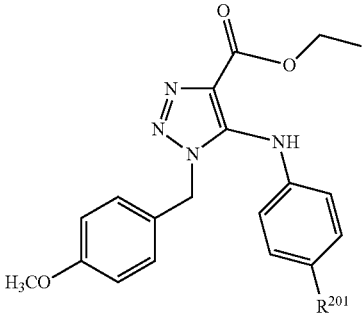 
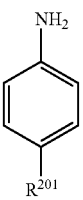
55

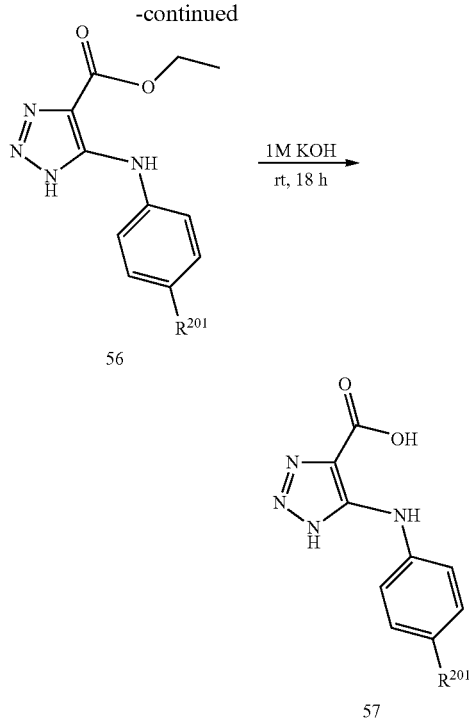

Scheme XII depicts a general method for the synthesis of N-linked 1H-1,2,3-triazole-4-carboxylic acids.

In certain embodiments, such as in the scheme above, each $R^{201}$, $R^{202}$, $R^{203}$, $R^{204}$, $R^{205}$, $R^{206}$, $R^{207}$, $R^{208}$, $R^{209}$, $R^{210}$, $R^{211}$, $R^{212}$, $R^{213}$, $R^{214}$, and $R^{215}$ is independently chosen from halogen, $C_1$-$C_6$ alkyl, $C_2$-$C_6$ alkenyl, $C_2$-$C_6$ alkynyl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ alkylsulfonyl, pentafluorosulfaneyl, sulfamoyl, $C_1$-$C_6$ alkylsulfamoyl, $C_1$-$C_6$ dialkylsulfamoyl, cyano, amino, $C_1$-$C_6$ alkylamino, $C_1$-$C_6$ dialkylamino, hydroxy, and $C_1$-$C_6$ hydroxyalkyl. Each $X^1$, $X^2$, and $X^3$ is independently chosen from N and CH.

General Sulfination Procedure by $S_NAr$

An oven-dried argon filled vial (A) (8 mL) containing a magnetic stir bar was charged with 36 mg sodium hydride (0.75 mmol, 1.1 equiv) and a thiophenol (0.780 mmol, 1.15 equiv). The vial was sealed with a screw cap and backfilled with argon three times. N,N-Dimethylformamide (3 mL) was then added via syringe and the solution stirred for 10 min. A second oven-dried argon filled vial (B) (8 mL) containing a magnetic stir bas was then charged with an aryl halide (0.68 mmol, 1.0 equiv), sealed with a screw cap and backfilled with argon three times. The contents of vial A were then transferred to vial B via syringe. Vial B was then placed in a pre-heated oil bath at 70° C. and stirred for 24 h. The reaction mixture was then cooled to room temperature, diluted with ethyl acetate (150 mL), washed with water (5×20 mL), brine (20 mL), and the filtrate concentrated in vacuo. The crude product was purified via flash chromatography on silica gel to yield the desired product.

General Sulfination Procedure by Cross-Coupling.

An oven-dried argon filled vial (A) (8 mL) containing a magnetic stir bar was charged with 52.7 mg potassium tert-butoxide (0.470 mmol, 1.10 equiv) and a thiophenol (0.490 mmol, 1.15 equiv). The vial was sealed with a screw cap and backfilled with argon three times. Toluene (1 mL) was then added via syringe and the solution stirred for 10 min. A second oven-dried argon filled vial (B) (8 mL) containing a magnetic stir bas was then charged with an aryl halide (0.43 mmol, 1.0 equiv), 2.8 mg lithium isopropoxide (0.043 mmol, 0.1 equiv), and 10.8 mg Pd-PEPPSI™-IP-ent$^{Cl}$-o-picoline (0.0129 mmol, 0.03 equiv). Vial B was then sealed with a screw cap, backfilled with argon three times, and toluene (3 mL) was added via syringe. The contents of vial B were then transferred to vial A via syringe and stirred for 24 h. The reaction mixture was then cooled to room temperature and passed through a plug of silica with ethyl acetate. The filtrate was concentrated in vacuo and the crude product was purified via flash chromatography on silica gel to yield the desired product.

General $S_NAr$ Procedure with Phenoxides

An oven-dried argon filled vial (A) (8 mL) containing a magnetic stir bar was charged with 36 mg sodium hydride (0.75 mmol, 1.1 equiv) and a phenol (0.780 mmol, 1.15 equiv). The vial was sealed with a screw cap and backfilled with argon three times. N,N-Dimethylformamide (3 mL) was then added via syringe and the solution stirred for 30 min. A second oven-dried argon filled vial (B) (8 mL) containing a magnetic stir bas was then charged with an aryl halide (0.68 mmol, 1.0 equiv), sealed with a screw cap and backfilled with argon three times. The contents of vial A were then transferred to vial B via syringe. Vial B was then placed in a pre-heated oil bath at 80° C. and stirred for 24 h. The reaction mixture was then cooled to room temperature, diluted with ethyl acetate (150 mL), washed with water (5×20 mL), brine (20 mL), and the filtrate concentrated in vacuo. The crude product was purified via flash chromatography on silica gel to yield the desired product.

General Procedure for the Preparation of Biaryls

An oven-dried argon filled vial (A) (8 mL) containing a magnetic stir bar was charged with an aryl-bromide (2.0 mmol) and capped with a screw cap. Tetrahydrofuran (2 mL) was added via syringe to the aryl-bromide followed by 1.0 mL n-butyllithium (2.2 mmol, 1.1 equiv) under argon at −78° C. The solution was stirred at −78° C. for 30 min, and then 2.4 mL zinc chloride solution in tetrahydrofuran (2.4 mmol, 1.2 equiv) was added at −78° C. and stirred at that temperature for 20 min to give the aryl-zinc. An oven-dried argon filled vial (B) (8 mL) containing a magnetic stir bar was charged with an aryl-bromide (0.50 mmol, 1.0 equiv) and Pd-PEPPSI™-IPent (0.02 mmol, 0.04 equiv). The vial was sealed with a screw cap and backfilled with argon three times. Tetrahydrofuran (TF) and N-methyl-2-pyrrolidone (NMP) were then added via syringe in amounts that give a final ratio of 2:1 THf:NMP in a total of 5 mL solvent. The organozinc reagent was then added via syringe and the vial was placed in a pre-heated oil bath at 50° C. and stirred for 24 h. The reaction mixture was then cooled to room temperature, diluted with ethyl acetate (150 mL), washed with 1 M ammonium chloride (2×20 mL), brine (20 mL), and the filtrate concentrated in vacuo. The crude product was purified via flash chromatography on silica gel to yield the desired product.

General PMB Group Removal Procedure

A vial (8 mL) containing a magnetic stir bar was charged with the molecule containing the PMB group (50 mg to 200 mg) and 3 mL trifluoroacetic acid. The vial was sealed with a screw cap, placed in a pre-heated oil bath at 70° C. and stirred for 24 h. The reaction mixture was then cooled to room temperature, diluted with ethyl acetate (150 mL), washed with 5% sodium bicarbonate (2×50 mL), brine (20 mL), and the filtrate concentrated in vacuo. The crude product was purified via flash chromatography on silica gel to yield the desired product.

General Ethyl Ester Hydrolysis Procedure

A vial (8 mL) containing a magnetic stir bar was charged with the ethyl ester (20 mg to 150 mg) and 5 mL 1 N KOH. The vial was then sealed with a screw cap and stirred at room temperature for 6 h. The pH was adjusted to between 2 and 3 using 0.1 N HCl and the contents of the vial were extracted with ethyl acetate (3×50 mL). The organic layers were combined, dried over anhydrous magnesium sulfate, filtered and concentrated in vacuo. The crude product was purified by trituration in diethyl ether to yield the desired product.

The following compounds are prepared by the methods of Schemes I-XII.

Synthesis of Ethyl 5-chloro-1-(4-methoxybenzyl)-1H-1,2,3-triazole-4-carboxylate

Step 1—Ethyl 5-chloro-1,2,3-triazole-4-carboxylate (1)

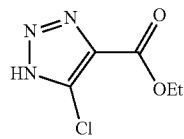

A 100-mL round bottom flask with a stir bar was charged with 6.2 mL ethyl diazoacetate (58 mmol, 2.0 equiv), sealed with a rubber septum and backfilled with argon three times. Acetonitrile (35 mL) was transferred to the flask via syringe and the flask was then cooled to 0° C. Next, 2.2 mL phosgene (29 mmol, 1.0 equiv) was added dropwise and the reaction mixture was stirred at room temperature for 20 h. The solvent was removed in vacuo and the crude product was purified by silica gel column chromatography (4% ethyl acetate/hexanes) to give 1 as a colorless oil (1.6 g, 26%).

Step 2—4-Methoxybenzyl chloride (5)

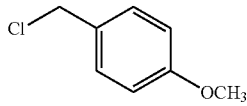

A 250-mL round bottom flask with a stir bar was charged with 4-methoxybenzyl alcohol (8.34 g, 6.00 mmol, 1.00 equiv), sealed with a rubber septum and backfilled with argon three times. The alcohol was then dissolved in 100 mL diethyl ether transferred via syringe, followed by 8.9 mL thionyl chloride (12 mmol, 2.0 equiv) added dropwise via syringe. The reaction mixture was stirred at room temperature for 5 h. The reaction mixture was then quenched by slowly adding water (50 mL). (Caution: HCl gas was developed). The aqueous and organic phases were separated, and the aqueous layer was extracted with dichloromethane (2×50 mL). The organic layers were combined and washed with saturated sodium bicarbonate (2×50 mL), water (2×50 mL), dried with anhydrous magnesium sulfate, filtered and the solvent removed in vacuo to give 4-methoxybenzyl chloride (8.9 g, 94%) as a colorless oil. $^1$H-NMR (300 MHz, CDCl$_3$) δ: 7.32 (d, 2H), 6.89 (d, 2H), 4.57 (s, 2H), 3.81 (s, 3H).

Step 3—4-Methoxybenzyl azide (6)

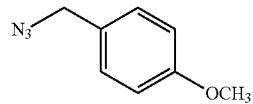 [SMILES: COc1ccc(CN=[N+]=[N-])cc1]

A 50-mL round bottom flask (A) with a stir bar was charged with 2.10 g sodium azide (31.8 mmol, 1.00 equiv), sealed with a rubber septum and backfilled with argon three times. A 50-mL round bottom flask (B) was charged with 5.00 g 5 (31.8 mmol, 1.00 equiv), sealed with a rubber septum and backfilled with argon three times. N,N-dimethylformamide (20 mL) was added to flask B to dissolve 5, then transferred to flask A and stirred for 24 hours at room temperature. The mixture was then diluted with water (200 mL) and extracted with diethyl ether (3×50 mL), the combined extracts were washed with water (5×50 mL), dried with anhydrous sodium sulfate, filtered and the solvent removed in vacuo to give 6 (4.94 g, 95%) as a colorless oil. $^1$H-NMR (400 MHz, CDCl$_3$) δ: 7.25 (d, 2H), 6.91 (d, 2H), 4.26 (s, 2H), 3.81 (s, 3H).

Step 4—Ethyl 5-hydroxy-1-(4-methoxybenzyl)-1H-1,2,3-triazole-4-carboxylate (7)

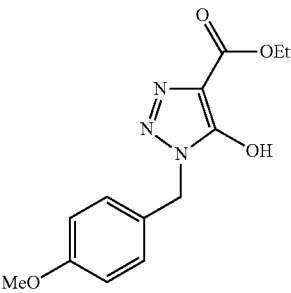 [SMILES: CCOC(=O)c1nnn(Cc2ccc(OC)cc2)c1O]

A 100-mL round bottom flask with a stir bar was charged with 4.19 g diethyl malonate (26.0 mmol, 1.00 equiv), 10.0 mL 30% sodium ethoxide in ethanol (26.0 mmol, 1.00 equiv) and ethanol (30 mL). The flask was sealed with a rubber septum and back filled with argon three times. After 30 min of stirring, a solution of 4.25 g 6 (26.0 mmol, 1.00 equiv) in ethanol (10 mL) was added dropwise with stirring, the mixture was then refluxed for 18 h. After cooling, the ethanol was removed in vacuo and water was added. The pH was adjusted to 2 with dilute hydrochloric acid to give a crystalline precipitate, which was filtered, washed with water, and dried in vacuo with P$_4$O$_{10}$ desiccant. Recrystallization from chloroform-pentanes gave 7 (4.6 g, 67%) as an off-white solid. $^1$H-NMR (400 MHz, DMSO-d$_6$) δ: 7.20 (d, 2H), 6.90 (d, 2H), 5.25 (s, 2H), 4.23 (q, 2H), 3.72 (s, 3H), 1.26 (t, 3H).

Step 5—Synthesis of ethyl 5-chloro-1-(4-methoxybenzyl)-1H-1,2,3-triazole-4-carboxylate (8)

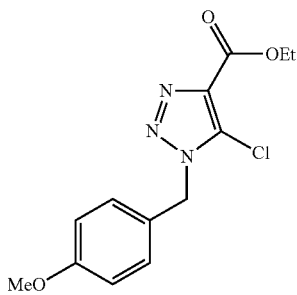 [SMILES: CCOC(=O)c1nnn(Cc2ccc(OC)cc2)c1Cl]

A 100-mL round bottom flask with a stir bar was charged with 3.70 g 7 (13.3 mmol, 1.00 equiv) and toluene (40 mL). With stirring, 3.0 g phosphorus pentachloride (14 mmol, 1.1 equiv) was added slowly to the round bottom flask. The mixture was stirred at 40° C. for 90 min under argon. The solvent was removed in vacuo and the residue dissolved in diethyl ether and washed with saturated sodium bicarbonate (3×50 mL), water (2×50 mL), dried with anhydrous magnesium sulfate, filtered and the solvent removed in vacuo. Recrystallization from diethyl ether-pentane gave pure 8 (2.53 g, 65%) as an off-white solid. $^1$HNMR (300 MHz, CDCl$_3$) δ: 7.26 (d, 2H), 6.87 (d, 2H), 5.50 (s, 2H), 4.42 (q, 2H), 3.79 (s, 3H), 1.40 (t, 3H).

Synthesis of [1,1'-Biphenyl]-4-thiol (24)

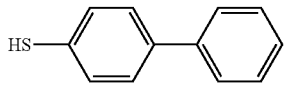 [SMILES: Sc1ccc(-c2ccccc2)cc1]

Step 1

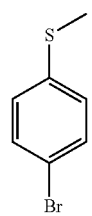

A 25-mL round bottom flask equipped with a stir-bar was charged with sodium hydride (141 mg, 5.88 mmol, 1.1 equiv.). The flask was sealed with a rubber septum and purged with argon (3×). 4-Bromobenzenethiol (20, 1.00 g, 5.34 mmol, 1.0 equiv.) in THF (5 mL) was added dropwise via a syringe, followed by MeI (289 mL, 5.88 mmol, 1.10 equiv.). Stirred at room temperature for 1 h. Quenched with the addition water and diluted with diethyl ether, washed with water (2×25 mL) and brine (25 mL). Dried over anhydrous MgSO4, filtered and concentrated under reduced pressure. The crude was purified by silica gel column chromatography to give (4-bromophenyl)(methyl)sulfane 21 as an off-white solid (480 mg, 44%). $^1$H-NMR (300 MHz, CDCl$_3$) δ: 7.39 (d, 2H), 7.11 (d, 2H), 2.45 (s, 3H).

Step 2

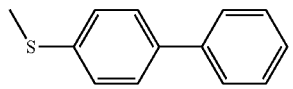

A 25-mL round bottom flask equipped with a stir-bar was charged with (4-bromophenyl)(methyl)sulfane (21, 460 mg, 2.46 mmol, 1 equiv.), Pd-PEPPSI-IPent (39 mg, 2 mol %), phenylboronic acid (22, 600 mg, 4.92 mmol, 2.0 equiv.), and potassium hydroxide (830 mg, 14.8 mmol, 6.0 equiv.). The flask was sealed with a rubber septum and purged with argon (3×). Dioxane (10.0 mL) was then added via syringe and the reaction was stirred at 65° C. for 4 h. The reaction mixture was diluted with diethyl ether (75 mL) and washed with 0.1N HCl (2×25 mL), water (2×25 mL) and brine (25 mL). Dried over anhydrous MgSO4 and filtered. The contents were concentrated under reduced pressure and the crude was passed through a pad of silica washing with 50% ethyl acetate/hexanes to give [1,1'-biphenyl]-4-yl(methyl)sulfane 23 as an off-white solid (407 mg, 90%). $^1$H-NMR (400 MHz, CDCl$_3$) δ: 7.55-7.45 (m, 4H), 7.44 (t, 2H), 7.35 (m, 3H), 3.71 (s, 3H).

Step 3

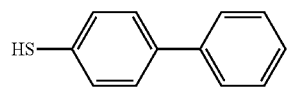 [SMILES: Sc1ccc(-c2ccccc2)cc1]

A 25-mL round bottom flask equipped with a stir-bar was charged with [1,1'-biphenyl]-4-yl(methyl)sulfane (23, 300 mg, 1.50 mmol, 1 equiv.) and sodium ethanethiolate (500 mg, 6.00 mmol, 4.0 equiv.). DMF (7 mL) was added and the flask was heated to 120° C. for 10 h. Cooled to room temperature and diluted with diethyl ether (100 mL). Washed with water (3×50 mL), brine (50 mL). Dried over anhydrous MgSO$_4$ and filtered. The contents were concentrated under reduced pressure and the crude was purified by silica gel column chromatography using 10% ethyl acetate/hexanes to give [1,1'-biphenyl]-4-thiol 24 as a pale-yellow solid (215 mg, 77%). $^1$H-NMR (300 MHz, CDCl$_3$) δ: 7.55 (d, 2H), 7.46 (m, 4H), 7.33 (m, 3H).

Synthesis of 4'-Methyl-[1,1'-biphenyl]-4-thiol (27)

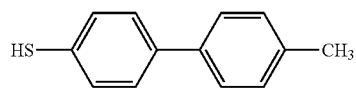

The title compound was prepared by the method described in Scheme V for compound 24 using p-tolylboronic acid (25, 669 mg, 4.92 mmol, 2.0 equiv.) a reagent in Step 2, to give 4'-methyl-[1,1'-biphenyl]-4-thiol 27 as a pale-yellow solid (217 mg, 44%, 2-steps).

Synthesis of 3-(Naphthalen-2-yl)phenol

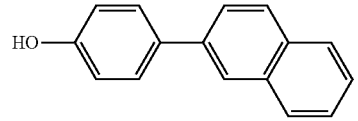

Referring to Scheme IX, a 10-mL round bottom flask equipped with a stir-bar was charged with 4-bromophenol (500 mg, 2.89 mmol, 1.0 equiv.), Pd-PEPPSI-IPent (45 mg, 2 mol %), 2-naphthylboronic acid (745 mg, 4.33 mmol, 1.5 equiv.), and potassium hydroxide (970 mg, 17.3 mmol, 6.0 equiv.). The flask was sealed with a rubber septum and purged with argon (3×). Dioxane (6.0 mL) was then added via syringe and the reaction was stirred at 70° C. for 5 h. The reaction mixture was diluted with diethyl ether (75 mL) and washed with 0.1N HCl (2×25 mL), water (2×25 mL) and brine (25 mL). Dried over anhydrous MgSO$_4$ and filtered. The contents were concentrated under reduced pressure and the crude was passed through a pad of silica washing with ethyl acetate to give 3-(naphthalen-2-yl)phenol (569 mg, 89%) as an off-white solid $^1$H-NMR (400 MHz, CDCl$_3$) δ: 7.98 (s, 1H), 7.87 (m, 3H), 7.72 (m, 1H), 7.60 (d, 2H), 7.48 (m, 2H), 6.95 (d, 2H).

Synthesis of 3-(Naphthalen-2-yl)phenol

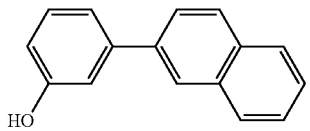

The title compound was prepared by the method described in Scheme IX using with 3-bromophenol (500 mg, 2.89 mmol, 1.00 equiv.) and 2-naphthylboronic acid (745 mg, 4.33 mmol, 1.50 equiv.) as reagents Scheme IX, to give 3-(naphthalen-2-yl)phenol (543 mg, 85%) as an off-white solid. $^1$H-NMR (400 MHz, CDCl$_3$) δ: 8.04 (s, 1H), 7.98-7.88 (m, 3H), 7.73 (d, 1H), 7.53 (m, 2H), 7.40-7.33 (m, 2H), 7.22 (s, 1H), 6.88 (d, 1H).

Synthesis of 4'-Fluoro-[1,1'-biphenyl]-4-ol

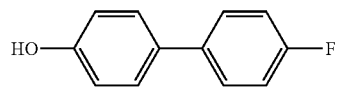

The title compound was prepared by the method described in Scheme IX using 4-methoxyphenol (92.4 mg, 0.74 mmol, 1.10 equiv.) as a reagent in Scheme IX, to give 4'-fluoro-[1,1'-biphenyl]-4-ol (262 mg, 55%) as a light-yellow solid. H-NMR (300 MHz, CDCl$_3$) δ: 7.48-7.41 (m, 4H), 7.10 (m, 2H), 6.90 (d, 2H).

Synthesis of 3-(Pyridin-4-yl)phenol

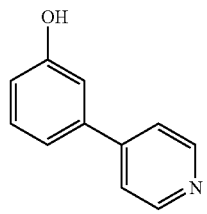 [SMILES: Oc1cccc(-c2ccncc2)c1]

A solution of 3-bromophenol (500 mg, 2.89 mmol, 1.00 equiv), pyridine-4-boronic acid (426 mg, 3.47 mmol, 1.20 equiv.), K$_2$CO$_3$ (2.49 g, 18.1 mmol, 6.25 equiv.), and Pd(PPh$_3$)$_4$ (168 mg, 0.15 mmol) in EtOH/H$_2$O was refluxed for 40 h. After removal of solvent under vacuum, the residue was purified by column chromatography to afford the 3-(pyridin-4-yl)phenol (406 mg, 82%) as a light-brown solid. $^1$H-NMR (300 MHz, DMSO-d$_6$) δ: 9.68 (brs, 1H), 8.61 (dd, 2H), 7.62 (dd, 2H), 7.32 (t, 1H), 7.21-7.18 (m, 1H), 7.13-7.12 (m, 1H), 6.87 (m, 1H).

Synthesis of 6-Phenylpyridin-3-ol

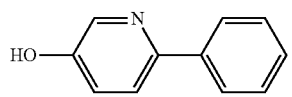

The title compound was prepared by the method described in Scheme IX using 6-bromopyridin-3-ol (500 mg, 2.87 mmol, 1.00 equiv.) and phenylboronic acid (695 mg, 5.74 mmol, 2.00 equiv.) as reagents in Scheme IX, to give 6-phenylpyridin-3-ol (132 mg, 26%) as an off-white solid. $^1$H-NMR (400 MHz, CDCl$_3$) δ: 8.32 (d, 1H), 7.87 (d, 2H), 7.61 (d, 1H), 7.45 (t, 2H), 7.37 (t, 1H).

Synthesis of 6-Phenylpyridin-3-ol

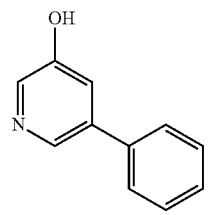 [SMILES: Oc1cncc(-c2ccccc2)c1]

The title compound was prepared by the method described in Scheme IX using 5-bromopyridin-3-ol (500 mg, 2.87 mmol, 1.00 equiv.) and phenylboronic acid (695 mg, 5.74 mmol, 2.00 equiv) as reagents in Scheme IX, to give 6-phenylpyridin-3-ol (187 mg, 37%) as an off-white solid. $^1$H-NMR (400 MHz, DMSO-d$_6$) δ: 10.05 (s, 1H), 8.34 (s, 1H), 8.13 (d, 1H), 7.66 (d, 2H), 7.50 (t, 2H), 7.41 (d, 1H), 7.37 (s, 1H).

Synthesis of 3-(Pyridin-3-yl)phenol

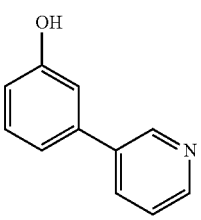 [SMILES: Oc1cccc(-c2cccnc2)c1]

The title compound was prepared by the method described in Scheme IX using 3-bromophenol (500 mg, 2.89 mmol, 1.00 equiv.) and pyridin-3-ylboronic acid (426 mg, 3.47 mmol, 1.20 equiv.) as reagents in Scheme IX, to give 3-(pyridin-3-yl)phenol (269 mg, 55%) as an off-white solid. ¹H-NMR (400 MHz, DMSO-d₆) δ: 9.63 (brs, 1H), 8.81 (d, 1H), 8.55 (dd, 1H), 8.00-7.98 (m, 1H), 7.46 (dd, 1H), 7.29 (t, 1H), 7.12-7.10 (m, 1H), 7.06 (t, 1H), 6.82 (m, 1H).

Synthesis of [3,3'-Bipyridin]-5-ol

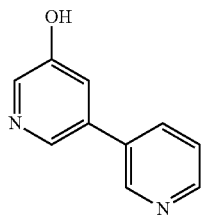 [SMILES: Oc1cncc(-c2cccnc2)c1]

The title compound was prepared by the method described in Scheme IX using 5-bromopyridin-3-ol (500 mg, 2.87 mmol, 1.00 equiv) and pyridin-3-ylboronic acid (426 mg, 3.47 mmol, 1.20 equiv.) as reagents in Scheme IX, to give [3,3'-bipyridin]-5-ol (266 mg, 54%) as a light brown solid. ¹H-NMR (400 MHz, CDCl₃) δ: 8.85 (s, 1H), 8.66 (s, 1H), 8.34 (s, 2H), 7.92 (s, 1H), 7.79 (d, 2H).

Synthesis of 4-(Pyridin-2-yl)phenol

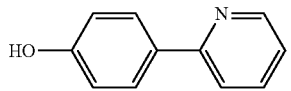

The title compound was prepared by the method described in Scheme IX using 5-bromopyridin-3-ol (500 mg, 2.89 mmol, 1.00 equiv.) and phenylboronic acid (685 mg, 5.66 mmol, 2.0 equiv.) as reagents in Step 1 of Scheme IX, to give 4-(pyridin-2-yl)phenol (267 mg, 54%) as an off-white solid. ¹H-NMR (400 MHz, CDCl₃) δ: 8.58 (d, 1H), 7.80 (d, 2H), 7.66 (t, 1H), 7.61 (d, 1H), 7.11 (t, 1H), 6.91 (d, 2H).

The invention is further illustrated by the following examples.

Example I-001: 5-((4-chlorophenyl)thio)-1H-1,2,3-triazole-4-carboxylic acid

Step 1—Ethyl 5-((4-chlorophenyl) thio)-1-(4-methoxybenzyl)-1H-1,2,3-triazole-4-carboxylate

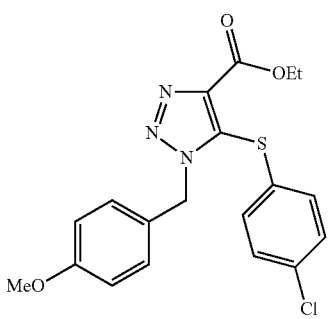 [SMILES: CCOC(=O)c1nnn(Cc2ccc(OC)cc2)c1Sc1ccc(Cl)cc1]

A 10-mL round bottom flask with a stir bar was charged with sodium hydride (50%, 36.0 mg, 0.744 mmol, 1.10 equiv), sealed with a rubber septum and backfilled with argon three times. The 4-chlorothiophenol (108 mg, 0.744 mmol, 1.10 equiv) was dissolved in anhydrous DMF (3 mL) was added dropwise at room temperature. Ethyl 5-chloro-1-(4-methoxybenzyl)-1H-1,2,3-triazole-4-carboxylate (200 mg, 0.676 mmol, 1.00 equiv) dissolved in anhydrous DMF (2 mL) was added dropwise and the reaction mixture was stirred in an oil-bath at 70° C. for 18 hours. The mixture was cooled to room temperature and quenched with water (2 mL). Extracted with ethyl acetate (3×25 mL), and the combined extracts were washed with water (5×20 mL), dried with anhydrous MgSO4, filtered and the solvent removed in vacuo. Flash column chromatography on silica gel gave ethyl 5-((4-chlorophenyl) thio)-1-(4-methoxybenzyl)-1H-1,2,3-triazole-4-carboxylate (180 mg, 66%) as a yellow oil. ¹H-NMR (400 MHz, CDCl₃) δ: 7.12 (d, 4H), 6.88 (d, 2H), 6.74 (d, 2H), 5.56 (s, 2H), 4.35 (q, 2H), 3.76 (s, 3H), 1.32 (t, 3H).

Step 2—Ethyl 5-((4-chlorophenyl)thio)-1H-1,2,3-triazole-4-carboxylate (I-002)

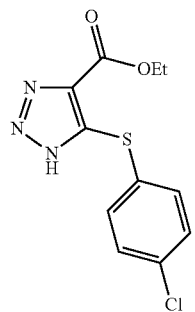 [SMILES: CCOC(=O)c1nn[nH]c1Sc1ccc(Cl)cc1]

A vial (8 mL) containing a magnetic stir bar was charged with ethyl 5-((4-chlorophenyl) thio)-1-(4-methoxybenzyl)-1H-1,2,3-triazole-4-carboxylate (200 mg, 0.495 mmol) and 3 mL of trifluoroacetic acid. The vial was sealed with a screw cap, placed in a pre-heated oil bath at 70° C. and stirred for 3 h. The reaction mixture was then cooled to room temperature, diluted with ethyl acetate (150 mL), washed with saturated aqueous sodium bicarbonate (2×50 mL), water (50 mL), brine (50 mL), and dried with anhydrous MgSO₄, filtered and the solvent removed in vacuo. Flash chromatography on silica gel gave ethyl 5-((4-chlorophenyl) thio)-1H-1,2,3-triazole-4-carboxylate (I-002, 99 mg, 71%) as an off-white solid. ¹H-NMR (400 MHz, CDCl₃) δ: 9.72 (bs, 1H), 7.51 (d, 2H), 7.38 (d, 2H), 4.44 (q, 2H), 1.40 (t, 3H).

Step 3—5-((4-Chlorophenyl)thio)-1H-1,2,3-triazole-4-carboxylic acid (I-001)

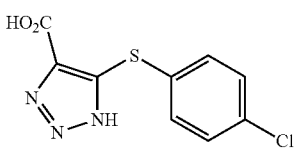 [SMILES: O=C(O)c1nn[nH]c1Sc1ccc(Cl)cc1]

A vial (8 mL) containing a magnetic stir bar was charged with the 5-((4-chlorophenyl) thio)-1H-1,2,3-triazole-4-carboxylate (70 mg, 0.247 mmol) and 5 mL of 1 N KOH. The vial was then sealed with a screw cap and stirred at room temperature for 6 hours. The pH was adjusted to between 2 and 3 using 0.1 N HCl. The contents of the vial were extracted with ethyl acetate (3×50 mL). The organic layers were combined, dried over anhydrous MgSO$_4$, filtered and concentrated in vacuo. The crude product was purified by trituration in diethyl ether to yield 5-((4-chlorophenyl)thio)-1H-1,2,3-triazole-4-carboxylic acid as white solid (I-001, 51 mg, 80%). $^1$H-NMR (400 MHz, DMSO-d$_6$) δ: 7.45 (s, 4H). HRMS-EI (calc. M+1) 255.9942, found 255.9940.

Example I-003:
5-(p-Tolylthio)-1H-1,2,3-triazole-4-carboxylic acid

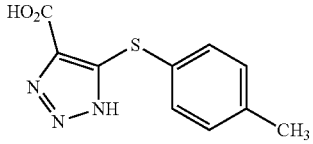 [SMILES: Cc1ccc(Sc2[nH]nnc2C(=O)O)cc1]

The title compound was prepared by the method described in Example I-001 using 4-methylthiophenol (92.4 mg, 0.744 mmol, 1.10 equiv) as a reagent in Step 1 of Example I-001, to give 5-(p-tolylthio)-1H-1,2,3-triazole-4-carboxylic acid (32.7 mg, 21%, 3-steps) as a white solid. $^1$HNMR (400 MHz, CDCl$_3$) δ: 7.37 (d, 2H), 7.11 (d, 2H), 2.28 (s, 3H).

Example I-004: 5-((4-Methoxyphenyl)thio)-1H-1,2,3-triazole-4-carboxylic acid

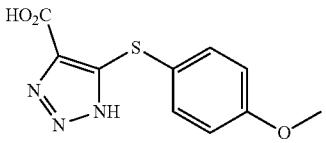 [SMILES: COc1ccc(Sc2[nH]nnc2C(=O)O)cc1]

The title compound was prepared by the method described in Step 3 of Example I-001, to give 5-((4-methoxyphenyl)thio)-1H-1,2,3-triazole-4-carboxylic acid (124 mg, 72%, 3-steps) as a yellowish solid. $^1$H-NMR (300 MHz, Acetone-d$_6$) δ: 7.54 (d, 2H), 7.00 (d, 2H), 3.99 (s, 3H).

Example I-005: Ethyl 5-((4-Methoxyphenyl)thio)-1H-1,2,3-triazole-4-carboxylate

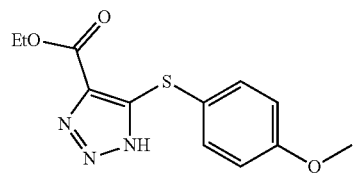 [SMILES: CCOC(=O)c1nn[nH]c1Sc1ccc(OC)cc1]

The title compound was prepared by the method described in Example I-001 using 4-methoxythiophenol (104 mg, mmol, 1.10 equiv) as a reagent in Step 1 of Example I-001, to give 5-((4-methoxyphenyl)thio)-1H-1,2,3-triazole-4-carboxylic acid (124 mg, 72%, 3-steps) as a yellowish solid. $^1$H-NMR (300 MHz, Acetone-d$_6$) δ: 7.54 (d, 2H), 7.00 (d, 2H), 3.99 (s, 3H).

Example I-006: 5-((2-Methoxyphenyl)thio)-1H-1,2,3-triazole-4-carboxylic acid

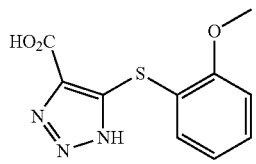 [SMILES: COc1ccccc1Sc1[nH]nnc1C(=O)O]

The title compound was prepared by the method described in Example I-001 using 2,4-dimethylthiophenol (104 mg, 0.744 mmol, 1.10 equiv) as a reagent in Step 1 of Example I-001, to give 5-((2,4-dimethylphenyl)thio)-1H-1,2,3-triazole-4-carboxylic acid (111 mg, 65%, 3-steps) as a white solid. $^1$H-NMR (400 MHz, DMSO-d$_6$) δ: 7.36 (s, 1H), 7.23 (s, 1H), 7.09 (d, 1H), 6.93 (dd, 1H), 3.78 (s, 3H).

Example I-007: 5-((4-Bromophenyl)thio)-1H-1,2,3-triazole-4-carboxylic acid

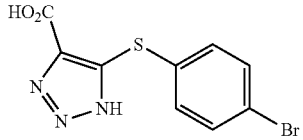

The title compound was prepared by the method described in Example I-001 using 4-bromothiophenol (141 mg, 0.744 mmol, 1.10 equiv) as a reagent in Step 1 of Example I-001, to give 5-((4-bromophenyl)thio)-1H-1,2,3-triazole-4-carboxylic acid (74.2 mg, 36%, 3-steps) as a white solid. $^1$H-NMR (400 MHz, CD$_3$OD) δ: 7.43 (d, 2H), 7.34 (d, 2H).

Example I-008: Ethyl 5-((4-bromophenyl)thio)-1H-1,2,3-triazole-4-carboxylate

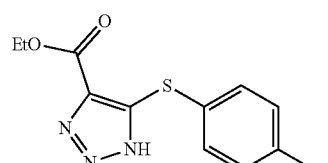

The title compound was prepared by the method described in Example I-001 using 4-bromothiophenol (141 mg, 0.744 mmol, 1.10 equiv.) as a reagent in Step 1 of Example I-001. $^1$H-NMR (300 MHz, CDCl$_3$) δ: 9.62 (bs, 1H), 7.46 (m, 4H), 4.40 (q, 2H), 1.35 (t, 3H).

Example I-009: 5-((2,4-Dimethylphenyl)thio)-1H-1,2,3-triazole-4-carboxylic acid

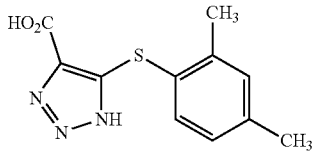 [SMILES: Cc1ccc(Sc2[nH]nnc2C(=O)O)c(C)c1]

The title compound was prepared by the method described in Example I-001 using 2,4-dimethylthiophenol (103 mg, 0.744 mmol, 1.10 equiv) as a reagent in Step 1 of Example I-001, to give 5-((2,4-dimethylphenyl)thio)-1H-1,2,3-triazole-4-carboxylic acid (52 mg, 31%, 3-steps) as an off-white solid. $^1$H-NMR (400 MHz, DMSO-d$_6$) δ: 7.32 (d, 1H), 7.16 (s, 1H), 7.02 (d, 1H), 2.27 (s, 6H).

Example I-010:
5-(o-Tolylthio)-1H-1,2,3-triazole-4-carboxylic acid

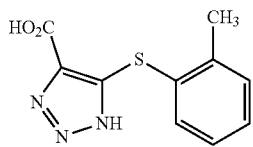

The title compound was prepared by the method described in Example I-001 using 2-methylthiophenol (92.4 mg, 0.744 mmol, 1.10 equiv) as a reagent in Step 1 of Example I-001, to give 5-(o-tolylthio)-1H-1,2,3-triazole-4-carboxylic acid (51.4 mg, 33%, 3-steps) as a white solid. $^1$HNMR (300 MHz, DMSO-d$_6$) δ: 7.40-7.30 (m, 3H), 7.22 (t, 1H), 3.09 (s, 3H).

Example I-011: 5-((2-Chlorophenyl)thio)-1H-1,2,3-triazole-4-carboxylic acid

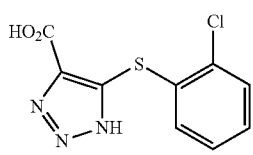 [SMILES: O=C(O)c1nn[nH]c1Sc1ccccc1Cl]

The title compound was prepared by the method described in Example I-001 using 2-chlorothiophenol (108 mg, 0.744 mmol, 1.10 equiv) as a reagent in Step 1 of Example I-001, to give 5-((2-chlorophenyl)thio)-1H-1,2,3-triazole-4-carboxylic acid (69.5 mg, 40%) as a white solid. $^1$H-NMR (400 MHz, DMSO-d$_6$) δ: 7.57 (d, 1H), 7.35 (m, 3H).

Example I-012: Ethyl 5-((2-chlorophenyl)thio)-1H-1,2,3-triazole-4-carboxylate

The title compound was prepared by the method described in Example I-001 using 2-chlorothiophenol (108 mg, 0.744 mmol, 1.10 equiv.) as a reagent in Step 1 of Example I-001. $^1$H-NMR (300 MHz, CDCl$_3$) δ: 7.51 (m, 2H), 7.33-7.25 (m, 2H), 4.42 (q, 2H), 1.36 (t, 3H).

Example I-013: 5-((2-Fluorophenyl)thio)-1H-1,2,3-triazole-4-carboxylic acid

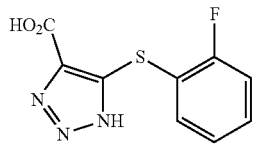

The title compound was prepared by the method described in Example I-001 using 2-fluorothiophenol (95.4 mg, 0.744 mmol, 1.10 equiv) as a reagent in Step 1 of Example I-001, to give 5-((2-fluorophenyl)thio)-1H-1,2,3-triazole-4-carboxylic acid (55.1 mg, 34%, 3-steps) as an off-white solid. $^1$H-NMR (400 MHz, CD$_3$CN) δ: 7.59 (t, 1H), 7.50 (q, 1H), 7.26 (t, 2H).

Example I-014: Ethyl 5-((2-fluorophenyl)thio)-1H-1,2,3-triazole-4-carboxylate

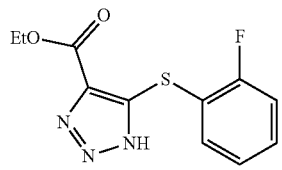 [SMILES: CCOC(=O)c1nn[nH]c1Sc1ccccc1F]

The title compound was prepared by the method described in Example I-001 using 2-fluorothiophenol (95.4 mg, 0.744 mmol, 1.10 equiv.) as a reagent in Step 1 of Example I-001. $^1$H-NMR (300 MHz, CDCl$_3$) δ: 11.4 (bs, 1H), 7.59 (t, 1H), 7.40 (q, 1H), 7.16 (m, 2H), 4.39 (q, 2H), 1.33 (t, 3H).

Example I-015: 5-((3-Fluorophenyl)thio)-1H-1,2,3-triazole-4-carboxylic acid

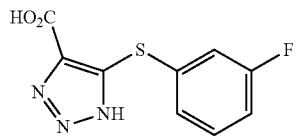 [SMILES: O=C(O)c1nn[nH]c1Sc1cccc(F)c1]

The title compound was prepared by the method described in Example I-001 using 3-fluorothiophenol (95.4 mg, 0.744 mmol, 1.10 equiv) as a reagent in Step 1 of Example I-001, to give 5-((3-fluorophenyl)thio)-1H-1,2,3-triazole-4-carboxylic acid (59.7 mg, 37%, 3-steps) as a white solid. $^1$H-NMR (400 MHz, CDCl$_3$) δ: 7.22-7.10 (m, 3H), 6.92 (t, 1H).

Example I-016: 5-((4-(Trifluoromethyl)phenyl)thio)-1H-1,2,3-triazole-4-carboxylic acid

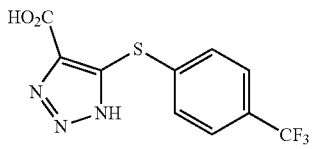

The title compound was prepared by the method described in Example I-001 using 4-(trifluoromethyl)thiophenol (133 mg, 0.744 mmol, 1.10 equiv) as a reagent in Step 1 of Example I-001, to give 5-((4-(trifluoromethyl)phenyl)thio)-1H-1,2,3-triazole-4-carboxylic acid (25.4 mg, 13%) as a white solid. $^1$H-NMR (400 MHz, DMSO-d$_6$) δ: 7.70 (d, 2H), 7.55 (d, 2H).

Example I-025: 5-((3,4-Dichlorophenyl)thio)-1H-1,2,3-triazole-4-carboxylic acid

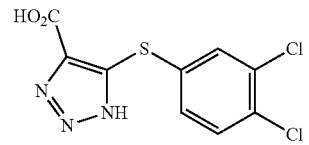 [SMILES: O=C(O)c1nn[nH]c1Sc1ccc(Cl)c(Cl)c1]

The title compound was prepared by the method described in Example I-001 using 3,4-dichlorothiophenol (133 mg, 0.744 mmol, 1.10 equiv) as a reagent in Step 1 of Example I-001, to give 5-((3,4-dichlorophenyl)thio)-1H-1,2,3-triazole-4-carboxylic acid (72 mg, 37%, 3-steps) as an off-white solid. $^1$H-NMR (400 MHz, DMSO-d$_6$) δ: 7.76 (s, 1H), 7.65 (d, 1H), 7.42 (d, 1H).

Example I-031: 5-(Naphthalen-2-ylthio)-1H-1,2,3-triazole-4-carboxylic acid

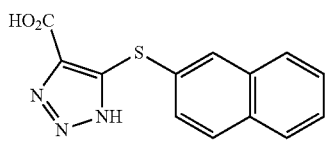 [SMILES: O=C(O)c1nn[nH]c1Sc1ccc2ccccc2c1]

The title compound was prepared by the method described in Example I-001 using naphthalene-2-thiol (119 mg, 0.744 mmol, 1.10 equiv) as a reagent in Step 1 of Example I-001, to give 5-(naphthalen-2-ylthio)-1H-1,2,3-triazole-4-carboxylic acid (46 mg, 26%, 3-steps) as a white solid. $^1$H-NMR (400 MHz, DMSO-d$_6$) δ: 8.07 (s, 1H), 7.92 (d, 3H), 7.56-7.49 (m, 3H).

Example I-032: 5-(Benzo[d]thiazol-2-ylthio)-1H-1,2,3-triazole-4-carboxylic acid

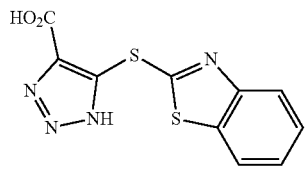 [SMILES: O=C(O)c1nn[nH]c1Sc1nc2ccccc2s1]

The title compound was prepared by the method described in Example I-001 using benzo[d]thiazole-2-thiol (124 mg, 0.744 mmol, 1.10 equiv) as a reagent in Step 1 of Example I-001, to give 5-(benzo[d]thiazol-2-ylthio)-1H-1,2,3-triazole-4-carboxylic acid (9.4 mg, 6%, 3-steps) as an off-white solid. $^1$H-NMR (400 MHz, CDCl$_3$) δ: 7.67 (d, 1H), 7.57 (d, 1H), 7.25 (t, 1H), 7.15 (t, 1H).

Example I-033: 5-(4-Chlorophenoxy)-1H-1,2,3-triazole-4-carboxylic acid

Step 1—Ethyl 5-(4-chlorophenoxy)-1-(4-methoxybenzyl)-1H-1,2,3-triazole-4-carboxylate

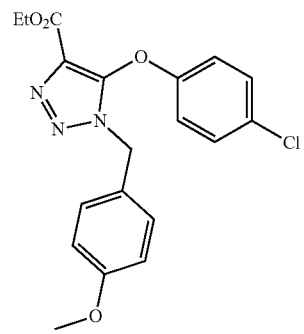 [SMILES: CCOC(=O)c1nnn(Cc2ccc(OC)cc2)c1Oc1ccc(Cl)cc1]

A 10-mL round bottom flask with a stir bar was charged with sodium hydride (50%, 36.0 mg, 0.744 mmol, 1.10 equiv.), sealed with a rubber septum and backfilled with argon three times. The 4-chlorophenol (95.6 mg, 0.744 mmol, 1.10 equiv.) was dissolved in anhydrous DMF (3 mL) was added dropwise at room temperature. Ethyl 5-chloro-1-(4-methoxybenzyl)-1H-1,2,3-triazole-4-carboxylate (200 mg, 0.676 mmol, 1.0 equiv.) dissolved in anhydrous DMF (2 mL) was added dropwise and the reaction flask was stirred in an oil-bath at 80° C. for 18 hours. The mixture was cooled to room temperature and quenched with water (2 mL). Extracted with ethyl acetate (3×50 mL), and the combined extracts were washed with water (5×25 mL), dried with anhydrous MgSO4, filtered and the solvent removed in vacuo. Flash column chromatograph gave ethyl 5-(4-chlorophenoxy)-1-(4-methoxybenzyl)-1H-1,2,3-triazole-4-carboxylate (183 mg, 70%) as a yellow oil. This was used without purification in the next step.

Step 2—Ethyl 5-(4-chlorophenoxy)-1H-1,2,3-triazole-4-carboxylate

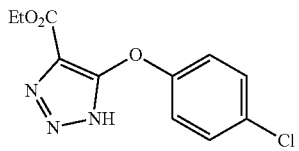 [SMILES: CCOC(=O)c1nn[nH]c1Oc1ccc(Cl)cc1]

A vial (8 mL) containing a magnetic stir bar was charged with ethyl 5-(4-chlorophenoxy)-1-(4-methoxybenzyl)-1H-1,2,3-triazole-4-carboxylate (150 mg, 0.464 mmol) and 3 mL of trifluoroacetic acid. The vial was sealed with a screw cap, placed in a pre-heated oil bath at 70° C. and stirred for 3 h. The reaction mixture was then cooled to room temperature, diluted with ethyl acetate (150 mL), washed with saturated aq. sodium bicarbonate (2×50 mL), water (50 mL), brine (50 mL), and dried with anhydrous MgSO4, filtered and the solvent removed in vacuo. Flash chromatography on silica gel gave ethyl 5-(4-chlorophenoxy)-1H-1,2,3-triazole-4-carboxylate (92 mg, 74%) as an off-white solid. $^1$H-NMR (400 MHz, CDCl$_3$) δ: 13.21 (bs, 1H), 7.30 (d, 2H), 7.09 (d, 2H), 4.39 (q, 2H), 1.30 (t, 3H).

Step 3—5-(4-Chlorophenoxy)-1H-1,2,3-triazole-4-carboxylic acid (I-033)

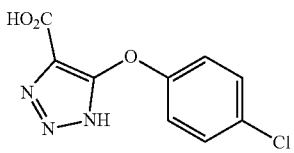 [SMILES: O=C(O)c1nn[nH]c1Oc1ccc(Cl)cc1]

A vial (8 mL) containing a magnetic stir bar was charged with the ethyl 5-(4-chlorophenoxy)-1H-1,2,3-triazole-4-carboxylate (70 mg, 0.262 mmol) and 3 mL of 1 N KOH. The vial was then sealed with a screw cap and stirred at room temperature for 18 hours. The pH was adjusted to between 2 and 3 using 0.1 N HCl and the contents of the vial were extracted with ethyl acetate (3×50 mL). The organic layers were combined, dried over anhydrous MgSO4, filtered and concentrated in vacuo. The crude product was purified by trituration in diethyl ether to yield 5-(4-chlorophenoxy)-1H-1,2,3-triazole-4-carboxylic acid (I-033) as a white solid (53 mg, 84%). $^1$H-NMR (400 MHz, DMSO-d$_6$) δ: 7.41 (d, 2H), 7.11 (d, 2H).

Example I-035: 5-(4-Methoxyphenoxy)-1H-1,2,3-triazole-4-carboxylic acid

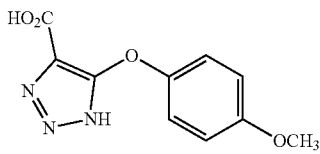

The title compound was prepared by the method described in Example I-033 using 4-methoxyphenol (92.4 mg, 0.744 mmol, 1.10 equiv.) as a reagent in Step 1 of Example I-033, to give 5-(4-methoxyphenoxy)-1H-1,2,3-triazole-4-carboxylic acid (I-035, 47.7 mg, 31%, 3-steps) as an off-white solid. $^1$H-NMR (400 MHz, DMSO-d$_6$) δ: 7.05 (d, 2H), 6.92 (d, 2H), 3.74 (s, 3H).

Example I-037: 5-(4-Bromo-3-methylphenoxy)-1H-1,2,3-triazole-4-carboxylic acid

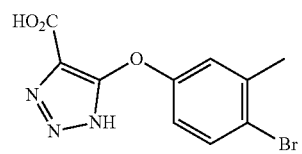

The title compound was prepared by the method described in Example I-033 using 4-bromo-3-methylphenol (139 mg, 0.744 mmol, 1.10 equiv.) as a reagent in Step 1 of Example I-033, to give 5-(4-bromo-3-methylphenoxy)-1H-1,2,3-triazole-4-carboxylic acid (I-037, 24.2 mg, 12%, 3-steps) as an off-white solid. $^1$H-NMR (300 MHz, CDCl$_3$) δ: 7.54 (d, 1H), 7.11 (d, 1H), 6.86 (dd, 1H), 2.32 (s, 3H).

Example I-039: 5-(3,4-Dimethylphenoxy)-1H-1,2,3-triazole-4-carboxylic acid

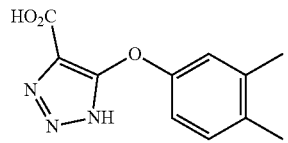 [SMILES: Cc1ccc(Oc2[nH]nnc2C(=O)O)cc1C]

The title compound was prepared by the method described in Example I-033 using 3,4-dimethylphenol (91.0 mg, 0.744 mmol, 1.10 equiv.) as a reagent in Step 1 of Example I-033, to give 5-(3,4-dimethylphenoxy)-1H-1,2,3-triazole-4-carboxylic acid (I-039, 23.6 mg, 15%, 3-steps) as an off-white solid. $^1$H-NMR (400 MHz, DMSO-d$_6$) δ: 7.10 (d, 1H), 6.84 (d, 1H), 6.77 (dd, 1H), 2.19 (s, 3H), 2.18 (s, 3H).

Example I-049: 5-(4-Pentafluorosulfanylphenoxy)-1H-1,2,3-triazole-4-carboxylic acid

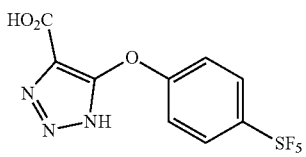

The title compound was prepared by the method described in Example I-033 using 4-pentafluorosulfanylphenol (164 mg, 0.744 mmol, 1.10 equiv.) as a reagent in Step 1 of Example I-033, to give 5-(4-pentafluorosulfanylphenoxy)-1H-1,2,3-triazole-4-carboxylic acid (34.8 mg, 13%, 3-steps) as an off-white solid. $^1$H-NMR (400 MHz, DMSO-d$_6$) δ: 7.90 (d, 2H), 7.23 (d, 2H).

Example I-050: 5-(3,4-Dichlorophenoxy)-1H-1,2,3-triazole-4-carboxylic acid

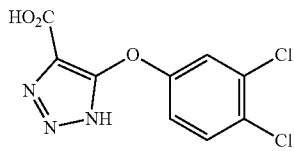 [SMILES: O=C(O)c1nn[nH]c1Oc1ccc(Cl)c(Cl)c1]

The title compound was prepared by the method described in Example I-033 using 3,4-dichlorophenol (121 mg, 0.744 mmol, 1.10 equiv.) as a reagent in Step 1 of Example I-033, to give 5-(3,4-dichlorophenoxy)-1H-1,2,3-triazole-4-carboxylic acid (I-050, 52 mg, 31%, 3-steps) as an off-white solid. $^1$H-NMR (400 MHz, DMSO-$d_6$) δ: 7.62 (d, 1H), 7.44 (m, 1H), 7.09 (d, 1H).

Example I-057: 5-Phenoxy-1H-1,2,3-triazole-4-carboxylic acid

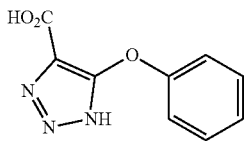

The title compound was prepared by the method described in Example I-033 using phenol (70 mg, 0.744 mmol, 1.10 equiv.) as a reagent in Step 1 of Example I-033, to give 5-phenoxy-1H-1,2,3-triazole-4-carboxylic acid (I-057, 26.3 mg, 19%, 3-steps) as an off-white solid. $^1$H-NMR (400 MHz, DMSO-$d_6$) δ: 7.22 (d, 2H), 6.96 (m, 3H).

Example I-058: 5-(Naphthalen-2-yloxy)-1H-1,2,3-triazole-4-carboxylic acid

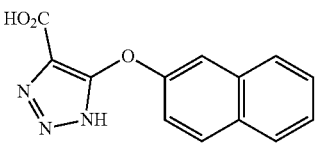 [SMILES: O=C(O)c1nn[nH]c1Oc1ccc2ccccc2c1]

The title compound was prepared by the method described in Example I-033 using naphthalen-2-ol (107 mg, 0.744 mmol, 1.10 equiv.) as a reagent in Step 1 of Example I-033, to give 5-(naphthalen-2-yloxy)-1H-1,2,3-triazole-4-carboxylic acid (20.7 mg, 12%, 3-steps) as an off-white solid. $^1$H-NMR (400 MHz, DMSO-$d_6$) δ: 7.97-7.91 (m, 2H), 7.85 (d, 1H), 7.52-7.44 (m, 3H), 7.37 (d, 1H).

Example I-085: 5-((4-Bromobenzyl)oxy)-1H-1,2,3-triazole-4-carboxylic acid

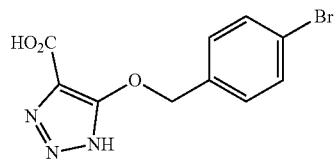 [SMILES: O=C(O)c1nn[nH]c1OCc1ccc(Br)cc1]

The title compound was prepared by the method described in Example I-033 using 1-bromo-4-(bromomethyl)benzene (186 mg, 0.744 mmol, 1.10 equiv.) as a reagent in Step 1 of Example I-033, to give 5-((4-bromobenzyl)oxy)-1H-1,2,3-triazole-4-carboxylic acid (26.2 mg, 13%, 3-steps) as a light-yellow solid. $^1$H-NMR (400 MHz, CDCl$_3$) δ: 7.48 (d, 2H), 7.20 (d, 2H), 5.74 (s, 2H).

Example I-128: 5-([1,1'-Biphenyl]-4-ylthio)-1H-1,2,3-triazole-4-carboxylic acid

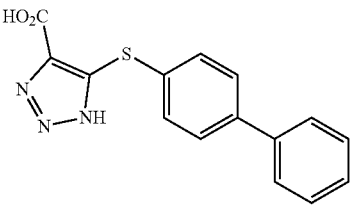 [SMILES: O=C(O)c1nn[nH]c1Sc1ccc(-c2ccccc2)cc1]

The title compound was prepared by the method described in Example I-001 using [1,1'-biphenyl]-4-thiol (139 mg, 0.744 mmol, 1.10 equiv) as a reagent in Step 1 of Example I-001, to give 5-([1,1'-biphenyl]-4-ylthio)-1H-1,2,3-triazole-4-carboxylic acid (111 mg, 37%, 3-steps) as a white solid. $^1$H-NMR (300 MHz, DMSO-$d_6$) δ: 7.71-7.68 (m, 4H), 7.56-7.46 (m, 4H), 7.39 (t, 1H).

Example I-129: 5-((4'-Methyl-[1,1'-biphenyl]-4-yl)thio)-1H-1,2,3-triazole-4-carboxylic acid

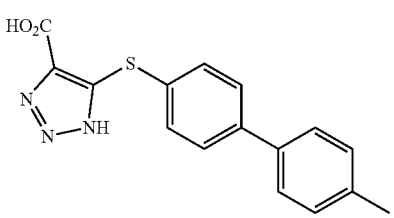

The title compound was prepared by the method described in Example I-001 using 4'-methyl-[1,1'-biphenyl]-4-thiol (149 mg, mmol, 1.10 equiv) as a reagent in Step 1 of Example I-001, to give 5-((4'-methyl-[1,1'-biphenyl]-4-yl)thio)-1H-1,2,3-triazole-4-carboxylic acid (99.5 mg, 47%) as an off-white solid. $^1$H-NMR (400 MHz, DMSO-$d_6$) δ: 7.65 (d, 2H), 7.56 (d, 2H), 7.50 (d, 2H), 7.27 (d, 2H) 2.33 (s, 3H).

Example I-146: 5-((4'-(Methylsulfonyl)-[1,1'-biphenyl]-4-yl)oxy)-1H-1,2,3-triazole-4-carboxylic acid

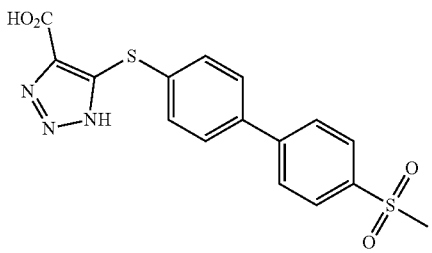 [SMILES: CS(=O)(=O)c1ccc(-c2ccc(Sc3[nH]nnc3C(=O)O)cc2)cc1]

The title compound was prepared by the method described in Example I-033 using 4'-(methylsulfonyl)-[1,1'-biphenyl]-4-ol (185 mg, 0.744 mmol, 1.10 equiv.) as a reagent in Step 1 of Example I-033, to give 5-((4'-(methylsulfonyl)-[1,1'-biphenyl]-4-yl)oxy)-1H-1,2,3-triazole-4-carboxylic acid (28.8 mg, 12%, 3-steps) as an off-white solid. $^1$H-NMR (400 MHz, DMSO-$d_6$) δ: 7.98 (d, 2H), 7.92 (d, 2H), 7.77 (d, 2H), 7.20 (d, 2H), 3.25 (s, 3H).

Example I-150: 5-([1,1'-Biphenyl]-4-yloxy)-1H-1,2,3-triazole-4-carboxylic acid

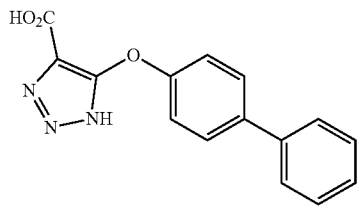 [SMILES: O=C(O)c1nn[nH]c1Oc1ccc(-c2ccccc2)cc1]

The title compound was prepared by the method described in Example I-033 using [1,1'-biphenyl]-4-ol (127 mg, 0.744 mmol, 1.10 equiv.) as a reagent in Step 1 of Example I-033, to give 5-([1,1'-biphenyl]-4-yloxy)-1H-1,2,3-triazole-4-carboxylic acid (I-150, 43.7 mg, 22%, 3-steps) as an off-white solid. $^1$H-NMR (400 MHz, DMSO-$d_6$) δ: 7.66 (m, 4H), 7.46 (t, 2H), 7.36 (t, 1H), 7.17 (d, 2H).

Example I-151: 5-((4'-Methyl-[1,1'-biphenyl]-4-yl)oxy)-1H-1,2,3-triazole-4-carboxylic acid

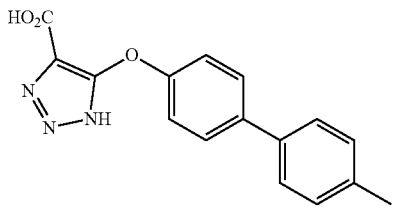 [SMILES: Cc1ccc(-c2ccc(Oc3[nH]nnc3C(=O)O)cc2)cc1]

The title compound was prepared by the method described in Example I-033 using 4'-methyl-[1,1'-biphenyl]-4-ol (137 mg, 0.744 mmol, 1.10 equiv.) as a reagent in Step 1 of Example I-033, to give 5-((4'-methyl-[1,1'-biphenyl]-4-yl)oxy)-1H-1,2,3-triazole-4-carboxylic acid (I-151, 27.9 mg, 14%, 3-steps) as an off-white solid. $^1$H-NMR (400 MHz, DMSO-$d_6$) δ: 7.52 (d, 2H), 7.41 (d, 2H), 7.19 (d, 4H), 2.35 (s, 3H).

Example I-152: 5-((4'-Chloro-[1,1'-biphenyl]-4-yl)oxy)-1H-1,2,3-triazole-4-carboxylic acid

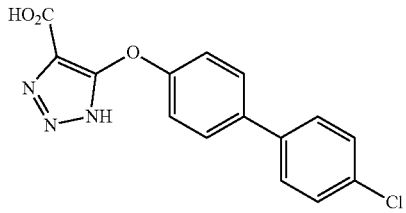 [SMILES: O=C(O)c1nn[nH]c1Oc1ccc(-c2ccc(Cl)cc2)cc1]

The title compound was prepared by the method described in Example I-033 using 4'-chloro-[1,1'-biphenyl]-4-ol (152 mg, 0.744 mmol, 1.10 equiv.) as a reagent in Step 1 of Example I-033, to give 5-((4'-chloro-[1,1'-biphenyl]-4-yl)oxy)-1H-1,2,3-triazole-4-carboxylic acid (42.7 mg, 20%, 3-steps) as an off-white solid. $^1$H-NMR (400 MHz, DMSO-$d_6$) δ: 7.68 (m, 4H), 7.50 (d, 2H), 7.15 (d, 2H).

Example I-153: 5-((4'-Methoxy-[1,1'-biphenyl]-4-yl)oxy)-1H-1,2,3-triazole-4-carboxylic acid

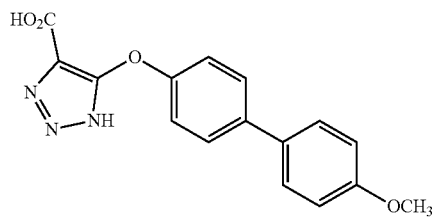 [SMILES: COc1ccc(-c2ccc(Oc3[nH]nnc3C(=O)O)cc2)cc1]

The title compound was prepared by the method described in Example I-033 using 4'-methoxy-[1,1'-biphenyl]-4-ol (149 mg, 0.744 mmol, 1.10 equiv.) as a reagent in Step 1 of Example I-033, to give 5-((4'-methoxy-[1,1'-biphenyl]-4-yl)oxy)-1H-1,2,3-triazole-4-carboxylic acid (I-153, 46.3 mg, 22%, 3-steps) as an off-white solid. H-NMR (400 MHz, DMSO-$d_6$) δ: 7.60 (m, 4H), 7.13 (d, 2H), 7.02 (d, 2H), 3.80 (s, 3H).

Example I-154: 5-((4'-Bromo-[1,1'-biphenyl]-4-yl)oxy)-1H-1,2,3-triazole-4-carboxylic acid

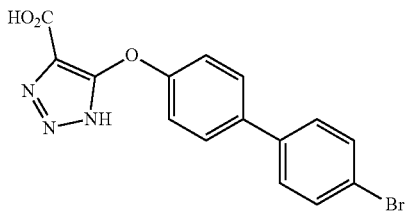

The title compound was prepared by the method described in Example I-033 using 4'-bromo-[1,1'-biphenyl]-4-ol (185 mg, 0.744 mmol, 1.10 equiv.) as a reagent in Step 1 of Example I-033, to give 5-((4'-bromo-[1,1'-biphenyl]-4-yl)oxy)-1H-1,2,3-triazole-4-carboxylic acid (I-154, 48.7 mg, 20%, 3-steps) as an off-white solid. $^1$H-NMR (400 MHz, DMSO-d$_6$) δ: 7.65 (m, 6H), 7.15 (d, 2H).

Example I-158: 5-((3'-Methoxy-[1,1'-biphenyl]-4-yl)oxy)-1H-1,2,3-triazole-4-carboxylic acid

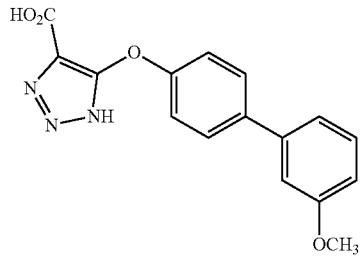 [SMILES: COc1cccc(-c2ccc(Oc3[nH]nnc3C(=O)O)cc2)c1]

The title compound was prepared by the method described in Example I-033 using 4'-methoxy-[1,1'-biphenyl]-4-ol (149 mg, 0.744 mmol, 1.10 equiv.) as a reagent in Step 1 of Example I-033, to give 5-((3'-methoxy-[1,1'-biphenyl]-4-yl)oxy)-1H-1,2,3-triazole-4-carboxylic acid (I-158, 54.6 mg, 26%, 3-steps) as an off-white solid. H-NMR (400 MHz, DMSO-d$_6$) δ: 7.56 (d, 2H), 7.37-7.23 (m, 3H), 7.14 (d, 1H), 7.08 (s, 1H), 6.88 (dd, 1H), 3.86 (s, 3H).

Example I-160: 5-((4'-Fluoro-[1,1'-biphenyl]-4-yl)oxy)-1H-1,2,3-triazole-4-carboxylic acid

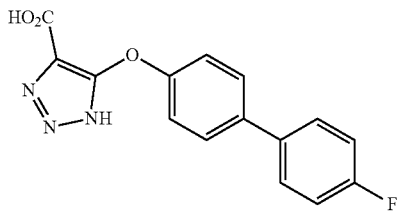 [SMILES: O=C(O)c1nn[nH]c1Oc1ccc(-c2ccc(F)cc2)cc1]

The title compound was prepared by the method described in Example I-033 using 4'-fluoro-[1,1'-biphenyl]-4-ol (140 mg, 0.744 mmol, 1.10 equiv.) as a reagent in Step 1 of Example I-033, to 5-((4'-fluoro-[1,1'-biphenyl]-4-yl)oxy)-1H-1,2,3-triazole-4-carboxylic acid (I-160, 32.3 mg, 16%, 3-steps) as an off-white solid. $^1$H-NMR (400 MHz, DMSO-d$_6$) δ: 7.66 (m, 4H), 7.28 (t, 2H), 7.15 (t, 2H).

Example I-171: 5-((3',4'-Dichloro-[1,1'-biphenyl]-4-yl)oxy)-1H-1,2,3-triazole-4-carboxylic acid

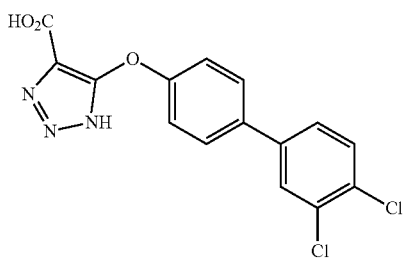 [SMILES: O=C(O)c1nn[nH]c1Oc1ccc(-c2ccc(Cl)c(Cl)c2)cc1]

The title compound was prepared by the method described in Example I-033 using 3',4'-dichloro-[1,1'-biphenyl]-4-ol (178 mg, 0.744 mmol, 1.10 equiv.) as a reagent in Step 1 of Example I-033, to give 5-((3',4'-dichloro-[1,1'-biphenyl]-4-yl)oxy)-1H-1,2,3-triazole-4-carboxylic acid (47 mg, 16%, 3-steps) as an off-white solid. $^1$H-NMR (400 MHz, DMSO-d$_6$) δ: 7.92 (s, 1H), 7.73-7.64 (m, 4H), 7.15 (d, 2H).

Example I-174: 5-((2'-Fluoro-[1,1'-biphenyl]-4-yl)oxy)-1H-1,2,3-triazole-4-carboxylic acid

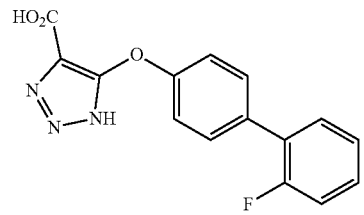 [SMILES: O=C(O)c1nn[nH]c1Oc1ccc(-c2ccccc2F)cc1]

The title compound was prepared by the method described in Example I-033 using 2'-fluoro-[1,1'-biphenyl]-4-ol (140 mg, 0.744 mmol, 1.10 equiv.) as a reagent in Step 1 of Example I-033, to give 5-((2'-fluoro-[1,1'-biphenyl]-4-yl)oxy)-1H-1,2,3-triazole-4-carboxylic acid (24.3 mg, 12%, 3-steps) as an off-white solid. $^1$H-NMR (400 MHz, DMSO-d$_6$) δ: 7.53 (m, 3H), 7.41 (m, 1H), 7.31 (m, 2H), 7.17 (d, 2H).

Example I-177: 5-(4-(Naphthalen-2-yl)phenoxy)-1H-1,2,3-triazole-4-carboxylic acid

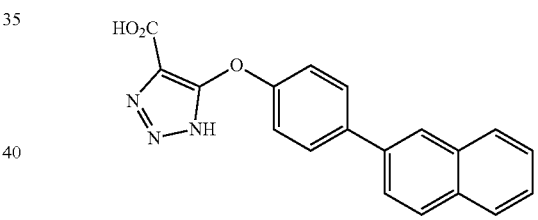

The title compound was prepared by the method described in Example I-033 using 4-(naphthalen-2-yl)phenol (164 mg, 0.744 mmol, 1.10 equiv.) as a reagent in Step 1 of Example I-033, to give 5-(4-(naphthalen-2-yl)phenoxy)-1H-1,2,3-triazole-4-carboxylic acid (24.6 mg, 11%, 3-steps) as an off-white solid. $^1$H-NMR (300 MHz, DMSO-d$_6$) δ: 8.21 (s, 1H), 7.97 (m, 3H), 7.83 (d, 3H), 7.52 (d, 2H), 7.21 (d, 2H).

Example I-178: 5-(3-(Naphthalen-2-yl)phenoxy)-1H-1,2,3-triazole-4-carboxylic acid

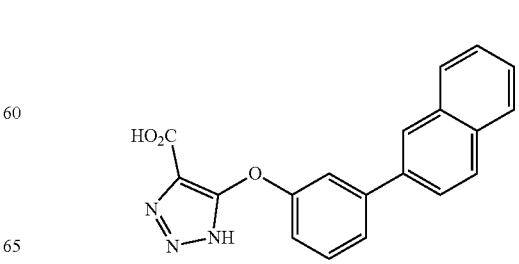

The title compound was prepared by the method described in Example I-033 using 3-(naphthalen-2-yl)phenol (164 mg, 0.744 mmol, 1.10 equiv.) as a reagent in Step 1 of Example I-033, to give 5-(3-(naphthalen-2-yl)phenoxy)-1H-1,2,3-triazole-4-carboxylic acid (I-178, 26.1 mg, 12%, 3-steps) as an off-white solid. ¹H-NMR (400 MHz, DMSO-d₆) δ: 8.21 (s, 1H), 7.99 (m, 3H), 7.83 (d, 3H), 7.54 (d, 2H), 7.21 (d, 2H).

Example I-249: 5-([1,1'-Biphenyl]-3-yloxy)-1H-1,2,3-triazole-4-carboxylic acid

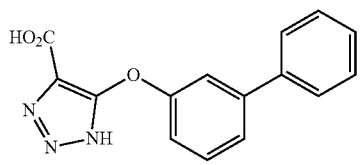 [SMILES: O=C(O)c1nn[nH]c1Oc1cccc(-c2ccccc2)c1]

The title compound was prepared by the method described in Example I-033 using [1,1'-biphenyl]-3-ol (127 mg, 0.744 mmol, 1.10 equiv.) as a reagent in Step 1 of Example I-033, to give 5-([1,1'-biphenyl]-3-yloxy)-1H-1,2,3-triazole-4-carboxylic acid (I-249, 53.2 mg, 28%, 3-steps) as an off-white solid. ¹H-NMR (300 MHz, DMSO-d₆) δ: 7.65 (m, 2H), 7.46 (m, 4H), 7.38 (m, 2H), 7.05 (m, 1H).

Example I-250: 5-((4'-Methoxy-[1,1'-biphenyl]-3-yl)oxy)-1H-1,2,3-triazole-4-carboxylic acid

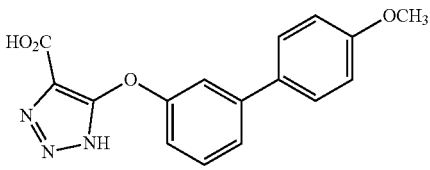 [SMILES: COc1ccc(-c2cccc(Oc3[nH]nnc3C(=O)O)c2)cc1]

The title compound was prepared by the method described in Example I-033 using (4'-methoxy-[1,1'-biphenyl]-3-ol (149 mg, 0.744 mmol, 1.10 equiv.) as a reagent in Step 1 of Example I-033, to give 5-((4'-methoxy-[1,1'-biphenyl]-3-yl)oxy)-1H-1,2,3-triazole-4-carboxylic acid (35.7 mg, 17%, 3-steps) as an off-white solid. ¹H-NMR (400 MHz, DMSO-d₆) δ: 7.59 (d, 2H), 7.40 (s, 2H), 7.31 (s, 1H), 7.00 (d, 3H), 3.79 (s, 3H).

Example I-251: 5-((4'-Methyl-[1,1'-biphenyl]-3-yl)oxy)-1H-1,2,3-triazole-4-carboxylic acid

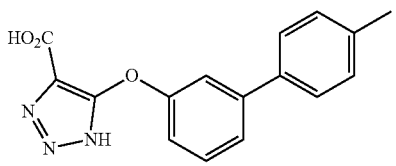 [SMILES: Cc1ccc(-c2cccc(Oc3[nH]nnc3C(=O)O)c2)cc1]

The title compound was prepared by the method described in Example I-033 using 4'-methyl-[1,1'-biphenyl]-3-ol (137 mg, 0.744 mmol, 1.10 equiv.) as a reagent in Step 1 of Example I-033, to give 5-((4'-methyl-[1,1'-biphenyl]-3-yl)oxy)-1H-1,2,3-triazole-4-carboxylic acid (43.8 mg, 22%, 3-steps) as an off-white solid. ¹H-NMR (400 MHz, DMSO-d₆) δ: 7.54 (d, 2H), 7.47-7.41 (m, 2H), 7.36-7.33 (m, 1H), 7.27 (d, 2H), 7.01 (m, 1H), 2.33 (s, 3H).

Example I-252: 5-((4'-Chloro-[1,1'-biphenyl]-3-yl)oxy)-1H-1,2,3-triazole-4-carboxylic acid

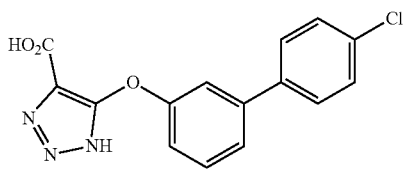 [SMILES: O=C(O)c1nn[nH]c1Oc1cccc(-c2ccc(Cl)cc2)c1]

The title compound was prepared by the method described in Example I-033 using 4'-chloro-[1,1'-biphenyl]-3-ol (152 mg, 0.744 mmol, 1.10 equiv.) as a reagent in Step 1 of Example I-033, to give 5-((4'-chloro-[1,1'-biphenyl]-3-yl)oxy)-1H-1,2,3-triazole-4-carboxylic acid (40.5 mg, 19%, 3-steps) as an off-white solid. ¹H-NMR (400 MHz, DMSO-d₆) δ: 7.69 (d, 2H), 7.50 (d, 2H), 7.46 (d, 2H), 7.39 (s, 1H), 7.06 (t, 1H).

Example I-253: 5-((3'-Chloro-[1,1'-biphenyl]-3-yl)oxy)-1H-1,2,3-triazole-4-carboxylic acid

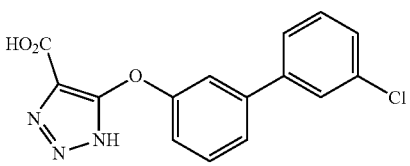 [SMILES: O=C(O)c1nn[nH]c1Oc1cccc(-c2cccc(Cl)c2)c1]

The title compound was prepared by the method described in Example I-033 using 3'-chloro-[1,1'-biphenyl]-3-ol (152 mg, 0.744 mmol, 1.10 equiv.) as a reagent in Step 1 of Example I-033, to give 5-((3'-chloro-[1,1'-biphenyl]-3-yl)oxy)-1H-1,2,3-triazole-4-carboxylic acid (38.2 mg, 18%, 3-steps) as an off-white solid. ¹H-NMR (400 MHz, DMSO-d₆) δ: 7.72 (s, 1H), 7.63 (d, 1H), 7.47 (m, 5H), 7.08 (d, 1H).

Example I-254: 5-((2'-Fluoro-[1,1'-biphenyl]-3-yl)oxy)-1H-1,2,3-triazole-4-carboxylic acid

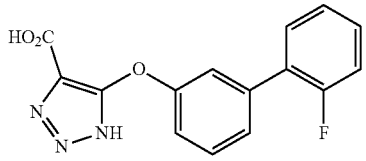 [SMILES: O=C(O)c1nn[nH]c1Oc1cccc(-c2ccccc2F)c1]

The title compound was prepared by the method described in Example I-033 using 2'-fluoro-[1,1'-biphenyl]-3-ol) (140 mg, 0.744 mmol, 1.10 equiv.) as a reagent in Step 1 of Example I-033, to give 5-((2'-fluoro-[1,1'-biphenyl]-3-yl)oxy)-1H-1,2,3-triazole-4-carboxylic acid (22.2 mg, 11%, 3-steps) as an off-white solid. ¹H-NMR (400 MHz, DMSO-d₆) δ: 7.54-7.40 (m, 3H), 7.34-7.25 (m, 4H), 7.11 (d, 1H).

Example I-255: 5-((3',4'-Dichloro-[1,1'-biphenyl]-3-yl)oxy)-1H-1,2,3-triazole-4-carboxylic acid

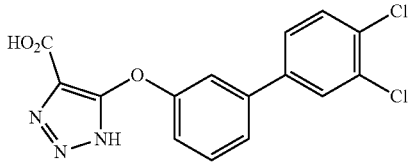 [SMILES: O=C(O)c1nn[nH]c1Oc1cccc(-c2ccc(Cl)c(Cl)c2)c1]

The title compound was prepared by the method described in Example I-033 using 3',4'-dichloro-[1,1'-biphenyl]-3-ol (178 mg, 0.744 mmol, 1.10 equiv.) as a reagent in Step 1 of Example I-033, to give 5-((3',4'-dichloro-[1,1'-biphenyl]-3-yl)oxy)-1H-1,2,3-triazole-4-carboxylic acid (42.2 mg, 14%, 3-steps) as an off-white solid. $^1$H-NMR (400 MHz, DMSO-$d_6$) δ: 7.95 (s, 1H), 7.70 (m, 2H), 7.49 (m, 3H), 7.10 (d, 1H).

Example I-256: 5-((3'-Cyano-[1,1'-biphenyl]-4-yl)oxy)-1H-1,2,3-triazole-4-carboxylic acid

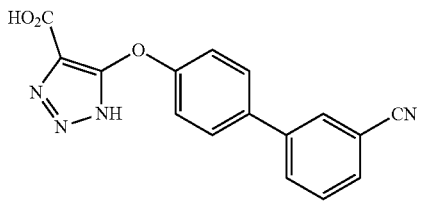 [SMILES: N#Cc1cccc(-c2ccc(Oc3[nH]nnc3C(=O)O)cc2)c1]

The title compound was prepared by the method described in Example I-033 using 3'-cyano-[1,1'-biphenyl]-4-ol (145 mg, 0.744 mmol, 1.10 equiv.) as a reagent in Step 1 of Example I-033, to give 5-((3'-cyano-[1,1'-biphenyl]-4-yl)oxy)-1H-1,2,3-triazole-4-carboxylic acid (18.6 mg, 9%, 3-steps) as an off-white solid. $^1$H-NMR (400 MHz, DMSO-$d_6$) δ: 8.14-7.99 (m, 2H), 7.79-7.65 (m, 4H), 7.16 (m, 2H).

Example I-257: 5-((4'-(Methylsulfonyl)-[1,1'-biphenyl]-3-yl)oxy)-1H-1,2,3-triazole-4-carboxylic acid

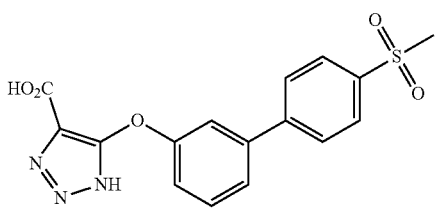 [SMILES: CS(=O)(=O)c1ccc(-c2cccc(Oc3[nH]nnc3C(=O)O)c2)cc1]

The title compound was prepared by the method described in Example I-033 using 4'-(methylsulfonyl)-[1,1'-biphenyl]-3-ol (185 mg, 0.744 mmol, 1.10 equiv.) as a reagent in Step 1 of Example I-033, to give 5-((4'-(methylsulfonyl)-[1,1'-biphenyl]-3-yl)oxy)-1H-1,2,3-triazole-4-carboxylic acid (14.5 mg, 6%, 3-steps) as an off-white solid. $^1$H-NMR (400 MHz, DMSO-$d_6$) δ: 8.00-7.93 (m, 4H), 7.57-7.49 (m, 3H), 7.14 (d, 1H), 3.25 (s, 3H).

Example I-258: 5-(4-Chloro-3-methylphenoxy)-1H-1,2,3-triazole-4-carboxylic acid

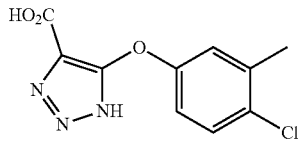 [SMILES: Cc1cc(Oc2[nH]nnc2C(=O)O)ccc1Cl]

The title compound was prepared by the method described in Example I-033 using 4-chloro-3-methylphenol (106 mg, 0.744 mmol, 1.10 equiv.) as a reagent in Step 1 of Example I-033, to give 5-(4-chloro-3-methylphenoxy)-1H-1,2,3-triazole-4-carboxylic acid (48.0 mg, 28%, 3-steps) as an off-white solid. $^1$H-NMR (400 MHz, DMSO-$d_6$) δ: 7.38 (d, 1H), 7.10 (s, 1H), 6.92 (d, 1H), 2.29 (s, 3H).

Example I-259: 5-(3-(Pyridin-3-yl)phenoxy)-1H-1,2,3-triazole-4-carboxylic acid

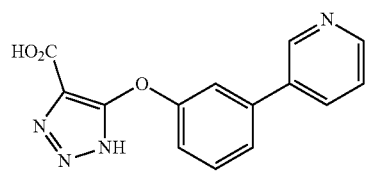 [SMILES: O=C(O)c1nn[nH]c1Oc1cccc(-c2cccnc2)c1]

The title compound was prepared by the method described in Example I-033 using 3-(pyridin-3-yl)phenol (103 mg, 0.744 mmol, 1.10 equiv.) as a reagent in Step 1 of Example I-033, to give 5-(3-(pyridin-3-yl)phenoxy)-1H-1,2,3-triazole-4-carboxylic acid (26.7 mg, 14%, 3-steps) as an off-white solid. $^1$H-NMR (400 MHz, DMSO-$d_6$) δ: 8.89 (s, 1H), 8.58 (d, 1H), 8.08 (d, 1H), 7.51 (m, 4H), 7.10 (d, 1H).

Example I-260: 5-(3-(Pyridin-4-yl)phenoxy)-1H-1,2,3-triazole-4-carboxylic acid

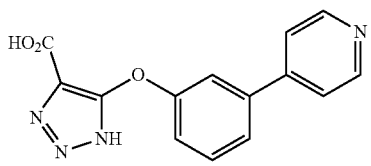 [SMILES: O=C(O)c1nn[nH]c1Oc1cccc(-c2ccncc2)c1]

The title compound was prepared by the method described in Example I-033 using 3-(pyridin-4-yl)phenol (127 mg, 0.744 mmol, 1.10 equiv.) as a reagent in Step 1 of Example I-033, to give 5-(3-(pyridin-4-yl)phenoxy)-1H-1,2,3-triazole-4-carboxylic acid (17.2 mg, 9%, 3-steps) as an off-white solid. $^1$H-NMR (300 MHz, DMSO-$d_6$) δ: 8.78 (d, 2H), 8.05 (d, 2H), 7.69-7.57 (m, 3H), 7.25 (m, 1H).

Example I-261: 5-(4-(Pyridin-2-yl)phenoxy)-1H-1,2,3-triazole-4-carboxylic acid

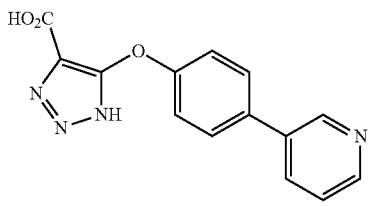 [SMILES: O=C(O)c1nn[nH]c1Oc1ccc(-c2cccnc2)cc1]

The title compound was prepared by the method described in Example I-033 using 4-(pyridin-2-yl)phenol (127 mg, 0.744 mmol, 1.10 equiv.) as a reagent in Step 1 of Example I-033, to give 5-(4-(pyridin-2-yl)phenoxy)-1H-1,2,3-triazole-4-carboxylic acid (36.2 mg, 19%, 3-steps) as an off-white solid. $^1$H-NMR (400 MHz, DMSO-$d_6$) δ: 8.61 (d, 1H), 7.92 (d, 2H), 7.77 (m, 2H), 7.22 (m, 1H), 6.88 (d, 2H).

Example I-262: 5-((5-Phenylpyridin-3-yl)oxy)-1H-1,2,3-triazole-4-carboxylic acid

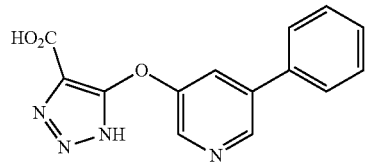 [SMILES: O=C(O)c1nn[nH]c1Oc1cncc(-c2ccccc2)c1]

The title compound was prepared by the method described in Example I-033 using 5-phenylpyridin-3-ol (127 mg, 0.744 mmol, 1.10 equiv.) as a reagent in Step 1 of Example I-033, to give 5-((5-phenylpyridin-3-yl)oxy)-1H-1,2,3-triazole-4-carboxylic acid (32.3 mg, 17%, 3-steps) as an off-white solid. $^1$H-NMR (400 MHz, DMSO-$d_6$) δ: 8.56 (s, 1H), 8.05 (d, 2H), 7.99 (d, 1H), 7.62 (dd, 1H), 7.49 (t, 2H), 7.42 (t, 1H).

Example I-263: 5-((6-Phenylpyridin-3-yl)oxy)-1H-1,2,3-triazole-4-carboxylic acid

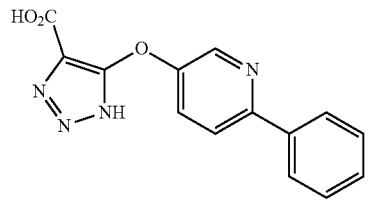 [SMILES: O=C(O)c1nn[nH]c1Oc1ccc(-c2ccccc2)nc1]

The title compound was prepared by the method described in Example I-033 using 6-phenylpyridin-3-ol (127 mg, 0.744 mmol, 1.10 equiv.) as a reagent in Step 1 of Example I-033, to give 5-((6-phenylpyridin-3-yl)oxy)-1H-1,2,3-triazole-4-carboxylic acid (28.5 mg, 15%, 3-steps) as an off-white solid. $^1$H-NMR (400 MHz, DMSO-$d_6$) δ: 8.74 (s, 1H), 8.45 (d, 1H), 7.89 (s, 1H), 7.74 (d, 2H), 7.50 (t, 2H), 7.45 (m, 1H).

Example I-264: 5-([3,3'-Bipyridin]-5-yloxy)-1H-1,2,3-triazole-4-carboxylic acid

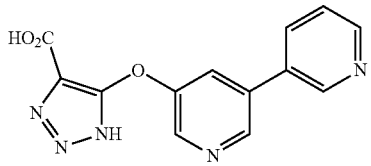 [SMILES: O=C(O)c1nn[nH]c1Oc1cncc(-c2cccnc2)c1]

The title compound was prepared by the method described in Example I-033 using [3,3'-bipyridin]-5-ol (128 mg, 0.744 mmol, 1.10 equiv.) as a reagent in Step 1 of Example I-033, to give 5-([3,3'-bipyridin]-5-yloxy)-1H-1,2,3-triazole-4-carboxylic acid (23.0 mg, 12%, 3-steps) as an off-white solid. $^1$H-NMR (400 MHz, DMSO-$d_6$) δ: 8.96 (s, 1H), 8.78 (s, 1H), 8.62 (d, 1H), 8.50 (s, 1H), 8.17 (d, 1H), 8.00 (s, 1H), 7.52 (q, 1H).

Example I-265: 5-(4-Cyclopentylphenoxy)-1H-1,2,3-triazole-4-carboxylic acid

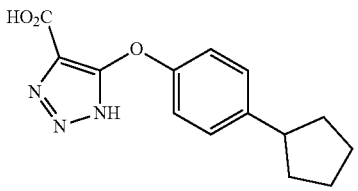 [SMILES: O=C(O)c1nn[nH]c1Oc1ccc(C2CCCC2)cc1]

The title compound was prepared by the method described in Example I-033 using 4-cyclopentylphenol (121 mg, 0.744 mmol, 1.10 equiv.) as a reagent in Step 1 of Example I-033, to give 5-(4-cyclopentylphenoxy)-1H-1,2,3-triazole-4-carboxylic acid (61.0 mg, 33%, 3-steps) as an off-white solid. $^1$H-NMR (400 MHz, DMSO-$d_6$) δ: 7.23 (d, 2H), 6.98 (d, 2H), 2.95 (m, 1H), 2.03-1.96 (m, 2H), 1.81-1.71 (m, 2H), 1.68-159 (m, 2H), 1.54-1.45 (m, 2H).

Example I-266: 5-(4-Cyclohexylphenoxy)-1H-1,2,3-triazole-4-carboxylic acid

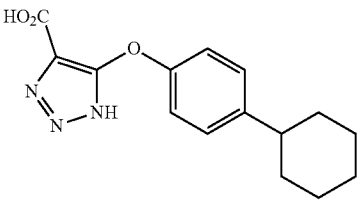 [SMILES: O=C(O)c1nn[nH]c1Oc1ccc(C2CCCCC2)cc1]

The title compound was prepared by the method described in Example I-033 using 4-cyclohexylphenol (131 mg, 0.744 mmol, 1.10 equiv.) as a reagent in Step 1 of Example I-033, to give 5-(4-cyclohexylphenoxy)-1H-1,2,3-triazole-4-carboxylic acid (74.0 mg, 39%, 3-steps) as an off-white solid. $^1$H-NMR (300 MHz, DMSO-$d_6$) δ: 7.20 (d, 2H), 6.97 (d, 2H), 2.47 (m, 1H), 1.79-1.67 (m, 5H), 1.43-1.23 (m, 5H).

Example I-267: 5-(3-Cyclopentylphenoxy)-1H-1,2,3-triazole-4-carboxylic acid

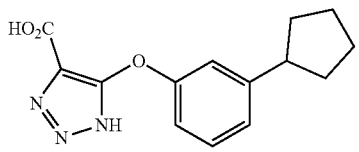 [SMILES: O=C(O)c1nn[nH]c1Oc1cccc(C2CCCC2)c1]

The title compound was prepared by the method described in Example I-033 using 3-cyclopentylphenol (121 mg, 0.744 mmol, 1.10 equiv.) as a reagent in Step 1 of Example I-033, to give 5-(3-cyclopentylphenoxy)-1H-1,2,3-triazole-4-carboxylic acid (70.2 mg, 38%, 3-steps) as an off-white solid. $^1$H-NMR (300 MHz, DMSO-$d_6$) δ: 7.27 (m, 1H), 7.03 (d, 1H), 6.96 (t, 1H), 6.85 (m, 1H), 2.96 (m, 1H), 2.03-1.96 (m, 2H), 1.79-1.69 (m, 2H), 1.68-1.57 (m, 2H), 1.56-1.45 (m, 2H).

Example I-268: 5-(3-Cyclohexylphenoxy)-1H-1,2,3-triazole-4-carboxylic acid

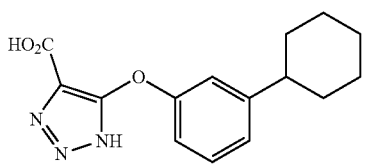 [SMILES: O=C(O)c1nn[nH]c1Oc1cccc(C2CCCCC2)c1]

The title compound was prepared by the method described in Example I-033 using 3-cyclohexylphenol (131 mg, 0.744 mmol, 1.10 equiv.) as a reagent in Step 1 of Example I-033, to give 5-(3-cyclohexylphenoxy)-1H-1,2,3-triazole-4-carboxylic acid (71.9 mg, 37%, 3-steps) as an off-white solid. $^1$H-NMR (400 MHz, DMSO-$d_6$) δ: 7.26 (t, 1H), 7.00 (d, 1H), 6.93 (s, 1H), 6.84 (d, 1H), 2.50 (m, 1H), 1.78-1.66 (m, 5H), 1.38-1.23 (m, 5H).

Example I-269: 5-(3-Pentafluorosulfanylphenoxy)-1H-1,2,3-triazole-4-carboxylic acid

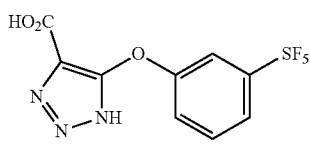

The title compound was prepared by the method described in Example I-033 using 3-pentafluorosulfanylphenol (164 mg, 0.744 mmol, 1.10 equiv.) as a reagent in Step 1 of Example I-033, to give 5-(3-pentafluorosulfanylphenoxy)-1H-1,2,3-triazole-4-carboxylic acid (38.2 mg, 14%, 3-steps) as an off-white solid. $^1$H-NMR (400 MHz, DMSO-$d_6$) δ: 7.69 (d, 2H), 7.63 (t, 1H), 7.40 (d, 1H).

Example I-270: 5-((3',4'-Dimethoxy-[1,1'-biphenyl]-4-yl)oxy)-1H-1,2,3-triazole-4-carboxylic acid

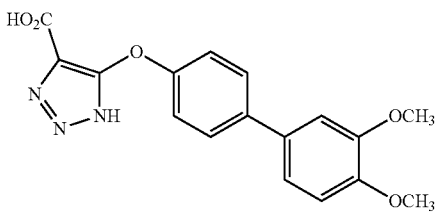 [SMILES: COc1ccc(-c2ccc(Oc3[nH]nnc3C(=O)O)cc2)cc1OC]

The title compound was prepared by the method described in Example I-033 using 3',4'-dimethoxy-[1,1'-biphenyl]-4-ol (171 mg, 0.744 mmol, 1.10 equiv.) as a reagent in Step 1 of Example I-033, to give 5-((3',4'-dimethoxy-[1,1'-biphenyl]-4-yl)oxy)-1H-1,2,3-triazole-4-carboxylic acid (36.9 mg, 16%, 3-steps) as an off-white solid. $^1$H-NMR (400 MHz, DMSO-$d_6$) δ: 7.61 (d, 2H), 7.18-7.08 (m, 4H), 7.01 (d, 2H), 3.82 (s, 3H), 3.77 (s, 3H).

Example I-271: 5-((4'-Fluoro-3'-methoxy-[1,1'-biphenyl]-4-yl)oxy)-1H-1,2,3-triazole-4-carboxylic acid

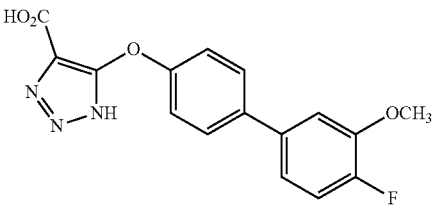 [SMILES: COc1cc(-c2ccc(Oc3[nH]nnc3C(=O)O)cc2)ccc1F]

The title compound was prepared by the method described in Example I-033 using 4'-fluoro-3'-methoxy-[1,1'-biphenyl]-4-ol (162 mg, 0.744 mmol, 1.10 equiv.) as a reagent in Step 1 of Example I-033, to give 5-((4'-fluoro-3'-methoxy-[1,1'-biphenyl]-4-yl)oxy)-1H-1,2,3-triazole-4-carboxylic acid (28.9 mg, 13%, 3-steps) as a light-yellow solid. H-NMR (400 MHz, DMSO-$d_6$) δ: 7.67 (d, 2H), 7.37 (d, 1H), 7.27 (t, 1H), 7.15 (m, 3H), 3.92 (s, 3H).

Example I-272: 5-(4-(Pentan-3-yl)phenoxy)-1H-1,2,3-triazole-4-carboxylic acid Step 1—Ethyl 1-(4-methoxybenzyl)-5-(4-(pentan-3-yl)phenoxy)-1H-1,2,3-triazole-4-carboxylate

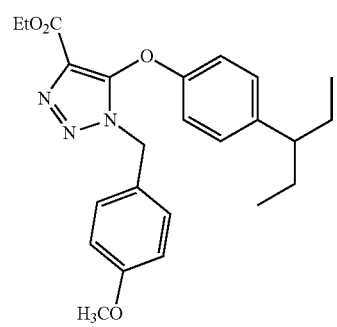 [SMILES: CCOC(=O)c1nnn(Cc2ccc(OC)cc2)c1Oc1ccc(C(CC)CC)cc1]

A 10-mL round bottom flask with a stir bar were charged with ethyl 5-(4-bromophenoxy)-1-(4-methoxybenzyl)-1H-1,2,3-triazole-4-carboxylate (32, 250.0 mg, 0.58 mmol, 1.00 equiv.) and Pd-PEPPSI-IHept$^{Cl}$ (12.0 mg, 0.012 mmol, 2 mol %), sealed with a rubber septum and backfilled with argon three times. Toluene (2 mL) was added followed by the dropwise addition of 3-pentylzinc bromide (0.62 mL, 1.40 M, 0.87 mmol, 1.50 equiv.) and the reaction flask was stirred in an oil-bath at 40° C. for 18 hours. The mixture was cooled to room temperature and quenched with water (2 mL). Extracted with Ethyl acetate (3×50 mL), and the combined extracts were washed with water (2×25 mL) and brine (25 mL), dried with anhydrous MgSO4, filtered and the solvent removed in vacuo. Flash column chromatography gave ethyl 1-(4-methoxybenzyl)-5-(4-(pentan-3-yl)phenoxy)-1H-1,2,3-triazole-4-carboxylate (171 mg, 70%) as a yellow oil. $^1$H-NMR (300 MHz, CDCl$_3$) δ: 7.21 (d, 2H), 7.03 (d, 2H), 6.76 (d, 2H), 6.68 (d, 2H), 5.36 (s, 2H), 4.14 (q, 2H), 2.27 (m, 1H), 1.68 (m, 2H), 1.48 (m, 2H), 1.06 (t, 3H), 0.74 (t, 3H).

Step 2—Ethyl 5-(4-chlorophenoxy)-1H-1,2,3-triazole-4-carboxylate

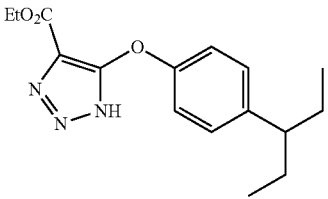

A vial (8 mL) containing a magnetic stir bar was charged with ethyl 1-(4-methoxybenzyl)-5-(4-(pentan-3-yl)phenoxy)-1H-1,2,3-triazole-4-carboxylate (170 mg, 0.402 mmol) and 3 mL of trifluoroacetic acid. The vial was sealed with a screw cap, placed in a pre-heated oil bath at 70° C. and stirred for 3 h. The reaction mixture was then cooled to room temperature, diluted with ethyl acetate (150 mL), washed with saturated aq. sodium bicarbonate (2×50 mL), water (50 mL), brine (50 mL), and dried with anhydrous MgSO4, filtered and the solvent removed in vacuo. Flash chromatography on silica gel gave ethyl 5-(4-(pentan-3-yl)phenoxy)-1H-1,2,3-triazole-4-carboxylate (94 mg, 77%) as an off-white solid. $^1$H-NMR (400 MHz, CDCl$_3$) δ: 7.10 (s, 4H), 4.39 (q, 2H), 2.32 (quint, 1H), 1.68 (q, 2H), 1.53 (q, 2H), 1.32 (t, 3H), 0.78 (t, 3H).

Step 3—5-(4-(Pentan-3-yl)phenoxy)-1H-1,2,3-triazole-4-carboxylic acid (I-272)

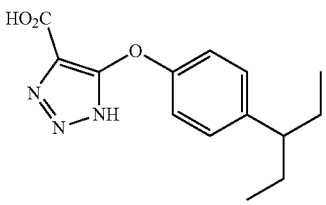 [SMILES: CCC(CC)c1ccc(Oc2[nH]nnc2C(=O)O)cc1]

A vial (8 mL) containing a magnetic stir bar was charged with the ethyl 5-(4-(pentan-3-yl)phenoxy)-1H-1,2,3-triazole-4-carboxylate (90 mg, 0.297 mmol) and 3 mL of 1 N KOH. The vial was then sealed with a screw cap and stirred at room temperature for 18 hours. The pH was adjusted to between 2 and 3 using 0.1 N HCl and the contents of the vial were extracted with ethyl acetate (3×50 mL). The organic layers were combined, dried over anhydrous MgSO$_4$, filtered and concentrated in vacuo. The crude product was purified by trituration in diethyl ether/pentane to yield 5-(4-(pentan-3-yl)phenoxy)-1H-1,2,3-triazole-4-carboxylic acid as a white solid (I-272, 65 mg, 79%). $^1$H-NMR (300 MHz, DMSO-d$_6$) δ: 7.15 (d, 2H), 7.01 (d, 2H), 2.30 (m, 1H), 1.64 (q, 2H), 1.47 (q, 2H), 0.75 (t, 6H).

Example I-273: 5-(4-(Pentan-2-yl)phenoxy)-1H-1,2,3-triazole-4-carboxylic acid

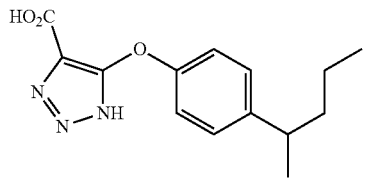 [SMILES: CCCC(C)c1ccc(Oc2[nH]nnc2C(=O)O)cc1]

The title compound was prepared by the method described in Example I-272 using 2-pentylzinc bromide (0.62 mL, 1.40 M, 0.87 mmol, 1.50 equiv.) and 5-(4-bromophenoxy)-1-(4-methoxybenzyl)-1H-1,2,3-triazole-4-carboxylate (250 mg, 0.58 mmol, 1.00 equiv.) as reagents in Step 1 of Example I-272, to give 5-(4-methoxyphenoxy)-1H-1,2,3-triazole-4-carboxylic acid (60.4 mg, 39%, 3-steps) as an off-white solid. $^1$H-NMR (400 MHz, DMSO-d$_6$) δ: 7.17 (d, 2H), 7.08 (d, 2H), 2.69 (m, 1H), 1.47 (m, 2H), 1.19-1.09 (m, 5H), 0.84 (t, 3H).

Example I-274: 5-(4-Isopropylphenoxy)-1H-1,2,3-triazole-4-carboxylic acid

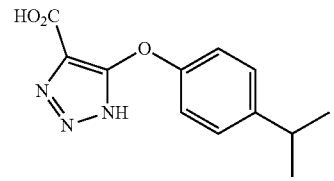 [SMILES: CC(C)c1ccc(Oc2[nH]nnc2C(=O)O)cc1]

The title compound was prepared by the method described in Example I-272 using isopropylzinc bromide (0.80 mL, 0.87 mmol, 1.50 equiv.) and 5-(4-bromophenoxy)-1-(4-methoxybenzyl)-1H-1,2,3-triazole-4-carboxylate (250 mg, 0.58 mmol, 1.00 equiv.) as reagents in Step 1 of Example I-272, to give 5-(4-methoxyphenoxy)-1H-1,2,3-triazole-4-carboxylic acid (48.4 mg, 29%, 3-steps) as an off-white solid. $^1$H-NMR (400 MHz, DMSO-d$_6$) δ: 7.23 (d, 2H), 6.99 (d, 2H), 2.88 (quint, 1H), 1.19 (d, 6H).

Example I-275: 5-(4-Cyclobutylphenoxy)-1H-1,2,3-triazole-4-carboxylic acid

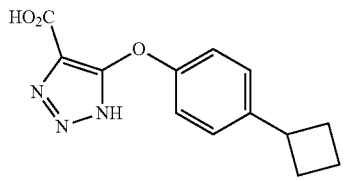 [SMILES: O=C(O)c1nn[nH]c1Oc1ccc(C2CCC2)cc1]

The title compound was prepared by the method described in Example I-272 using cyclobutylzinc bromide (1.20 mL, 0.70 M, 0.87 mmol, 1.50 equiv.) and 5-(4-bromophenoxy)-1-(4-methoxybenzyl)-1H-1,2,3-triazole-4-carboxylate (250 mg, 0.58 mmol, 1.00 equiv.) as reagents in Step 1 of Example I-272, to give 5-(4-methoxyphenoxy)-1H-1,2,3-triazole-4-carboxylic acid (21.0 mg, 12%, 3-steps) as an off-white solid. $^{1}$H-NMR (400 MHz, DMSO-$d_6$) δ: 7.18 (d, 2H), 6.96 (d, 2H), 2.29 (m, 2H), 2.10-1.90 (m, 3H), 1.80 (m, 1H), 1.60 (m, 1H).

Example I-276: 5-(3-(Pentan-3-yl)phenoxy)-1H-1,2,3-triazole-4-carboxylic acid

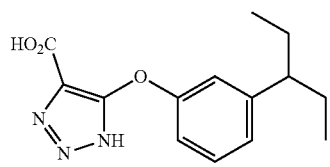 [SMILES: CCC(CC)c1cccc(Oc2[nH]nnc2C(=O)O)c1]

The title compound was prepared by the method described in Example I-272 using 3-pentylzinc bromide (0.62 mL, 1.40 M, 0.868 mmol, 1.50 equiv.) and 5-(3-bromophenoxy)-1-(4-methoxybenzyl)-1H-1,2,3-triazole-4-carboxylate (250 mg, 0.57 mmol, 1.00 equiv.) as reagents in Step 1 of Example I-272, to give 5-(4-methoxyphenoxy)-1H-1,2,3-triazole-4-carboxylic acid (64.0 mg, 41%, 3-steps) as an off-white solid. $^{1}$H-NMR (400 MHz, DMSO-$d_6$) δ: 7.27 (t, 1H), 6.94 (m, 1H), 6.85 (m, 2H), 2.30 (m, 1H), 1.66-1.59 (m, 2H), 1.48 (m, 2H), 0.72 (t, 6H).

Example I-277: 5-(3-(Pentan-2-yl)phenoxy)-1H-1,2,3-triazole-4-carboxylic acid

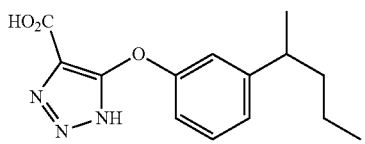 [SMILES: CCCC(C)c1cccc(Oc2[nH]nnc2C(=O)O)c1]

The title compound was prepared by the method described in Example I-272 using 2-pentylzinc bromide (0.62 mL, 1.40 M, 0.868 mmol, 1.50 equiv.) and 5-(3-bromophenoxy)-1-(4-methoxybenzyl)-1H-1,2,3-triazole-4-carboxylate (250 mg, 0.57 mmol, 1.00 equiv.) as reagents in Step 1 of Example I-272, to give 5-(4-methoxyphenoxy)-1H-1,2,3-triazole-4-carboxylic acid (56 mg, 36%, 3-steps) as an off-white solid. $^{1}$H-NMR (400 MHz, DMSO-$d_6$) δ: 7.26 (t, 1H), 6.99 (d, 1H), 6.85 (s, 1H), 6.84 (d, 1H), 2.69 (m, 1H), 1.48 (m, 2H), 1.20-1.09 (m, 5H), 0.83 (t, 3H).

Example I-278: 5-(3-Isopropylphenoxy)-1H-1,2,3-triazole-4-carboxylic acid

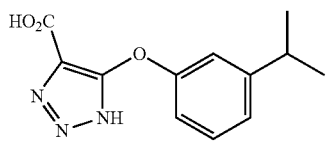 [SMILES: CC(C)c1cccc(Oc2[nH]nnc2C(=O)O)c1]

The title compound was prepared by the method described in Example I-272 using isopropylzinc bromide (0.80 mL, 0.87 mmol, 1.50 equiv.) and 5-(3-bromophenoxy)-1-(4-methoxybenzyl)-1H-1,2,3-triazole-4-carboxylate (250 mg, 0.58 mmol, 1.00 equiv) as reagents in Step 1 of Example I-272, to give 5-(4-methoxyphenoxy)-1H-1,2,3-triazole-4-carboxylic acid (36.8 mg, 22%, 3-steps) as an off-white solid. $^{1}$H-NMR (400 MHz, DMSO-$d_6$) δ: 7.25 (m, 1H), 6.97 (m, 2H), 6.83 (s, 1H), 2.85 (m, 1H), 1.19 (t, 6H).

Example I-279: 5-(3-Cyclobutylphenoxy)-1H-1,2,3-triazole-4-carboxylic acid

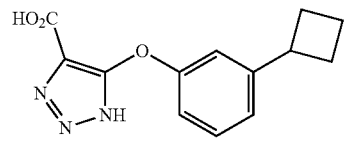 [SMILES: O=C(O)c1nn[nH]c1Oc1cccc(C2CCC2)c1]

The title compound was prepared by the method described in Example I-272 using cyclobutylzinc bromide (1.20 mL, 0.70 M, 0.87 mmol, 1.50 equiv.) and 5-(3-bromophenoxy)-1-(4-methoxybenzyl)-1H-1,2,3-triazole-4-carboxylate (250 mg, 0.58 mmol, 1.0 equiv.) as reagents in Step 1 of Example I-272, to give 5-(4-methoxyphenoxy)-1H-1,2,3-triazole-4-carboxylic acid (19.3 mg, 11%, 3-steps) as an off-white solid. $^{1}$H-NMR (400 MHz, DMSO-$d_6$) δ: 7.23 (t, 1H), 6.87 (m, 3H), 2.51 (m, 1H), 2.30 (m, 2H), 1.82 (m, 2H), 1.72 (m, 2H).

Example I-280: 5-(3-(Azepan-1-yl)phenoxy)-1H-1,2,3-triazole-4-carboxylic acid Step 1—Ethyl 5-(3-bromophenoxy)-1-(4-methoxybenzyl)-1H-1,2,3-triazole-4-carboxylate

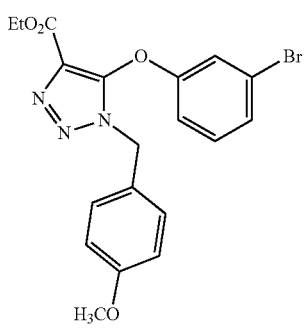 [SMILES: CCOC(=O)c1nnn(Cc2ccc(OC)cc2)c1Oc1cccc(Br)c1]

A 25 mL round bottom flask with a stir bar was charged with NaH (50%, 72.0 mg, 1.49 mmol, 1.10 equiv.), sealed with a rubber septum and backfilled with argon three times. The 3-bromophenol (258 mg, 1.49 mmol, 1.10 equiv.) was dissolved in anhydrous DMF (6 mL) was added dropwise at room temperature. Ethyl 5-chloro-1-(4-methoxybenzyl)-1H-1,2,3-triazole-4-carboxylate (400 mg, 1.35 mmol, 1.00 equiv.) dissolved in anhydrous DMF (8 mL) was added dropwise and the reaction flask was stirred in an oil-bath at 80° C. for 18 hours. The mixture was cooled to room temperature and quenched with water (5 mL). Extracted with EtOAc (3×100 mL), and the combined extracts were washed with water (5×50 mL), brine (50 mL) dried with anhydrous MgSO$_4$, filtered and the solvent removed in vacuo. Flash column chromatograph gave ethyl 5-(3-bromophenoxy)-1-(4-methoxybenzyl)-1H-1,2,3-triazole-4-carboxylate (396 mg, 68%) as a yellow oil. $^1$H-NMR (400 MHz, CDCl$_3$) δ: 7.22-7.12 (m, 3H), 7.10 (t, 1H), 6.76 (d, 3H), 6.68 (d, 1H), 5.37 (s, 2H), 4.19 (q, 2H), 3.72 (s, 3H), 1.11 (t, 3H).

Step 2—Ethyl 5-(3-(azepan-1-yl)phenoxy)-1-(4-methoxybenzyl)-1H-1,2,3-triazole-4-carboxylate

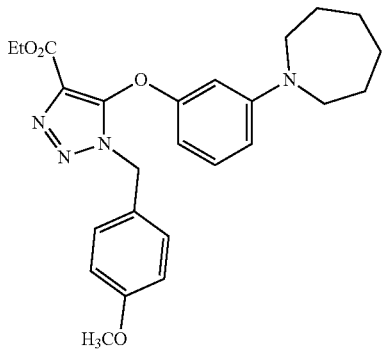 [SMILES: CCOC(=O)c1nnn(Cc2ccc(OC)cc2)c1Oc1cccc(N2CCCCCC2)c1]

A 10-mL round bottom flask with a stir bar was charged with Cs$_2$CO$_3$ (880 mg, 2.70 mmol, 3.00 equiv.), Pd-PEPPSI-IPent$^{Cl}$ (30 mg, 0.04 mmol, 0.04 equiv.) and 5-(3-bromophenoxy)-1-(4-methoxybenzyl)-1H-1,2,3-triazole-4-carboxylate (389 mg, 0.90 mmol, 1.00 equiv.), sealed with a rubber septum and backfilled with argon three times. The azepan (129 mg, 1.30 mmol, 1.50 equiv.) was dissolved in anhydrous DME (2 mL) was added dropwise at room temperature. The reaction flask was stirred in an oil-bath at 80° C. for 18 hours. The mixture was cooled to room temperature and extracted with EtOAc (3×50 mL), and the combined extracts were washed with water (3×25 mL), brine (25 mL), dried over anhydrous MgSO4, filtered and the solvent removed in vacuo. Flash column chromatography gave ethyl 5-(3-(azepan-1-yl)phenoxy)-1-(4-methoxybenzyl)-1H-1,2,3-triazole-4-carboxylate (227 mg, 56%) as a yellow oil. $^1$H-NMR (400 MHz, CDCl$_3$) δ: 7.24 (d, 2H), 7.06 (d, 1H), 6.82 (m, 2H), 6.44 (d, 1H) 6.10 (s, 1H), 6.03 (d, 1H), 5.33 (s, 2H), 4.22 (q, 2H), 3.79 (s, 3H), 3.36 (t, 4H), 1.72 (m, 4H), 1.53 (m, 4H), 1.15 (t, 3H).

Step 3—Ethyl 5-(3-(azepan-1-yl)phenoxy)-1H-1,2,3-triazole-4-carboxylate

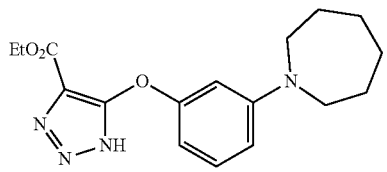 [SMILES: O=C(O)c1nn[nH]c1Oc1cccc(N2CCCCCC2)c1]

A vial (8 mL) containing a magnetic stir bar was charged with ethyl 5-(3-(azepan-1-yl)phenoxy)-1-(4-methoxybenzyl)-1H-1,2,3-triazole-4-carboxylate (150 mg, 0.33 mmol) and 3 mL of trifluoroacetic acid. The vial was sealed with a screw cap, placed in a pre-heated oil bath at 70° C. and stirred for 3 h. The reaction mixture was then cooled to room temperature, diluted with ethyl acetate (150 mL), washed with saturated aq. sodium bicarbonate (2×50 mL), water (50 mL), brine (50 mL), and dried over anhydrous MgSO4, filtered and the solvent removed in vacuo. Flash chromatography on silica gel gave ethyl 5-(3-(azepan-1-yl)phenoxy)-1H-1,2,3-triazole-4-carboxylate (50.6 mg, 46%) as a yellow oil. $^1$H-NMR (400 MHz, CDCl$_3$) δ: 7.13 (t, 1H), 6.47 (m, 2H), 6.34 (d, 1H), 4.40 (q, 2H), 3.42 (m, 4H), 1.75 (m, 4H), 1.53 (m, 4H), 1.33 (t, 3H).

Step 3—5-(3-(Azepan-1-yl)phenoxy)-1H-1,2,3-triazole-4-carboxylic acid (I-280)

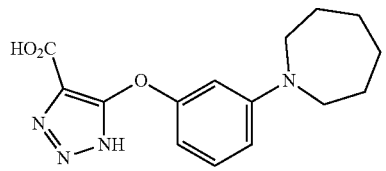

A vial (8 mL) containing a magnetic stir bar was charged with the ethyl 5-(3-(azepan-1-yl)phenoxy)-1H-1,2,3-triazole-4-carboxylate (50 mg, 0.151 mmol) and 3 mL of 1 N KOH. The vial was then sealed with a screw cap and stirred at room temperature for 18 hours. The pH was adjusted to between 2 and 3 using 0.1 N HCl and the contents of the vial were extracted with ethyl acetate (3×50 mL). The organic layers were combined, dried over anhydrous MgSO4, filtered and concentrated in vacuo. The crude product was purified by trituration in dichloromethane/pentane mixture to yield 5-(3-(azepan-1-yl)phenoxy)-1H-1,2,3-triazole-4-carboxylic acid as a pale-yellow solid (I-280, 36.6 mg, 80%). $^1$H-NMR (400 MHz, DMSO-d$_6$) δ: 7.04 (t, 1H), 6.44 (d, 1H), 6.34 (s, 1H), 6.14 (d, 1H), 2.05 (m, 4H), 1.69 (m, 4H), 1.45 (m, 4H).

Example I-281: 5-(3-(Piperidin-1-yl)phenoxy)-1H-1,2,3-triazole-4-carboxylic acid

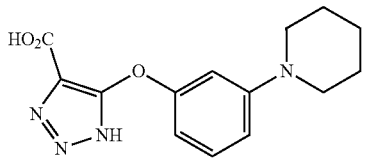 [SMILES: O=C(O)c1nn[nH]c1Oc1cccc(N2CCCCC2)c1]

The title compound was prepared by the method described in Example I-280 using piperidine (111 mg, 1.30 mmol, 1.50 equiv.) as a reagent in Step 2 of Example I-280, to give 5-(3-(piperidin-1-yl)phenoxy)-1H-1,2,3-triazole-4-carboxylic acid (38.2 mg, 15%, 3-steps) as a red solid. $^{1}$H-NMR (400 MHz, DMSO-$d_6$) δ: 7.14 (t, 1H), 6.70 (d, 1H), 6.62 (s, 1H), 6.35 (d, 1H), 3.13 (m, 4H), 1.58-1.153 (m, 6H).

Example I-282: 5-(3-Morpholinophenoxy)-1H-1,2,3-triazole-4-carboxylic acid

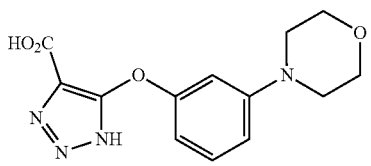 [SMILES: O=C(O)c1nn[nH]c1Oc1cccc(N2CCOCC2)c1]

The title compound was prepared by the method described in Example I-280 using morpholine (113 mg, 1.30 mmol, 1.50 equiv.) as a reagent in Step 2 of Example I-280, to give 5-(3-morpholinophenoxy)-1H-1,2,3-triazole-4-carboxylic acid (36.5 mg, 14%, 3-steps) as a pale-yellow solid. $^{1}$H-NMR (400 MHz, DMSO-$d_6$) δ: 7.18 (t, 1H), 6.72 (d, 1H), 6.65 (s, 1H), 6.41 (d, 1H), 3.71 (t, 4H), 3.09 (t, 4H).

Example I-283: 5-(3-(Pyrrolidin-1-yl)phenoxy)-1H-1,2,3-triazole-4-carboxylic acid

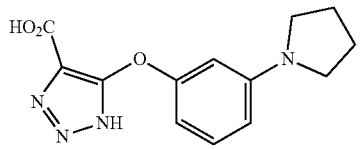 [SMILES: O=C(O)c1nn[nH]c1Oc1cccc(N2CCCC2)c1]

The title compound was prepared by the method described in Example I-280 using piperidine (94.0 mg, 1.30 mmol, 1.50 equiv.) as a reagent in Step 2 of Example I-280, to give 5-(3-(pyrrolidin-1-yl)phenoxy)-1H-1,2,3-triazole-4-carboxylic acid (27.1 mg, 11%, 3-steps) as a pale-yellow solid. $^{1}$H-NMR (400 MHz, CDCl$_3$) δ: 7.20 (t, 1H), 6.47-6.42 (m, 3H), 3.27 (m, 4H), 2.01 (m, 4H).

Example I-284: 5-(3-Vinylphenoxy)-1H-1,2,3-triazole-4-carboxylic acid

Step 1—Ethyl 5-(3-formylphenoxy)-1-(4-methoxybenzyl)-1H-1,2,3-triazole-4-carboxylate

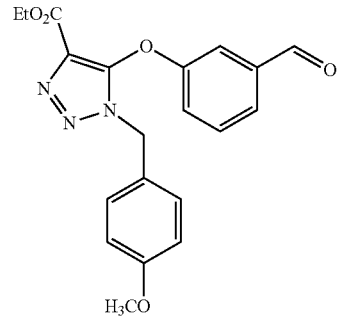 [SMILES: CCOC(=O)c1nnn(Cc2ccc(OC)cc2)c1Oc1cccc(C=O)c1]

A 25-mL round bottom flask with a stir bar was charged with NaH (50%, 116.0 mg, 2.4 mmol, 1.20 equiv), sealed with a rubber septum and backfilled with argon three times. The 3-hydroxybenzaldehyde (308 mg, 2.40 mmol, 1.20 equiv) was dissolved in anhydrous DMF (5 mL) was added dropwise at room temperature and stirred for 30 minutes. Ethyl 5-chloro-1-(4-methoxybenzyl)-1H-1,2,3-triazole-4-carboxylate (590 mg, 2.00 mmol, 1.00 equiv) dissolved in anhydrous DMF (4 mL) was added dropwise and the reaction flask was stirred in an oil-bath at 80° C. for 18 hours. The mixture was cooled to room temperature and quenched with water (2 mL). Extracted with EtOAc (3×50 mL), and the combined extracts were washed with water (5×25 mL), dried over anhydrous MgSO$_4$, filtered and the solvent removed in vacuo. Flash column chromatograph gave ethyl 5-(3-formylphenoxy)-1-(4-methoxybenzyl)-1H-1,2,3-triazole-4-carboxylate (587 mg, 77%) as a yellow oil. $^{1}$H-NMR (400 MHz, CDCl$_3$) δ: 9.88 (s, 1H), 7.63n (m, 1H), 7.46 (t, 1H), 7.20 (m, 2H), 7.11-7.04 (m, 2H), 6.75 (m, 2H), 5.42 (s, 2H), 4.16 (q, 2H), 3.75 (s, 3H), 1.13 (t, 3H).

Step 2—Ethyl 5-(3-formylphenoxy)-1H-1,2,3-triazole-4-carboxylate

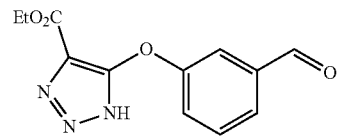 [SMILES: CCOC(=O)c1nn[nH]c1Oc1cccc(C=O)c1]

A vial (8 mL) containing a magnetic stir bar was charged with ethyl 5-(4-chlorophenoxy)-1-(4-methoxybenzyl)-1H-1,2,3-triazole-4-carboxylate (580 mg, 1.52 mmol) and 3 mL of trifluoroacetic acid. The vial was sealed with a screw cap, placed in a pre-heated oil bath at 70° C. and stirred for 2 h. The reaction mixture was then cooled to room temperature, diluted with ethyl acetate (150 mL), washed with saturated aq. sodium bicarbonate (2×50 mL), water (50 mL), brine (50 mL), and dried over anhydrous MgSO$_4$, filtered and the solvent removed in vacuo. Flash chromatography on silica gel gave ethyl 5-(3-formylphenoxy)-1H-1,2,3-triazole-4-carboxylate (217 mg, 54%) as a pale-yellow solid. $^{1}$H-NMR (400 MHz, CDCl$_3$) δ: 13.59 (bs, 1H), 9.98 (s, 1H), 7.68 (m, 2H), 7.55 (m, 1H), 7.46 (m, 1H), 4.34 (q, 2H), 1.24 (t, 3H).

Step 3—Ethyl 5-(3-vinylphenoxy)-1H-1,2,3-triazole-4-carboxylate

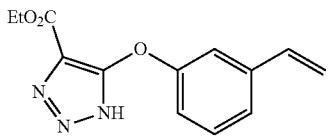 [SMILES: C=Cc1cccc(Oc2[nH]nnc2C(=O)OCC)c1]

To a solution of methyltriphenylphosphonium bromide (643 mg, 1.80 mmol, 2.60 equiv) in dry THF (5 mL), t-BuOK (216 mg, 1.93 mmol, 2.80 equiv) was added and stirred under argon for 1 h. Ethyl 5-(3-formylphenoxy)-1H-1,2,3-triazole-4-carboxylate (180 mg, 0.69 mmol, 1.00 equiv) was added and stirred for 24 h. The reaction mixture was diluted with dichloromethane (50 mL) and washed with water (2×25 mL) and brine (25 mL), dried over anhydrous Na$_2$SO$_4$, filtered and the solvent removed in vacuo. Flash chromatography on silica gel with 20% ethyl acetate/hexanes gave ethyl 5-(3-vinylphenoxy)-1H-1,2,3-triazole-4-carboxylate (114 mg, 64%) as a yellow oil. $^1$H-NMR (400 MHz, CDCl$_3$) δ:13.60 (bs, 1H), 7.37-7.30 (m, 2H), 7.2 (m, 1H), 6.71 (m, 1H), 5.75 (d, 1H), 5.30 (d, 1H), 4.41 (q, 2H), 1.31 (t, 3H).

Step 4—5-(3-Vinylphenoxy)-1H-1,2,3-triazole-4-carboxylic acid (I-284)

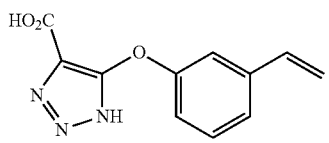 [SMILES: C=Cc1cccc(Oc2[nH]nnc2C(=O)O)c1]

A vial (8 mL) containing a magnetic stir bar was charged with the ethyl 5-(4-chlorophenoxy)-1H-1,2,3-triazole-4-carboxylate (100 mg, 0.39 mmol) and 3 mL of 1 N KOH. The vial was then sealed with a screw cap and stirred at room temperature for 18 hours. The pH was adjusted to between 2 and 3 using 1 N HCl and the contents of the vial were extracted with ethyl acetate (3×50 mL). The organic layers were combined, dried over anhydrous MgSO$_4$, filtered and concentrated in vacuo. The crude product was purified by trituration in diethyl ether/pentane to yield 5-(3-vinylphenoxy)-1H-1,2,3-triazole-4-carboxylic acid as pale-yellow solid (62.5 mg, 70%). $^1$H-NMR (400 MHz, DMSO-d$_6$) δ: 7.29 (m, 1H), 7.23 (m, 1H), 7.12 (s, 1H), 6.78 (m, 1H), 6.73 (m, 1H), 5.81 (d, 1H), 5.27 (d, 1H).

Example I-285: 5-(4-Vinylphenoxy)-1H-1,2,3-triazole-4-carboxylic acid

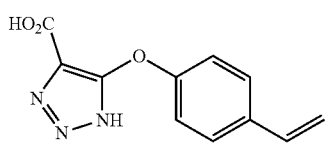 [SMILES: C=Cc1ccc(Oc2[nH]nnc2C(=O)O)cc1]

The title compound was prepared by the method described in Example I-284 using 4-hydroxybenzaldehyde (308 mg, 2.40 mmol, 1.20 equiv) as a reagent in Step 1 of Example I-284, to give 5-(4-vinylphenoxy)-1H-1,2,3-triazole-4-carboxylic acid (58.1 mg, 18%, 4-steps) as a pale-yellow solid. $^1$H-NMR (400 MHz, DMSO-d$_6$) δ: 7.44 (d, 2H), 7.01 (d, 2H), 6.68 (m, 1H), 5.74 (m, 1H), 5.20 (m, 1H).

Example I-286: 5-(3-(2-Methylprop-1-en-1-yl)phenoxy)-1H-1,2,3-triazole-4-carboxylic acid

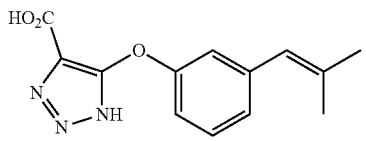 [SMILES: CC(C)=Cc1cccc(Oc2[nH]nnc2C(=O)O)c1]

The title compound was prepared by the method described in Example I-284 using 3-hydroxybenzaldehyde (308 mg, 2.40 mmol, 1.20 equiv.) as a reagent in Step 1 of Example I-284, to give 5-(3-(2-methylprop-1-en-1-yl)phenoxy)-1H-1,2,3-triazole-4-carboxylic acid (87.2 mg, 14%, 4-steps) as a pale-yellow solid. $^1$H-NMR (400 MHz, DMSO-d$_6$) δ: 7.31 (d, 1H), 6.99 (d, 1H), 6.87 (s, 2H), 6.24 (s, 1H), 0.86 (s, 3H), 0.84 (s, 3H).

Example I-287: 5-(4-(2-Methylprop-1-en-1-yl)phenoxy)-1H-1,2,3-triazole-4-carboxylic acid

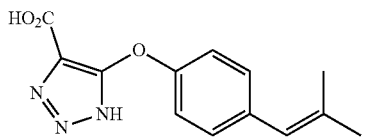 [SMILES: CC(C)=Cc1ccc(Oc2[nH]nnc2C(=O)O)cc1]

The title compound was prepared by the method described in Example I-284 using 4-hydroxybenzaldehyde (308 mg, 2.40 mmol, 1.20 equiv.) as a reagent in Step 1 of Example I-284, to give 5-(4-(2-methylprop-1-en-1-yl)phenoxy)-1H-1,2,3-triazole-4-carboxylic acid (73.1 mg, 12%, 4-steps) as a pale-yellow solid. $^1$H-NMR (400 MHz, DMSO-d$_6$) δ: 7.21 (d, 2H), 7.02 (d, 2H), 6.24 (s, 1H), 1.87 (s, 3H), 1.81 (s, 3H).

Example I-288: 5-(3-ethynylphenoxy)-1H-1,2,3-triazole-4-carboxylic acid

Step 1—Ethyl 5-(3-((triisopropylsilyl)ethynyl)phenoxy)-1H-1,2,3-triazole-4-carboxylate

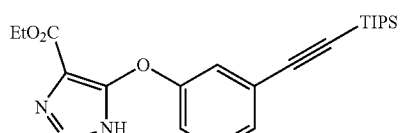

A 10-mL round bottom flask with a stir bar was charged with ethyl 5-(3-bromophenoxy)-1H-1,2,3-triazole-4-carboxylate (265 mg, 0.85 mmol, 1.00 equiv.), ethynyltriisopropylsilane (0.25 mL, 2.55 mmol, 3.00 equiv), (Ph$_3$P)$_2$PdCl$_2$ (120 mg, 0.17 mmol, 0.20 equiv.), and CuI (34.0 mg, 0.17 mmol, 0.20 equiv.) sealed with a rubber septum and backfilled with argon three times. The diisopropylamine (4 mL) was added at room temperature and the flask was heated to 80° C. for 48 hours. Cooled to room temperature and diluted with ethyl acetate (50 mL) and filtered through a pad of Celite. The filtrate was washed with water (3×25 mL), brine (25 mL), dried over anhydrous Na$_2$SO$_4$, filtered and concentrated under reduced pressure. The crude was purified by silica gel column chromatography with 5% diethyl ether/dichloromethane to yield ethyl 5-(3-((triisopropylsilyl)ethynyl)phenoxy)-1H-1,2,3-triazole-4-carboxylate as a yellow oil (105 mg, 30%). $^1$H-NMR (400 MHz, CDCl$_3$) δ: 7.33 (m, 3H), 7.09 (s, 1H), 4.38 (q, 2H), 1.27 (m, 6H), 1.10 (s, 18H).

Step 2—Ethyl 5-(3-ethynylphenoxy)-1H-1,2,3-triazole-4-carboxylate

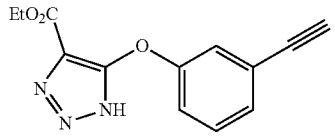 [SMILES: C#Cc1cccc(Oc2[nH]nnc2C(=O)OCC)c1]

A 10-mL round bottom flask with a stir bar was charged with ethyl 5-(3-((triisopropylsilyl)ethynyl)phenoxy)-1H-1,2,3-triazole-4-carboxylate as a yellow oil (98.0 mg, 0.24 mmol, 1.00 equiv), sealed with a rubber septum and backfilled with argon three times. THF (1 mL) was added followed by TBAF (0.48 mL, 0.48 mmol, 2.00 equiv) in THF. Stirred at room temperature for 2 h. Diluted with ethyl acetate (50 mL) and washed with water (3×25 mL), brine (25 mL), dried over anhydrous Na$_2$SO$_4$, filtered and concentrated under reduced pressure. The crude was purified by silica gel column chromatography with 5% diethyl ether/dichloromethane to yield ethyl 5-(3-ethynylphenoxy)-1H-1,2,3-triazole-4-carboxylate as yellow oil (44.0 mg, 71%). The crude was used without purification in the next step.

Step 3—5-(3-Ethynylphenoxy)-1H-1,2,3-triazole-4-carboxylic acid

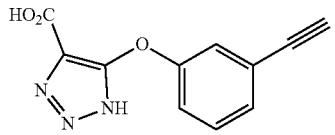 [SMILES: C#Cc1cccc(Oc2[nH]nnc2C(=O)O)c1]

A vial (8 mL) containing a magnetic stir bar was charged with the ethyl 5-(3-ethynylphenoxy)-1H-1,2,3-triazole-4-carboxylate as yellow oil (40 mg, 0.16 mmol) and 3 mL of 1 N KOH. The vial was then sealed with a screw cap and stirred at room temperature for 18 hours. The pH was adjusted to between 2 and 3 using 1 N HCl and the contents of the vial were extracted with ethyl acetate (3×50 mL). The organic layers were combined, dried over anhydrous MgSO4, filtered and concentrated in vacuo. The crude product was purified by trituration in dichloromethane/pentane mixture to yield 5-(3-ethynylphenoxy)-1H-1,2,3-triazole-4-carboxylic acid as a light-yellow solid (19.2 mg, 55%). $^1$H-NMR (400 MHz, Acetone-d$_6$) δ: 7.42 (d, 1H), 7.30-7.21 (m, 3H), 3.72 (s, 1H).

Example I-289: Ethyl 5-((4-methoxyphenyl)amino)-1H-1,2,3-triazole-4-carboxylic acid Step 1—Ethyl 1-(4-methoxybenzyl)-5-((4-methoxyphenyl)amino)-1H-1,2,3-triazole-4-carboxylate

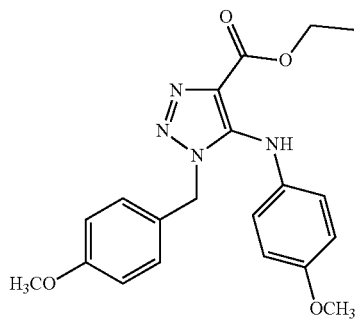 [SMILES: CCOC(=O)c1nnn(Cc2ccc(OC)cc2)c1Nc1ccc(OC)cc1]

A 25-mL round bottom flask with a stir bar was charged with sodium chromanoxide (245 mg, 1.01 mmol, 1.50 equiv.), Pd-PEPPSI-IPent$^{Cl}$ (17.6 mg, 0.02 mmol, 3 mol %), and Ethyl 5-chloro-1-(4-methoxybenzyl)-1H-1,2,3-triazole-4-carboxylate (200 mg, 0.676 mmol, 1.00 equiv), sealed with a rubber septum and backfilled with argon three times. Anhydrous toluene (7 mL) was added at room temperature and the reaction flask was stirred in an oil-bath at 100° C. for 18 hours. The mixture was cooled to room temperature and filtered through a pad of silica and the solvent was removed in vacuo. Flash column chromatograph gave ethyl 1-(4-methoxybenzyl)-5-((4-methoxyphenyl)amino)-1H-1,2,3-triazole-4-carboxylate (64.1 mg, 25%) as a yellow oil. $^1$H-NMR (400 MHz, CDCl$_3$) δ: 7.69 (s, 1H), 7.41 (d, 2H), 6.89 (d, 2H), 4.48 (q, 2H), 3.79 (s, 6H), 1.45 (t, 3H).

Step 2—Ethyl 5-((4-methoxyphenyl)amino)-1H-1,2,3-triazole-4-carboxylate (I-289)

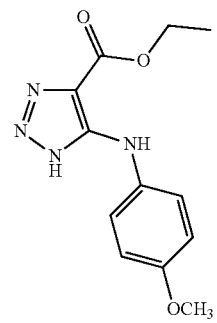 [SMILES: CCOC(=O)c1nn[nH]c1Nc1ccc(OC)cc1]

A vial (8 mL) containing a magnetic stir bar was charged with ethyl 1-(4-methoxybenzyl)-5-((4-methoxyphenyl)amino)-1H-1,2,3-triazole-4-carboxylate (64 mg, 0.166 mmol) and 3 mL of trifluoroacetic acid. The vial was sealed with a screw cap, placed in a pre-heated oil bath at 70° C. and stirred for 3 h. The reaction mixture was then cooled to room temperature, diluted with ethyl acetate (150 mL), washed with saturated aq. sodium bicarbonate (2×50 mL), water (50 mL), brine (50 mL), and dried with anhydrous MgSO4, filtered and the solvent removed in vacuo. Flash chromatography on silica gel gave ethyl 5-((4-methoxyphenyl)amino)-1H-1,2,3-triazole-4-carboxylate (29 mg, 67%) as an off-white solid. ¹H-NMR (400 MHz, CDCl₃) δ: 7.71 (s, 1H), 7.41 (d, 2H), 6.91 (d, 2H), 4.46 (q, 2H), 3.80 Is, 3H), 1.45 (t, 3H).

Example I-290: 5-((4-Methoxyphenyl)amino)-1H-1,2,3-triazole-4-carboxylic acid (I-289)

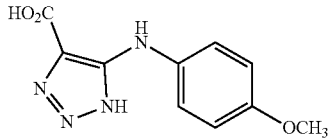 [SMILES: COc1ccc(Nc2[nH]nnc2C(=O)O)cc1]

A vial (8.0 mL) containing a magnetic stir bar was charged with the ethyl 5-((4-methoxyphenyl)amino)-1H-1,2,3-triazole-4-carboxylate (I-289, 29 mg, 110 mmol) and 3 mL of 1 N KOH. The vial was then sealed with a screw cap and stirred at room temperature for 18 hours. The pH was adjusted to between 2 and 3 using 1 N HCl and the contents of the vial were extracted with ethyl acetate (3×50 mL). The organic layers were combined, dried over anhydrous MgSO4, filtered and concentrated in vacuo. The crude product was purified by trituration in diethyl ether to yield 5-((4-methoxyphenyl)amino)-1H-1,2,3-triazole-4-carboxylic acid as white solid (I-290, 18.7 mg, 75%). ¹H-NMR (400 MHz, DMSO-d₆) δ: 8.15 (bs, 1H), 7.46 (d, 2H), 6.87 (d, 2H), 3.70 (s, 3H).

Example I-292: 5-(p-Tolylamino)-1H-1,2,3-triazole-4-carboxylic acid

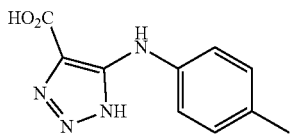

The title compound was prepared by the method described in Example I-289 using p-toluidine (146 mg, 1.36 mmol, 2.00 equiv.) as a reagent in Step 1 of Example I-289, to give ethyl 5-(p-tolylamino)-1H-1,2,3-triazole-4-carboxylate (I-291) and after saponification 5-(p-tolylamino)-1H-1,2,3-triazole-4-carboxylic acid (I-292, 6.9 mg, 5%, 3-steps) as a light-brown solid. ¹H-NMR (300 MHz, CDCl₃) δ: 7.25 (d, 2H), 7.00 (d, 2H), 2.18 (s, 3H).

Example I-293: 5-(3-Cyclopropylphenoxy)-1H-1,2,3-triazole-4-carboxylic acid

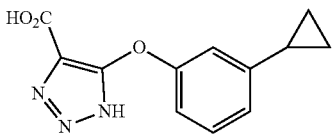 [SMILES: O=C(O)c1nn[nH]c1Oc1cccc(C2CC2)c1]

The title compound was prepared by the method described in Example I-272 using cyclopropylzinc bromide (1.1 mL, 0.74 M, 0.87 mmol, 1.50 equiv.) and 5-(3-bromophenoxy)-1-(4-methoxybenzyl)-1H-1,2,3-triazole-4-carboxylate (250 mg, 0.58 mmol, 1.0 equiv.) as reagents in Step 1 of Example I-272, to give 5-(3-cyclopropylphenoxy)-1H-1,2,3-triazole-4-carboxylic acid (19.4 mg, 11%, 3-steps) as an off-white solid. ¹H-NMR (400 MHz, DMSO-d₆) δ: 7.20 (m, 1H), 6.81 (m, 3H), 1.91 (m, 1H), 0.94 (m, 2H), 0.65 (m, 2H).

Example I-294: 5-(4-Cyclopropylphenoxy)-1H-1,2,3-triazole-4-carboxylic acid

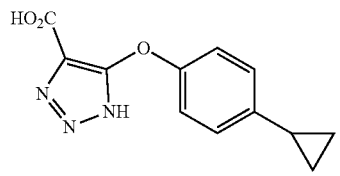 [SMILES: O=C(O)c1nn[nH]c1Oc1ccc(C2CC2)cc1]

The title compound was prepared by the method described in Example I-272 using cyclopropylzinc bromide (1.1 mL, 0.74 M, 0.87 mmol, 1.50 equiv.) and 5-(4-bromophenoxy)-1-(4-methoxybenzyl)-1H-1,2,3-triazole-4-carboxylate (250 mg, 0.58 mmol, 1.0 equiv.) as reagents in Step 1 of Example I-272, to give 5-(4-cyclopropylphenoxy)-1H-1,2,3-triazole-4-carboxylic acid (24.5 mg, 14%, 3-steps) as an off-white solid. ¹H-NMR (400 MHz, DMSO-d₆) δ: 7.05 (d, 2H), 6.93 (d, 2H), 1.91 (m, 1H), 0.91 (m, 2H), 0.62 (m, 2H).

Example I-295: 5-(3-Ethylphenoxy)-1H-1,2,3-triazole-4-carboxylic acid

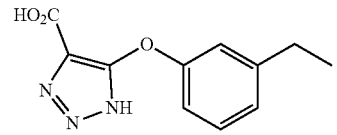 [SMILES: CCc1cccc(Oc2[nH]nnc2C(=O)O)c1]

The title compound was prepared by the method described in Example I-272 using ethylzinc bromide (1.05 mL, 0.80 M, 0.87 mmol, 1.50 equiv.) and 5-(3-bromophenoxy)-1-(4-methoxybenzyl)-1H-1,2,3-triazole-4-carboxylate (250 mg, 0.58 mmol, 1.0 equiv.) as reagents in Step 1 of Example I-272, to give 5-(3-ethylphenoxy)-1H-1,2,3-triazole-4-carboxylic acid (29.8 mg, 17%, 3-steps) as an off-white solid. 1H-NMR (400 MHz, DMSO-d₆) δ: 7.26 (t, 1H), 6.99 (d, 1H), 6.87 (d, 1H), 6.84 (t, 1H), 2.59 (q, 2H), 1.16 (t, 3H).

Example I-296: 5-(3-Isobutylphenoxy)-1H-1,2,3-triazole-4-carboxylic acid

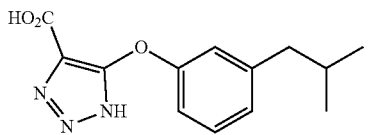 [SMILES: CC(C)Cc1cccc(Oc2[nH]nnc2C(=O)O)c1]

The title compound was prepared by the method described in Example I-272 using isobutyllzinc bromide (1.00 mL, 0.83 M, 0.87 mmol, 1.50 equiv.) and 5-(3-bromophenoxy)-1-(4-methoxybenzyl)-1H-1,2,3-triazole-4-carboxylate (250 mg, 0.58 mmol, 1.0 equiv.) as reagents in Step 1 of Example I-272, to give 5-(3-isobutylphenoxy)-1H-1,2,3-triazole-4-carboxylic acid (24.6 mg, 14%, 3-steps) as an off-white solid. $^1$H-NMR (400 MHz, DMSO-$d_6$) δ: 7.27 (d, 1H), 6.95 (d, 1H), 6.87 (m, 2H), 2.44 (d, 2H), 1.91 (m, 1H), 0.85 (d, 6H).

Example I-297: 5-(4-Ethynylphenoxy)-1H-1,2,3-triazole-4-carboxylic acid

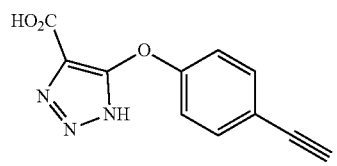 [SMILES: C#Cc1ccc(Oc2[nH]nnc2C(=O)O)cc1]

The title compound was prepared by the method described in Example I-288 using ethyl 5-(4-bromophenoxy)-1H-1,2,3-triazole-4-carboxylate (265 mg, 0.85 mmol, 1.00 equiv.) and ethynyltriisopropylsilane (0.25 mL, 2.55 mmol, 3.00 equiv) as reagents in Step 1 of Example I-288, to give 5-(4-ethynylphenoxy)-1H-1,2,3-triazole-4-carboxylic acid as a light-yellow solid (19.9 mg, 12%). $^1$H-NMR (400 MHz, DMSO-$d_6$) δ: 7.61 (d, 2H), 7.11 (d, 2H). 3.33 (s, 1H).

Example I-298: 5-(4-Ethylphenoxy)-1H-1,2,3-triazole-4-carboxylic acid

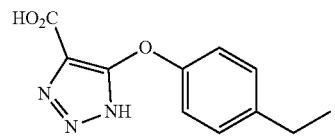 [SMILES: CCc1ccc(Oc2[nH]nnc2C(=O)O)cc1]

The title compound was prepared by the method described in Example I-272 using ethylzinc bromide (1.05 mL, 0.80 M, 0.87 mmol, 1.50 equiv.) and 5-(4-bromophenoxy)-1-(4-methoxybenzyl)-1H-1,2,3-triazole-4-carboxylate (250 mg, 0.58 mmol, 1.0 equiv.) as reagents in Step 1 of Example I-272, to give 5-(4-ethylphenoxy)-1H-1,2,3-triazole-4-carboxylic acid (26.3 mg, 15%, 3-steps) as an off-white solid. $^1$H-NMR (400 MHz, DMSO-$d_6$) δ: 7.19 (d, 2H), 6.98 (d, 2H), 2.57 (q, 2H), 1.16 (t, 3H).

Example I-299: 5-(4-Isobutylphenoxy)-1H-1,2,3-triazole-4-carboxylic acid

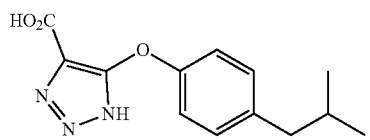 [SMILES: CC(C)Cc1ccc(Oc2[nH]nnc2C(=O)O)cc1]

The title compound was prepared by the method described in Example I-272 using isobutyllzinc bromide (1.00 mL, 0.83 M, 0.87 mmol, 1.50 equiv.) and 5-(4-bromophenoxy)-1-(4-methoxybenzyl)-1H-1,2,3-triazole-4-carboxylate (250 mg, 0.58 mmol, 1.0 equiv.) as reagents in Step 1 of Example I-272, to give 5-(4-isobutylphenoxy)-1H-1,2,3-triazole-4-carboxylic acid (24.5 mg, 14%, 3-steps) as an off-white solid. $^1$H-NMR (400 MHz, DMSO-$d_6$) δ: 7.13 (d, 2H), 6.97 (d, 2H), 2.41 (d, 2H), 1.79 (m, 1H), 0.85 (d, 6H).

Example I-300: 5-((3',5'-Dichloro-[1,1'-biphenyl]-4-yl)oxy)-1H-1,2,3-triazole-4-carboxylic acid

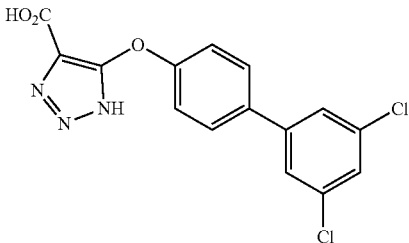 [SMILES: O=C(O)c1nn[nH]c1Oc1ccc(-c2cc(Cl)cc(Cl)c2)cc1]

The title compound was prepared by the method described in Example I-033 using 3',5'-dichloro-[1,1'-biphenyl]-4-ol (178 mg, 0.744 mmol, 1.10 equiv.) as a reagent in Step 1 of Example I-033, to give 5-((3',5'-dichloro-[1,1'-biphenyl]-4-yl)oxy)-1H-1,2,3-triazole-4-carboxylic acid (47.2 mg, 16%, 3-steps) as an off-white solid. $^1$H-NMR (400 MHz, DMSO-$d_6$) δ: 7.75 (d, 2H), 7.73 (d, 2H), 7.58 (t, 1H), 7.14 (d, 2H).

Example I-301: 5-((3',5'-Dimethoxy-[1,1'-biphenyl]-4-yl)oxy)-1H-1,2,3-triazole-4-carboxylic acid

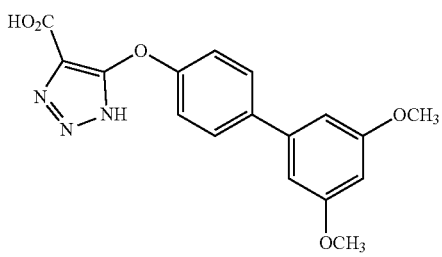 [SMILES: COc1cc(OC)cc(-c2ccc(Oc3[nH]nnc3C(=O)O)cc2)c1]

The title compound was prepared by the method described in Example I-033 1 using 3',5'-dimethoxy-[1,1'-biphenyl]-4-ol (171 mg, 0.744 mmol, 1.10 equiv.) as a reagent in Step 1 of Example I-033, to give 5-((3',5'-dimethoxy-[1,1'-biphenyl]-4-yl)oxy)-1H-1,2,3-triazole-4-carboxylic acid (36.9 mg, 16%, 3-steps) as an off-white solid. $^1$H-NMR (300 MHz, DMSO-$d_6$) δ: 7.17 (d, 2H), 7.01 (d, 2H), 6.90 (t, 1H), 6.56 (d, 2H), 3.65 (s, 6H).

Example I-302: 5-((3',5'-Dichloro-[1,1'-biphenyl]-3-yl)oxy)-1H-1,2,3-triazole-4-carboxylic acid

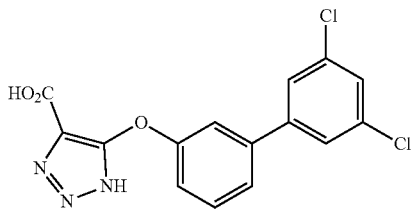 [SMILES: O=C(O)c1nn[nH]c1Oc1cccc(-c2cc(Cl)cc(Cl)c2)c1]

The title compound was prepared by the method described in Example I-033 using 3',5'-dichloro-[1,1'-biphenyl]-3-ol (178 mg, 0.744 mmol, 1.10 equiv.) as a reagent in Step 1 of Example I-033, to give 5-((3',5'-dichloro-[1,1'-biphenyl]-3-yl)oxy)-1H-1,2,3-triazole-4-carboxylic acid (42.2 mg, 14%, 3-steps) as an off-white solid. $^1$H-NMR (300 MHz, DMSO-$d_6$) δ: 7.75 (d, 2H), 7.62 (t, 1H), 7.55-7.53 (m, 2H), 7.47 (t, 1H), 7.13-7.09 (m, 1H).

Example I-303: 5-((3',5'-Dimethoxy-[1,1'-biphenyl]-3-yl)oxy)-1H-1,2,3-triazole-4-carboxylic acid

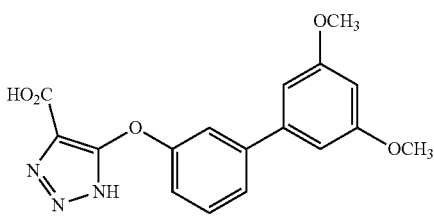 [SMILES: COc1cc(OC)cc(-c2cccc(Oc3[nH]nnc3C(=O)O)c2)c1]

The title compound was prepared by the method described in Example I-033 using 3',5'-dimethoxy-[1,1'-biphenyl]-3-ol (171 mg, 0.744 mmol, 1.10 equiv.) as a reagent in Step 1 of Example I-033, to give 5-((3',5'-dimethoxy-[1,1'-biphenyl]-3-yl)oxy)-1H-1,2,3-triazole-4-carboxylic acid (32.3 mg, 14%, 3-steps) as an off-white solid. $^1$H-NMR (300 MHz, DMSO-$d_6$) δ: 7.31 (d, 2H), 7.10 (t, 1H), 6.99-6.94 (m, 2H), 6.87-6.85 (m, 1H), 6.73 (d, 2H), 3.66 (s, 6H).

Example I-304: 5-(4-(Benzo[d][1,3]dioxol-5-yl)phenoxy)-1H-1,2,3-triazole-4-carboxylic acid

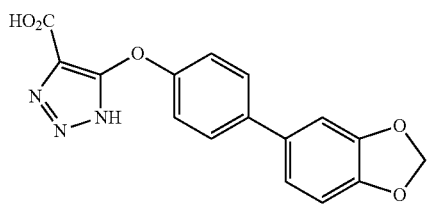 [SMILES: O=C(O)c1nn[nH]c1Oc1ccc(-c2ccc3c(c2)OCO3)cc1]

The title compound was prepared by the method described in Example I-272 using benzo[d][1,3]dioxol zinc chloride (2.7 mL, 0.3 M, 0.87 mmol, 1.50 equiv.) and 5-(4-bromophenoxy)-1-(4-methoxybenzyl)-1H-1,2,3-triazole-4-carboxylate (250 mg, 0.58 mmol, 1.0 equiv.) as reagents in Step 1 of Example I-272, to give 5-(4-(benzo[d][1,3]dioxol-5-yl)phenoxy)-1H-1,2,3-triazole-4-carboxylic acid (29.7 mg, 17%, 3-steps) as an off-white solid. $^1$H-NMR (400 MHz, DMSO-$d_6$) δ: 7.59 (d, 2H), 7.22 (s, 1H), 7.11 (m, 3H), 6.98 (d, 1H), 6.06 (s, 2H).

Example I-305: 5-(3-(Benzo[d][1,3]dioxol-5-yl)phenoxy)-1H-1,2,3-triazole-4-carboxylic acid

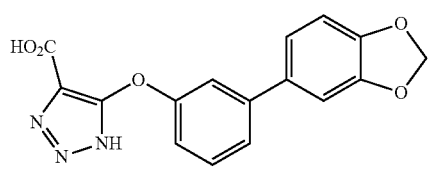 [SMILES: O=C(O)c1nn[nH]c1Oc1cccc(-c2ccc3c(c2)OCO3)c1]

The title compound was prepared by the method described in Example I-272 using benzo[d][1,3]dioxol zinc chloride (2.7 ml, 0.3 M, 0.87 mmol, 1.50 equiv.) and 5-(3-bromophenoxy)-1-(4-methoxybenzyl)-1H-1,2,3-triazole-4-carboxylate (250 mg, 0.58 mmol, 1.0 equiv.) as reagents in Step 1 of Example I-272, to give 5-(4-(benzo[d][1,3]dioxol-5-yl)phenoxy)-1H-1,2,3-triazole-4-carboxylic acid (22.6 mg, 13%, 3-steps) as an off-white solid. $^1$H-NMR (300 MHz, DMSO-$d_6$) δ: 7.40 (m, 2H), 7.33 (t, 1H), 7.25 (d, 1H), 7.14 (dd, 1H), 7.00 (m, 2H), 6.07 (s, 2H).

Example I-306: 5-(4-Fluoro-3-methylphenoxy)-1H-1,2,3-triazole-4-carboxylic acid

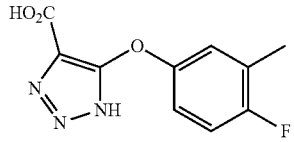 [SMILES: Cc1cc(Oc2[nH]nnc2C(=O)O)ccc1F]

The title compound was prepared by the method described in Example I-033 using 4-fluoro-3-methylphenol (94.0 mg, 0.744 mmol, 1.10 equiv.) as a reagent in Step 1 of Example I-033, to give 5-(4-fluoro-3-methylphenoxy)-1H-1,2,3-triazole-4-carboxylic acid (32.1 mg, 20%, 3-steps) as an off-white solid. $^1$H-NMR (300 MHz, DMSO-$d_6$) δ: 7.13 (t, 1H), 7.06 (m, 1H), 6.94 (m, 1H), 2.22 (d, 3H).

Example I-307: 5-(3,4-Difluorophenoxy)-1H-1,2,3-triazole-4-carboxylic acid

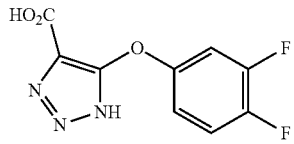 [SMILES: O=C(O)c1nn[nH]c1Oc1ccc(F)c(F)c1]

The title compound was prepared by the method described in Example I-033 using 3,4-difluorophenol (97.0 mg, 0.744 mmol, 1.10 equiv.) as a reagent in Step 1 of Example I-033, to give 5-(3,4-difluorophenoxy)-1H-1,2,3-triazole-4-carboxylic acid (27.6 mg, 17%, 3-steps) as an off-white solid. $^1$H-NMR (300 MHz, DMSO-$d_6$) δ: 7.44 (q, 1H), 7.37-7.30 (m, 1H), 6.96 (m, 1H).

Example I-308: 5-(4-Chloro-3-fluorophenoxy)-1H-1,2,3-triazole-4-carboxylic acid

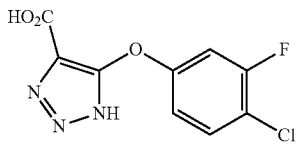 [SMILES: O=C(O)c1nn[nH]c1Oc1ccc(Cl)c(F)c1]

The title compound was prepared by the method described in Example I-033 using 4-chloro-3-fluorophenol (109 mg, 0.744 mmol, 1.10 equiv.) as a reagent in Step 1 of Example I-033, to give 5-(4-chloro-3-fluorophenoxy)-1H-1,2,3-triazole-4-carboxylic acid (42.0 mg, 16%, 3-steps) as an off-white solid. $^1$H-NMR (300 MHz, DMSO-$d_6$) δ: 7.58 (t, 1H), 7.29 (dd, 1H), 6.96 (dd, 1H).

Example I-309: 5-(3-Chloro-4-fluorophenoxy)-1H-1,2,3-triazole-4-carboxylic acid

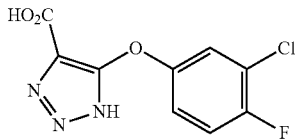 [SMILES: O=C(O)c1nn[nH]c1Oc1ccc(F)c(Cl)c1]

The title compound was prepared by the method described in Example I-033 using 3-chloro-4-fluorophenol (109 mg, 0.744 mmol, 1.10 equiv.) as a reagent in Step 1 of Example I-033, to give 5-(3-chloro-4-fluorophenoxy)-1H-1,2,3-triazole-4-carboxylic acid (39.8 mg, 15%, 3-steps) as an off-white solid. $^1$H-NMR (300 MHz, DMSO-$d_6$) δ: 7.42 (m, 2H), 7.15 (m, 1H).

Example I-310: 5-((3'-Fluoro-4'-(trifluoromethoxy)-[1,1'-biphenyl]-4-yl)oxy)-1H-1,2,3-triazole-4-carboxylic acid

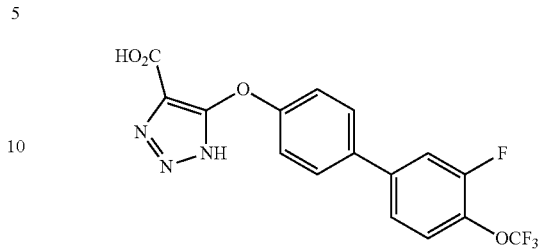

The title compound was prepared by the method described in Example I-033 using 5-((3'-fluoro-4'-(trifluoromethoxy)-[1,1'-biphenyl]-4-ol (203 mg, 0.744 mmol, 1.10 equiv.) as a reagent in Step 1 of Example I-033, to give 5-((3'-fluoro-4'-(trifluoromethoxy)-[1,1'-biphenyl]-4-yl)oxy)-1H-1,2,3-triazole-4-carboxylic acid (43.2 mg, 11%, 3-steps) as an off-white solid. $^1$H-NMR (300 MHz, DMSO-$d_6$) δ: 7.85 (d, 1H), 7.74 (d, 2H), 7.62 (m, 2H), 7.17 (d, 2H).

Example I-311: 5-((3'-Fluoro-4'-(trifluoromethoxy)-[1,1'-biphenyl]-3-yl)oxy)-1H-1,2,3-triazole-4-carboxylic acid

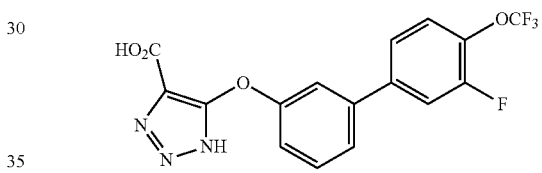

The title compound was prepared by the method described in Example I-033 using 5-((3'-fluoro-4'-(trifluoromethoxy)-[1,1'-biphenyl]-3-ol (203 mg, 0.744 mmol, 1.10 equiv.) as a reagent in Step 1 of Example I-033, to give 5-((3'-fluoro-4'-(trifluoromethoxy)-[1,1'-biphenyl]-3-yl)oxy)-1H-1,2,3-triazole-4-carboxylic acid (45.8 mg, 12%, 3-steps) as an off-white solid. $^1$HNMR (300 MHz, DMSO-$d_6$) δ: 7.82 (d, 1H), 7.67-7.57 (m, 2H), 7.45 (m, 3H), 7.03 (m, 1H).

The following compounds in Table 1 have been made or prepared using the methods set for above I-001-I-016, I-025, I-031-I-033, I-035, I-037, I-039, I-049, I-050, I-057, I-058, I-085, I-128, I-129, I-0146, I-150-I-154, I-158, I-160, I-170, I-174, I-177, I-178, and I-249-I-311. The other compounds in Table 1 can be prepared by the methods set forth above.

TABLE 1

| Ex. No. | Structure | IUPAC Name | Chemical Formula | MW (g/mol) |
|---|---|---|---|---|
| I-001 | 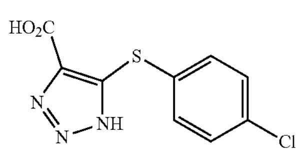 [SMILES: O=C(O)c1nn[nH]c1Sc1ccc(Cl)cc1] | 5-((4-chlorophenyl)thio)-1H-1,2,3-triazole-4-carboxylic acid | $C_9H_6ClN_3O_2S$ | 255.68 |

Example compounds.

TABLE 1-continued

Example compounds.

| Ex. No. | Structure | IUPAC Name | Chemical Formula | MW (g/mol) |
|---|---|---|---|---|
| I-002 | 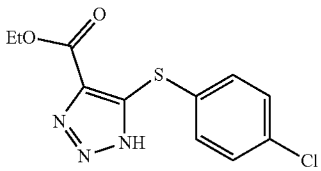 [SMILES: CCOC(=O)c1nn[nH]c1Sc1ccc(Cl)cc1] | Ethyl 5-((4-chlorophenyl)thio)-1H-1,2,3-triazole-4-carboxylate | $C_{11}H_{10}ClN_3O_2S$ | 283.73 |
| I-003 | 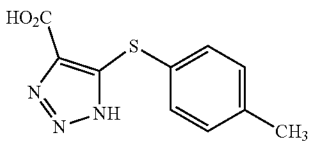 [SMILES: Cc1ccc(Sc2[nH]nnc2C(=O)O)cc1] | 5-(p-tolylthio)-1H-1,2,3-triazole-4-carboxylic acid | $C_{10}H_9N_3O_2S$ | 235.26 |
| I-004 | 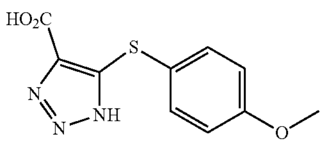 [SMILES: COc1ccc(Sc2[nH]nnc2C(=O)O)cc1] | 5-((4-methoxyphenyl)thio)-1H-1,2,3-triazole-4-carboxylic acid | $C_{10}H_9N_3O_3S$ | 251.26 |
| I-005 | 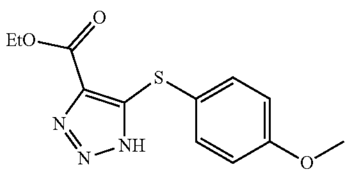 [SMILES: CCOC(=O)c1nn[nH]c1Sc1ccc(OC)cc1] | Ethyl 5-((4-methoxyphenyl)thio)-1H-1,2,3-triazole-4-carboxylate | $C_{12}H_{13}N_3O_3S$ | 279.31 |
| I-006 | 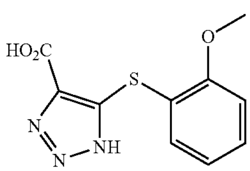 [SMILES: COc1ccccc1Sc1[nH]nnc1C(=O)O] | 5-((2-methoxyphenyl)thio)-1H-1,2,3-triazole-4-carboxylic acid | $C_{10}H_9N_3O_3S$ | 251.26 |
| I-007 | 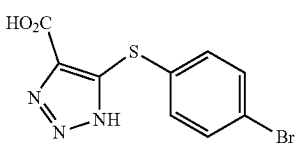 [SMILES: O=C(O)c1nn[nH]c1Sc1ccc(Br)cc1] | 5-((4-bromophenyl)thio)-1H-1,2,3-triazole-4-carboxylic acid | $C_9H_6BrN_3O_2S$ | 300.13 |
| I-008 | 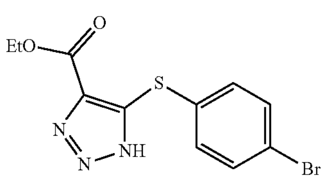 [SMILES: CCOC(=O)c1nn[nH]c1Sc1ccc(Br)cc1] | Ethyl 5-((4-bromophenyl)thio)-1H-1,2,3-triazole-4-carboxylate | $C_{11}H_{10}BrN_3O_2S$ | 328.18 |
| I-009 | 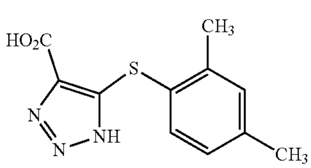 [SMILES: Cc1ccc(Sc2[nH]nnc2C(=O)O)c(C)c1] | 5-((2,4-dimethylphenyl)thio)-1H-1,2,3-triazole-4-carboxylic acid | $C_{11}H_{11}N_3O_2S$ | 249.29 |
| I-010 | 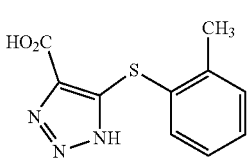 | 5-(o-tolylthio)-1H-1,2,3-triazole-4-carboxylic acid | $C_{10}H_9N_3O_2S$ | 235.26 |

TABLE 1-continued

Example compounds.

| Ex. No. | Structure | IUPAC Name | Chemical Formula | MW (g/mol) |
|---|---|---|---|---|
| I-011 | 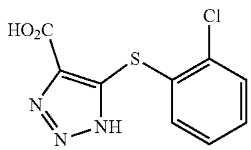 [SMILES: O=C(O)c1nn[nH]c1Sc1ccccc1Cl] | 5-((2-chlorophenyl)thio)-1H-1,2,3-triazole-4-carboxylic acid | $C_9H_6ClN_3O_2S$ | 255.68 |
| I-012 | 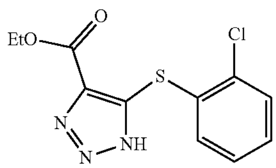 [SMILES: CCOC(=O)c1nn[nH]c1Sc1ccccc1Cl] | Ethyl 5-((2-chlorophenyl)thio)-1H-1,2,3-triazole-4-carboxylate | $C_9H_6ClN_3O_2S$ | 255.68 |
| I-013 | 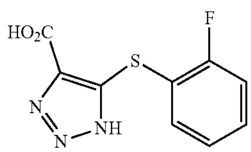 [SMILES: O=C(O)c1nn[nH]c1Sc1ccccc1F] | 5-((2-fluorophenyl)thio)-1H-1,2,3-triazole-4-carboxylic acid | $C_9H_6FN_3O_2S$ | 239.22 |
| I-014 | 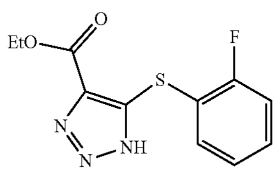 [SMILES: CCOC(=O)c1nn[nH]c1Sc1ccccc1F] | Ethyl 5-((2-fluorophenyl)thio)-1H-1,2,3-triazole-4-carboxylate | $C_{11}H_{10}FN_3O_2S$ | 267.28 |
| I-015 | 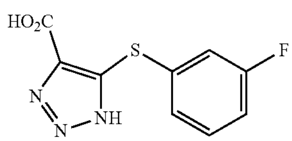 [SMILES: O=C(O)c1nn[nH]c1Sc1cccc(F)c1] | 5-((3-fluorophenyl)thio)-1H-1,2,3-triazole-4-carboxylic acid | $C_9H_6FN_3O_2S$ | 239.22 |
| I-016 | 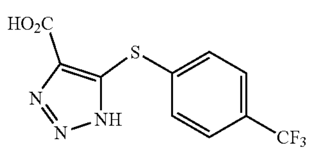 | 5-((4-(trifluoromethyl)phenyl)thio)-1H-1,2,3-triazole-4-carboxylic acid | $C_{10}H_6F_3N_3O_2S$ | 289.23 |
| I-017 | 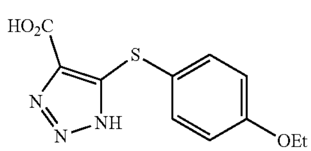 | 5-((4-ethoxyphenyl)thio)-1H-1,2,3-triazole-4-carboxylic acid | $C_{11}H_{11}N_3O_3S$ | 265.29 |
| I-018 | 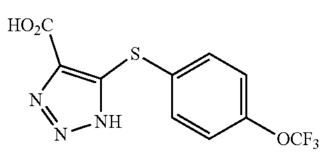 | 5-((4-(trifluoromethoxy)phenyl)thio)-1H-1,2,3-triazole-4-carboxylic acid | $C_{10}H_6F_3N_3O_3S$ | 305.23 |
| I-019 | 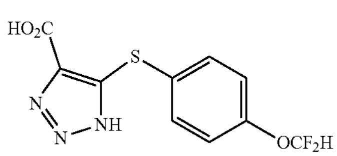 | 5-((4-(difluoromethoxy)phenyl)thio)-1H-1,2,3-triazole-4-carboxylic acid | $C_{10}H_7F_2N_3O_3S$ | 287.24 |

TABLE 1-continued

Example compounds.

| Ex. No. | Structure | IUPAC Name | Chemical Formula | MW (g/mol) |
|---|---|---|---|---|
| I-020 | 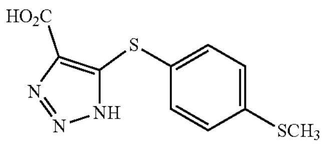 | 5-((4-(methylthio)phenyl)thio)-1H-1,2,3-triazole-4-carboxylic acid | $C_{10}H_9N_3O_2S_2$ | 267.32 |
| I-021 | 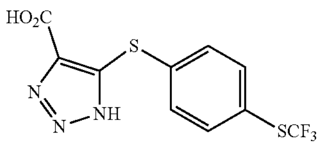 | 5-((4-((trifluoromethyl)thio)phenyl)thio)-1H-1,2,3-triazole-4-carboxylic acid | $C_{10}H_6F_3N_3O_2S_2$ | 321.29 |
| I-022 | 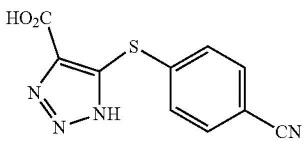 [SMILES: N#Cc1ccc(Sc2[nH]nnc2C(=O)O)cc1] | 5-((4-cyanophenyl)thio)-1H-1,2,3-triazole-4-carboxylic acid | $C_{10}H_6N_4O_2S$ | 246.24 |
| I-023 | 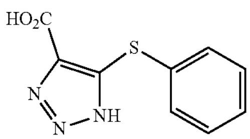 [SMILES: O=C(O)c1nn[nH]c1Sc1ccccc1] | 5-(phenylthio)-1H-1,2,3-triazole-4-carboxylic acid | $C_9H_7N_3O_2S$ | 221.23 |
| I-024 | 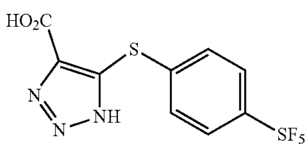 | 5-((4-(pentafluoro-$\lambda^6$-sulfaneyl)phenyl)thio)-1H-1,2,3-triazole-4-carboxylic acid | $C_9H_6F_5N_3O_2S_2$ | 347.28 |
| I-025 | 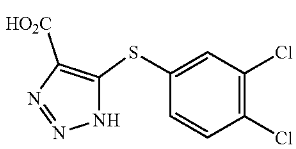 [SMILES: O=C(O)c1nn[nH]c1Sc1ccc(Cl)c(Cl)c1] | 5-((3,4-dichlorophenyl)thio)-1H-1,2,3-triazole-4-carboxylic acid | $C_9H_5Cl_2N_3O_2S$ | 290.12 |
| I-026 | 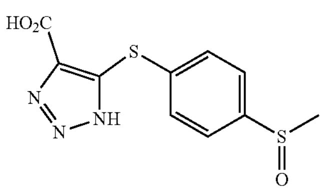 [SMILES: CS(=O)c1ccc(Sc2[nH]nnc2C(=O)O)cc1] | 5-((4-(methylsulfinyl)phenyl)thio)-1H-1,2,3-triazole-4-carboxylic acid | $C_{10}H_9N_3O_3S_2$ | 283.32 |
| I-027 | 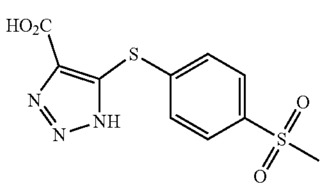 [SMILES: CS(=O)(=O)c1ccc(Sc2[nH]nnc2C(=O)O)cc1] | 5-((4-(methylsulfonyl)phenyl)thio)-1H-1,2,3-triazole-4-carboxylic acid | $C_{10}H_9N_3O_4S_2$ | 299.32 |
| I-028 | 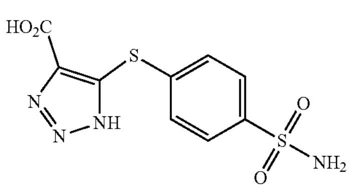 [SMILES: NS(=O)(=O)c1ccc(Sc2[nH]nnc2C(=O)O)cc1] | 5-((4-sulfamoylphenyl)thio)-1H-1,2,3-triazole-4-carboxylic acid | $C_9H_8N_4O_4S_2$ | 300.31 |

TABLE 1-continued

Example compounds.

| Ex. No. | Structure | IUPAC Name | Chemical Formula | MW (g/mol) |
|---|---|---|---|---|
| I-029 | 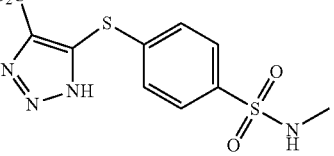 | 5-((4-(N-methylsulfamoyl)phenyl)thio)-1H-1,2,3-triazole-4-carboxylic acid | $C_{10}H_{10}N_4O_4S_2$ | 314.33 |
| I-030 | 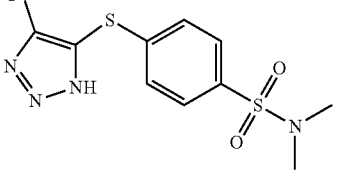 | 5-((4-(N,N-dimethylsulfamoyl)phenyl)thio)-1H-1,2,3-triazole-4-carboxylic acid | $C_{11}H_{12}N_4O_4S_2$ | 328.36 |
| I-031 | 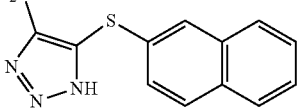 | 5-(naphthalen-2-ylthio)1H-1,2,3-triazole-4-carboxylic acid | $C_{13}H_9N_3O_2S$ | 271.29 |
| I-032 | 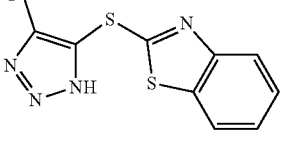 | 5-(benzo[d]thiazol-2-ylthio)-1H-1,2,3-triazole-4-carboxylic acid | $C_{10}H_6N_4O_2S_2$ | 278.30 |
| I-033 | 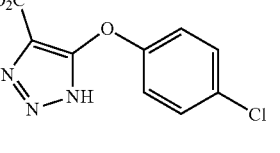 | 5-(4-chlorophenoxy)-1H-1,2,3-triazole-4-carboxylic acid | $C_9H_6ClN_3O_3$ | 239.62 |
| I-034 | 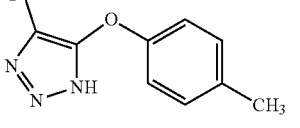 | 5-(p-tolyloxy)-1H-1,2,3-triazole-4-carboxylic acid | $C_{10}H_9N_3O_3$ | 219.20 |
| I-035 | 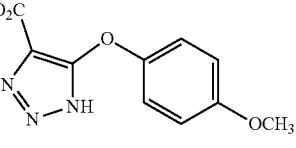 | 5-(4-methoxyphenoxy)-1H-1,2,3-triazole-4-carboxylic acid | $C_{10}H_9N_3O_4$ | 235.20 |
| I-036 | 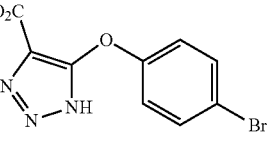 | 5-(4-bromophenoxy)-1H-1,2,3-triazole-4-carboxylic acid | $C_9H_6BrN_3O_3$ | 284.07 |
| I-037 | 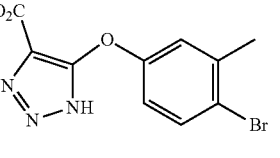 | 5-(4-bromo-3-methylphenoxy)-1H-1,2,3-triazole-4-carboxylic acid | $C_{10}H_8BrN_3O_3$ | 298.10 |

TABLE 1-continued

Example compounds.

| Ex. No. | Structure | IUPAC Name | Chemical Formula | MW (g/mol) |
|---|---|---|---|---|
| I-038 | 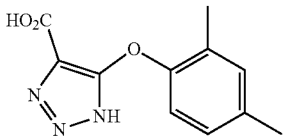 [SMILES: Cc1ccc(Oc2[nH]nnc2C(=O)O)c(C)c1] | 5-(2,4-dimethylphenoxy)-1H-1,2,3-triazole-4-carboxylic acid | $C_{11}H_{11}N_3O_3$ | 233.23 |
| I-039 | 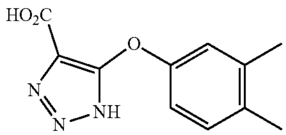 [SMILES: Cc1ccc(Oc2[nH]nnc2C(=O)O)cc1C] | 5-(3,4-dimethylphenoxy)-1H-1,2,3-triazole-4-carboxylic acid | $C_{11}H_{11}N_3O_3$ | 233.23 |
| I-040 | 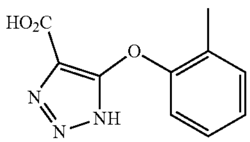 [SMILES: Cc1ccccc1Oc1[nH]nnc1C(=O)O] | 5-(o-tolyloxy)-1H-1,2,3-triazole-4-carboxylic acid | $C_{10}H_9N_3O_3$ | 219.20 |
| I-041 | 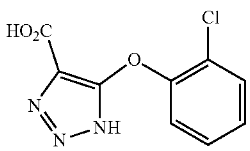 [SMILES: O=C(O)c1nn[nH]c1Oc1ccccc1F] | 5-(2-chlorophenoxy)-1H-1,2,3-triazole-4-carboxylic acid | $C_9H_6ClN_3O_3$ | 239.62 |
| I-042 | 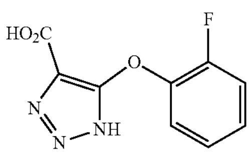 | 5-(2-chlorophenoxy)-1H-1,2,3-triazole-4-carboxylic acid | $C_9H_6FN_3O_3$ | 223.16 |
| I-043 | 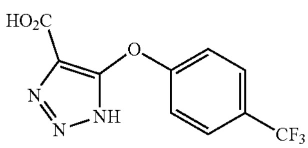 | 5-(4-(trifluoromethyl)phenoxy)-1H-1,2,3-triazole-4-carboxylic acid | $C_{10}H_6F_3N_3O_3$ | 273.17 |
| I-044 | 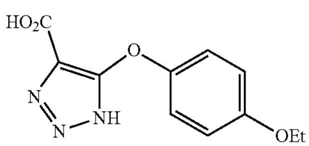 [SMILES: CCOc1ccc(Oc2[nH]nnc2C(=O)O)cc1] | 5-(4-ethoxyphenoxy)-1H-1,2,3-triazole-4-carboxylic acid | $C_{11}H_{11}N_3O_4$ | 249.23 |
| I-045 | 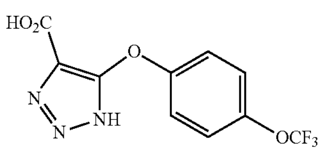 [SMILES: CSc1ccc(Oc2[nH]nnc2C(=O)O)cc1] | 5-(4-(trifluoromethoxy)phenoxy)-1H-1,2,3-triazole-4-carboxylic acid | $C_{10}H_6F_3N_3O_4$ | 289.17 |
| I-046 | 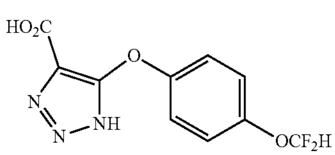 | 5-(4-(difluoromethoxy)phenoxy)-1H-1,2,3-triazole-4-carboxylic acid | $C_{10}H_7F_2N_3O_4$ | 271.18 |
| I-047 | 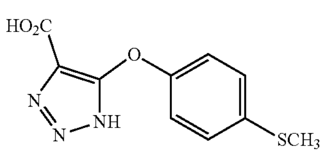 | 5-(4-(methylthio)phenoxy)-1H-1,2,3-triazole-4-carboxylic acid | $C_{10}H_9N_3O_3S$ | 251.26 |

TABLE 1-continued

Example compounds.

| Ex. No. | Structure | IUPAC Name | Chemical Formula | MW (g/mol) |
|---|---|---|---|---|
| I-048 | 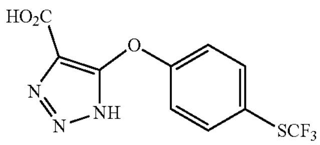 | 5-(4-((trifluoromethyl)thio)phenoxy)-1H-1,2,3-triazole-4-carboxylic acid | $C_{10}H_6F_3N_3O_3S$ | 305.23 |
| I-049 | 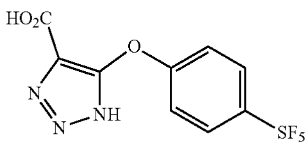 | 5-((4-(pentafluoro-$\lambda^6$-sulfaneyl)phenoxy)-1H-1,2,3-triazole-4-carboxylic acid | $C_9H_6F_5N_3O_3S$ | 331.22 |
| I-050 | 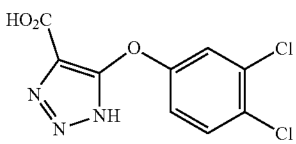 [SMILES: O=C(O)c1nn[nH]c1Oc1ccc(Cl)c(Cl)c1] | 5-(3,4-dichlorophenoxy)-1H-1,2,3-triazole-4-carboxylic acid | $C_9H_5Cl_2N_3O_3$ | 274.06 |
| I-051 | 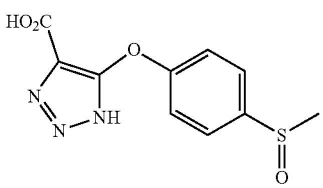 [SMILES: CS(=O)c1ccc(Oc2[nH]nnc2C(=O)O)cc1] | 5-(4-(methylsulfinyl)phenoxy)-1H-1,2,3-triazole-4-carboxylic acid | $C_{10}H_9N_3O_4S$ | 267.26 |
| I-052 | 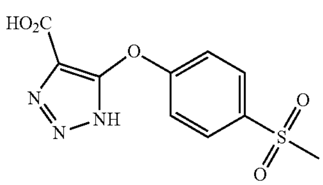 [SMILES: CS(=O)(=O)c1ccc(Oc2[nH]nnc2C(=O)O)cc1] | 5-(4-(methylsulfonyl)phenoxy)-1H-1,2,3-triazole-4-carboxylic acid | $C_{10}H_9N_3O_5S$ | 283.26 |
| I-053 | 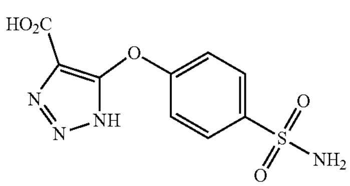 [SMILES: NS(=O)(=O)c1ccc(Oc2[nH]nnc2C(=O)O)cc1] | 5-(4-sulfamoylphenoxy)-1H-1,2,3-triazole-4-carboxylic acid | $C_9H_8N_4O_5S$ | 284.25 |
| I-054 | 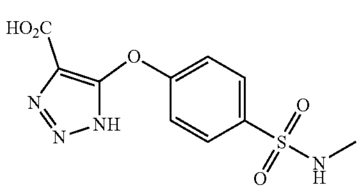 [SMILES: CNS(=O)(=O)c1ccc(Oc2[nH]nnc2C(=O)O)cc1] | 5-(4-(N-methylsulfamoyl)phenoxy)-1H-1,2,3-triazole-4-carboxylic acid | $C_{10}H_{10}N_4O_5S$ | 298.27 |
| I-055 | 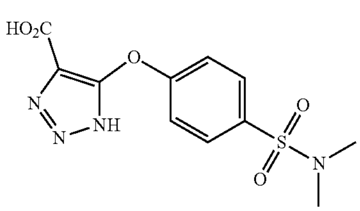 [SMILES: CN(C)S(=O)(=O)c1ccc(Oc2[nH]nnc2C(=O)O)cc1] | 5-(4-(N,N-dimethylsulfamoyl)phenoxy)-1H-1,2,3-triazole-4-carboxylic acid | $C_{11}H_{12}N_4O_5S$ | 312.30 |

TABLE 1-continued

Example compounds.

| Ex. No. | Structure | IUPAC Name | Chemical Formula | MW (g/mol) |
|---|---|---|---|---|
| I-056 | 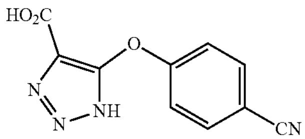 [SMILES: N#Cc1ccc(Oc2[nH]nnc2C(=O)O)cc1] | 5-(4-cyanophenoxy)-1H-1,2,3-triazole-4-carboxylic acid | $C_{10}H_6N_4O_3$ | 230.18 |
| I-057 | 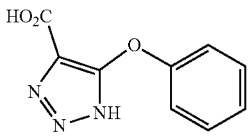 [SMILES: O=C(O)c1nn[nH]c1Oc1ccccc1] | 5-phenoxy-1H-1,2,3-triazole-4-carboxylic acid | $C_9H_7N_3O_3$ | 205.17 |
| I-058 | 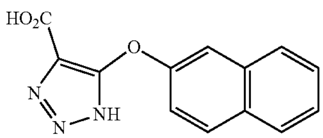 | 5-(naphthalen-2-yloxy)-1H-1,2,3-triazole-4-carboxylic acid | $C_{13}H_9N_3O_3$ | 255.23 |
| I-059 | 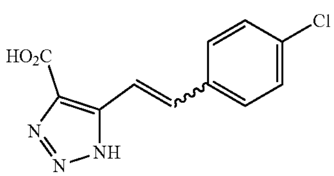 | 5-(4-chlorostyryl)-1H-1,2,3-triazole-4-carboxylic acid | $C_{11}H_8ClN_3O_2$ | 249.65 |
| I-060 | 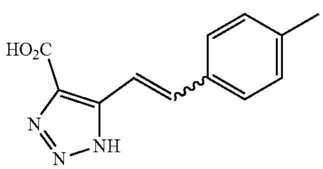 [SMILES: Cc1ccc(C=Cc2[nH]nnc2C(=O)O)cc1] | 5-(4-methylstyryl)-1H-1,2,3-triazole-4-carboxylic acid | $C_{12}H_{11}N_3O_2$ | 229.24 |
| I-061 | 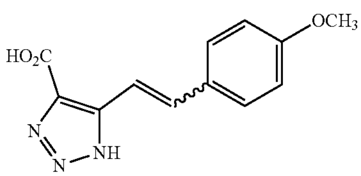 [SMILES: COc1ccc(C=Cc2[nH]nnc2C(=O)O)cc1] | 5-(4-methoxystyryl)-1H-1,2,3-triazole-4-carboxylic acid | $C_{12}H_{11}N_3O_3$ | 245.24 |
| I-062 | 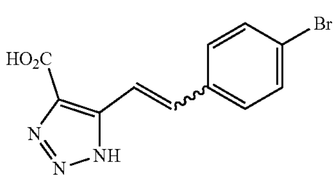 [SMILES: O=C(O)c1nn[nH]c1C=Cc1ccc(Br)cc1] | 5-(4-bromostyryl)-1H-1,2,3-triazole-4-carboxylic acid | $C_{11}H_8BrN_3O_2$ | 294.11 |
| I-063 | 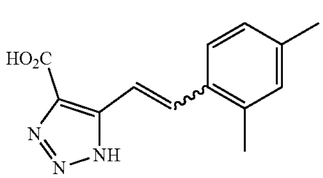 [SMILES: Cc1ccc(C=Cc2[nH]nnc2C(=O)O)c(C)c1] | 5-(2,4-dimethylstyryl)-1H-1,2,3-triazole-4-carboxylic acid | $C_{13}H_{13}N_3O_2$ | 243.27 |
| I-064 | 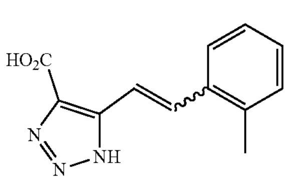 [SMILES: Cc1ccccc1C=Cc1[nH]nnc1C(=O)O] | 5-(2-methylstyryl)-1H-1,2,3-triazole-4-carboxylic acid | $C_{12}H_{11}N_3O_2$ | 229.24 |

TABLE 1-continued

Example compounds.

| Ex. No. | Structure | IUPAC Name | Chemical Formula | MW (g/mol) |
|---|---|---|---|---|
| I-065 | 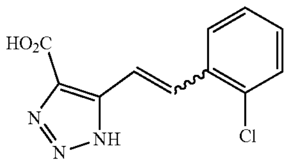 [SMILES: O=C(O)c1nn[nH]c1C=Cc1ccccc1Cl] | 5-(2-chlorostyryl)-1H-1,2,3-triazole-4-carboxylic acid | $C_{11}H_8ClN_3O_2$ | 249.65 |
| I-066 | 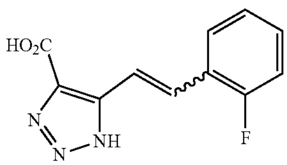 | 5-(2-fluorostyryl)-1H-1,2,3-triazole-4-carboxylic acid | $C_{11}H_8FN_3O_2$ | 233.20 |
| I-067 | 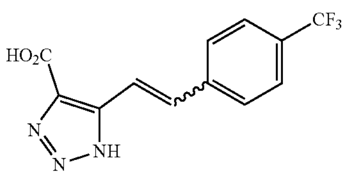 | 5-(4-(trifluoromethyl)styryl)-1H-1,2,3-triazole-4-carboxylic acid | $C_{12}H_8F_3N_3O_2$ | 283.21 |
| I-068 | 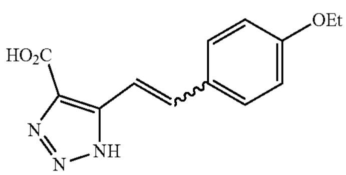 [SMILES: CCOc1ccc(C=Cc2[nH]nnc2C(=O)O)cc1] | 5-(4-ethoxystyryl)-1H-1,2,3-triazole-4-carboxylic acid | $C_{13}H_{13}N_3O_3$ | 259.27 |
| I-069 | 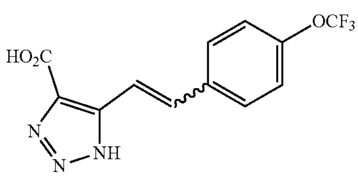 [SMILES: O=C(O)c1nn[nH]c1C=Cc1ccc(OC(F)(F)F)cc1] | 5-(4-(trifluoromethoxy)styryl)-1H-1,2,3-triazole-4-carboxylic acid | $C_{12}H_8F_3N_3O_3$ | 299.21 |
| I-070 | 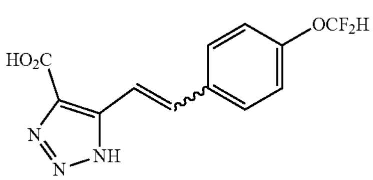 | 5-(4-(difluoromethoxy)styryl)-1H-1,2,3-triazole-4-carboxylic acid | $C_{12}H_9F_2N_3O_3$ | 281.22 |
| I-071 | 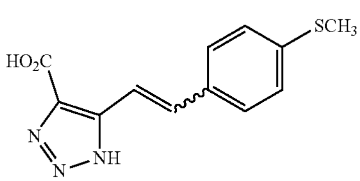 | 5-(4-(methylthio)styryl)-1H-1,2,3-triazole-4-carboxylic acid | $C_{12}H_{11}N_3O_2S$ | 261.30 |
| I-072 | 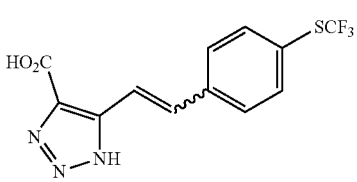 | 5-(4-((trifluoromethyl)thio)styryl)-1H-1,2,3-triazole-4-carboxylic acid | $C_{12}H_8F_3N_3O_2S$ | 315.27 |

TABLE 1-continued

Example compounds.

| Ex. No. | Structure | IUPAC Name | Chemical Formula | MW (g/mol) |
|---|---|---|---|---|
| I-073 | 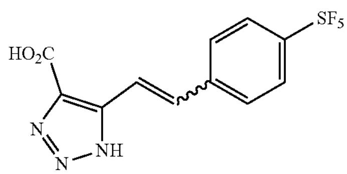 | 5-((4-(pentafluoro-λ⁶-sulfaneyl)phenoxy)-1H-1,2,3-triazole-4-carboxylic acid | $C_{11}H_8F_5N_3O_2S$ | 341.26 |
| I-074 | 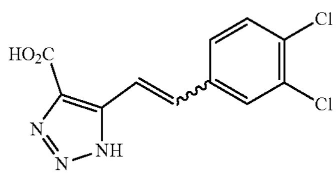 [SMILES: O=C(O)c1nn[nH]c1C=Cc1ccc(Cl)c(Cl)c1] | 5-(3,4-dichlorostyryl)-1H-1,2,3-triazole-4-carboxylic acid | $C_{11}H_7Cl_2N_3O_2$ | 284.10 |
| I-075 | 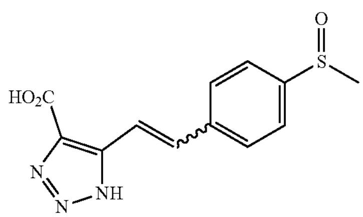 [SMILES: CS(=O)c1ccc(C=Cc2[nH]nnc2C(=O)O)cc1] | 5-(4-(methylsulfinyl)styryl)-1H-1,2,3-triazole-4-carboxylic acid | $C_{12}H_{11}N_3O_3S$ | 277.30 |
| I-076 | 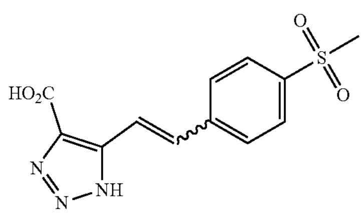 [SMILES: CS(=O)(=O)c1ccc(C=Cc2[nH]nnc2C(=O)O)cc1] | 5-(4-(methylsulfonyl)styryl)-1H-1,2,3-triazole-4-carboxylic acid | $C_{12}H_{11}N_3O_4S$ | 293.30 |
| I-077 | 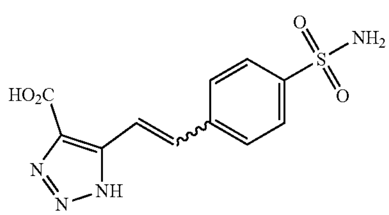 [SMILES: NS(=O)(=O)c1ccc(C=Cc2[nH]nnc2C(=O)O)cc1] | 5-(4-sulfamoylstyryl)-1H-1,2,3-triazole-4-carboxylic acid | $C_{11}H_{10}N_4O_4S$ | 294.29 |
| I-078 | 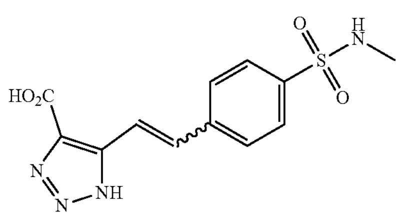 [SMILES: CNS(=O)(=O)c1ccc(C=Cc2[nH]nnc2C(=O)O)cc1] | 5-(4-(N-methylsulfamoyl)styryl)-1H-1,2,3-triazole-4-carboxylic acid | $C_{12}H_{12}N_4O_4S$ | 308.31 |
| I-079 | 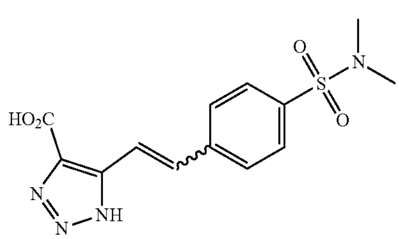 [SMILES: CN(C)S(=O)(=O)c1ccc(C=Cc2[nH]nnc2C(=O)O)cc1] | 5-(4-(N,N-dimethylsulfamoyl)styryl)-1H-1,2,3-triazole-4-carboxylic acid | $C_{13}H_{14}N_4O_4S$ | 322.34 |

TABLE 1-continued

Example compounds.

| Ex. No. | Structure | IUPAC Name | Chemical Formula | MW (g/mol) |
|---|---|---|---|---|
| I-080 | 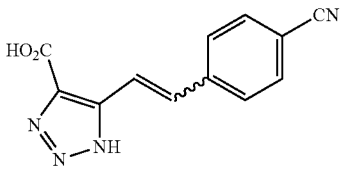 [SMILES: N#Cc1ccc(C=Cc2[nH]nnc2C(=O)O)cc1] | 5-(4-cyanostyryl)-1H-1,2,3-triazole-4-carboxylic acid | $C_{12}H_8N_4O_2$ | 240.22 |
| I-081 | 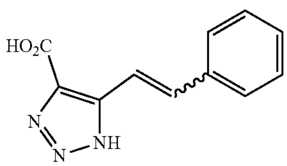 [SMILES: O=C(O)c1nn[nH]c1C=Cc1ccccc1] | 5-styryl-1H-1,2,3-triazole-4-carboxylic acid | $C_{11}H_9N_3O_2$ | 215.21 |
| I-082 | 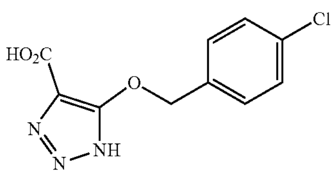 [SMILES: O=C(O)c1nn[nH]c1OCc1ccc(Cl)cc1] | 5-((4-chlorobenzyl)oxy)-1H-1,2,3-triazole-4-carboxylic acid | $C_{10}H_8ClN_3O_3$ | 253.64 |
| I-083 | 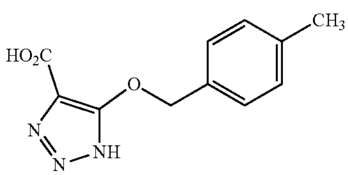 [SMILES: Cc1ccc(COc2[nH]nnc2C(=O)O)cc1] | 5-((4-methylbenzyl)oxy)-1H-1,2,3-triazole-4-carboxylic acid | $C_{11}H_{11}N_3O_3$ | 233.23 |
| I-084 | 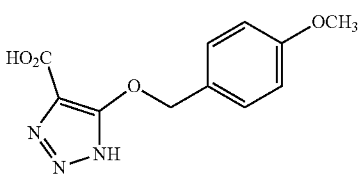 [SMILES: COc1ccc(COc2[nH]nnc2C(=O)O)cc1] | 5-((4-methoxybenzyl)oxy)-1H-1,2,3-triazole-4-carboxylic acid | $C_{11}H_{11}N_3O_4$ | 249.23 |
| I-085 | 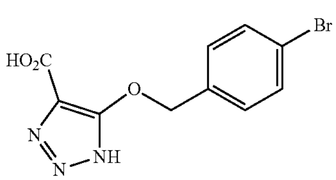 [SMILES: O=C(O)c1nn[nH]c1OCc1ccc(Br)cc1] | 5-((4-bromobenzyl)oxy)-1H-1,2,3-trazole-4-carboxylic acid | $C_{10}H_8BrN_3O_3$ | 298.10 |
| I-086 | 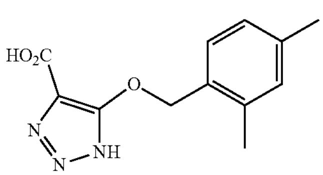 [SMILES: Cc1ccc(COc2[nH]nnc2C(=O)O)c(C)c1] | 5-((2,4-dimethylbenzyl)oxy)-1H-1,2,3-triazole-4-carboxylic acid | $C_{12}H_{13}N_3O_3$ | 247.25 |
| I-087 | 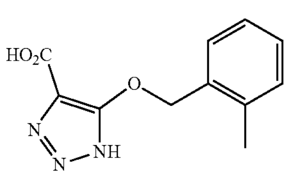 [SMILES: Cc1ccccc1COc1[nH]nnc1C(=O)O] | 5-((2-methylbenzyl)oxy)-1H-1,2,3-triazole-4-carboxylic acid | $C_{11}H_{11}N_3O_3$ | 233.23 |

TABLE 1-continued

Example compounds.

| Ex. No. | Structure | IUPAC Name | Chemical Formula | MW (g/mol) |
|---|---|---|---|---|
| I-088 | 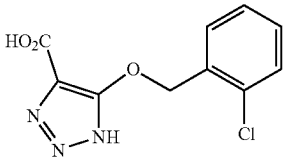 | 5-((2-chlorobenzyl)oxy)-1H-1,2,3-triazole-4-carboxylic acid | $C_{10}H_8ClN_3O_3$ | 253.64 |
| I-089 | 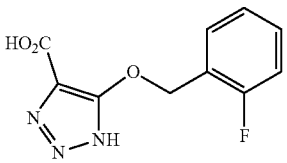 [SMILES: O=C(O)c1nn[nH]c1OCc1ccccc1F] | 5-((2-fluorobenzyl)oxy)-1H-1,2,3-triazole-4-carboxylic acid | $C_{10}H_8FN_3O_3$ | 237.19 |
| I-090 | 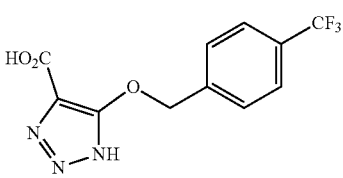 | 5-((4-(trifluoromethyl)benzyl)oxy)-1H-1,2,3-triazole-4-carboxylic acid | $C_{11}H_8F_3N_3O_3$ | 287.20 |
| I-091 | 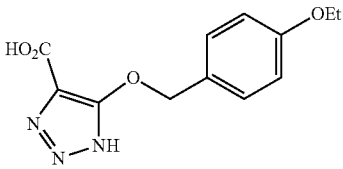 [SMILES: CCOc1ccc(COc2[nH]nnc2C(=O)O)cc1] | 5-((4-ethoxybenzyl)oxy)-1H-1,2,3-triazole-4-carboxylic acid | $C_{12}H_{13}N_3O_4$ | 263.25 |
| I-092 | 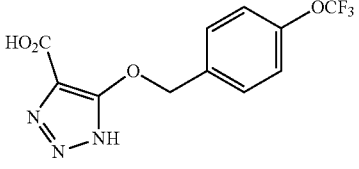 [SMILES: O=C(O)c1nn[nH]c1OCc1ccc(OC(F)(F)F)cc1] | 5-((4-(trifluoromethoxy)benzyl)oxy)-1H-1,2,3-triazole-4-carboxylic acid | $C_{11}H_8F_3N_3O_4$ | 303.20 |
| I-093 | 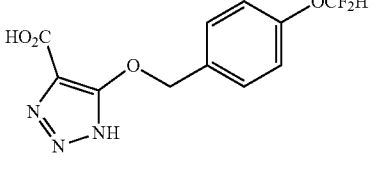 | 5-((4-(difluoromethoxy)benzyl)oxy)-1H-1,2,3-triazole-4-carboxylic acid | $C_{11}H_9F_2N_3O_4$ | 285.21 |
| I-094 | 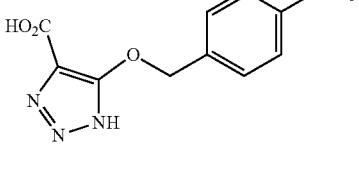 | 5-((4-(methylthio)benzyl)oxy)-1H-1,2,3-triazole-4-carboxylic acid | $C_{11}H_{11}N_3O_3S$ | 265.29 |
| I-095 | 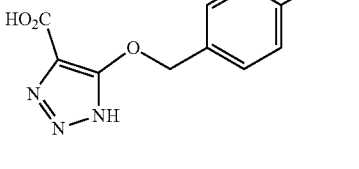 | 5-((4-((trifluoromethyl)thio)benzyl)oxy)-1H-1,2,3-triazole-4-carboxylic acid | $C_{11}H_8F_3N_3O_3S$ | 319.26 |

TABLE 1-continued

Example compounds.

| Ex. No. | Structure | IUPAC Name | Chemical Formula | MW (g/mol) |
|---|---|---|---|---|
| I-096 | 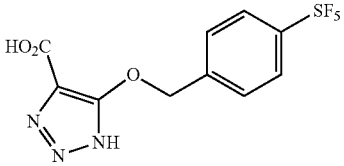 | 5-((4-(pentafluoro-λ⁶-sulfaneylbenzyl)oxy)-1H-1,2,3-triazole-4-carboxylic acid | $C_{10}H_8F_5N_3O_3S$ | 345.24 |
| I-097 | 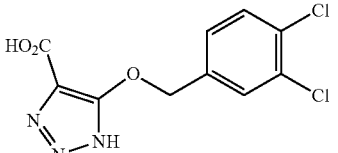 | 5-((3,4-dichlorobenzyl)oxy)-1H-1,2,3-triazole-4-carboxylic acid | $C_{10}H_7Cl_2N_3O_3$ | 288.08 |
| I-098 | 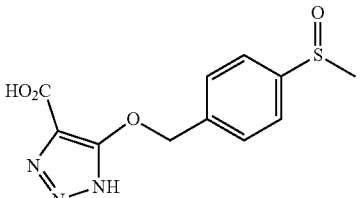 | 5-((4-(methylsulfinyl)benzyl)oxy)-1H-1,2,3-triazole-4-carboxylic acid | $C_{11}H_{11}N_3O_4S$ | 281.29 |
| I-099 | 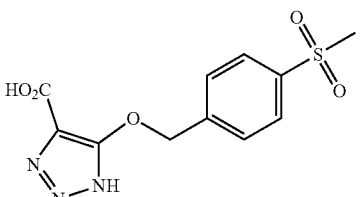 | 5-((4-(methylsulfonyl)benzyl)oxy)-1H-1,2,3-triazole-4-carboxylic acid | $C_{11}H_{11}N_3O_5S$ | 297.29 |
| I-100 | 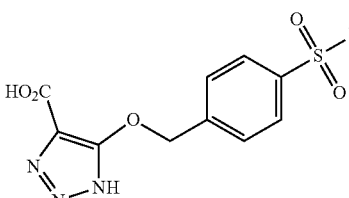 | 5-((4-sulfamoylbenzyl)oxy)-1H-1,2,3-triazole-4-carboxylic acid | $C_{10}H_{10}N_4O_5S$ | 298.27 |
| I-101 | 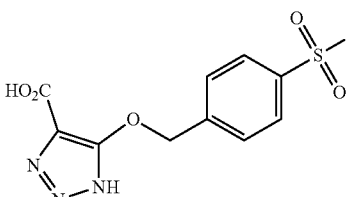 | 5-((4-(N-methylsulfamoyl)benzyl)oxy)-1H-1,2,3-triazole-4-carboxylic acid | $C_{11}H_{12}N_4O_5S$ | 312.30 |
| I-102 | 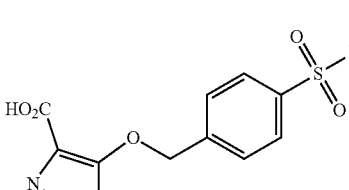 | 5-((4-(N,N-dimethylsulfamoyl)benzyl)oxy)-1H-1,2,3-triazole-4-carboxylic acid | $C_{12}H_{14}N_4O_5S$ | 326.33 |

TABLE 1-continued

Example compounds.

| Ex. No. | Structure | IUPAC Name | Chemical Formula | MW (g/mol) |
|---|---|---|---|---|
| I-103 | 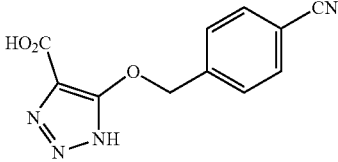 | 5-((4-cyanobenzyl)oxy)-1H-1,2,3-triazole-4-carboxylic acid | $C_{11}H_8N_4O_3$ | 244.21 |
| I-104 | 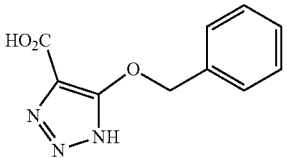 [SMILES: O=C(O)c1nn[nH]c1OCc1ccccc1] | 5-(benzyloxy)-1H-1,2,3-triazole-4-carboxylic acid | $C_{10}H_9N_3O_3$ | 219.20 |
| I-105 | 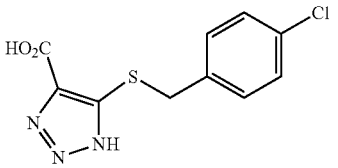 | 5-((4-chlorobenzyl)thio)-1H-1,2,3-triazole-4-carboxylic acid | $C_{10}H_8ClN_3O_2S$ | 269.70 |
| I-106 | 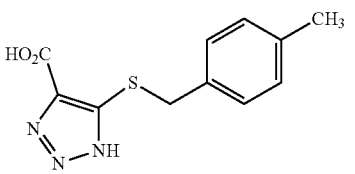 | 5-((4-methylbenzyl)thio)-1H-1,2,3-triazole-4-carboxylic acid | $C_{11}H_{11}N_3O_2S$ | 249.29 |
| I-107 | 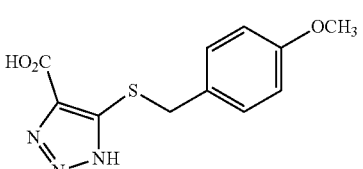 | 5-((4-methoxybenzyl)thio)-1H-1,2,3-triazole-4-carboxylic acid | $C_{11}H_{11}N_3O_3S$ | 265.29 |
| I-108 | 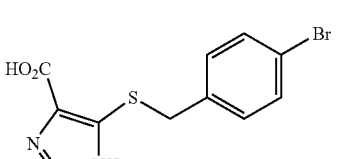 | 5-((4-bromobenzyl)thio)-1H-1,2,3-trazole-4-carboxylic acid | $C_{10}H_8BrN_3O_2S$ | 314.16 |
| I-109 | 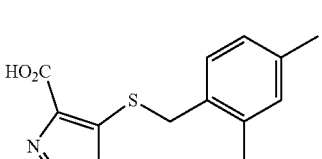 | 5-((2,4-dimethylbenzyl)thio)-1H-1,2,3-triazole-4-carboxylic acid | $C_{12}H_{13}N_3O_2S$ | 263.32 |
| I-110 | 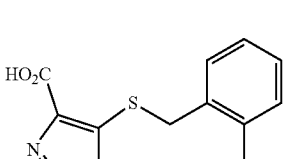 | 5-((2-methylbenzyl)thio)-1H-1,2,3-triazole-4-carboxylic acid | $C_{11}H_{11}N_3O_2S$ | 249.29 |

TABLE 1-continued

Example compounds.

| Ex. No. | Structure | IUPAC Name | Chemical Formula | MW (g/mol) |
|---|---|---|---|---|
| I-111 | 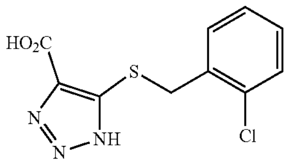 | 5-((2-chlorobenzyl)thio)-1H-1,2,3-triazole-4-carboxylic acid | $C_{10}H_8ClN_3O_2S$ | 269.70 |
| I-112 | 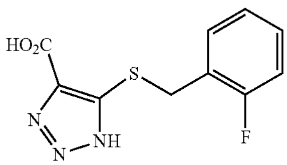 | 5-((2-fluorobenzyl)thio)-1H-1,2,3-triazole-4-carboxylic acid | $C_{10}H_8FN_3O_2S$ | 253.25 |
| I-113 | 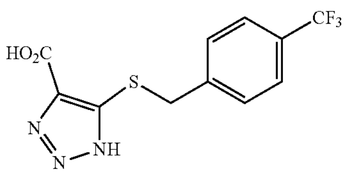 | 5-((4-(trifluoromethyl)benzyl)thio)-1H-1,2,3-triazole-4-carboxylic acid | $C_{11}H_8F_3N_3O_2S$ | 303.26 |
| I-114 | 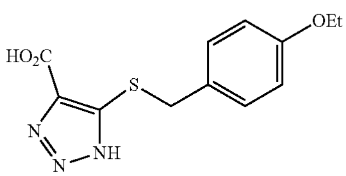 | 5-((4-ethoxybenzyl)thio)-1H-1,2,3-triazole-4-carboxylic acid | $C_{12}H_{13}N_3O_3S$ | 279.31 |
| I-115 | 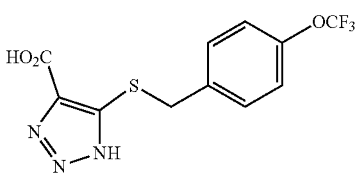 | 5-((4-(trifluoromethoxy)benzyl)thio)-1H-1,2,3-triazole-4-carboxylic acid | $C_{11}H_8F_3N_3O_3S$ | 319.26 |
| I-116 | 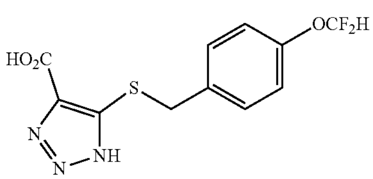 | 5-((4-(difluoromethoxy)benzyl)thio)-1H-1,2,3-triazole-4-carboxylic acid | $C_{11}H_9F_2N_3O_3S$ | 301.27 |
| I-117 | 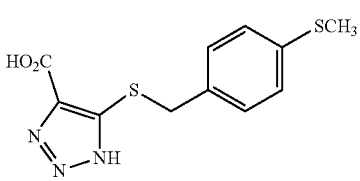 [SMILES: COc1ccc(CSc2[nH]nnc2C(=O)O)cc1] | 5-((4-(methylthio)benzyl)thio)-1H-1,2,3-triazole-4-carboxylic acid | $C_{11}H_{11}N_3O_2S_2$ | 281.35 |
| I-118 | 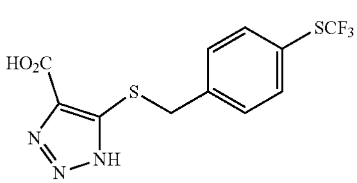 [SMILES: O=C(O)c1nn[nH]c1SCc1ccc(OC(F)(F)F)cc1] | 5-((4-((trifluoromethyl)thio)benzyl)thio)-1H-1,2,3-triazole-4-carboxylic acid | $C_{11}H_8F_3N_3O_2S_2$ | 335.32 |

TABLE 1-continued

Example compounds.

| Ex. No. | Structure | IUPAC Name | Chemical Formula | MW (g/mol) |
|---|---|---|---|---|
| I-119 | 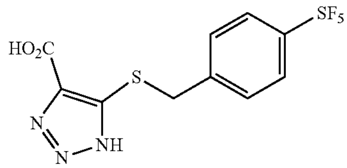 | 5-((4-(pentafluoro-$\lambda^6$-sulfaneylbenzyl)thio)-1H-1,2,3-triazole-4-carboxylic acid | $C_{10}H_8F_5N_3O_2S_2$ | 361.31 |
| I-120 | 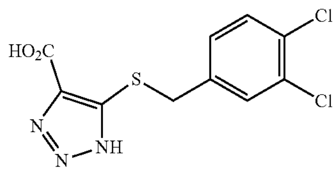 [SMILES: O=C(O)c1nn[nH]c1SCc1ccc(Cl)c(Cl)c1] | 5-((3,4-dichlorobenzyl)thio)-1H-1,2,3-triazole-4-carboxylic acid | $C_{10}H_7Cl_2N_3O_2S$ | 304.15 |
| I-121 | 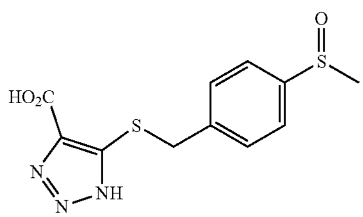 [SMILES: CS(=O)c1ccc(CSc2[nH]nnc2C(=O)O)cc1] | 5-((4-(methylsulfinyl)benzyl)thio)-1H-1,2,3-triazole-4-carboxylic acid | $C_{11}H_{11}N_3O_3S_2$ | 297.35 |
| I-122 | 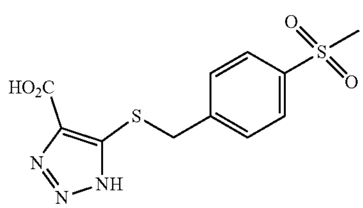 [SMILES: CS(=O)(=O)c1ccc(CSc2[nH]nnc2C(=O)O)cc1] | 5-((4-(methylsulfonyl)benzyl)thio)-1H-1,2,3-triazole-4-carboxylic acid | $C_{11}H_{11}N_3O_4S_2$ | 313.35 |
| I-123 | 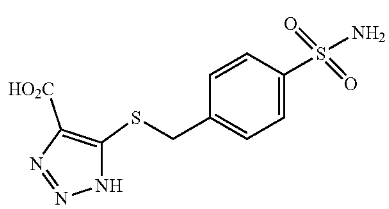 [SMILES: NS(=O)(=O)c1ccc(CSc2[nH]nnc2C(=O)O)cc1] | 5-((4-sulfamoylbenzyl)thio)-1H-1,2,3-triazole-4-carboxylic acid | $C_{10}H_{10}N_4O_4S_2$ | 314.33 |
| I-124 | 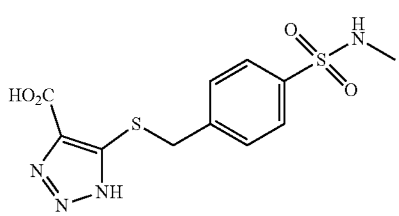 [SMILES: CNS(=O)(=O)c1ccc(CSc2[nH]nnc2C(=O)O)cc1] | 5-((4-(N-methylsulfamoyl)benzyl)thio)-1H-1,2,3-triazole-4-carboxylic acid | $C_{11}H_{12}N_4O_4S_2$ | 328.36 |
| I-125 | 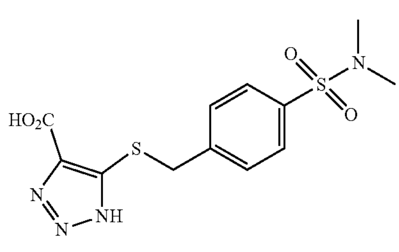 [SMILES: CN(C)S(=O)(=O)c1ccc(CSc2[nH]nnc2C(=O)O)cc1] | 5-((4-(N,N-dimethylsulfamoyl)benzyl)thio)-1H-1,2,3-triazole-4-carboxylic acid | $C_{12}H_{14}N_4O_4S_2$ | 342.39 |

TABLE 1-continued

Example compounds.

| Ex. No. | Structure | IUPAC Name | Chemical Formula | MW (g/mol) |
|---|---|---|---|---|
| I-126 | 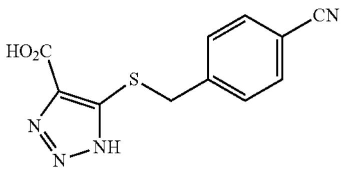 [SMILES: N#Cc1ccc(CSc2[nH]nnc2C(=O)O)cc1] | 5-((4-cyanobenzyl)thio)-1H-1,2,3-triazole-4-carboxylic acid | $C_{11}H_8N_4O_2S$ | 260.27 |
| I-127 | 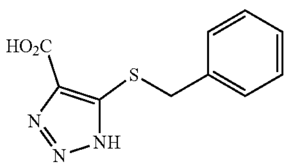 [SMILES: O=C(O)c1nn[nH]c1SCc1ccccc1] | 5-(benzylthio)-1H-1,2,3-triazole-4-carboxylic acid | $C_{10}H_9N_3O_2S$ | 235.26 |
| I-128 | 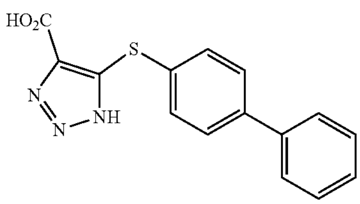 [SMILES: O=C(O)c1nn[nH]c1Sc1ccc(-c2ccccc2)cc1] | 5-([1,1'-biphenyl]-4-ylthio)-1H-1,2,3-triazole-4-carboxylic acid | $C_{15}H_{11}N_3O_2S$ | 297.33 |
| I-129 | 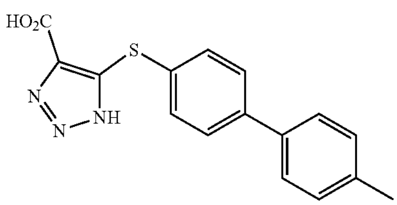 | 5-((4'-methyl-[1,1'-biphenyl]-4-yl)thio)-1H-1,2,3-triazole-4-carboxylic acid | $C_{16}H_{13}N_3O_2S$ | 311.36 |
| I-130 | 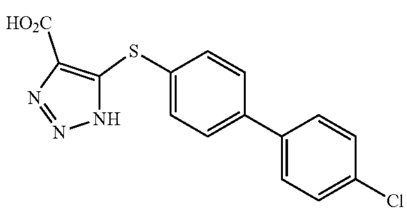 | 5-((4'-chloro-[1,1'-biphenyl]-4-yl)thio)-1H-1,2,3-triazole-4-carboxylic acid | $C_{15}H_{10}ClN_3O_2S$ | 331.77 |
| I-131 | 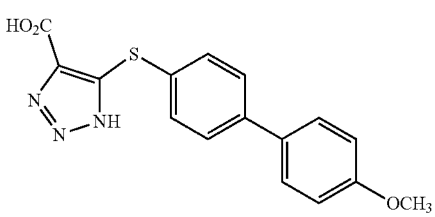 [SMILES: COc1ccc(-c2ccc(Sc3[nH]nnc3C(=O)O)cc2)cc1] | 5-((4'-methoxy-[1,1'-biphenyl]-4-yl)thio)-1H-1,2,3-triazole-4-carboxylic acid | $C_{16}H_{13}N_3O_3S$ | 327.36 |
| I-132 | 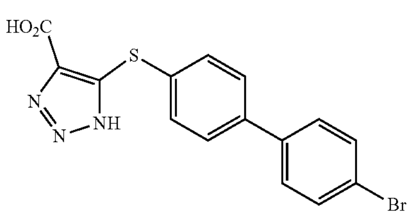 | 5-((4'-bromo-[1,1'-biphenyl]-4-yl)thio)-1H-1,2,3-triazole-4-carboxylic acid | $C_{15}H_{10}BrN_3O_2S$ | 376.23 |

TABLE 1-continued

Example compounds.

| Ex. No. | Structure | IUPAC Name | Chemical Formula | MW (g/mol) |
|---|---|---|---|---|
| I-133 | 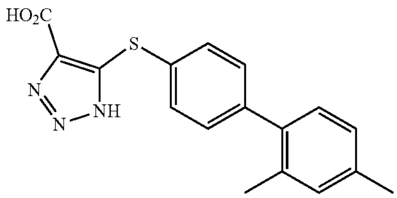 | 5-((2',4'-dimethyl-[1,1'-biphenyl]-4-yl)thio)-1H-1,2,3-triazole-4-carboxylic acid | $C_{17}H_{15}N_3O_2S$ | 325.39 |
| I-134 | 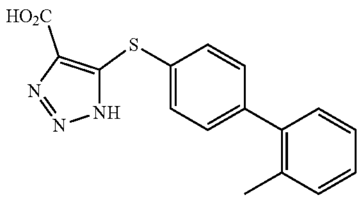 [SMILES: Cc1ccccc1-c1ccc(Sc2[nH]nnc2C(=O)O)cc1] | 5-((2'-methyl-[1,1'-biphenyl]-4-yl)thio)-1H-1,2,3-triazole-4-carboxylic acid | $C_{16}H_{13}N_3O_2S$ | 311.36 |
| I-135 | 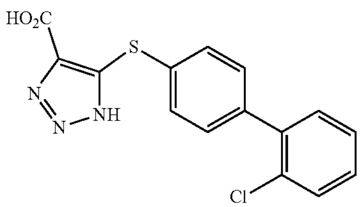 [SMILES: O=C(O)c1nn[nH]c1Sc1ccc(-c2ccccc2Cl)cc1] | 5-((2'-chloro-[1,1'-biphenyl]-4-yl)thio)-1H-1,2,3-triazole-4-carboxylic acid | $C_{15}H_{10}ClN_3O_2S$ | 331.77 |
| I-136 | 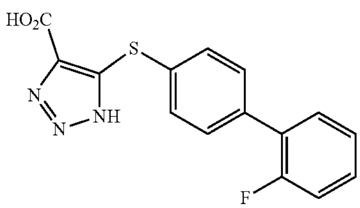 [SMILES: O=C(O)c1nn[nH]c1Sc1ccc(-c2ccccc2F)cc1] | 5-((2'-fluoro-[1,1'-biphenyl]-4-yl)thio)-1H-1,2,3-triazole-4-carboxylic acid | $C_{15}H_{10}FN_3O_2S$ | 315.32 |
| I-137 | 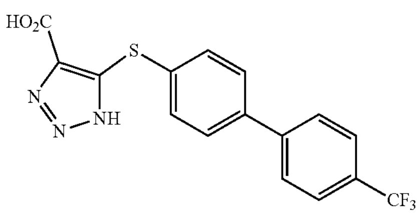 | 5-((4'-(trifluoromethyl)-[1,1'-biphenyl]-4-yl)thio)-1H-1,2,3-triazole-4-carboxylic acid | $C_{16}H_{10}F_3N_3O_2S$ | 365.33 |
| I-138 | 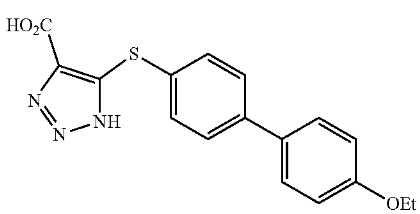 | 5-((4'-ethoxy-[1,1'-biphenyl]-4-yl)thio)-1H-1,2,3-triazole-4-carboxylic acid | $C_{17}H_{15}N_3O_3S$ | 341.39 |
| I-139 | 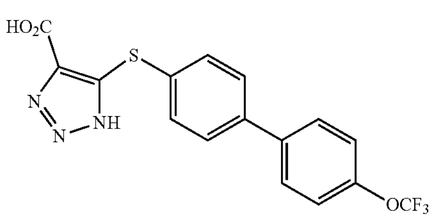 [SMILES: CSc1ccc(-c2ccc(Sc3[nH]nnc3C(=O)O)cc2)cc1] | 5-((4'-(trifluoromethoxy)-[1,1'-biphenyl]-4-yl)thio)-1H-1,2,3-triazole-4-carboxylic acid | $C_{16}H_{10}F_3N_3O_3S$ | 381.33 |

TABLE 1-continued

| Ex. No. | Structure | IUPAC Name | Chemical Formula | MW (g/mol) |
|---|---|---|---|---|
| I-140 | 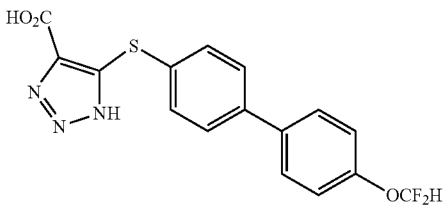 | 5-((4'-(difluoromethoxy)-[1,1'-biphenyl]-4-yl)thio)-1H-1,2,3-triazole-4-carboxylic acid | $C_{16}H_{11}F_3N_3O_3S$ | 363.34 |
| I-141 | 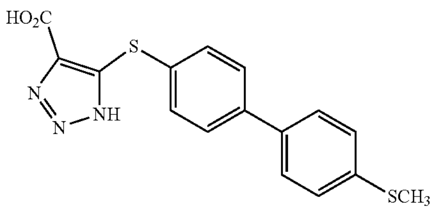 | 5-((4'-(methylthio)-[1,1'-biphenyl]-4-yl)thio)-1H-1,2,3-triazole-4-carboxylic acid | $C_{16}H_{13}N_3O_2S_2$ | 343.42 |
| I-142 | 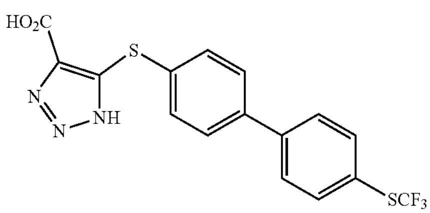 | 5-((4'-((trifluoromethyl)thio)-[1,1'-biphenyl]-4-yl)thio)-1H-1,2,3-triazole-4-carboxylic acid | $C_{16}H_{10}F_3N_3O_2S_2$ | 397.39 |
| I-143 | 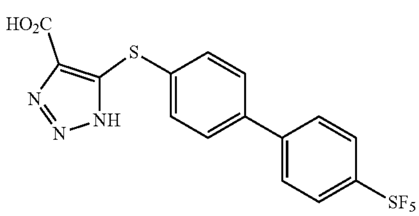 | 5-((4'-(pentafluoro-$\lambda^6$-sulfaneyl)-[1,1'-biphenyl]-4-yl)thio)-1H-1,2,3-triazole-4-carboxylic acid | $C_{15}H_{10}F_6N_3O_2S_2$ | 423.38 |
| I-144 | 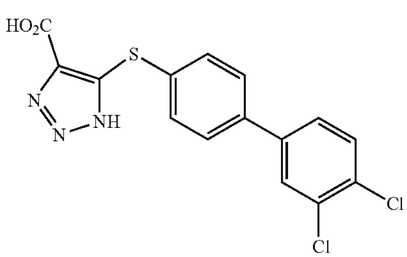 | 5-((3',4'-dichloro-[1,1'-biphenyl]-4-yl)thio)-1H-1,2,3-triazole-4-carboxylic acid | $C_{15}H_9Cl_2N_3O_2S$ | 366.22 |
| I-145 | 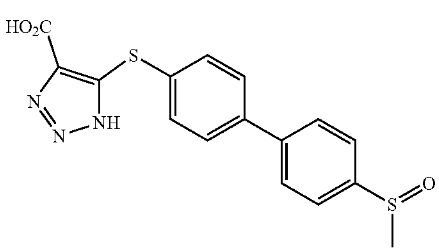 [SMILES: CS(=O)c1ccc(-c2ccc(Sc3[nH]nnc3C(=O)O)cc2)cc1] | 5-((4'-(methylsulfinyl)-[1,1'-biphenyl]-4-yl)thio)-1H-1,2,3-triazole-4-carboxylic acid | $C_{16}H_{13}N_3O_3S_2$ | 358.42 |

TABLE 1-continued

Example compounds.

| Ex. No. | Structure | IUPAC Name | Chemical Formula | MW (g/mol) |
|---|---|---|---|---|
| I-146 | 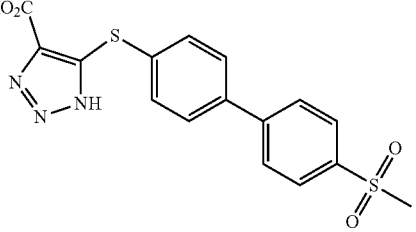 | 5-((4'-(methylsulfonyl)-[1,1'-biphenyl]-4-yl)thio)-1H-1,2,3-triazole-4-carboxylic acid | $C_{16}H_{13}N_3O_4S_2$ | 375.42 |
| I-147 | 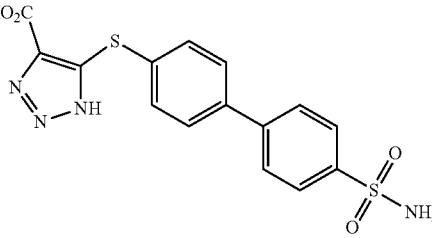 | 5-((4'-sulfamoyl-[1,1'-biphenyl]-4-yl)thio)-1H-1,2,3-triazole-4-carboxylic acid | $C_{15}H_{12}N_4O_4S_2$ | 376.41 |
| I-148 | 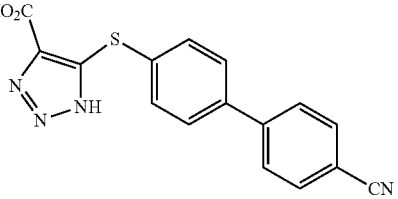 | 5-((4'-cyano-[1,1'-biphenyl]-4-yl)thio)-1H-1,2,3-triazole-4-carboxylic acid | $C_{16}H_{10}N_4O_2S_2$ | 322.34 |
| I-149 | 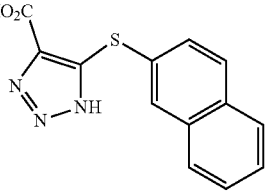 | 5-(naphthalen-2-ylthio)-1H-1,2,3-triazole-4-carboxylic acid | $C_{13}H_9N_3O_2S$ | 271.29 |
| I-150 | 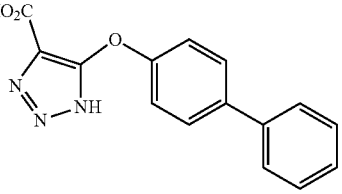 | 5-([1,1'-biphenyl]-4-yloxy)-1H-1,2,3-triazole-4-carboxylic acid | $C_{15}H_{11}N_3O_3$ | 281.27 |
| I-151 | 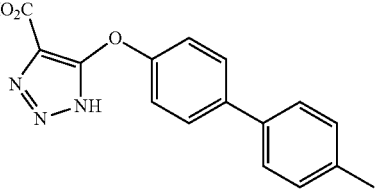 | 5-((4'-methyl-[1,1'-biphenyl]-4-yl)oxy)-1H-1,2,3-triazole-4-carboxylic acid | $C_{16}H_{13}N_3O_3$ | 295.30 |
| I-152 | 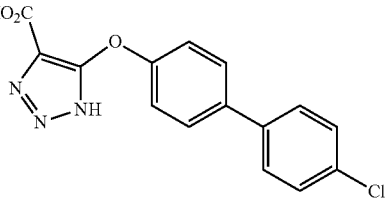 | 5-((4'-chloro-[1,1'-biphenyl]-4-yl)oxy)-1H-1,2,3-triazole-4-carboxylic acid | $C_{15}H_{10}ClN_3O_3$ | 315.71 |

TABLE 1-continued

Example compounds.

| Ex. No. | Structure | IUPAC Name | Chemical Formula | MW (g/mol) |
|---|---|---|---|---|
| I-153 | 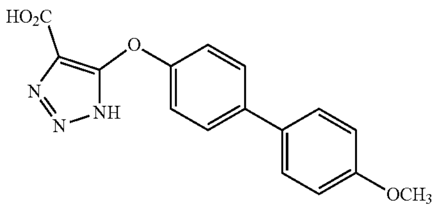 [SMILES: COc1ccc(-c2ccc(Oc3[nH]nnc3C(=O)O)cc2)cc1] | 5-((4'-methoxy-[1,1'-biphenyl]-4-yl)oxy)-1H-1,2,3-triazole-4-carboxylic acid | $C_{16}H_{13}N_3O_4$ | 311.30 |
| I-154 | 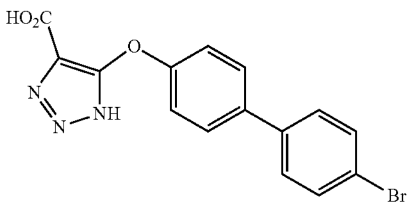 [SMILES: O=C(O)c1nn[nH]c1Oc1ccc(-c2ccc(Br)cc2)cc1] | 5-((4'-bromo-[1,1'-biphenyl]-4-yl)oxy)-1H-1,2,3-triazole-4-carboxylic acid | $C_{15}H_{10}BrN_3O_3$ | 360.17 |
| I-155 | 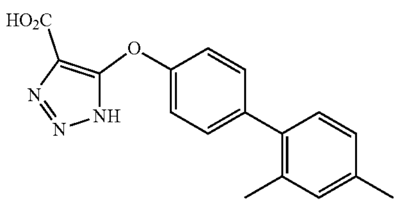 [SMILES: Cc1ccc(-c2ccc(Oc3[nH]nnc3C(=O)O)cc2)c(C)c1] | 5-((2',4'-dimethyl-[1,1'-biphenyl]-4-yl)oxy)-1H-1,2,3-triazole-4-carboxylic acid | $C_{17}H_{15}N_3O_3$ | 309.33 |
| I-156 | 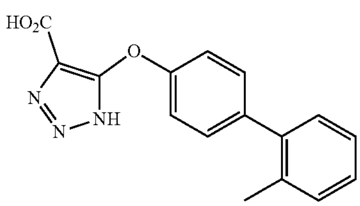 [SMILES: Cc1ccccc1-c1ccc(Oc2[nH]nnc2C(=O)O)cc1] | 5-((2'-methyl-[1,1'-biphenyl]-4-yl)oxy)-1H-1,2,3-triazole-4-carboxylic acid | $C_{16}H_{13}N_3O_3$ | 295.30 |
| I-157 | 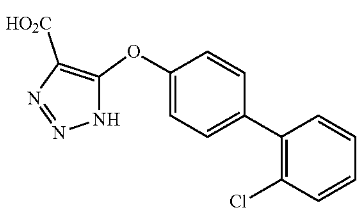 [SMILES: O=C(O)c1nn[nH]c1Oc1ccc(-c2ccccc2Cl)cc1] | 5-((2'-chloro-[1,1'-biphenyl]-4-yl)oxy)-1H-1,2,3-triazole-4-carboxylic acid | $C_{15}H_{10}ClN_3O_3$ | 315.71 |
| I-158 | 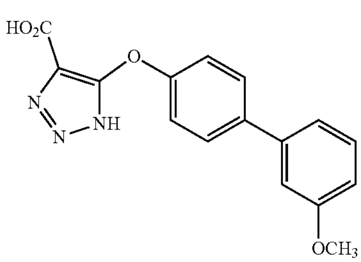 [SMILES: COc1cccc(-c2ccc(Oc3[nH]nnc3C(=O)O)cc2)c1] | 5-((3'-methoxy-[1,1'-biphenyl]-4-yl)oxy)-1H-1,2,3-triazole-4-carboxylic acid | $C_{16}H_{13}N_3O_4$ | 311.30 |

TABLE 1-continued

Example compounds.

| Ex. No. | Structure | IUPAC Name | Chemical Formula | MW (g/mol) |
|---|---|---|---|---|
| I-159 | 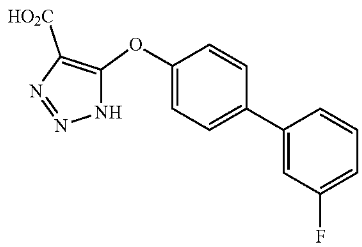 [SMILES: O=C(O)c1nn[nH]c1Oc1ccc(-c2cccc(F)c2)cc1] | 5-((3'-fluoro-[1,1'-biphenyl]-4-yl)oxy)-1H-1,2,3-triazole-4-carboxylic acid | $C_{15}H_{10}FN_3O_3$ | 299.26 |
| I-160 | 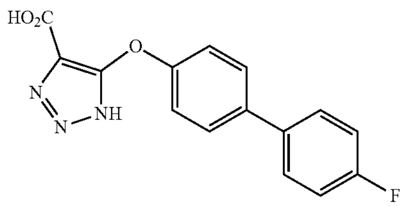 [SMILES: O=C(O)c1nn[nH]c1Oc1ccc(-c2ccc(F)cc2)cc1] | 5-((4'-fluoro-[1,1'-biphenyl]-4-yl)oxy)-1H-1,2,3-triazole-4-carboxylic acid | $C_{15}H_{10}FN_3O_3$ | 299.26 |
| I-161 | 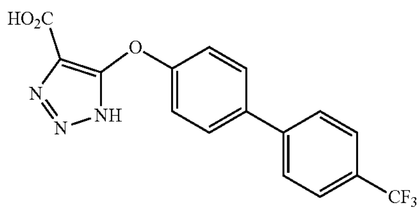 [SMILES: O=C(O)c1nn[nH]c1Oc1ccc(-c2ccc(C(F)(F)F)cc2)cc1] | 5-((4'-(trifluoromethyl)-[1,1'-biphenyl]-4-yl)oxy)-1H-1,2,3-triazole-4-carboxylic acid | $C_{16}H_{10}F_3N_3O_3$ | 349.27 |
| I-162 | 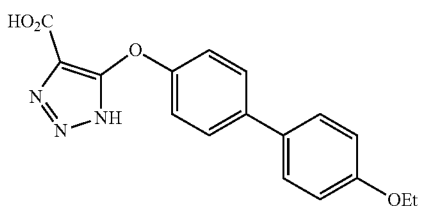 [SMILES: CCOc1ccc(-c2ccc(Oc3[nH]nnc3C(=O)O)cc2)cc1] | 5-((4'-ethoxy-[1,1'-biphenyl]-4-yl)oxy)-1H-1,2,3-triazole-4-carboxylic acid | $C_{17}H_{15}N_3O_4$ | 352.32 |
| I-163 | 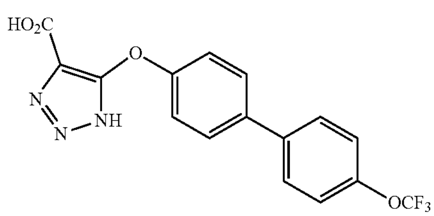 | 5-((4'-(trifluoromethoxy)-[1,1'-biphenyl]-4-yl)oxy)-1H-1,2,3-triazole-4-carboxylic acid | $C_{16}H_{10}F_3N_3O_4$ | 365.27 |
| I-164 | 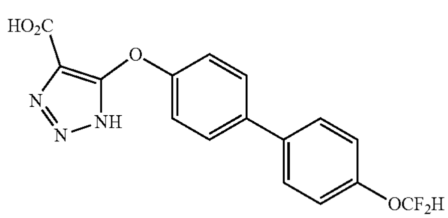 | 5-((4'-(difluoromethoxy)-[1,1'-biphenyl]-4-yl)oxy)-1H-1,2,3-triazole-4-carboxylic acid | $C_{16}H_{11}F_2N_3O_4$ | 347.28 |
| I-165 | 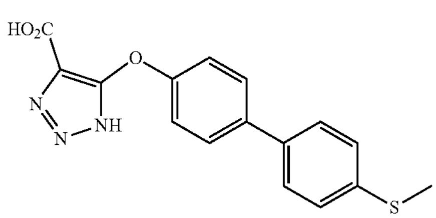 [SMILES: CSc1ccc(-c2ccc(Oc3[nH]nnc3C(=O)O)cc2)cc1] | 5-((4'-(methylthio)-[1,1'-biphenyl]-4-yl)oxy)-1H-1,2,3-triazole-4-carboxylic acid | $C_{16}H_{13}N_3O_3S$ | 327.36 |

TABLE 1-continued

Example compounds.

| Ex. No. | Structure | IUPAC Name | Chemical Formula | MW (g/mol) |
|---|---|---|---|---|
| I-166 | 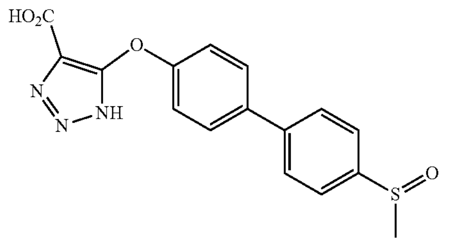 [SMILES: CS(=O)c1ccc(-c2ccc(Oc3[nH]nnc3C(=O)O)cc2)cc1] | 5-((4'-(methylsulfinyl)-[1,1'-biphenyl]-4-yl)oxy)-1H-1,2,3-triazole-4-carboxylic acid | $C_{16}H_{13}N_3O_4S$ | 343.36 |
| I-167 | 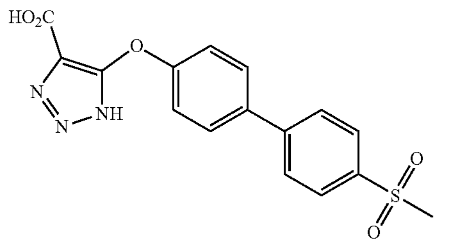 | 5-((4'-(methylsulfonyl)-[1,1'-biphenyl]-4-yl)oxy)-1H-1,2,3-triazole-4-carboxylic acid | $C_{16}H_{13}N_3O_5S$ | 359.36 |
| I-168 | 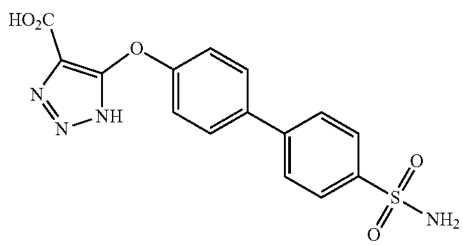 | 5-((4'-sulfamoyl-[1,1'-biphenyl]-4-yl)oxy)-1H-1,2,3-triazole-4-carboxylic acid | $C_{15}H_{12}N_4O_5S$ | 360.34 |
| I-169 | 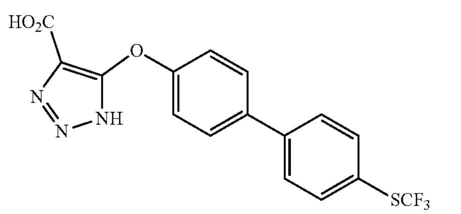 | 5-((4'-((trifluoromethyl)thio)-[1,1'-biphenyl]-4-yl)oxy)-1H-1,2,3-triazole-4-carboxylic acid | $C_{16}H_{10}F_3N_3O_3S$ | 381.33 |
| I-170 | 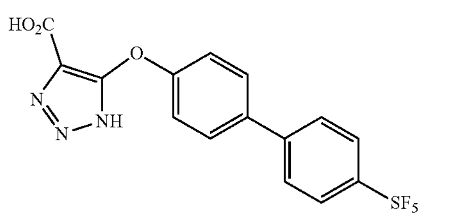 | 5-((4'-(pentafluoro-$\lambda^6$-sulfaneyl)-[1,1'-biphenyl]-4-yl)oxy)-1H-1,2,3-triazole-4-carboxylic acid | $C_{15}H_{10}F_5N_3O_3S$ | 407.32 |
| I-171 | 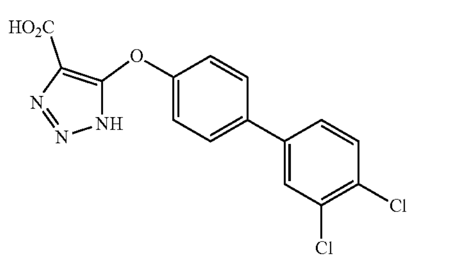 | 5-((3',4'-dichloro-[1,1'-biphenyl]-4-yl)oxy)-1H-1,2,3-triazole-4-carboxylic acid | $C_{15}H_9Cl_2N_3O_3$ | 350.16 |

TABLE 1-continued

Example compounds.

| Ex. No. | Structure | IUPAC Name | Chemical Formula | MW (g/mol) |
|---|---|---|---|---|
| I-172 | 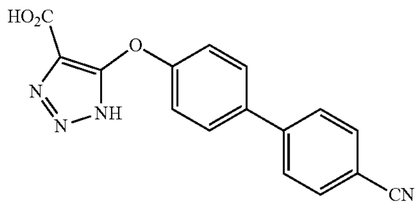 | 5-((4'-cyano-[1,1'-biphenyl]-4-yl)oxy)-1H-1,2,3-triazole-4-carboxylic acid | $C_{16}H_{10}N_4O_3$ | 306.28 |
| I-173 | 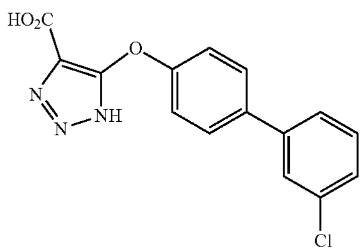 [SMILES: O=C(O)c1nn[nH]c1Oc1ccc(-c2cccc(Cl)c2)cc1] | 5-((3'-chloro-[1,1'-biphenyl]-3-yl)oxy)-1H-1,2,3-triazole-4-carboxylic acid | $C_{15}H_{10}ClN_3O_3$ | 315.71 |
| I-174 | 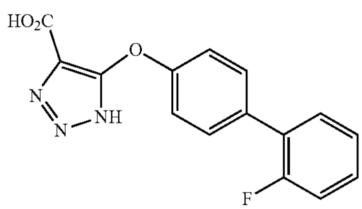 [SMILES: O=C(O)c1nn[nH]c1Oc1ccc(-c2ccccc2F)cc1] | 5-((2'-fluoro-[1,1'-biphenyl]-3-yl)oxy)-1H-1,2,3-triazole-4-carboxylic acid | $C_{15}H_{10}FN_3O_3$ | 299.07 |
| I-175 | 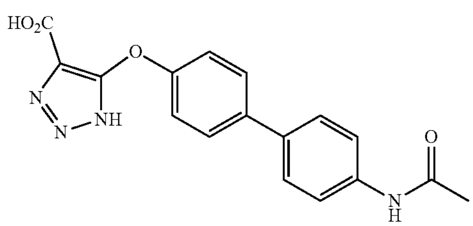 [SMILES: CC(=O)Nc1ccc(-c2ccc(Oc3[nH]nnc3C(=O)O)cc2)cc1] | 5-((4'-acetamido-[1,1'-biphenyl]-3-yl)oxy)-1H-1,2,3-triazole-4-carboxylic acid | $C_{17}H_{14}N_4O_4$ | 338.32 |
| I-176 | 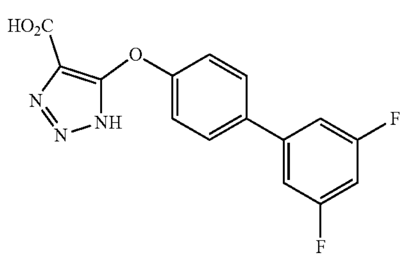 [SMILES: O=C(O)c1nn[nH]c1Oc1ccc(-c2cc(F)cc(F)c2)cc1] | 5-((3',5'-difluoro-[1,1'-biphenyl]-3-yl)oxy)-1H-1,2,3-triazole-4-carboxylic acid | $C_{15}H_9F_2N_3O_3$ | 317.25 |
| I-177 | 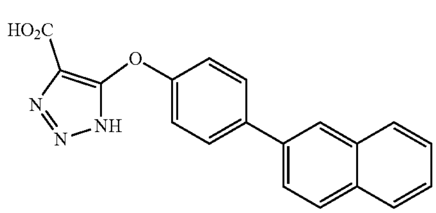 [SMILES: O=C(O)c1nn[nH]c1Oc1ccc(-c2ccc3ccccc3c2)cc1] | 5-(4-(naphthalen-2-yl)phenoxy)-1H-1,2,3-triazole-4-carboxylic acid | $C_{19}H_{13}N_3O_3$ | 331.33 |

TABLE 1-continued

Example compounds.

| Ex. No. | Structure | IUPAC Name | Chemical Formula | MW (g/mol) |
|---|---|---|---|---|
| I-178 | 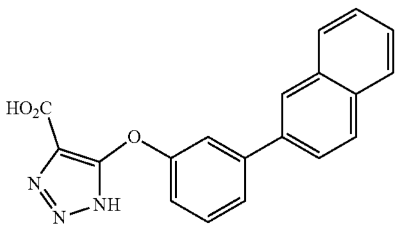 [SMILES: O=C(O)c1nn[nH]c1Oc1cccc(-c2ccc3ccccc3c2)c1] | 5-(3-(naphthalen-2-yl)phenoxy)-1H-1,2,3-triazole-4-carboxylic acid | $C_{19}H_{13}N_3O_3$ | 331.33 |
| I-179 | 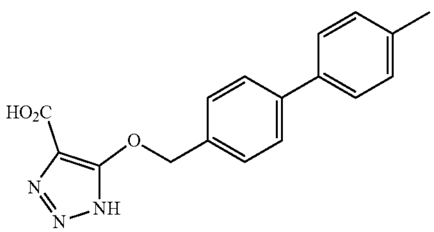 [SMILES: Cc1ccc(-c2ccc(COc3[nH]nnc3C(=O)O)cc2)cc1] | 5-((4'-methyl-[1,1'-biphenyl]-4-yl)methoxy)-1H-1,2,3-triazole-4-carboxylic acid | $C_{17}H_{15}N_3O_3$ | 309.33 |
| I-180 | 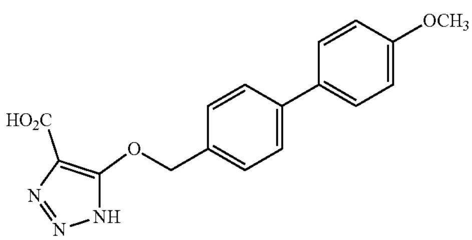 [SMILES: COc1ccc(-c2ccc(COc3[nH]nnc3C(=O)O)cc2)cc1] | 5-((4'-methoxy-[1,1'-biphenyl]-4-yl)methoxy)-1H-1,2,3-triazole-4-carboxylic acid | $C_{17}H_{15}N_3O_4$ | 352.32 |
| I-181 | 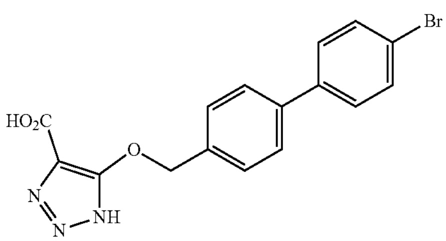 [SMILES: O=C(O)c1nn[nH]c1OCc1ccc(-c2ccc(Br)cc2)cc1] | 5-((4'-bromo-[1,1'-biphenyl]-4-yl)methoxy)-1H-1,2,3-triazole-4-carboxylic acid | $C_{16}H_{12}BrN_3O_3$ | 374.19 |
| I-182 | 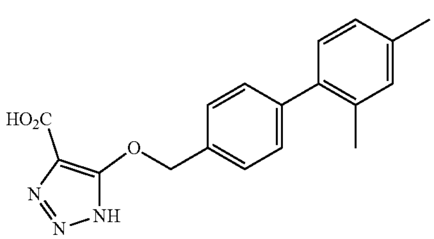 [SMILES: Cc1ccc(-c2ccc(COc3[nH]nnc3C(=O)O)cc2)c(C)c1] | 5-((2',4'-dimethyl-[1,1'-biphenyl]-4-yl)methoxy)-1H-1,2,3-triazole-4-carboxylic acid | $C_{18}H_{17}N_3O_3$ | 323.35 |
| I-183 | 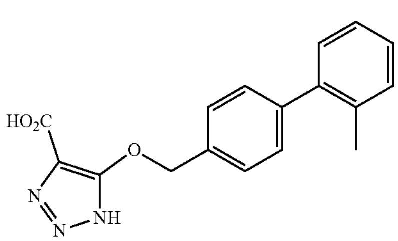 [SMILES: Cc1ccccc1-c1ccc(COc2[nH]nnc2C(=O)O)cc1] | 5-((2'-methyl-[1,1'-biphenyl]-4-yl)methoxy)-1H-1,2,3-triazole-4-carboxylic acid | $C_{17}H_{15}N_3O_3$ | 309.33 |

TABLE 1-continued

Example compounds.

| Ex. No. | Structure | IUPAC Name | Chemical Formula | MW (g/mol) |
|---|---|---|---|---|
| I-184 | 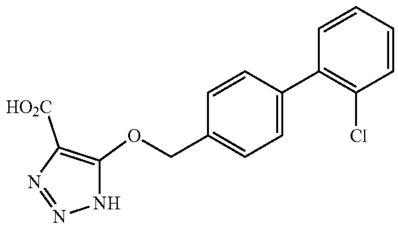 [SMILES: O=C(O)c1nn[nH]c1OCc1ccc(-c2ccccc2F)cc1] | 5-((2'-chloro-[1,1'-biphenyl]-4-yl)methoxy)-1H-1,2,3-triazole-4-carboxylic acid | $C_{16}H_{12}ClN_3O_3$ | 329.74 |
| I-185 | 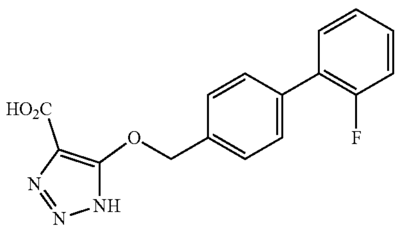 | 5-((2'-fluoro-[1,1'-biphenyl]-4-yl)methoxy)-1H-1,2,3-triazole-4-carboxylic acid | $C_{16}H_{12}FN_3O_3$ | 313.29 |
| I-186 | 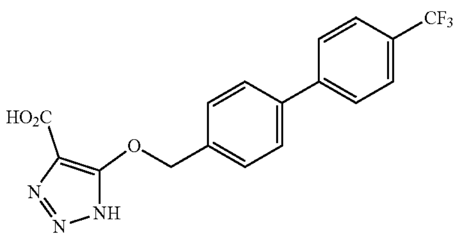 [SMILES: CCOc1ccc(-c2ccc(COc3[nH]nnc3C(=O)O)cc2)cc1] | 5-((4'-(trifluoromethyl)-[1,1'-biphenyl]-4-yl)methoxy)-1H-1,2,3-triazole-4-carboxylic acid | $C_{17}H_{12}F_3N_3O_3$ | 363.30 |
| I-187 | 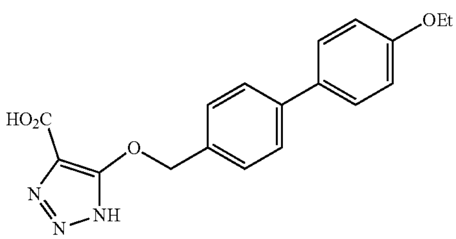 | 5-((4'-ethoxy-[1,1'-biphenyl]-4-yl)methoxy)-1H-1,2,3-triazole-4-carboxylic acid | $C_{18}H_{17}N_3O_4$ | 339.35 |
| I-188 | 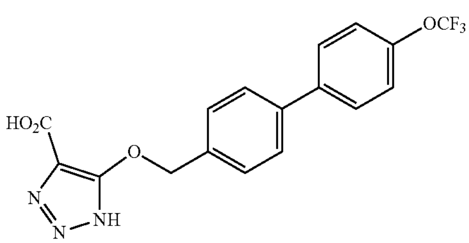 | 5-((4'-(trifluoromethoxy)-[1,1'-biphenyl]-4-yl)methoxy)-1H-1,2,3-triazole-4-carboxylic acid | $C_{17}H_{12}F_3N_3O_4$ | 379.30 |
| I-189 | 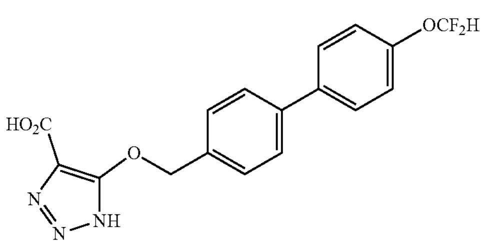 | 5-((4'-(difluoromethoxy)-[1,1'-biphenyl]-4-yl)methoxy)-1H-1,2,3-triazole-4-carboxylic acid | $C_{17}H_{13}F_2N_3O_4$ | 361.30 |

TABLE 1-continued

Example compounds.

| Ex. No. | Structure | IUPAC Name | Chemical Formula | MW (g/mol) |
|---|---|---|---|---|
| I-190 | 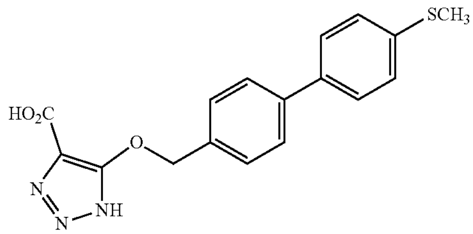 | 5-((4'-(methylthio)-[1,1'-biphenyl]-4-yl)methoxy)-1H-1,2,3-triazole-4-carboxylic acid | $C_{17}H_{15}N_3O_3S$ | 341.39 |
| I-191 | 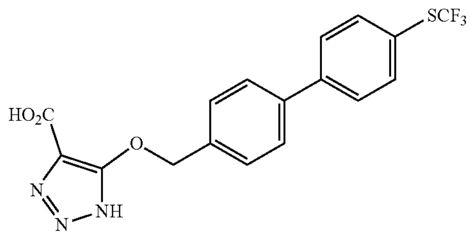 [SMILES: O=C(O)c1nn[nH]c1OCc1ccc(-c2ccc(OC(F)(F)F)cc2)cc1] | 5-((4'-((trifluoromethyl)thio)-[1,1'-biphenyl]-4-yl)methoxy)-1H-1,2,3-triazole-4-carboxylic acid | $C_{17}H_{12}F_3N_3O_3S$ | 395.36 |
| I-192 | 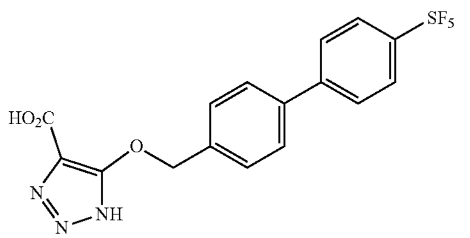 | 5-((4'-(pentafluoro-$\lambda^6$-sulfaneyl)-[1,1'-biphenyl]-4-yl)methoxy)-1H-1,2,3-triazole-4-carboxylic acid | $C_{16}H_{12}F_5N_3O_3S$ | 421.34 |
| I-193 | 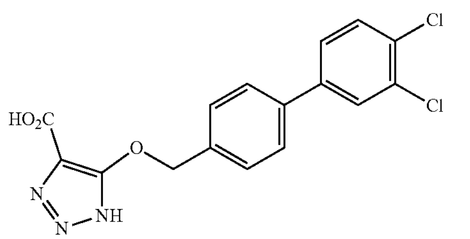 [SMILES: O=C(O)c1nn[nH]c1OCc1ccc(-c2ccc(Cl)c(Cl)c2)cc1] | 5-((3',4'-dichloro-[1,1'-biphenyl]-4-yl)methoxy)-1H-1,2,3-triazole-4-carboxylic acid | $C_{16}H_{11}Cl_2N_3O_3$ | 364.18 |
| I-194 | 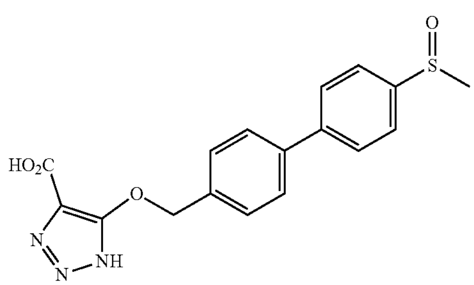 [SMILES: CS(=O)c1ccc(-c2ccc(COc3[nH]nnc3C(=O)O)cc2)cc1] | 5-((4'-(methylsulfinyl)-[1,1'-biphenyl]-4-yl)methoxy)-1H-1,2,3-triazole-4-carboxylic acid | $C_{17}H_{16}N_3O_4S$ | 357.38 |
| I-195 | 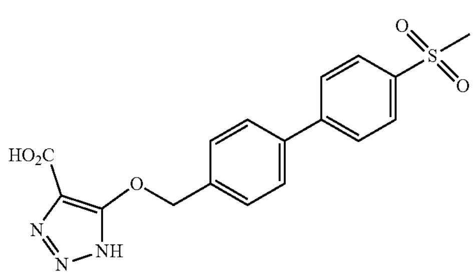 [SMILES: CS(=O)(=O)c1ccc(-c2ccc(COc3[nH]nnc3C(=O)O)cc2)cc1] | 5-((4'-(methylsulfonyl)-[1,1'-biphenyl]-4-yl)methoxy)-1H-1,2,3-triazole-4-carboxylic acid | $C_{17}H_{15}N_3O_5S$ | 373.38 |

TABLE 1-continued

Example compounds.

| Ex. No. | Structure | IUPAC Name | Chemical Formula | MW (g/mol) |
|---|---|---|---|---|
| I-196 | 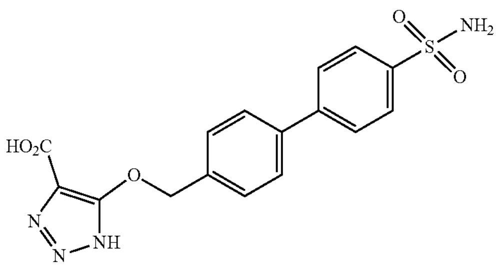 | 5-((4'-sulfamoyl-[1,1'-biphenyl]-4-yl)methoxy)-1H-1,2,3-triazole-4-carboxylic acid | $C_{16}H_{14}N_4O_5S$ | 374.37 |
| I-197 | 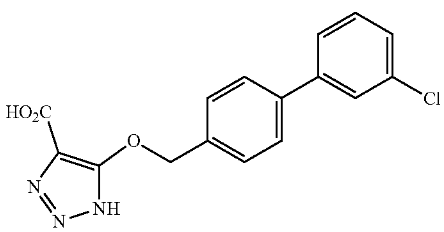 [SMILES: O=C(O)c1nn[nH]c1OCc1ccc(-c2cccc(Cl)c2)cc1] | 5-((3'-chloro-[1,1'-biphenyl]-4-yl)methoxy)-1H-1,2,3-triazole-4-carboxylic acid | $C_{16}H_{12}ClN_3O_3$ | 329.74 |
| I-198 | 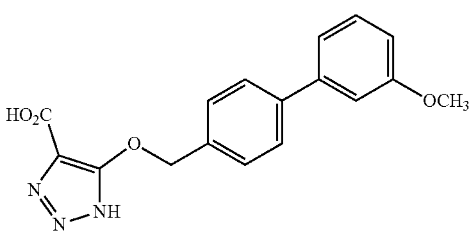 | 5-((3'-methoxy-[1,1'-biphenyl]-4-yl)methoxy)-1H-1,2,3-triazole-4-carboxylic acid | $C_{17}H_{15}N_3O_4$ | 325.32 |
| I-199 | 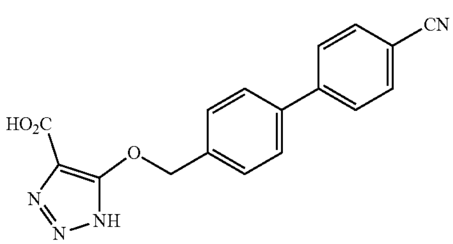 [SMILES: N#Cc1ccc(-c2ccc(COc3[nH]nnc3C(=O)O)cc2)cc1] | 5-((4'-cyano-[1,1'-biphenyl]-4-yl)methoxy)-1H-1,2,3-triazole-4-carboxylic acid | $C_{17}H_{12}N_4O_3$ | 320.31 |
| I-200 | 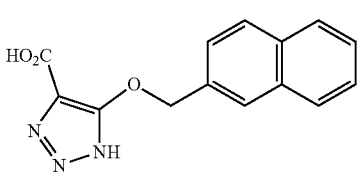 [SMILES: O=C(O)c1nn[nH]c1OCc1ccc2ccccc2c1] | 5-(naphthalen-2-ylmethoxy)-1H-1,2,3-triazole-4-carboxylic acid | $C_{14}H_{11}N_3O_3$ | 269.26 |
| I-201 | 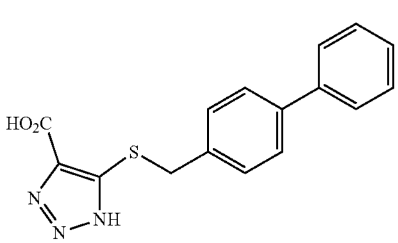 [SMILES: O=C(O)c1nn[nH]c1SCc1ccc(-c2ccccc2)cc1] | 5-(([1,1'-biphenyl]-4-ylmethyl)thio)-1H-1,2,3-triazole-4-carboxylic acid | $C_{16}H_{13}N_3O_2S$ | 311.36 |

TABLE 1-continued

Example compounds.

| Ex. No. | Structure | IUPAC Name | Chemical Formula | MW (g/mol) |
|---|---|---|---|---|
| I-202 | 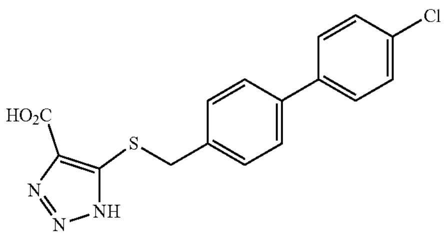 [SMILES: O=C(O)c1nn[nH]c1SCc1ccc(-c2ccc(Br)cc2)cc1] | 5-(((4'-chloro-[1,1'-biphenyl]-4-yl)methyl)thio)-1H-1,2,3-triazole-4-carboxylic acid | $C_{16}H_{12}ClN_3O_2S$ | 345.80 |
| I-203 | 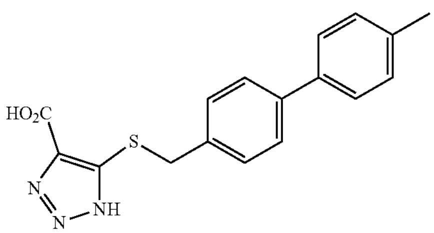 | 5-(((4'-methyl-[1,1'-biphenyl]-4-yl)methyl)thio)-1H-1,2,3-triazole-4-carboxylic acid | $C_{17}H_{15}N_3O_2S$ | 325.39 |
| I-204 | 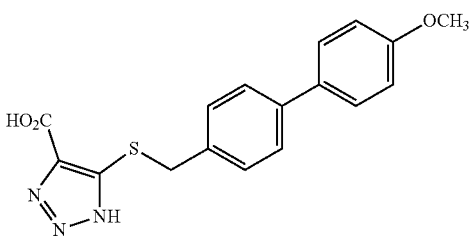 | 5-(((4'-methoxy-[1,1'-biphenyl]-4-yl)methyl)thio)-1H-1,2,3-triazole-4-carboxylic acid | $C_{17}H_{15}N_3O_3S$ | 341.39 |
| I-205 | 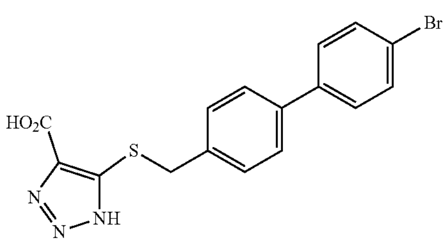 | 5-(((4'-bromo-[1,1'-biphenyl]-4-yl)methyl)thio)-1H-1,2,3-triazole-4-carboxylic acid | $C_{16}H_{12}BrN_3O_2S$ | 390.26 |
| I-206 | 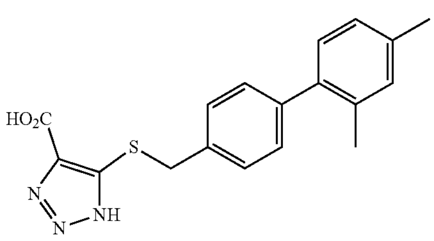 [SMILES: Cc1ccc(-c2ccc(CSc3[nH]nnc3C(=O)O)cc2)c(C)c1] | 5-(((2',4'-dimethyl-[1,1'-biphenyl]-4-yl)methyl)thio)-1H-1,2,3-triazole-4-carboxylic acid | $C_{18}H_{17}N_3O_2S$ | 339.41 |
| I-207 | 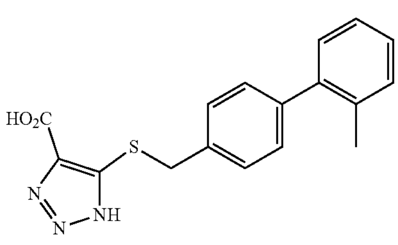 | 5-(((2'-methyl-[1,1'-biphenyl]-4-yl)methyl)thio)-1H-1,2,3-triazole-4-carboxylic acid | $C_{17}H_{15}N_3O_2S$ | 325.39 |

TABLE 1-continued

Example compounds.

| Ex. No. | Structure | IUPAC Name | Chemical Formula | MW (g/mol) |
|---|---|---|---|---|
| I-208 | 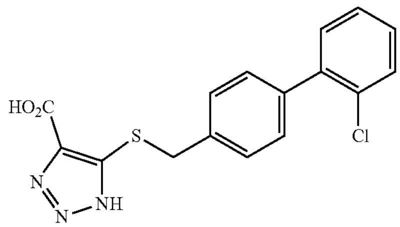 | 5-(((2'-chloro-[1,1'-biphenyl]-4-yl)methyl)thio)-1H-1,2,3-triazole-4-carboxylic acid | $C_{16}H_{12}ClN_3O_2S$ | 345.80 |
| I-209 | 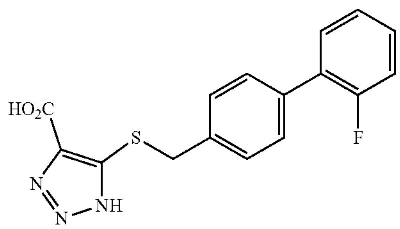 | 5-(((2'-fluoro-[1,1'-biphenyl]-4-yl)methyl)thio)-1H-1,2,3-triazole-4-carboxylic acid | $C_{16}H_{12}FN_3O_2S$ | 329.35 |
| I-210 | 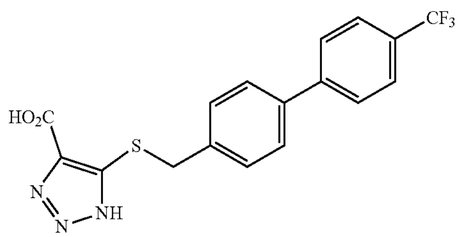 | 5-(((4'-(trifluoromethyl)-[1,1'-biphenyl]-4-yl)methyl)thio)-1H-1,2,3-triazole-4-carboxylic acid | $C_{17}H_{12}F_3N_3O_2S$ | 379.36 |
| I-211 | 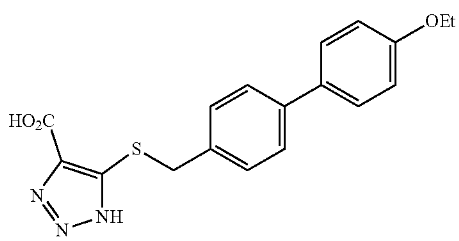 [SMILES: CCOc1ccc(-c2ccc(CSc3[nH]nnc3C(=O)O)cc2)cc1] | 5-(((4'-ethoxy-[1,1'-biphenyl]-4-yl)methyl)thio)-1H-1,2,3-triazole-4-carboxylic acid | $C_{18}H_{17}N_3O_3S$ | 355.41 |
| I-212 | 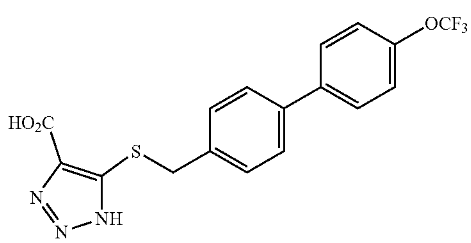 | 5-(((4'-(trifluoromethoxy)-[1,1'-biphenyl]-4-yl)methyl)thio)-1H-1,2,3-triazole-4-carboxylic acid | $C_{17}H_{12}F_3N_3O_3S$ | 395.36 |
| I-213 | 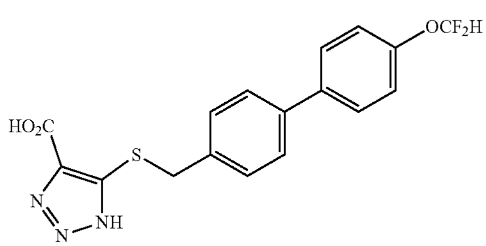 | 5-(((4'-(difluoromethoxy)-[1,1'-biphenyl]-4-yl)methyl)thio)-1H-1,2,3-triazole-4-carboxylic acid | $C_{17}H_{13}F_3N_3O_3S$ | 377.37 |

TABLE 1-continued

Example compounds.

| Ex. No. | Structure | IUPAC Name | Chemical Formula | MW (g/mol) |
|---|---|---|---|---|
| I-214 | 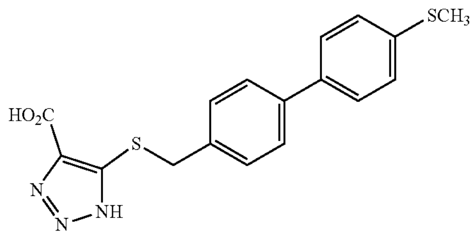 | 5-(((4'-(methylthio)-[1,1'-biphenyl]-4-yl)methyl)thio)-1H-1,2,3-triazole-4-carboxylic acid | $C_{17}H_{15}N_3O_2S_2$ | 357.45 |
| I-215 | 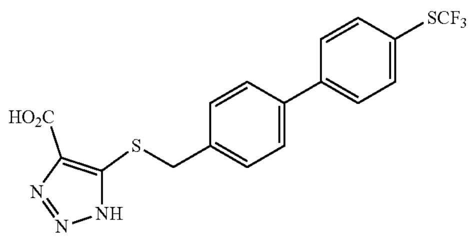 [SMILES: O=C(O)c1nn[nH]c1SCc1ccc(-c2ccc(OC(F)(F)F)cc2)cc1] | 5-(((4'-((trifluoromethyl)thio)-[1,1'-biphenyl]-4-yl)methyl)thio)-1H-1,2,3-triazole-4-carboxylic acid | $C_{17}H_{12}F_3N_3O_2S_2$ | 411.42 |
| I-216 | 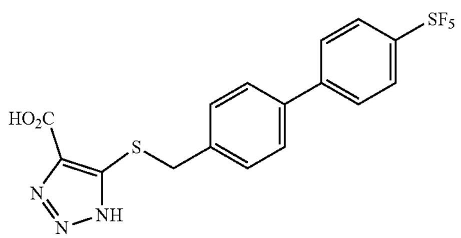 | 5-(((4'-(pentafluoro-$\lambda^6$-sulfaneyl)-[1,1'-biphenyl]-4-yl)methyl)thio)-1H-1,2,3-triazole-4-carboxylic acid | $C_{16}H_{12}F_3N_3O_2S_2$ | 437.40 |
| I-217 | 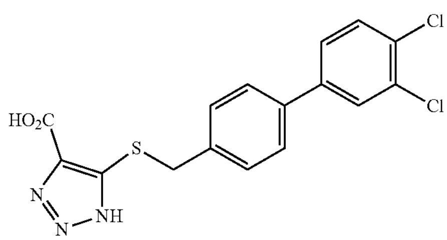 [SMILES: O=C(O)c1nn[nH]c1SCc1ccc(-c2ccc(Cl)c(Cl)c2)cc1] | 5-(((3',4'-dichloro-[1,1'-biphenyl]-4-yl)methyl)thio)-1H-1,2,3-triazole-4-carboxylic acid | $C_{16}H_{11}Cl_2N_3O_2S$ | 380.24 |
| I-218 | 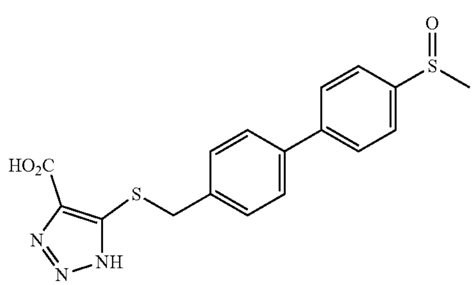 [SMILES: CS(=O)c1ccc(-c2ccc(CSc3[nH]nnc3C(=O)O)cc2)cc1] | 5-(((4'-(methylsulfinyl)-[1,1'-biphenyl]-4-yl)methyl)thio)-1H-1,2,3-triazole-4-carboxylic acid | $C_{17}H_{15}N_3O_2S_2$ | 373.45 |
| I-219 | 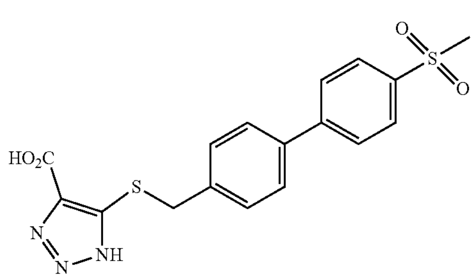 [SMILES: CS(=O)(=O)c1ccc(-c2ccc(CSc3[nH]nnc3C(=O)O)cc2)cc1] | 5-(((4'-(methylsulfonyl)-[1,1'-biphenyl]-4-yl)methyl)thio)-1H-1,2,3-triazole-4-carboxylic acid | $C_{17}H_{15}N_3O_4S_2$ | 389.44 |

TABLE 1-continued

Example compounds.

| Ex. No. | Structure | IUPAC Name | Chemical Formula | MW (g/mol) |
|---|---|---|---|---|
| I-220 | 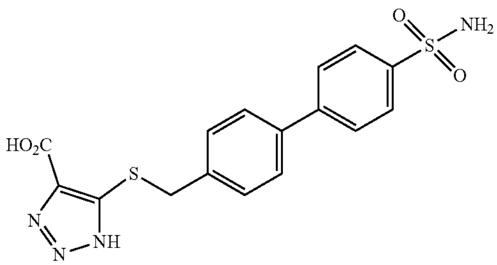 [SMILES: NS(=O)(=O)c1ccc(-c2ccc(CSc3[nH]nnc3C(=O)O)cc2)cc1] | 5-(((4'-sulfamoyl-[1,1'-biphenyl]-4-yl)methyl)thio)-1H-1,2,3-triazole-4-carboxylic acid | $C_{16}H_{14}N_4O_4S_2$ | 390.43 |
| I-221 | 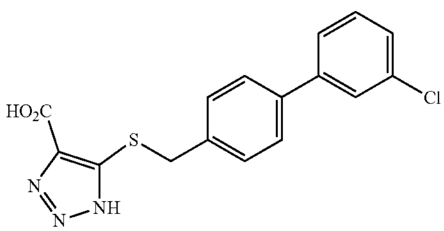 [SMILES: O=C(O)c1nn[nH]c1SCc1ccc(-c2cccc(Cl)c2)cc1] | 5-(((3'-chloro-[1,1'-biphenyl]-4-yl)methyl)thio)-1H-1,2,3-triazole-4-carboxylic acid | $C_{16}H_{12}ClN_3O_2S$ | 345.80 |
| I-222 | 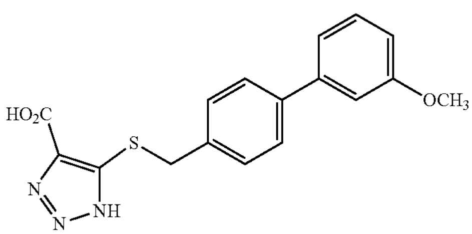 | 5-(((3'-methoxy-[1,1'-biphenyl]-4-yl)methyl)thio)-1H-1,2,3-triazole-4-carboxylic acid | $C_{17}H_{15}N_3O_3S$ | 341.39 |
| I-223 | 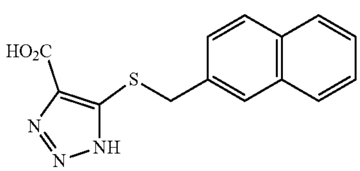 [SMILES: O=C(O)c1nn[nH]c1SCc1ccc2ccccc2c1] | 5-((naphthalen-2-ylmethyl)thio)-1H-1,2,3-triazole-4-carboxylic acid | $C_{14}H_{11}N_3O_2S$ | 285.32 |
| I-224 | 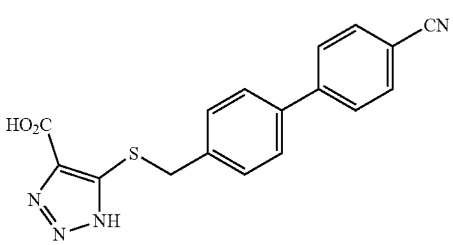 | 5-(((4'-cyano-[1,1'-biphenyl]-4-yl)methyl)thio)-1H-1,2,3-triazole-4-carboxylic acid | $C_{17}H_{12}N_4O_2S$ | 336.37 |
| I-225 | 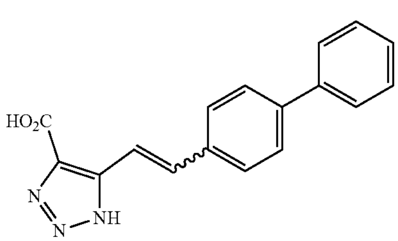 [SMILES: O=C(O)c1nn[nH]c1C=Cc1ccc(-c2ccccc2)cc1] | 5-(2-([1,1'-biphenyl]-4-yl)vinyl)-1H-1,2,3-triazole-4-carboxylic acid | $C_{17}H_{13}N_3O_2$ | 291.31 |

TABLE 1-continued

Example compounds.

| Ex. No. | Structure | IUPAC Name | Chemical Formula | MW (g/mol) |
|---|---|---|---|---|
| I-226 | 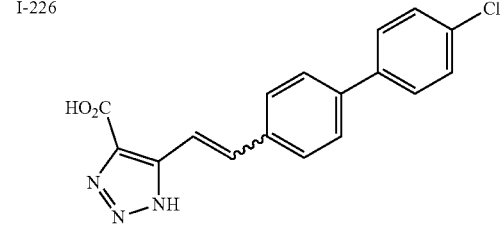 | 5-(2-(4'-chloro-[1,1'-biphenyl]-4-yl)vinyl)-1H-1,2,3-triazole-4-carboxylic acid | $C_{17}H_{12}ClN_3O_2$ | 325.75 |
| I-227 | 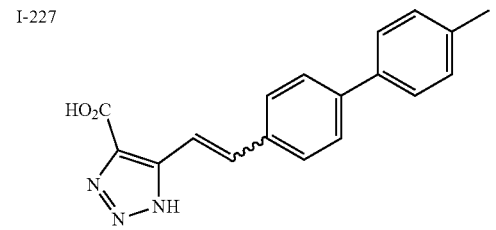 | 5-(2-(4'-methyl-[1,1'-biphenyl]-4-yl)vinyl)-1H-1,2,3-triazole-4-carboxylic acid | $C_{18}H_{15}N_3O_2$ | 305.34 |
| I-228 | 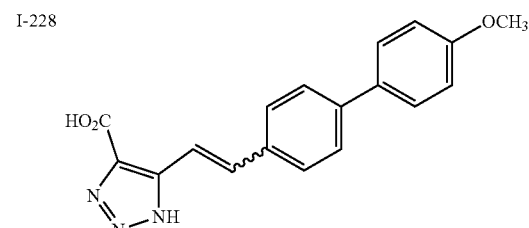 | 5-(2-(4'-methoxy-[1,1'-biphenyl]-4-yl)vinyl)-1H-1,2,3-triazole-4-carboxylic acid | $C_{18}H_{15}N_3O_3$ | 321.34 |
| I-229 | 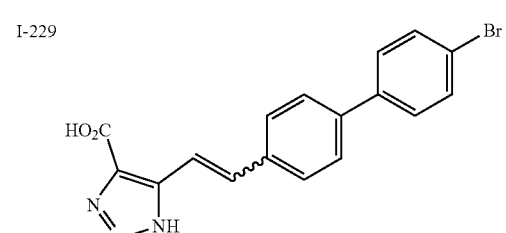 | 5-(2-(4'-bromo-[1,1'-biphenyl]-4-yl)vinyl)-1H-1,2,3-triazole-4-carboxylic acid | $C_{17}H_{12}BrN_3O_2$ | 370.21 |
| I-230 | 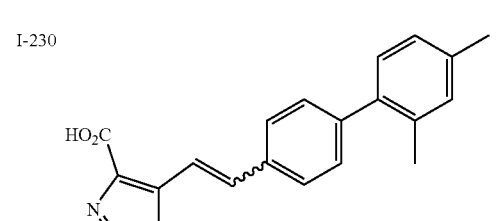 | 5-(2-(2',4'-dimethyl-[1,1'-biphenyl]-4-yl)vinyl)-1H-1,2,3-triazole-4-carboxylic acid | $C_{19}H_{17}N_3O_2$ | 319.36 |
| I-231 | 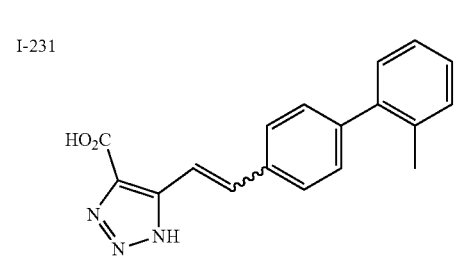 | 5-(2-(2'-methyl-[1,1'-biphenyl]-4-yl)vinyl)-1H-1,2,3-triazole-4-carboxylic acid | $C_{18}H_{15}N_3O_2$ | 305.34 |

TABLE 1-continued

Example compounds.

| Ex. No. | Structure | IUPAC Name | Chemical Formula | MW (g/mol) |
|---|---|---|---|---|
| I-232 | 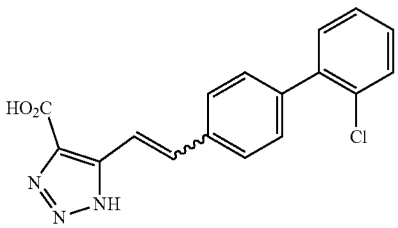 [SMILES: Cc1ccccc1-c1ccc(C=Cc2[nH]nnc2C(=O)O)cc1] | 5-(2-(2'-chloro-[1,1'-biphenyl]-4-yl)vinyl)-1H-1,2,3-triazole-4-carboxylic acid | $C_{17}H_{12}ClN_3O_2$ | 325.75 |
| I-233 | 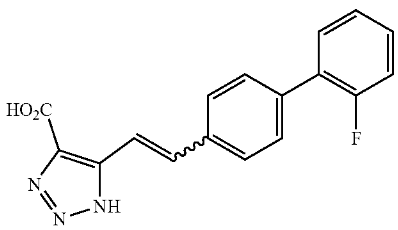 | 5-(2-(2'-fluoro-[1,1'-biphenyl]-4-yl)vinyl)-1H-1,2,3-triazole-4-carboxylic acid | $C_{17}H_{12}FN_3O_2$ | 309.30 |
| I-234 | 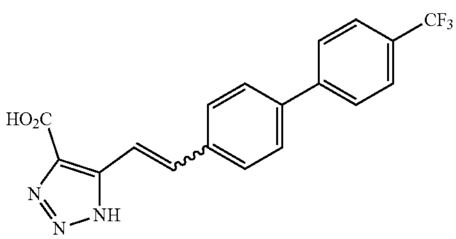 [SMILES: CCOc1ccc(-c2ccc(C=Cc3[nH]nnc3C(=O)O)cc2)cc1] | 5-(2-(4'-(trifluoromethyl)-[1,1'-biphenyl]-4-yl)vinyl)-1H-1,2,3-triazole-4-carboxylic acid | $C_{18}H_{12}F_3N_3O_2$ | 359.31 |
| I-235 | 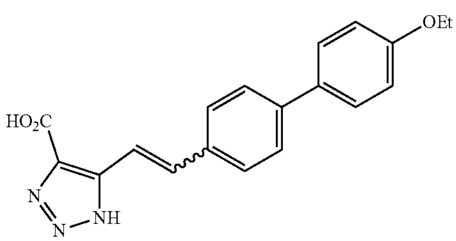 | 5-(2-(4'-ethoxy-[1,1'-biphenyl]-4-yl)vinyl)-1H-1,2,3-triazole-4-carboxylic acid | $C_{19}H_{17}N_3O_3$ | 335.36 |
| I-236 | 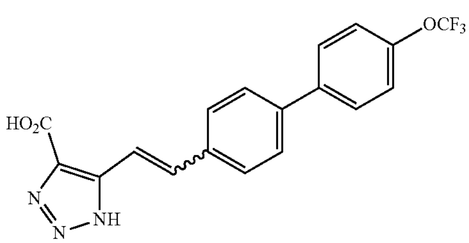 | 5-(2-(4'-(trifluoromethoxy)-[1,1'-biphenyl]-4-yl)vinyl)-1H-1,2,3-triazole-4-carboxylic acid | $C_{18}H_{12}F_3N_3O_3$ | 375.31 |
| I-237 | 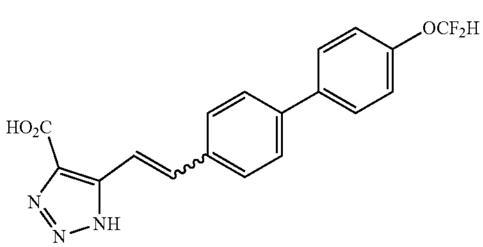 | 5-(2-(4'-(difluoromethoxy)-[1,1'-biphenyl]-4-yl)vinyl)-1H-1,2,3-triazole-4-carboxylic acid | $C_{18}H_{13}F_3N_3O_3$ | 357.32 |

TABLE 1-continued

Example compounds.

| Ex. No. | Structure | IUPAC Name | Chemical Formula | MW (g/mol) |
|---|---|---|---|---|
| I-238 | 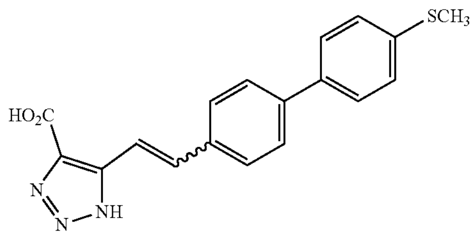 | 5-(2-(4'-(methylthio)-[1,1'-biphenyl]-4-yl)vinyl)-1H-1,2,3-triazole-4-carboxylic acid | $C_{18}H_{15}N_3O_2S$ | 337.40 |
| I-239 | 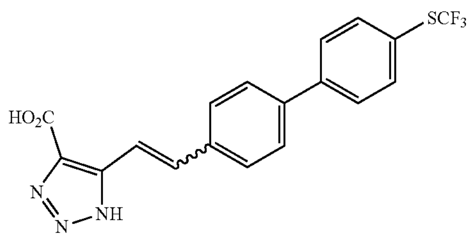 [SMILES: O=C(O)c1nn[nH]c1C=Cc1ccc(-c2ccc(OC(F)(F)F)cc2)cc1] | 5-(2-(4'-((trifluoromethyl)thio)-[1,1'-biphenyl]-4-yl)vinyl)-1H-1,2,3-triazole-4-carboxylic acid | $C_{18}H_{12}F_3N_3O_2S$ | 391.37 |
| I-240 | 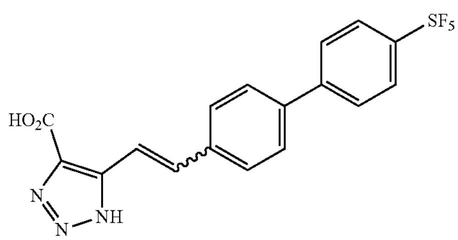 | 5-(2-(4'-(pentafluoro-$\lambda^6$-sulfaneyl)-[1,1'-biphenyl]-4-yl)vinyl)-1H-1,2,3-triazole-4-carboxylic acid | $C_{17}H_{12}F_3N_3O_2S$ | 417.35 |
| I-241 | 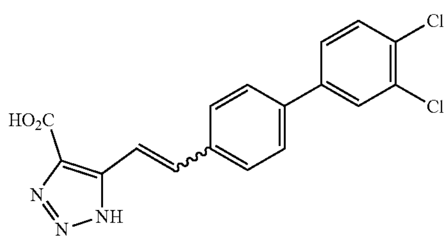 [SMILES: O=C(O)c1nn[nH]c1C=Cc1ccc(-c2ccc(Cl)c(Cl)c2)cc1] | 5-(2-(3',4'-dichloro-[1,1'-biphenyl]-4-yl)vinyl)-1H-1,2,3-triazole-4-carboxylic acid | $C_{17}H_{11}Cl_2N_3O_2$ | 360.19 |
| I-242 | 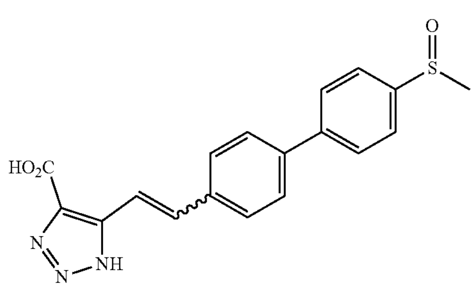 [SMILES: CS(=O)c1ccc(-c2ccc(C=Cc3[nH]nnc3C(=O)O)cc2)cc1] | 5-(2-(4'-(methylsulfinyl)-[1,1'-biphenyl]-4-yl)vinyl)-1H-1,2,3-triazole-4-carboxylic acid | $C_{18}H_{15}N_3O_2S$ | 353.40 |
| I-243 | 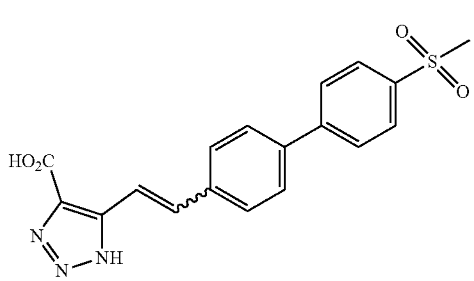 [SMILES: CS(=O)(=O)c1ccc(-c2ccc(C=Cc3[nH]nnc3C(=O)O)cc2)cc1] | 5-(2-(4'-(methylsulfonyl)-[1,1'-biphenyl]-4-yl)vinyl)-1H-1,2,3-triazole-4-carboxylic acid | $C_{18}H_{15}N_3O_4S$ | 369.40 |

TABLE 1-continued

Example compounds.

| Ex. No. | Structure | IUPAC Name | Chemical Formula | MW (g/mol) |
|---|---|---|---|---|
| I-244 | 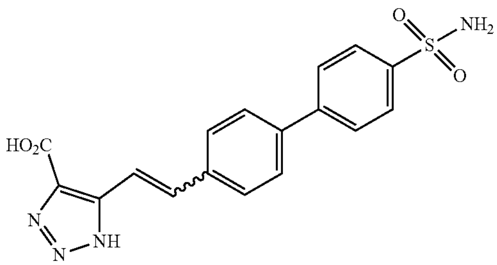 [SMILES: NS(=O)(=O)c1ccc(-c2ccc(C=Cc3[nH]nnc3C(=O)O)cc2)cc1] | 5-(2-(4'-sulfamoyl-[1,1'-biphenyl]-4-yl)vinyl)-1H-1,2,3-triazole-4-carboxylic acid | $C_{17}H_{14}N_4O_4S$ | 370.38 |
| I-245 | 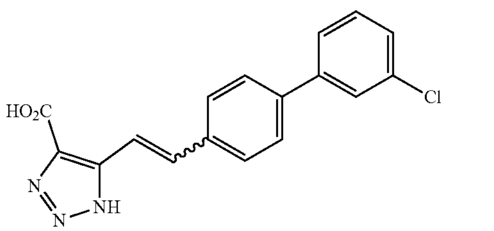 [SMILES: O=C(O)c1nn[nH]c1C=Cc1ccc(-c2cccc(Cl)c2)cc1] | 5-(2-(3'-chloro-[1,1'-biphenyl]-4-yl)vinyl)-1H-1,2,3-triazole-4-carboxylic acid | $C_{17}H_{12}ClN_3O_2$ | 325.75 |
| I-246 | 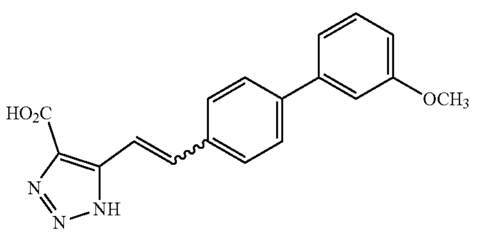 [SMILES: COc1cccc(-c2ccc(C=Cc3[nH]nnc3C(=O)O)cc2)c1] | 5-(2-(3'-methoxy-[1,1'-biphenyl]-4-yl)vinyl)-1H-1,2,3-triazole-4-carboxylic acid | $C_{18}H_{15}N_3O_3$ | 321.34 |
| I-247 | 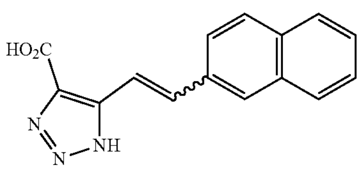 [SMILES: O=C(O)c1nn[nH]c1C=Cc1ccc2ccccc2c1] | 5-(2-(naphthalen-2-yl)vinyl)-1H-1,2,3-triazole-4-carboxylic acid | $C_{15}H_{11}N_3O_2$ | 265.27 |
| I-248 | 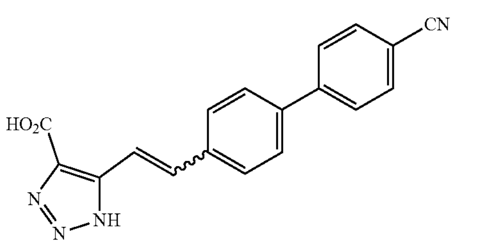 | 5-(2-(4'-cyano-[1,1'-biphenyl]-4-yl)vinyl)-1H-1,2,3-triazole-4-carboxylic acid | $C_{18}H_{12}N_4O_2$ | 316.32 |
| I-249 | 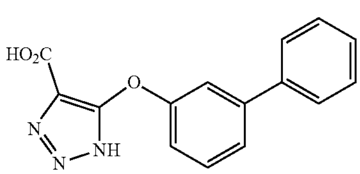 [SMILES: O=C(O)c1nn[nH]c1Oc1cccc(-c2ccccc2)c1] | 5-([1,1'-biphenyl]-3-yloxy)-1H-1,2,3-triazole-4-carboxylic acid | C15H11N3O3 | 281.08 |
| I-250 | 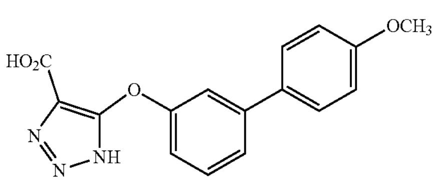 [SMILES: COc1ccc(-c2cccc(Oc3[nH]nnc3C(=O)O)c2)cc1] | 5-((4'-methoxy-[1,1'-biphenyl]-3-yl)oxy)-1H-1,2,3-triazole-4-carboxylic acid | C16H13N3O4 | 311.09 |

TABLE 1-continued

Example compounds.

| Ex. No. | Structure | IUPAC Name | Chemical Formula | MW (g/mol) |
|---|---|---|---|---|
| I-251 | 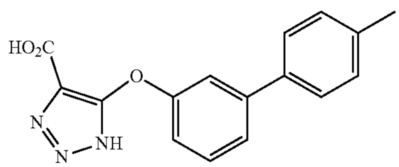 [SMILES: Cc1ccc(-c2cccc(Oc3[nH]nnc3C(=O)O)c2)cc1] | 5-((4'-methyl-[1,1'-biphenyl]-3-yl)oxy)-1H-1,2,3-triazole-4-carboxylic acid | $C_{16}H_{13}N_3O_3$ | 295.10 |
| I-252 | 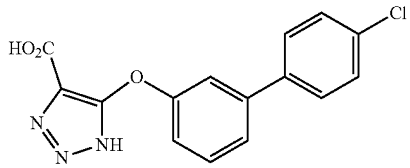 [SMILES: O=C(O)c1nn[nH]c1Oc1cccc(-c2ccc(Cl)cc2)c1] | 5-((4'-chloro-[1,1'-biphenyl]-3-yl)oxy)-1H-1,2,3-triazole-4-carboxylic acid | $C_{16}H_{10}ClN_3O_3$ | 315.71 |
| I-253 | 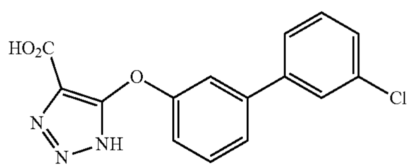 [SMILES: O=C(O)c1nn[nH]c1Oc1cccc(-c2cccc(Cl)c2)c1] | 5-((3'-chloro-[1,1'-biphenyl]-3-yl)oxy)-1H-1,2,3-triazole-4-carboxylic acid | $C_{16}H_{10}ClN_3O_3$ | 315.71 |
| I-254 | 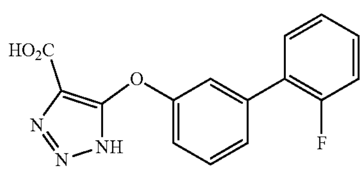 [SMILES: O=C(O)c1nn[nH]c1Oc1cccc(-c2ccccc2F)c1] | 5-((2'-fluoro-[1,1'-biphenyl]-3-yl)oxy)-1H-1,2,3-triazole-4-carboxylic acid | $C_{16}H_{10}FN_3O_3$ | 299.26 |
| I-255 | 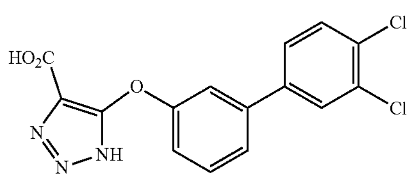 [SMILES: O=C(O)c1nn[nH]c1Oc1cccc(-c2ccc(Cl)c(Cl)c2)c1] | 5-((3',4'-dichloro-[1,1'-biphenyl]-3-yl)oxy)-1H-1,2,3-triazole-4-carboxylic acid | $C_{16}H_9Cl_2N_3O_3$ | 350.16 |
| I-256 | 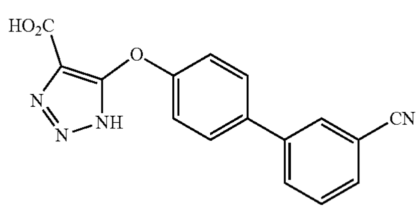 [SMILES: N#Cc1cccc(-c2ccc(Oc3[nH]nnc3C(=O)O)cc2)c1] | 5-((3'-cyano-[1,1'-biphenyl]-4-yl)oxy)-1H-1,2,3-triazole-4-carboxylic acid | $C_{16}H_{10}N_4O_3$ | 306.28 |
| I-257 | 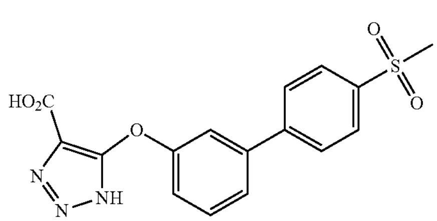 [SMILES: CS(=O)(=O)c1ccc(-c2cccc(Oc3[nH]nnc3C(=O)O)c2)cc1] | 5-((4'-(methylsulfonyl)-[1,1'-biphenyl]-3-yl)oxy)-1H-1,2,3-triazole-4-carboxylic acid | $C_{16}H_{13}N_3O_5S$ | 359.36 |
| I-258 | 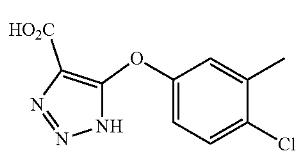 [SMILES: Cc1cc(Oc2[nH]nnc2C(=O)O)ccc1Cl] | 5-(4-chloro-3-methylphenoxy)-1H-1,2,3-triazole-4-carboxylic acid | $C_{10}H_{18}ClN_3O_3$ | 253.64 |

TABLE 1-continued

Example compounds.

| Ex. No. | Structure | IUPAC Name | Chemical Formula | MW (g/mol) |
|---|---|---|---|---|
| I-259 | 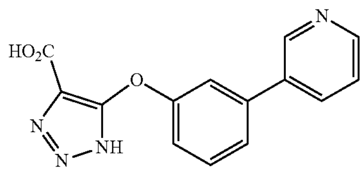 [SMILES: O=C(O)c1nn[nH]c1Oc1cccc(-c2cccnc2)c1] | 5-(3-(pyridin-3-yl)phenoxy)-1H-1,2,3-triazole-4-carboxylic acid | $C_{14}H_{10}N_4O_3$ | 282.26 |
| I-260 | 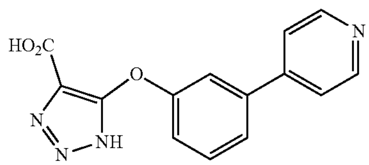 [SMILES: O=C(O)c1nn[nH]c1Oc1cccc(-c2ccncc2)c1] | 5-(3-(pyridin-4-yl)phenoxy)-1H-1,2,3-triazole-4-carboxylic acid | $C_{14}H_{10}N_4O_3$ | 282.26 |
| I-261 | 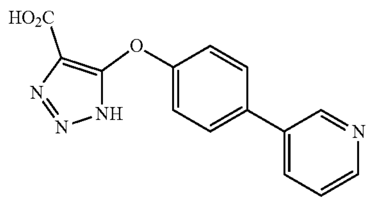 [SMILES: O=C(O)c1nn[nH]c1Oc1ccc(-c2cccnc2)cc1] | 5-(4-(pyridin-2-yl)phenoxy)-1H-1,2,3-triazole-4-carboxylic acid | $C_{14}H_{10}N_4O_3$ | 282.26 |
| I-262 | 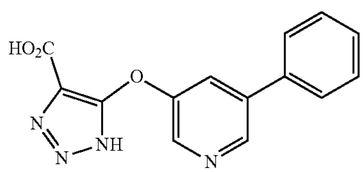 [SMILES: O=C(O)c1nn[nH]c1Oc1cncc(-c2ccccc2)c1] | 5-((5-phenylpyridin-3-yl)oxy)-1H-1,2,3-triazole-4-carboxylic acid | $C_{14}H_{10}N_4O_3$ | 282.26 |
| I-263 | 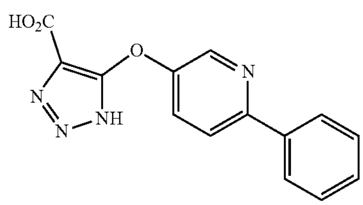 [SMILES: O=C(O)c1nn[nH]c1Oc1ccc(-c2ccccc2)nc1] | 5-((6-phenylpyridin-3-yl)oxy)-1H-1,2,3-triazole-4-carboxylic acid | $C_{14}H_{10}N_4O_3$ | 282.26 |
| I-264 | 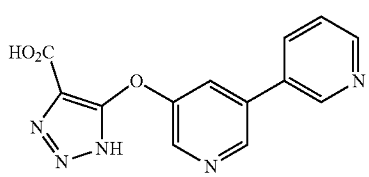 [SMILES: O=C(O)c1nn[nH]c1Oc1cncc(-c2cccnc2)c1] | 5-([3,3'-bipyridin]-5-yloxy)-1H-1,2,3-triazole-4-carboxylic acid | $C_{13}H_9N_5O_3$ | 283.25 |
| I-265 | 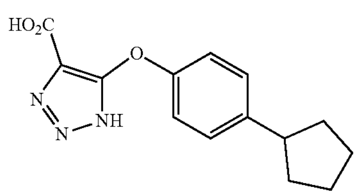 [SMILES: O=C(O)c1nn[nH]c1Oc1ccc(C2CCCC2)cc1] | 5-(4-cyclopentylphenoxy)-1H-1,2,3-triazole-4-carboxylic acid | $C_{14}H_{15}N_3O_3$ | 273.29 |
| I-266 | 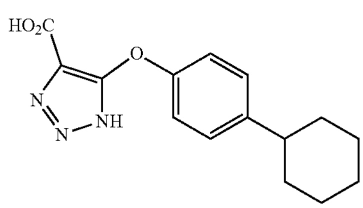 [SMILES: O=C(O)c1nn[nH]c1Oc1ccc(C2CCCCC2)cc1] | 5-(4-cyclohexylphenoxy)-1H-1,2,3-triazole-4-carboxylic acid | $C_{15}H_{17}N_3O_3$ | 287.32 |

TABLE 1-continued

Example compounds.

| Ex. No. | Structure | IUPAC Name | Chemical Formula | MW (g/mol) |
|---|---|---|---|---|
| I-267 | 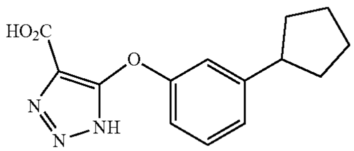 [SMILES: O=C(O)c1nn[nH]c1Oc1cccc(C2CCCC2)c1] | 5-(3-cyclopentylphenoxy)-1H-1,2,3-triazole-4-carboxylic acid | $C_{14}H_{15}N_3O_3$ | 273.29 |
| I-268 | 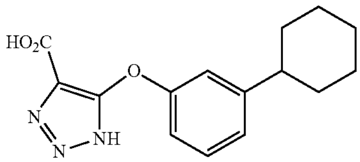 [SMILES: O=C(O)c1nn[nH]c1Oc1cccc(C2CCCCC2)c1] | 5-(3-cyclohexylphenoxy)-1H-1,2,3-triazole-4-carboxylic acid | $C_{15}H_{17}N_3O_3$ | 287.32 |
| I-269 | 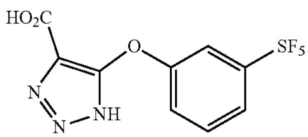 | 5-((3-(pentafluoro-$\lambda^6$-sulfaneyl)phenoxy)-1H-1,2,3-triazole-4-carboxylic acid | $C_9H_6F_5N_3O_3S$ | 331.22 |
| I-270 | 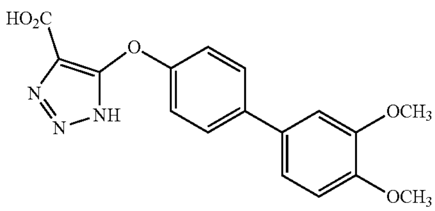 [SMILES: COc1ccc(-c2ccc(Oc3[nH]nnc3C(=O)O)cc2)cc1OC] | 5-((3',4'-dimethoxy-[1,1'-biphenyl]-4-yl)oxy)-1H-1,2,3-triazole-4-carboxylic acid | $C_{17}H_{15}N_3O_5$ | 341.32 |
| I-271 | 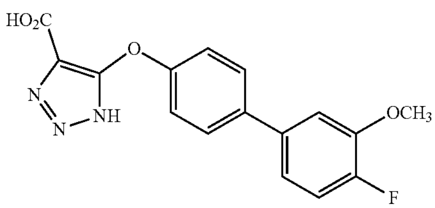 [SMILES: COc1cc(-c2ccc(Oc3[nH]nnc3C(=O)O)cc2)ccc1F] | 5-((4'-fluoro-3'-methoxy-[1,1'-biphenyl]-4-yl)oxy)-1H-1,2,3-triazole-4-carboxylic acid | $C_{16}H_{12}FN_3O_4$ | 329.29 |
| I-272 | 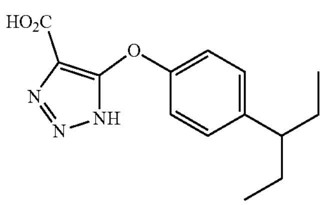 [SMILES: CCC(CC)c1ccc(Oc2[nH]nnc2C(=O)O)cc1] | 5-(4-(pentan-3-yl)phenoxy)-1H-1,2,3-triazole-4-carboxylic acid | $C_{14}H_{17}N_3O_3$ | 275.31 |
| I-273 | 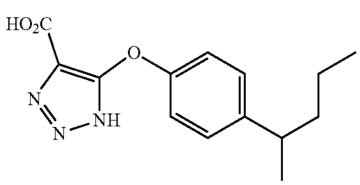 [SMILES: CCCC(C)c1ccc(Oc2[nH]nnc2C(=O)O)cc1] | 5-(4-(pentan-2-yl)phenoxy)-1H-1,2,3-triazole-4-carboxylic acid | $C_{14}H_{17}N_3O_3$ | 275.31 |
| I-274 | 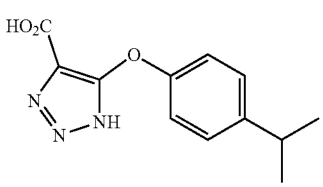 [SMILES: CC(C)c1ccc(Oc2[nH]nnc2C(=O)O)cc1] | 5-(4-isopropylphenoxy)-1H-1,2,3-triazole-4-carboxylic acid | $C_{12}H_{13}N_3O_3$ | 247.25 |

TABLE 1-continued

Example compounds.

| Ex. No. | Structure | IUPAC Name | Chemical Formula | MW (g/mol) |
|---|---|---|---|---|
| I-275 | 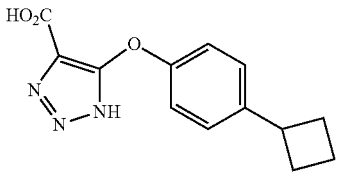 [SMILES: O=C(O)c1nn[nH]c1Oc1ccc(C2CCC2)cc1] | 5-(4-cyclobutylphenoxy)-1H-1,2,3-triazole-4-carboxylic acid | $C_{13}H_{13}N_3O_3$ | 259.27 |
| I-276 | 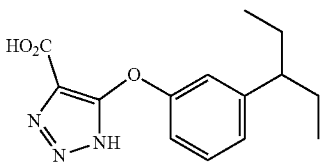 [SMILES: CCC(CC)c1cccc(Oc2[nH]nnc2C(=O)O)c1] | 5-(3-(pentan-3-yl)phenoxy)-1H-1,2,3-triazole-4-carboxylic acid | $C_{14}H_{17}N_3O_3$ | 275.31 |
| I-277 | 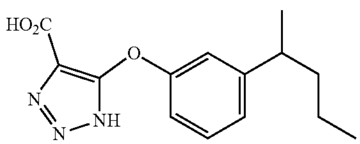 [SMILES: CCCC(C)c1cccc(Oc2[nH]nnc2C(=O)O)c1] | 5-(3-(pentan-2-yl)phenoxy)-1H-1,2,3-triazole-4-carboxylic acid | $C_{14}H_{17}N_3O_3$ | 275.31 |
| I-278 | 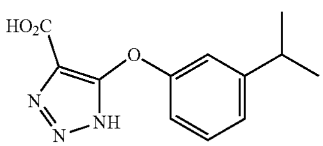 [SMILES: CC(C)c1cccc(Oc2[nH]nnc2C(=O)O)c1] | 5-(3-isopropylphenoxy)-1H-1,2,3-triazole-4-carboxylic acid | $C_{12}H_{13}N_3O_3$ | 247.25 |
| I-279 | 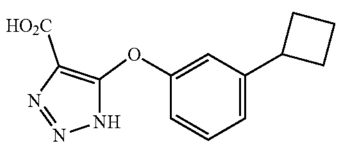 [SMILES: O=C(O)c1nn[nH]c1Oc1cccc(C2CCC2)c1] | 5-(3-cyclobutylphenoxy)-1H-1,2,3-triazole-4-carboxylic acid | $C_{13}H_{13}N_3O_3$ | 259.27 |
| I-280 | 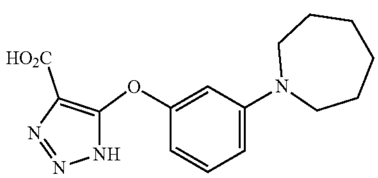 [SMILES: O=C(O)c1nn[nH]c1Oc1cccc(N2CCCCCC2)c1] | 5-(3-(azepan-1-yl)phenoxy)-1H-1,2,3-triazole-4-carboxylic acid | $C_{15}H_{18}N_4O_3$ | 302.33 |
| I-281 | 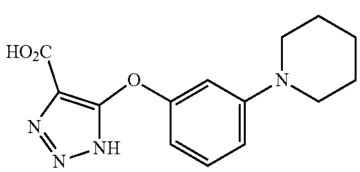 [SMILES: O=C(O)c1nn[nH]c1Oc1cccc(N2CCCCC2)c1] | 5-(3-(piperidin-1-yl)phenoxy)-1H-1,2,3-triazole-4-carboxylic acid | $C_{14}H_{16}N_4O_3$ | 288.31 |
| I-282 | 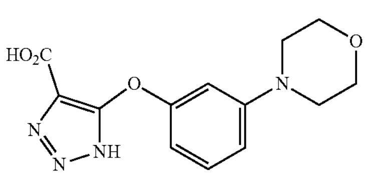 [SMILES: O=C(O)c1nn[nH]c1Oc1cccc(N2CCOCC2)c1] | 5-(3-morpholinophenoxy)-1H-1,2,3-triazole-4-carboxylic acid | $C_{13}H_{14}N_4O_4$ | 290.28 |
| I-283 | 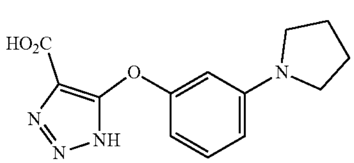 [SMILES: O=C(O)c1nn[nH]c1Oc1cccc(N2CCCC2)c1] | 5-(3-(pyrrolidin-1-yl)phenoxy)-1H-1,2,3-triazole-4-carboxylic acid | $C_{13}H_{14}N_4O_3$ | 274.28 |

TABLE 1-continued

Example compounds.

| Ex. No. | Structure | IUPAC Name | Chemical Formula | MW (g/mol) |
|---|---|---|---|---|
| I-284 | 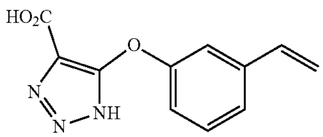 [SMILES: C=Cc1cccc(Oc2[nH]nnc2C(=O)O)c1] | 5-(3-vinylphenoxy)-1H-1,2,3-triazole-4-carboxylic acid | $C_{11}H_9N_3O_3$ | 231.21 |
| I-285 | 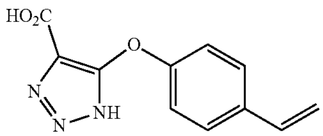 [SMILES: C=Cc1ccc(Oc2[nH]nnc2C(=O)O)cc1] | 5-(4-vinylphenoxy)-1H-1,2,3-triazole-4-carboxylic acid | $C_{11}H_9N_3O_3$ | 231.21 |
| I-286 | 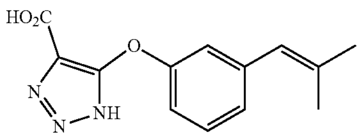 [SMILES: CC(C)=Cc1cccc(Oc2[nH]nnc2C(=O)O)c1] | 5-(3-(2-methylprop-1-en-1-yl)phenoxy)-1H-1,2,3-triazole-4-carboxylic acid | $C_{13}H_{13}N_3O_3$ | 259.27 |
| I-287 | 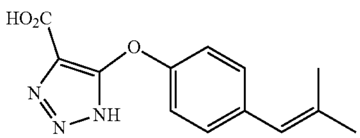 [SMILES: CC(C)=Cc1ccc(Oc2[nH]nnc2C(=O)O)cc1] | 5-(4-(2-methylprop-1-en-1-yl)phenoxy)-1H-1,2,3-triazole-4-carboxylic acid | $C_{13}H_{13}N_3O_3$ | 259.27 |
| I-288 | 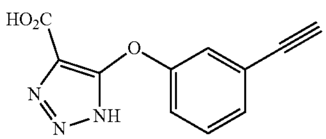 [SMILES: C#Cc1cccc(Oc2[nH]nnc2C(=O)O)c1] | 5-(3-ethynylphenoxy)-1H-1,2,3-triazole-4-carboxylic acid | $C_{11}H_7N_3O_3$ | 229.20 |
| I-289 | 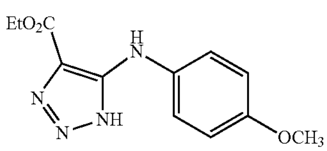 [SMILES: CCOC(=O)c1nn[nH]c1Nc1ccc(OC)cc1] | ethyl 5-((4-methoxyphenyl)amino)-1H-1,2,3-triazole-4-carboxylic acid | $C_{12}H_{14}N_4O_3$ | 262.27 |
| I-290 | 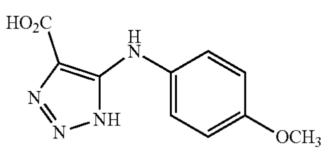 [SMILES: COc1ccc(Nc2[nH]nnc2C(=O)O)cc1] | 5-((4-methoxyphenyl)amino)-1H-1,2,3-triazole-4-carboxylic acid | $C_{10}H_{10}N_4O_3$ | 234.22 |
| I-291 | 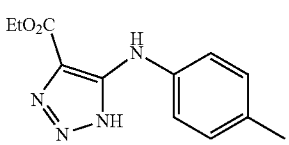 | ethyl 5-(p-tolylamino)-1H-1,2,3-triazole-4-carboxylate | $C_{12}H_{14}N_4O_2$ | 246.27 |
| I-292 | 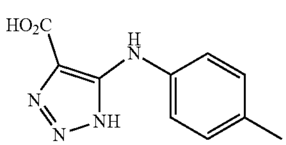 [SMILES: Cc1ccc(Nc2[nH]nnc2C(=O)O)cc1] | 5-(p-tolylamino)-1H-1,2,3-triazole-4-carboxylic acid | $C_{10}H_{10}N_4O_2$ | 218.22 |
| I-293 | 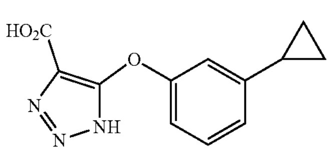 [SMILES: O=C(O)c1nn[nH]c1Oc1cccc(C2CC2)c1] | 5-(3-cyclopropylphenoxy)-1H-1,2,3-triazole-4-carboxylic acid | $C_{12}H_{11}N_3O_3$ | 245.24 |

TABLE 1-continued

Example compounds.

| Ex. No. | Structure | IUPAC Name | Chemical Formula | MW (g/mol) |
|---|---|---|---|---|
| I-294 | 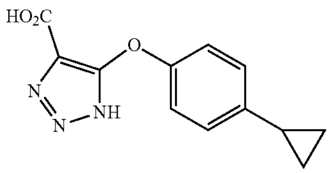 [SMILES: O=C(O)c1nn[nH]c1Oc1ccc(C2CC2)cc1] | 5-(4-cyclopropylphenoxy)-1H-1,2,3-triazole-4-carboxylic acid | $C_{12}H_{11}N_3O_3$ | 245.24 |
| I-295 | 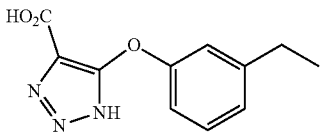 [SMILES: CCc1cccc(Oc2[nH]nnc2C(=O)O)c1] | 5-(3-ethylphenoxy)-1H-1,2,3-triazole-4-carboxylic acid | $C_{11}H_{11}N_3O_3$ | 233.08 |
| I-296 | 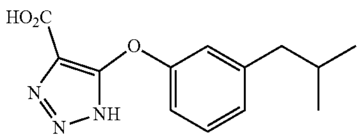 [SMILES: CC(C)Cc1cccc(Oc2[nH]nnc2C(=O)O)c1] | 5-(3-isobutylphenoxy)-1H-1,2,3-triazole-4-carboxylic acid | $C_{13}H_{15}N_3O_3$ | 261.28 |
| I-297 | 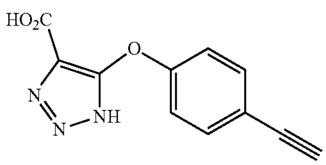 [SMILES: C#Cc1ccc(Oc2[nH]nnc2C(=O)O)cc1] | 5-(4-ethynylphenoxy)-1H-1,2,3-triazole-4-carboxylic acid | $C_{11}H_7N_3O_3$ | 229.20 |
| I-298 | 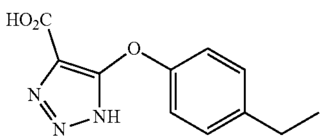 [SMILES: CCc1ccc(Oc2[nH]nnc2C(=O)O)cc1] | 5-(4-ethylphenoxy)-1H-1,2,3-triazole-4-carboxylic acid | $C_{11}H_{11}N_3O_3$ | 233.08 |
| I-299 | 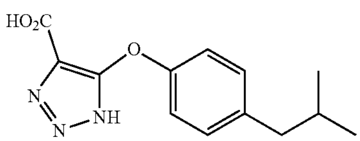 [SMILES: CC(C)Cc1ccc(Oc2[nH]nnc2C(=O)O)cc1] | 5-(4-isobutylphenoxy)-1H-1,2,3-triazole-4-carboxylic acid | $C_{13}H_{15}N_3O_3$ | 261.28 |
| I-300 | 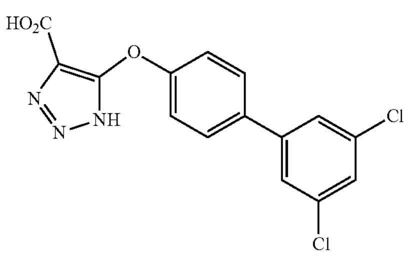 [SMILES: O=C(O)c1nn[nH]c1Oc1ccc(-c2cc(Cl)cc(Cl)c2)cc1] | 5-((3',5'-dichloro-[1,1'-biphenyl]-4-yl)oxy)-1H-1,2,3-triazole-4-carboxylic acid | $C_{15}H_9Cl_2N_3O_3$ | 350.16 |
| I-301 | 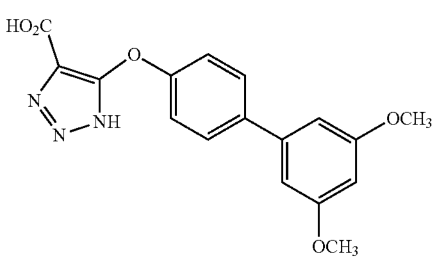 [SMILES: COc1cc(OC)cc(-c2ccc(Oc3[nH]nnc3C(=O)O)cc2)c1] | 5-((3',5'-dimethoxy-[1,1'-biphenyl]-4-yl)oxy)-1H-1,2,3-triazole-4-carboxylic acid | $C_{17}H_{15}N_3O_5$ | 341.32 |

TABLE 1-continued

Example compounds.

| Ex. No. | Structure | IUPAC Name | Chemical Formula | MW (g/mol) |
|---|---|---|---|---|
| I-302 | 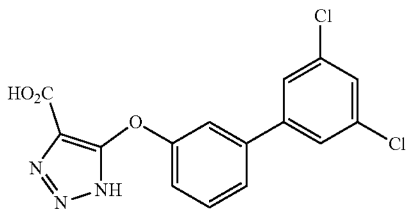 [SMILES: O=C(O)c1nn[nH]c1Oc1cccc(-c2cc(Cl)cc(Cl)c2)c1] | 5-((3',5'-dichloro-[1,1'-biphenyl]-3-yl)oxy)-1H-1,2,3-triazole-4-carboxylic acid | $C_{15}H_9Cl_2N_3O_3$ | 350.16 |
| I-303 | 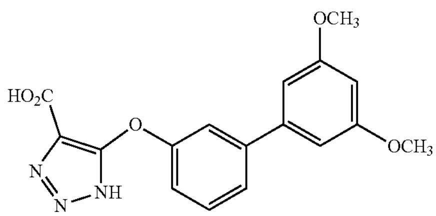 [SMILES: COc1cc(OC)cc(-c2cccc(Oc3[nH]nnc3C(=O)O)c2)c1] | 5-((3',5'-dimethoxy-[1,1'-biphenyl]-3-yl)oxy)-1H-1,2,3-triazole-4-carboxylic acid | $C_{17}H_{15}N_3O_5$ | 341.32 |
| I-304 | 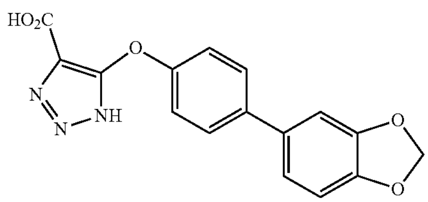 [SMILES: O=C(O)c1nn[nH]c1Oc1ccc(-c2ccc3c(c2)OCO3)cc1] | 5-(4-(benzo[d][1,3]dioxol-5-yl)phenoxy)-1H-1,2,3-triazole-4-carboxylic acid | $C_{16}H_{11}N_3O_5$ | 325.28 |
| I-305 | 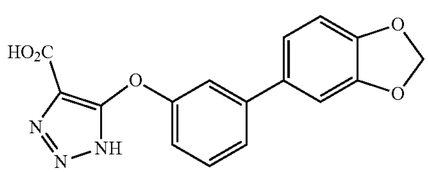 [SMILES: O=C(O)c1nn[nH]c1Oc1cccc(-c2ccc3c(c2)OCO3)c1] | 5-(3-(benzo[d][1,3]dioxol-5-yl)phenoxy)-1H-1,2,3-triazole-4-carboxylic acid | $C_{16}H_{11}N_3O_5$ | 325.28 |
| I-306 | 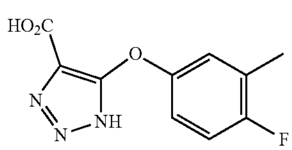 [SMILES: Cc1cc(Oc2[nH]nnc2C(=O)O)ccc1F] | 5-(4-fluoro-3-methylphenoxy)-1H-1,2,3-triazole-4-carboxylic acid | $C_{10}H_8FN_3O_3$ | 237.19 |
| I-307 | 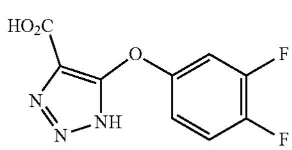 [SMILES: O=C(O)c1nn[nH]c1Oc1ccc(F)c(F)c1] | 5-(3,4-difluorophenoxy)-1H-1,2,3-triazole-4-carboxylic acid | $C_9H_5F_2N_3O_3$ | 241.15 |
| I-308 | 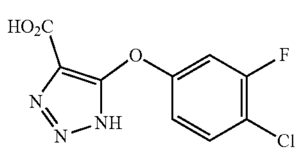 [SMILES: O=C(O)c1nn[nH]c1Oc1ccc(Cl)c(F)c1] | 5-(4-chloro-3-fluorophenoxy)-1H-1,2,3-triazole-4-carboxylic acid | $C_9H_5ClFN_3O_3$ | 257.61 |
| I-309 | 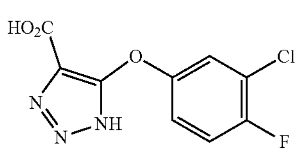 [SMILES: O=C(O)c1nn[nH]c1Oc1ccc(F)c(Cl)c1] | 5-(3-chloro-4-fluorophenoxy)-1H-1,2,3-triazole-4-carboxylic acid | $C_9H_5ClFN_3O_3$ | 257.61 |

TABLE 1-continued

Example compounds.

| Ex. No. | Structure | IUPAC Name | Chemical Formula | MW (g/mol) |
|---|---|---|---|---|
| I-310 | [structure] | 5-((3'-fluoro-4'-(trifluoromethoxy)-[1,1'-biphenyl]-4-yl)oxy)-1H-1,2,3-triazole-4-carboxylic acid | $C_{16}H_9F_4N_3O_4$ | 383.26 |
| I-311 | [structure] | 5-((3'-fluoro-4'-(trifluoromethoxy)-[1,1'-biphenyl]-3-yl)oxy)-1H-1,2,3-triazole-4-carboxylic acid | $C_{16}H_9F_4N_3O_4$ | 383.26 |

Also provided are alkyl esters of the compounds disclosed above, which can be made by the methods above and may be useful as, inter alia, prodrugs. Ethyl esters are shown, and other esters, such as methyl, n-propyl, isopropyl, and so on, are also provided herein. Such alkyl esters may be used as prodrugs of the compounds disclosed herein, and as disclosed above, are often made en route to the carboxylic acid compounds disclosed herein. Similarly, de-esterification may be used to produce the carboxylic acid analogue of esters disclosed herein.

Biological Activity Assay: In-Vitro Human Glycolate Oxidase (hGOX) Assay

The in-vitro glycolate oxidase assay was performed using recombinant full-length human hydroxyacid oxidase 1 (HAO1), the equivalent of hGOX. The enzyme was obtained from AbCam (Catalog #ab113144) and was purified using conventional chromatography to >95% purity. Purified HAO1 was dissolved in assay buffer consisting of 10 mM NaCl, 110 mM KCl, 2 mM $MgCl_2$, 50 mM HEPES (pH 7.4) and 0.01% Triton™ X-100. The assay used Corning 3575 384-well flat bottom, low flange, non-binding surface, black polystyrene plates.

To determine HAO1 inhibition, 2 µL of compound concentrations in 100% DMSO were added to 28 µL of 36 nM HAO1 and incubated at room temperature for 10 min. Subsequently 40 µL of 100 µM Amplex red/0.2 U/mL horseradish peroxidase (HRP) was added followed by 10 µL of 680 µM glycolate (pH 7.4). Thus, final concentrations in the 80 µL reaction well were 12.5 nM HAO1, 50 µM Amplex Red, 0.1 U/mL HRP, and 85 µM glycolate in a final concentration of 2.5% DMSO. The fluorescence signal was measured every 53 seconds using a GENios microplate reader (Tecan) with Ex=530±10 nm and Em=585±10 nm. Linear data were plotted to calculate the reaction velocity values.

Table 2 shows the $IC_{50}$ values for the compounds tested in this in-vitro assay.

TABLE 2

Results from In-Vitro Human Glycolate Oxidase (hGOX) Assay

| Ex. No. | $IC_{50}$ (µM) |
|---|---|
| I-001 | 0.11 |
| I-003 | 0.16 |
| I-004 | 0.14 |
| I-005 | >500 |
| I-006 | 2.31 |
| I-007 | 0.07 |
| I-008 | >500 |
| I-009 | 0.23 |
| I-010 | 0.36 |
| I-011 | 0.27 |
| I-012 | 251 |
| I-013 | 0.20 |
| I-014 | 430 |
| I-015 | 0.13 |
| I-016 | 0.82 |
| I-025 | 0.043 |
| I-031 | 0.069 |
| I-032 | 4.86 |
| I-033 | 0.067 |
| I-035 | 0.26 |
| I-037 | 0.034 |
| I-039 | 0.056 |
| I-049 | 0.050 |
| I-050 | 0.012 |
| I-057 | 0.36 |
| I-058 | 0.050 |
| I-085 | >10 |
| I-128 | 0.227 |
| I-129 | 0.041 |
| I-150 | 0.023 |
| I-151 | 0.011 |
| I-152 | 0.017 |
| I-153 | 0.010 |
| I-154 | 0.005 |
| I-158 | 0.008 |
| I-160 | 0.012 |
| I-167 | 0.008 |
| I-171 | 0.010 |
| I-174 | 0.027 |
| I-177 | 0.012 |
| I-178 | 013 |
| I-249 | 0.019 |
| I-250 | 0.025 |
| I-251 | 0.013 |
| I-252 | 0.013 |
| I-253 | 0.009 |

TABLE 2-continued

Results from In-Vitro Human
Glycolate Oxidase (hGOX) Assay

| Ex. No. | IC$_{50}$ (μM) |
|---|---|
| I-254 | 0.017 |
| I-255 | 0.006 |
| I-256 | 0.022 |
| I-257 | 0.013 |
| I-258 | 0.044 |
| I-259 | 0.018 |
| I-260 | 0.021 |
| I-261 | 0.150 |
| I-262 | 0.191 |
| I-263 | 0.141 |
| I-264 | 0.380 |
| I-265 | 0.025 |
| I-266 | 0.030 |
| I-267 | 0.035 |
| I-268 | 0.051 |
| I-269 | 0.105 |
| I-270 | 0.013 |
| I-271 | 0.007 |
| I-272 | 0.084 |
| I-273 | 0.045 |
| I-274 | 0.112 |
| I-275 | 0.022 |
| I-276 | 0.023 |
| I-277 | 0.065 |
| I-278 | 0.230 |
| I-279 | 0.032 |
| I-280 | 0.222 |
| I-281 | 0.370 |
| I-282 | 0.539 |
| I-283 | 0.172 |
| I-284 | 0.089 |
| I-285 | 0.038 |
| I-286 | 0.014 |
| I-287 | 0.020 |
| I-288 | 0.024 |
| I-289 | >500 |
| I-290 | 6.53 |
| I-291 | >500 |
| I-292 | 3.76 |
| I-293 | 0.074 |
| I-294 | 0.053 |
| I-295 | 0.079 |
| I-296 | 0.076 |
| I-297 | 0.004 |
| I-298 | 0.034 |
| I-299 | 0.033 |
| I-300 | 0.033 |
| I-301 | 1.08 |
| I-302 | 0.003 |
| I-303 | 0.169 |
| I-304 | 0.004 |
| I-305 | 0.002 |
| I-306 | 0.061 |
| I-307 | 0.088 |
| I-308 | 0.034 |
| I-309 | 0.027 |
| I-310 | 0.005 |
| I-311 | 0.027 |

It is expected that these compounds and the other compounds disclosed herein will be effective in inhibiting human hydroxyacid oxidase 1 and human glycolate oxidase, and thus would be effective in treating diseases related to oxalate accumulation, for example hyperoxaluria. In particular, compounds with linker L being O were generally 4 to 10 times more potent than the analogous compound having S as L.

HepaRG-CAR Cell-Based Assay for Quantitation of Glycolate Oxidase Inhibition

A HepaRG human hepatic cell line was transfected for stable overexpression of the constitutive androstane receptor (i.e., HepaRG-CAR cells), as reported by van der Mark et al. (Drug Metab. Dispos., 2017, 45:56-67. Overexpression of CAR in these cells resulted in higher levels of glycolate oxidase (GOX) expression compared to the parental HepaRG cells. HepaRG-CAR cells were plated in a 12-wells plate and incubated for 4 weeks until fully differentiated.

To measure cellular glycolate flux, the HepaRG-CAR cells were incubated in Williams medium supplemented with 10% fetal bovine serum (FBS), 5 μg/mL insulin, 50 μM hydrocortisone hemisuccinate, 2 mM glutamine, 5000 U/mL penicillin and 5 mg/mL streptomycin. Test compounds were added to the medium at 0, 0.3, 1, 3 or 10 μM and incubated for 30 minutes, after which 500 μM glycolate was also added. After incubation for 48 hours, 400 μL medium was taken from the culture plate and added to 60 μL 37% HCl. Internal standards (2,2-d$_2$ glycolate, 1,2-$^{13}$C2 oxalate and $^{13}$C2-glyoxylate) and hydroxylamine were added followed by another 30 minute incubation at 80° C. The acids were extracted using ethyl acetate with NaCl. The organic phase was dried under nitrogen and derivatized with N-tert-butyldimethylsilyl-N-methyl trifluoroacetamide (MTB-STFA) for 30 minutes at 80° C. The amounts of glycolate, glyoxylate and oxalate were determined by gas chromatography-mass spectrometry (GC-MS) analysis, using a 25 meter CP-Sil 5 CB low bleed column. A standard curve was used to calculate the concentrations of each acid in the culture medium. The IC$_{50}$ values of human glycolate oxidase inhibitors from the foregoing in-vitro human HepaRG-CAR cell-based assay are reported below at Table 3.

TABLE 3

IC$_{50}$ Value of Human Glycolate
Oxidase Inhibitors in an In-Vitro
Human HepaRG-CAR Cell-based Assay

| Ex. No. | IC$_{50}$ (μM) |
|---|---|
| I-001 | 1 |
| I-037 | 0.4 |
| I-058 | 2 |
| I-152 | 10 |
| I-154 | >10 |
| I-158 | 5 |
| I-160 | 2.5 |
| I-171 | >10 |
| I-174 | 3 |
| I-249 | 2 |
| I-250 | >5 |
| I-251 | 2.5 |
| I-252 | 2 |
| I-253 | 2.5 |
| I-254 | 2.5 |
| I-255 | 5 |
| I-256 | 10 |
| I-257 | 2.5 |
| I-258 | 0.3 |
| I-259 | 2 |
| I-260 | 2.5 |
| I-261 | >10 |
| I-262 | >10 |
| I-263 | >10 |
| I-264 | >10 |

Solubility, Metabolic Stability, and Protein Binding Assays

Solubility at relevant physiologic conditions and metabolic stability of compounds are both properties that can be important for suitability of use as a pharmaceutical composition and medicament without resort to complicated formulation. Accordingly, representative compounds disclosed herein were tested for aqueous and saline solubility, for metabolic stability in liver microsomes and in human plasma, and, as disclosed below.

Solubility.

For testing compound solubility in phosphate buffered saline (PBS), compound stock solutions were prepared at 10 mM in 100% DMSO. For testing in aqueous solution, the phosphate buffer was replaced with deionized, distilled water. Eleven grams $Na_2HPO_4$ (FW: 141.96 g/mol) and 3.5 g $NaH_2PO_4.2H_2O$ (FW: 156.03 g/mol) was added to 1 L Milli-Q water and adjusted to a pH to 7.4 with phosphoric acid or sodium hydroxide. For incubation, media were preheated to 37° C. Eight μL aliquots of reference and test compound stock solutions (10 mM) were added into 792 μL of 100 mM phosphate buffer (pH 7.4). The final DMSO concentration was 1%. Sample tubes were shaken for 1 hour at 1000 rpm at room temperature.

The calibration curve was prepared with 300-μM spiking solution (SS) in MeOH:acetonitrile (4:1). Six μL of 10 mM compound was added in 194 μL MeOH/acetonitrile (4:1). Samples were centrifuged for 10 minutes at 12,000 rpm to precipitate undissolved particles. Supernatants were transferred to a new tube or plate and dilute 10-fold and 100-fold with 100 mM buffer. Samples were prepared for LC-MS/MS analysis by adding 5 μL each sample (undiluted, 10-fold diluted, and 100-fold diluted) and 5 μL of standard curve samples to 95 μL of acetonitrile (containing internal standard).

Metabolic Stability.

For evaluating the metabolic stability in human liver microsomal preparation, three buffers were prepared. Buffer A had 1.0 L of 0.1 M monobasic potassium phosphate buffer containing 1.0 mM EDTA. Buffer B had 1.0 L of 0.1 M dibasic potassium phosphate buffer containing 1.0 mM EDTA. Buffer C had 0.1 M potassium phosphate buffer, 1.0 mM EDTA, adjusted to a pH 7.4 via titrating 700 mL buffer B with buffer A. Reference compound (ketanserin) and test compounds spiking solutions (500 μM) were prepared by adding 10 μL of 10 mM DMSO stock compound solution into 190 μL acetonitrile. A volume of 1.5 μL 500 μM spiking solution and 18.75 μL 20 mg/mL human liver microsomes were added into 479.75 μL of Buffer C on ice. A stock solution of 6 mM NADPH was prepared by dissolving NADPH into Buffer C.

Wells on an assay plate were iced and filled with 30 μL 1.5-μM spiking solution containing 0.75 mg/mL microsomes solution and designated for different timepoints (0-, 5-, 15-, 30-, 45-min). For the 0-min timepoint, 135 μL acetonitrile containing internal standard were added followed by 15 μL of NADPH stock solution (6 mM). All other plates were preincubated at 37° C. for 5 minutes and 15 μL NADPH stock solution (6 mM) were added to the plates to start the reaction. At 5-min, 15-min, 30-min, and 45-min, 135 μL acetonitrile containing internal standard were added to the wells of corresponding plates, respectively, to stop the reaction. After quenching, the plates were shaken on the vibrator (IKA, MTS 2/4) for 10 min at 600 rpm and then centrifuged at 5594×g for 15 minutes (Thermo Multifuge× 3R). Fifty μL supernatant from each well were transported into a 96-well sample plate containing 50 μL of ultra-pure water (Millipore, ZMQS50F01) for LC/MS analysis.

Table 4 shows the in vitro Drug Metabolism-Pharmacokinetic (DMPK) results, including aqueous solubility (μM) of the compound in PBS and in water (μM), metabolic stability half-life ($t_{1/2}$ in min), metabolic stability $Cl_{int}$ (mL/min/kg).

TABLE 4

In vitro DMPK results for human glycolate oxidase inhibitors

| Ex. No. | Aqueous Solubility PBS (μM) | Aqueous Solubility $H_2O$ (μM) | Metabolic Stability $t_{1/2}$ (min) | Metabolic Stability $Cl_{int}$ (mL/min/kg) |
|---|---|---|---|---|
| I-001 | 94.45 | 83.80 | 1455.6 | 1.19 |
| I-031 | 121 | 110 | 786.12 | 2.21 |
| I-033 | 121 | 107.5 | >5000 | <0.15 |
| I-037 | 96.80 | 96.10 | >5000 | <0.15 |
| I-050 | 120.5 | 102 | 704.77 | 2.47 |
| I-058 | 90.85 | 81.55 | 827.78 | 2.10 |
| I-128 | 122.5 | 106 | 171.91 | 10.11 |
| I-129 | 116 | 72.70 | 80.68 | 21.55 |
| I-150 | 95.70 | 83.10 | 527.01 | 3.04 |
| I-151 | 83.20 | 52.95 | >5000 | <0.15 |
| I-154 | 93.65 | 29.10 | >5000 | <0.15 |
| I-158 | 106 | 101 | >5000 | <0.15 |
| I-160 | 101.2 | 64.60 | 248.56 | 6.99 |
| I-167 | 116.5 | 112.5 | 1021.06 | 1.70 |
| I-171 | 96.30 | 45.75 | 120.54 | 14.42 |
| I-174 | 89.80 | 70.35 | 701.23 | 2.48 |
| I-177 | 89.30 | 45.70 | 565.7 | 3.07 |
| I-178 | 97.90 | 83.40 | 245.59 | 7.08 |
| I-249 | 103.45 | 107.5 | 347.65 | 5.00 |
| I-250 | 109.5 | 99.40 | 194.33 | 8.95 |
| I-251 | 108 | 101 | 98.43 | 17.66 |
| I-252 | 104 | 97.95 | 226.93 | 7.66 |
| I-253 | 102 | 91.70 | 315.45 | 5.51 |
| I-254 | 114 | 106 | 454.86 | 3.82 |
| I-255 | 97.10 | 80.95 | >5000 | <0.15 |
| I-256 | 90.45 | 86.90 | 4296.35 | 0.40 |
| I-257 | 91.85 | 89.80 | 1139.76 | 1.53 |
| I-258 | 95.75 | 93.55 | >5000 | <0.15 |
| I-259 | 93.10 | 96.10 | 3859.98 | 0.45 |
| I-260 | 100.5 | 94.40 | 618.21 | 2.81 |
| I-261 | 101.5 | 105 | 1098.06 | 1.58 |
| I-262 | 97.25 | 94.15 | >5000 | <0.15 |
| I-263 | 106 | 98.95 | 700.44 | 2.48 |
| I-264 | 107.5 | 105 | 10396.14 | 0.17 |
| I-265 | 107 | 100.4 | 93.26 | 18.64 |
| I-266 | 96.45 | 108 | 65.78 | 26.43 |
| I-267 | 79.85 | 82.60 | >5000 | <0.15 |
| I-268 | 97.60 | 111 | 20.64 | 84.24 |
| I-269 | 108.8 | 103.2 | >5000 | <0.15 |
| I-270 | <0.2 | 109.0 | 638.78 | 2.72 |
| I-271 | 110.0 | 90.10 | 498.79 | 3.49 |
| I-272 | 102.7 | 96.60 | 26.60 | 65.35 |
| I-273 | 112 | 108 | 49.33 | 35.24 |
| I-275 | 114.8 | 110.0 | 94.8 | 18.34 |
| I-276 | 108.8 | 103.2 | 292.03 | 5.95 |
| I-277 | 112.8 | 97.20 | 203.03 | 8.56 |
| I-279 | 112.4 | 110.8 | 349.39 | 4.98 |
| I-285 | 101.3 | 97.60 | >5000 | <0.15 |
| I-286 | 92.60 | 95.80 | 114.93 | 15.13 |
| I-287 | 85.70 | 82.50 | 129.56 | 13.42 |
| I-288 | 92.40 | 80.60 | 558.60 | 3.11 |
| I-294 | 107.6 | 107.7 | 511.17 | 3.40 |
| I-299 | 103.6 | 98.40 | 153.13 | 11.35 |
| I-302 | 111.5 | 90.65 | >5000 | <0.15 |
| I-304 | 111.2 | 115 | 317.84 | 5.47 |

Stability in Human Plasma.

Stock compounds were prepared for testing the stability in human plasma. First, 0.05 M sodium phosphate and 0.07 M NaCl buffer, pH 7.4, were pre-heated. In deionized water, 14.505 g/L $Na_2HPO\ 12H_2O$, 1.483 g/L $NaH_2PO_4.2H_2O$ and 4.095 g/L NaCl were dissolved. The basic solution was titrated with the phosphoric acid to pH 7.40. Frozen plasma was quickly thawed at 37° C. The plasma was centrifuged at 3,000 rpm for 8 minutes to remove clots, then pipetted and pooled as the plasma stock for the experiment. Only plasma within the range of pH 7.4 to pH 8 was used. If higher than pH 8, the plasma was discarded. The initial pH of the plasma was not adjusted to pH 7.4 with acid or by bubbling with carbon dioxide. By using a 5% carbon dioxide incubator and PBS buffer, a pH of 7.4 will be reached after the 4-hour equilibrium dialysis time. Plasma was iced until use.

Spiking solution A with 0.5 mM testing compounds was prepared by adding 10 μL of 10 mM test compounds stock solution to 190 μL DMSO. Spiking solution B with 0.02 mM testing compound was prepared by adding 40 μL of spiking solution A to 960 μL of 0.05 mM sodium phosphate buffer with 0.5% BSA. The plasma and spiking solution B were prewarmed at 37° C. for 5 minutes. Ten μL of pre-warmed spiking solution B was added into the wells designated for all the time points (5, 15, 30, 45, 60 minutes). For the 0-minute timepoint, 400 μL acetonitrile containing internal standard were added to the wells of 0-minute plate and then 90 μL plasma were added. For the other timepoints, 90 μL of pre-warmed plasma were added into the wells (0, 5, 15, 30, 45, 60 minutes) and the timing was started. At 5, 15, 30, 45, 60 minutes, 400 μL acetonitrile containing internal standard were added to the wells of corresponding plates, respectively, to stop the reaction. After quenching, the plates were shaken on a vibrator (IKA, MTS 2/4) for 10 minutes at 600 rpm and then centrifuged at 5594×g for 15 minutes (Thermo Multifuge×3R). Fifty μL of supernatant was transferred from each well into a 96-well sample plate containing 50 μL ultra-pure water (Millipore, ZMQS50F01) for LC/MS analysis.

Caco-2 Permeability.

Stock compounds solubilized in dimethyl sulfoxide (DMSO) were tested using luciferase yellow (LY) dye. For donor solutions in the apical to basolateral (A-to-B) direction, Hanks Balanced Salt Solution (HBSS) buffer with 0.3% DMSO and 5 μM LY was prepared by adding 150 μL DMSO and 50 μL LY (5 mM) into 50 mL HBSS buffer (pH 7.4). HBSS buffer with 0.1% DMSO and 5 μM LY was prepared by adding 50 μL DMSO and 50 μL LY (5 mM) into 50 mL HBSS buffer (pH 7.4). For donor solutions in the basolateral to apical (B-to-A) direction, HBSS buffer with 0.3% DMSO was prepared by adding 150 μL DMSO into 50 mL HBSS buffer (pH 7.4). HBSS buffer with 0.1% DMSO was prepared by adding 50 μL DMSO into 50 mL HBSS buffer (pH 7.4).

The receiver solution buffer for the A-to-B direction used HBSS buffer with 0.4% DMSO prepared by adding 200 μL DMSO into 50 mL HBSS buffer (pH 7.4). For B-to-A direction, HBSS buffer with 0.4% DMSO and 5 μM LY was prepared by adding 200 μL DMSO and 50 μL LY (5 mM) into 50 mL HBSS buffer (pH 7.4)

Transepithelial electrical resistance (TEER) was measured at room temperature after cell culture plates were removed from the incubator, cell monolayers were washed with HBSS buffer. The compound solution was centrifuged at 4000 rpm for 5 minutes before loading samples to donor chambers. Solutions were added as shown in Table 5.

TABLE 5

Donor and Receiver Chamber Solutions

| Position | Transport Direction | Volume added | Final volume |
|---|---|---|---|
| Apical | A--B (Donor chamber) | 600 μL of A-to-B dosing solution (100 μL for LY measurement and 100 μL for Backup) | 400 μL |
| Basolateral | A--B (Receiver chamber) | 800 μL 0.4% DMSO HBSS | 800 μL |
| Basolateral | B--A (Donor chamber) | 900 μL B-to-A dosing solution (100 μL for Backup) | 800 μL |
| Apical | B--A (Receiver chamber) | 500 μL 0.4% DMSO HBSS+ LY (100 μL for LY measurement) | 400 μL |

To determine LY concentration in the apical chamber, 100 μL sample was transferred from apical chambers and into an opaque plate for LYT0. Apical and basolateral plates were warmed to 37° C. for about 5 minutes, and the apical plate was placed onto the basolateral plate. The assembled plates were incubated at 37° C. for 90 minutes.

For the standard curve, a 20× solution of compound was prepared. For 300 μM compound solution, 6 μL of compound stock solution was added into 192 μL of MeOH/H$_2$O (1:1). After 90 minutes of incubation, the apical plate was separated from the basolateral plate after. One hundred μL samples were transferred from the basolateral plate to an opaque plate as LYT90. The LY concentrations were measured for LYT0 and LYT90 using a fluorometer at an excitation of 485 nm and emission of 535 nm. Samples for LC-MS/MS analysis were prepared from the donor and receiver chambers by diluting with 0.4% DMSO HBSS, then mixing with acetonitrile containing an internal standard of either osalmid or imipramine.

Protein Binding.

For testing protein binding of stock compounds solubilized in DMSO, spiking solutions of test and reference compounds were prepared. Solution A (0.5 mM) was prepared by adding 10 μL of 10 mM stock solution into 190 μL of DMSO. Solution B (0.02 mM) was prepared by adding 8 μL of Solution A into 192 μL of 0.05 M sodium phosphate buffer. The final DMSO concentration in Solution B was 4%.

To prepare test and reference compounds in plasma, a 96-well plate with 380 μL aliquots of plasma in the wells designed for plasma and buffer, respectively. Twenty μL of Solution B (0.02 mM of test and reference compounds) were spiked into the pre-loaded plasma in the 96-well plate. The final test concentration is 1 μM containing 0.2% DMSO.

For dialysis sample loading a plasma again buffer system was prepared by applying aliquots of 100 μL of blank dialysis buffer to the receiver side of dialysis chambers and then applying aliquots of 100 μL of the plasma spiked with test and reference compounds to the donor side of the dialysis chamber. A 25-μL aliquot of the plasma spiked with test and reference compounds was added into a 96-well sample preparation plate as T"0" plasma samples. Aliquots were mixed with the same volume of blank buffer (50:50, volume:volume). Samples were quenched with 200 μL of acetonitrile containing internal standard. The dialysis block was covered and a shaken at 60 rpm for 5 hours at 37° C.

After a 5-hour incubation, dialyzed samples were prepared from 25-μL aliquots from both the donor and receiver sides of the dialysis apparatus into new sample preparation plates. The aliquots were mixed with same volume of opposite matrixes. The samples were quenched with 200 μL acetonitrile containing internal standard. All 0-hour and 5-hour samples were vortexed at 600 rpm for 10 min followed by centrifugation at 5594×g for 15 minutes (Thermo Multifuge×3R). Fifty μL of the supernatants were transferred to anew 96-well plate and mixed with 50 μL Milli-Q water. The sample plate was covered and frozen at −20° C. until LC/MS/MS analysis.

Table 6 shows the further DMPK results for plasma stability half-life ($T_{1/2}$ in min), Caco-2 permeability ($P_{app}$, B-A/A-B), and protein binding fraction bound (%), and protein binding recovery (%).

TABLE 6

Additional in vitro DMPK results for human glycolate oxidase inhibitors

| Ex. No. | Plasma Stability $T_{1/2}$ (min) | Caco-2 Permeability $P_{app}$ (basal-apical/ apical-basal) | Protein Binding Fraction Bound (%) | Protein Binding Recovery (%) |
|---|---|---|---|---|
| I-001 | 42.34 | 0.35 | 100.0 | 75.4 |
| I-031 | 74.93 | 1.26 | 100.0 | 117.2 |
| I-033 | 75.34 | 0.85 | 100.0 | 122.7 |
| I-037 | 47.15 | 0.78 | 100.0 | 104.9 |
| I-049 | 219.01 | 2.98 | 99.4 | 107.4 |
| I-050 | 141.08 | 0.61 | 100.0 | 71.2 |
| I-058 | 51.15 | 1.96 | 100.0 | 101.0 |
| I-128 | 45.30 | 5.12 | 100.0 | 126.5 |
| I-129 | 86.41 | 35.11 | 100.0 | 113.4 |
| I-150 | 44.81 | 2.63 | 100.0 | 100.0 |
| I-151 | 40.14 | 6.89 | 100.0 | 10.7.0 |
| I-152 | 193.11 | 24.46 | 100.0 | 97.7 |
| I-153 | 186.75 | 6.08 | 89.7 | 116.4 |
| I-154 | 111.00 | >3.65 | 100.0 | 98.5 |
| I-158 | 286.09 | 8.2 | 100.0 | 92.5 |
| I-160 | 172.51 | 2.03 | 100.0 | 93.6 |
| I-167 | 371.21 | 8.76 | 100.0 | 95.5 |
| I-171 | 115.99 | 27.84 | 100.0 | 87.5 |
| I-174 | 69.90 | 2.67 | 100.0 | 99.9 |
| I-177 | 67.20 | 152.82 | 100.0 | 99.3 |
| I-178 | 59.08 | 40.25 | 100.0 | 109.3 |
| I-249 | 222.83 | 7.64 | 100.0 | 99.2 |
| I-250 | 145.76 | >15.28 | 91.1 | 98.8 |
| I-251 | 292.08 | 16.93 | 100.0 | 98.2 |
| I-252 | 301.34 | 41.83 | 100.0 | 97.1 |
| I-253 | 106.97 | 45.91 | 100.0 | 111.6 |
| I-254 | 150.65 | 12.16 | 100.0 | 94.4 |
| I-255 | 201.15 | 46.58 | 100.0 | 102.2 |
| I-256 | 511.13 | 5.21 | 100.0 | 113.2 |
| I-257 | 182.29 | 1.79 | 97.8 | 101.6 |
| I-258 | 63.00 | 0.96 | 100.0 | 109.8 |
| I-259 | 79.81 | 6.06 | 77.9 | 105.2 |
| I-260 | 107.36 | 13.02 | 95.3 | 113.6 |
| I-261 | 79.67 | 6.14 | 100.0 | 111.0 |
| I-262 | 97.91 | 41.06 | 99.1 | 120.1 |
| I-263 | 90.71 | 9.3 | 98.6 | 110.6 |
| I-264 | 103.02 | >3.31 | 100.0 | 122.6 |
| I-265 | 86.68 | 0.63 | 100.0 | 110.0 |
| I-266 | 186.36 | 2.15 | 100.0 | 101.2 |
| I-267 | 68.84 | 1.60 | 100.0 | 113.4 |
| I-268 | 110.58 | 2.50 | 100.0 | 106.2 |
| I-269 | 131.29 | 4.69 | 99.0 | 91.8 |
| I-270 | 311.96 | 2.60 | 99.2 | 101.3 |
| I-271 | 169.38 | 25.21 | 99.0 | 109.9 |
| I-272 | 276.59 | 1.23 | 100.0 | 101.1 |
| I-273 | 131.94 | 0.47 | 99.7 | 99.9 |
| I-275 | 102.23 | 1.72 | 100.0 | 98.5 |
| I-276 | 192.00 | 1.60 | 99.4 | 108.5 |
| I-277 | 162.32 | 2.61 | 99.7 | 107.9 |
| I-279 | 156.65 | 2.62 | 100.0 | 98.2 |
| I-285 | 481.12 | 0.91 | 98.8 | 98.8 |
| I-286 | 206.73 | 2.00 | 99.8 | 103.0 |
| I-287 | 103.28 | 0.60 | 99.8 | 109.2 |
| I-288 | 117.62 | 2.64 | 97.5 | 109.9 |
| I-294 | 102.38 | 0.39 | 100.0 | 111.2 |
| I-299 | 73.39 | 1.88 | 99.8 | 113.8 |
| I-302 | 100.32 | 29.75 | 98.3 | 104.1 |
| I-304 | 400.75 | 8.02 | 99.3 | 104.7 |

Mouse Models of Hyperoxaluria for Determining In Vivo Efficacy of hGOX Inhibitors Male CD1 mice, 6-8 weeks of age (Charles River Labs, Wilmington, Mass.) were administered 1% ethylene glycol ad libitum their drinking water for 14 days. The mice were housed in individual cages, fed ad libitum and 24-h urine collections were initiated on days 1, 5, 9 and 14 using a 15-rack metabolic cage system equipped with a CCS2000 chiller system (Hatteras Instruments, Cary, N.C.) to maintain the samples at 4° C. during collection. Hydrochloric acid (100 µL of 6N) added to the collection vials to acidify the samples and prevent degradation of oxalate before evaluation.

Urine samples were maintained at 4° C. and urinary oxalate concentrations were determined within 24 hours of sample collection using a Trinity Biotech oxalate assay kit (Catalog #591-D). The assay was an enzymatic method based on the oxidation of oxalate by oxalate oxidase followed by measurement of hydrogen peroxide ($H_2O_2$) produced during the peroxidase-catalyzed reaction. Briefly, a 1-mL aliquot of each sample was diluted with an equal volume of assay diluent to bring the pH to between 5.0 and 7.0, then placed into purifier tubes (provided in the kit) and mixed for 5 min. The tubes were centrifuged for 5 min at 2000 rpm (1500×g) and the supernatants collected for the oxalate assay. The procedure was specific for oxalate with no special equipment and was easily adaptable for clinical automated analyzers. Each assay included a standard curve prepared with a standardized oxalate control sample (included in the kit) and internal assay control samples for both a normal (0.2-0.3 mmol/L) and elevated (0.86-1.21 mmol/L) level of oxalate.

To evaluate in vivo efficacy, mice were dosed by once-daily oral gavage of compound I-002 in an appropriate vehicle (e.g., phosphate-buffered saline, pH 7.4) at a dosage of 100 mg/kg. A control group was included which is dosed with the same volume of vehicle with no compound. Dosing was performed daily for 4 to 7 days. A final urine 24-urine collection was initiated immediately following dosing on day 7. Compound I-002 showed a statistically significant reduction in urinary oxalate at 100 mg/kg daily dosing and was subsequently evaluated with a dose-response study to determine the minimal efficacious dose and an $EC_{30}$ (efficacious dose causing a 30% reduction in urinary oxalate).

The effect of example I-001 in the ethylene glycol model using CD-1 mice was evaluated by twice-daily, oral gavage dosing at 50 mg/kg for 6 days (days 5-11). Total urinary oxalate values (µmole/24 hr/mL) were decreased by 24% and 32% in 24-hour urine collections after 3 and 6 days of drug treatment, respectively. These data indicate the compounds described herein should be effective in reducing urinary oxalate in a model of hyperoxaluria and thus would be effective treating diseases related to oxalate accumulation, for example hyperoxaluria.

Murine Knockout Model

In addition, a genetic model of hyperoxaluria was created by knocking out the mouse liver enzyme Agxt using CRISPR-Cas9 technology (Jackson Laboratories, Bar Harbor, Me.). The mice were housed in individual cages, fed ad libitum and 24-h urine collections were initiated on days 1, 5, 9 and 14 using a 15-rack metabolic cage system equipped with a CCS2000 chiller system (Hatteras Instruments, Cary, N.C.) to maintain the samples at 4° C. during collection. Hydrochloric acid (100 µL of 6 N) added to the collection vials to acidify the samples and prevent degradation of oxalate before evaluation. Samples from this assay may be analyzed as above using the oxalate assay kit, or may be analyzed using another suitable method, e.g., HPLC. It is expected that the compounds described herein should be effective in reducing urinary oxalate in this model of hyperoxaluria, and thus would be effective treating diseases related to oxalate accumulation, for example hyperoxaluria.

It is expected that compounds disclosed herein will be effective in reducing urinary oxalate, and thus would be effective in the treating diseases related to oxalate accumulation, for example hyperoxaluria.

It expected that compounds disclosed herein will be effective in reducing urinary oxalate, and thus would be effective in the treating diseases related to oxalate accumulation, for example hyperoxaluria.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:

1. A compound of structural Formula Ia

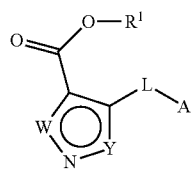

(Ia)

or a salt or tautomer thereof, wherein:
W is N or NH;
Y is N if W is NH; Y is NH if W is N;
$R^1$ is chosen from hydrogen and $C_1$-$C_6$ alkyl;
L is O;
A is chosen from monocyclic or bicyclic aryl, monocyclic or bicyclic heteroaryl, biaryl, and biheteroaryl, substituted with one or more $R^2$ groups; and
each $R^2$ is independently chosen from $C_2$-$C_6$ alkynyl.

2. The compound of claim 1, wherein A is chosen from aryl, biaryl, and biheteroaryl, any of which is substituted with one or more $R^2$ groups.

3. The compound of claim 2, wherein A is chosen from phenyl, biphenyl, naphthyl, pyridinylphenyl, phenylpyridinyl, and bipyridinyl, any of which is substituted with one or more $R^2$ groups.

4. The compound of claim 3, wherein A is substituted with ethynyl.

5. The compound of claim 3, wherein the phenyl is substituted with ethynyl.

6. The compound of claim 1, wherein $R^1$ is ethyl, methyl, or hydrogen.

7. The compound of claim 1, wherein $R^1$ is hydrogen.

8. A compound of structural Formula Id

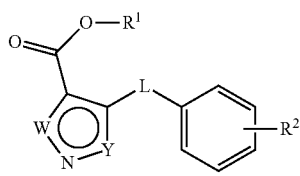

(Id)

or a salt or tautomer thereof, wherein:
W is N or NH;
Y is N if W is NH; Y is NH if W is N;
$R^1$ is chosen from hydrogen and $C_1$-$C_6$ alkyl;
L is O; and
each $R^2$ is independently chosen from $C_2$-$C_6$ alkynyl.

9. The compound of claim 8, wherein the phenyl is substituted with ethynyl.

10. The compound of claim 8, wherein $R^1$ is ethyl, methyl, or hydrogen.

11. A pharmaceutical composition comprising a compound of claim 1, a salt or tautomer thereof together with a pharmaceutically acceptable carrier.

12. The pharmaceutical composition of claim 11, formulated for oral administration.

13. The pharmaceutical composition of claim 11, additionally comprising another therapeutic agent.

14. A method of inhibiting glycolate oxidase (GOX) activity in a biological sample comprising contacting the biological sample with a pharmaceutical composition of claim 11, or a salt or tautomer thereof.

15. A method of treating an oxalate-related disease in a subject in need thereof, comprising the step of administering to the subject a compound of claim 11, or a pharmaceutical composition thereof, or a salt or tautomer thereof.

16. The method of claim 15, wherein the subject is a human.

17. The method of claim 16, wherein the oxalate-related disease is hyperoxaluria.

18. The method of claim 17, wherein the oxalate-related disease is primary hyperoxaluria.

19. A method of treating an oxalate-related disease in a subject in need thereof, comprising the sequential or co-administration of a compound of claim 8 or a pharmaceutical composition thereof; and a second therapeutic agent.

20. A compound of claim 8, wherein the compound is

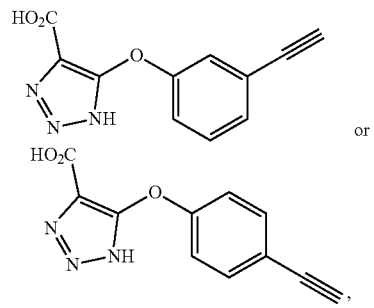

or a salt or tautomer thereof.

* * * * *